(12) United States Patent
Barbour et al.

(10) Patent No.: US 12,247,056 B2
(45) Date of Patent: Mar. 11, 2025

(54) MULTI-EPITOPE VACCINE FOR THE TREATMENT OF ALZHEIMER'S DISEASE

(71) Applicant: OTHAIR PROTHENA LIMITED, Dublin (IE)

(72) Inventors: Robin Barbour, Walnut Creek, CA (US); Gene Kinney, Boca Raton, FL (US); Wagner Zago, San Carlos, CA (US); Tarlochan S. Nijjar, Orinda, CA (US)

(73) Assignee: Othair Prothena Limited, Dublin (IE)

( * ) Notice: Subject to any disclaimer, the term of this patent is extended or adjusted under 35 U.S.C. 154(b) by 0 days.

(21) Appl. No.: 18/594,435

(22) Filed: Mar. 4, 2024

(65) Prior Publication Data

US 2024/0343769 A1 Oct. 17, 2024

Related U.S. Application Data

(62) Division of application No. 18/328,528, filed on Jun. 2, 2023, now Pat. No. 11,945,849, which is a division of application No. 17/925,813, filed as application No. PCT/US2021/033222 on May 19, 2021, now abandoned.

(60) Provisional application No. 63/140,917, filed on Jan. 24, 2021, provisional application No. 63/062,903, filed on Aug. 7, 2020, provisional application No. 63/027,150, filed on May 19, 2020.

(51) Int. Cl.
| | |
|---|---|
| *A61K 39/00* | (2006.01) |
| *A61K 38/00* | (2006.01) |
| *A61K 39/39* | (2006.01) |
| *A61P 25/28* | (2006.01) |
| *A61P 37/04* | (2006.01) |
| *C07K 14/47* | (2006.01) |

(52) U.S. Cl.
CPC ...... *C07K 14/4711* (2013.01); *A61K 39/0007* (2013.01); *A61K 39/39* (2013.01); *A61P 25/28* (2018.01); *A61P 37/04* (2018.01); *A61K 2039/53* (2013.01); *A61K 2039/545* (2013.01); *A61K 2039/55516* (2013.01); *A61K 2039/55544* (2013.01); *A61K 2039/55555* (2013.01); *A61K 2039/55572* (2013.01); *A61K 2039/55577* (2013.01); *A61K 2039/575* (2013.01); *A61K 2039/6037* (2013.01); *C07K 2319/00* (2013.01)

(58) Field of Classification Search
CPC ...... A61K 2039/53; A61K 2039/55516; A61K 39/39; A61P 37/04; C07K 2319/00
See application file for complete search history.

(56) References Cited

U.S. PATENT DOCUMENTS

| | | | |
|---|---|---|---|
| 5,057,540 | A | 10/1991 | Kensil |
| 5,208,036 | A | 5/1993 | Eppstein |
| 5,264,618 | A | 11/1993 | Felgner |
| 5,279,833 | A | 1/1994 | Rose |
| 5,283,185 | A | 2/1994 | Epand |
| 5,643,576 | A | 7/1997 | Johnston |
| 5,736,142 | A | 4/1998 | Sette |
| 5,840,838 | A | 11/1998 | Hensley et al. |
| 7,632,816 | B2 | 12/2009 | Wisniewski |
| 8,034,348 | B2 | 10/2011 | Schenk |
| 8,906,367 | B2 | 12/2014 | Nitsch |
| 10,501,531 | B2 | 12/2019 | Seubert |
| 2003/0175290 | A1 | 9/2003 | Renner et al. |
| 2008/0300204 | A1 | 12/2008 | Federoff et al. |
| 2010/0202968 | A1 | 8/2010 | Nitsch |
| 2011/0097351 | A1 | 4/2011 | Mandler et al. |
| 2014/0294839 | A1 | 10/2014 | Kuret |
| 2017/0239349 | A1 | 8/2017 | Agadjanyan |
| 2018/0327436 | A1 | 11/2018 | Gin |
| 2019/0330314 | A1 | 10/2019 | Barbour |
| 2019/0330316 | A1 | 10/2019 | Barbour |

FOREIGN PATENT DOCUMENTS

| | | |
|---|---|---|
| GB | 2220211 C | 1/1996 |
| WO | 1994012629 A1 | 6/1994 |
| WO | 1995007707 A1 | 3/1995 |
| WO | 1996034625 A1 | 11/1996 |
| WO | 1998040100 A1 | 9/1998 |
| WO | 2014058924 A2 | 4/2014 |
| WO | 2014165271 A2 | 10/2014 |
| WO | 2015165961 A1 | 11/2015 |
| WO | 2017191559 A1 | 11/2017 |

(Continued)

OTHER PUBLICATIONS

GenBank ID: BC108275.1. *Homo sapiens* synuclein, alpha. Submitted Nov. 3, 2005.

(Continued)

*Primary Examiner* — Barry A Chestnut
(74) *Attorney, Agent, or Firm* — McDonnell Boehnen Hulbert & Berghoff LLP

(57) ABSTRACT

The disclosure provides peptide compositions and immunotherapy compositions comprising an amyloid-beta (Aβ) peptide and a tau peptide. The disclosure also provides methods of treating or effecting prophylaxis of Alzheimer's disease or other diseases with beta-amyloid deposition in a subject, including methods of clearing deposits, inhibiting or reducing aggregation of Aβ and/or tau, blocking the uptake by neurons, clearing amyloid, and inhibiting propagation of tau seeds in a subject having or at risk of developing Alzheimer's disease or other diseases containing tau and/or amyloid-beta accumulations. The methods include administering to such patients the compositions comprising an amyloid-beta (Aβ) peptide and a tau peptide.

26 Claims, 40 Drawing Sheets

Specification includes a Sequence Listing.

(56) References Cited

FOREIGN PATENT DOCUMENTS

| WO | 2017191560 A1 | 11/2017 |
| --- | --- | --- |
| WO | 2017191561 A1 | 11/2017 |
| WO | 2018151821 A1 | 8/2018 |
| WO | 2018191598 A1 | 10/2018 |
| WO | 2018200656 A1 | 11/2018 |
| WO | 2018204546 A2 | 11/2018 |
| WO | 2018232369 A1 | 12/2018 |
| WO | 2019070480 A1 | 4/2019 |
| WO | 2019079160 A1 | 4/2019 |

OTHER PUBLICATIONS

Alexander, et al. (1994). "Development of high potency universal DR-restricted helper epitopes by modification of high affinity DR-blocking peptides." Immunity 1(9), 751-761.

Beissert, et al. (2020). "A trans-amplifying RNA vaccine strategy for induction of potent protective immunity." Mol. Ther. 28(1), 119-128.

Bett, et al. (1993). "Packaging capacity and stability of human adenovirus type 5 vectors." J. Virol. 67(10), 5911-5921.

Boris-Lawrie and Temin. (1993). "Recent advances in retrovirus vector technology." Curr. Opin. Genet. Develop. 3(1), 102-109.

Chen, et al. (2013). "Fusion Protein Linkers: Property, Design and Functionality." Adv. Drug Deliv. Rev. 65(10), 1357-1369.

Cunningham, et al. (2016). "Efficacy of the Herpes Zoster Subunit Vaccine in Adults 70 Years of Age or Older." N. Engl. J. Med. 375(11), 1019-1032.

Dubensky, et al. (1996). "Sindbis virus DNA-based expression vectors: utility for in vitro and in vivo gene transfer." J. Virol. 70(1), 508-519.

Gilman, et al. (2005). "Clinical effects of Abeta immunization (AN1792) in patients with AD in an interrupted trial." Neurology 64(9), 1553-1562.

Hull, et al. (2017). "Long-term extensions of randomized vaccination trials of ACC-001 and QS-21 in mild to moderate Alzheimer's disease." Curr. Alzheimer Res. 14(7), 696-708.

Jansen, et al. (1982). "Immunotoxins: Hybrid Molecules Combining High Specificity and Potent Cytotoxicity" Immunol. Rev. 62(1), 185-216.

McGee, et al. (1997). "The encapsulation of a model protein in poly (D,L lactide-co-glycolide) microparticles of various sizes: an evaluation of process reproducibility." J. Microencapsul. 14(2), 197-210.

NCT00960531. (2009-2013). "A Long Term Extension Study Evaluating ACC-001 With QS-21 in Subjects With Mild to Moderate Alzheimer's Disease." <https://clinicaltrials.gov/study/NCT00960531>.

Ohe, et al. (1995). "Construction of a novel bovine papillomavirus vector without detectable transforming activity suitable for gene transfer." Hum. Gene Ther. 6(3), 325-333.

Powilleit, et al. (2007). "Exploiting the Yeast L-A Viral Capsid for the In Vivo Assembly of Chimeric VLPs as Platform in Vaccine Development and Foreign Protein Expression." PLoS ONE 2(5), e415.

Stoute, et al. (1997). "A preliminary evaluation of a recombinant circumsporozite protein vaccine against Plasmodium falciparum malaria." N. Engl. J. Med. 336(2), 86-91.

Strejan, et al. (1984). "Suppression of chronic-relapsing experimental allergic encephalomyelitis in strain-13 guinea pigs by administration of liposome-associated myelin basic protein." J. Neuroimmunol. 7, 27-41.

Wald, et al. (2011). "Safety and immunogenicity of long HSV-2 peptides complexed with rhHsc70 in HSV-2 seropositive persons." Vaccine 29(47), 8520-8529.

Xiao and Brandsma. (1996). "High efficiency, long-term clinical expression of cottontail rabbit papillomavirus (CRPV) DNA in rabbit skin following particle-mediated DNA transfer." Nucleic Acids Res. 24(13), 2620-2622.

Zago, et al. (2012). "Neutralization of Soluble, Synaptotoxic Amyloid B Species by Antibodies is Epitope Specific." J. Neurosci. 32(8), 2696-2702.

Zhou. et al. (1994). "Adeno-associated virus 2-mediated high efficiency gene transfer into immature and mature subsets of hematopoietic progenitor cells in human umbilical cord blood." J. Exp. Med. 179(6), 1867-1875.

The International Search Report for International Application No. PCT/US2021/33222; mailed on Nov. 4, 2021, pp. 1-5.

Brain AD 04-33 – Vaccine Serum 2 – Dilution 1-300

Arrows: tau pathology
Arrowheads: A-beta pathology
Vaccine Serum 2: serum from vaccinated Guinea pig number 2
Immunogen 9  DAEFRHDRRQIVYKPVGGC Brain AD 04-33 - Vaccine Serum 2 – Dilution 1-300

Arrows: tau pathology
Arrowheads: A-beta pathology
Vaccine Serum 2: serum from vaccinated Guinea pig number 2
Immunogen 9  DAEFRHDRRQIVYKPVGGC Brain AD 04-33 - Vaccine Serum 2 – Dilution 1-1500

Arrows: tau pathology
Arrowheads: A-beta pathology
Vaccine Serum 2: serum from vaccinated Guinea pig number 2

Brain AD 04-33 – Control Serum – Dilution 1-300

Brain AD 04-33 - Control Serum – Dilution 1-300

Brain AD 04-33 – Control Serum – Dilution 1-1500

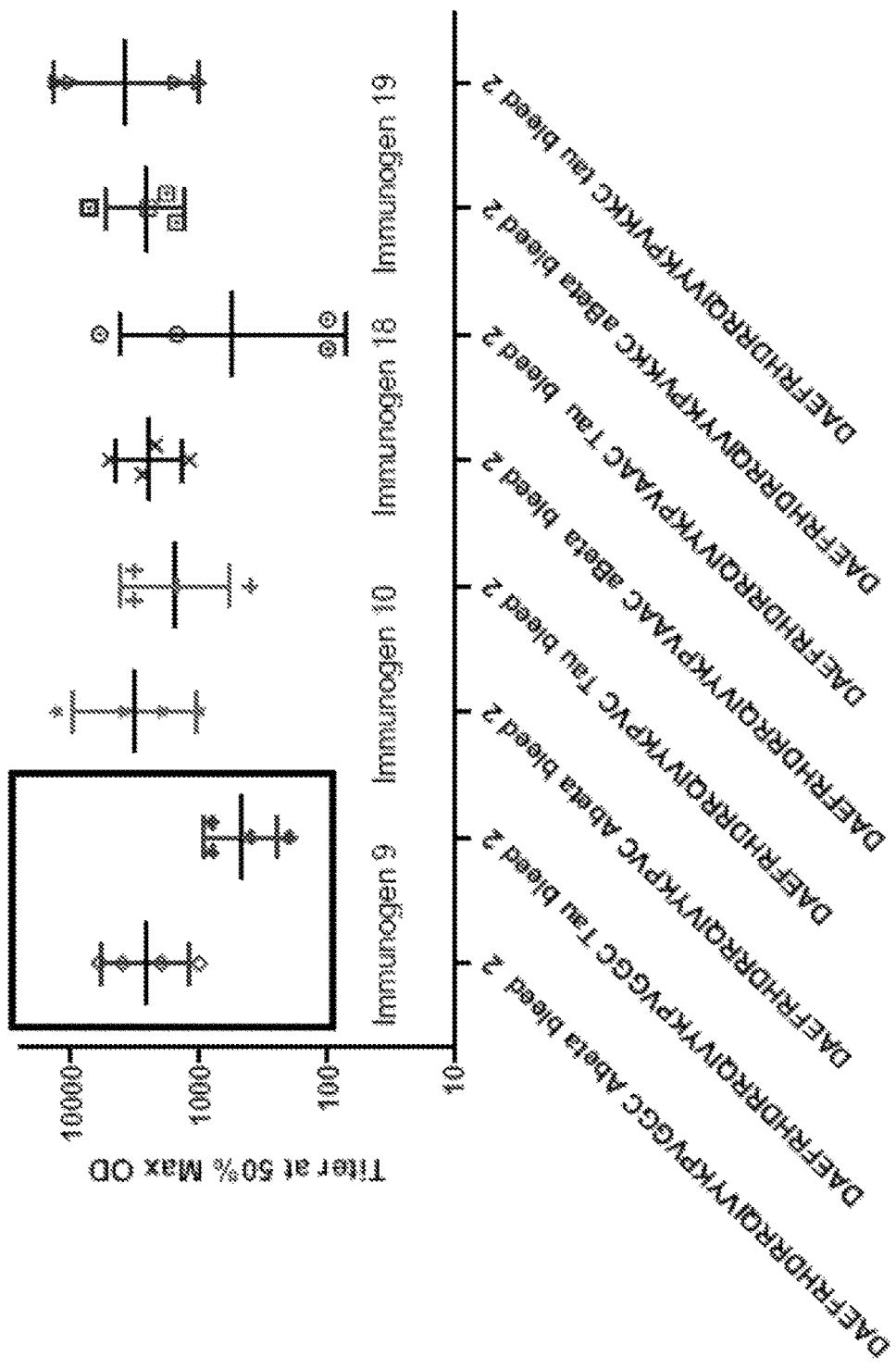

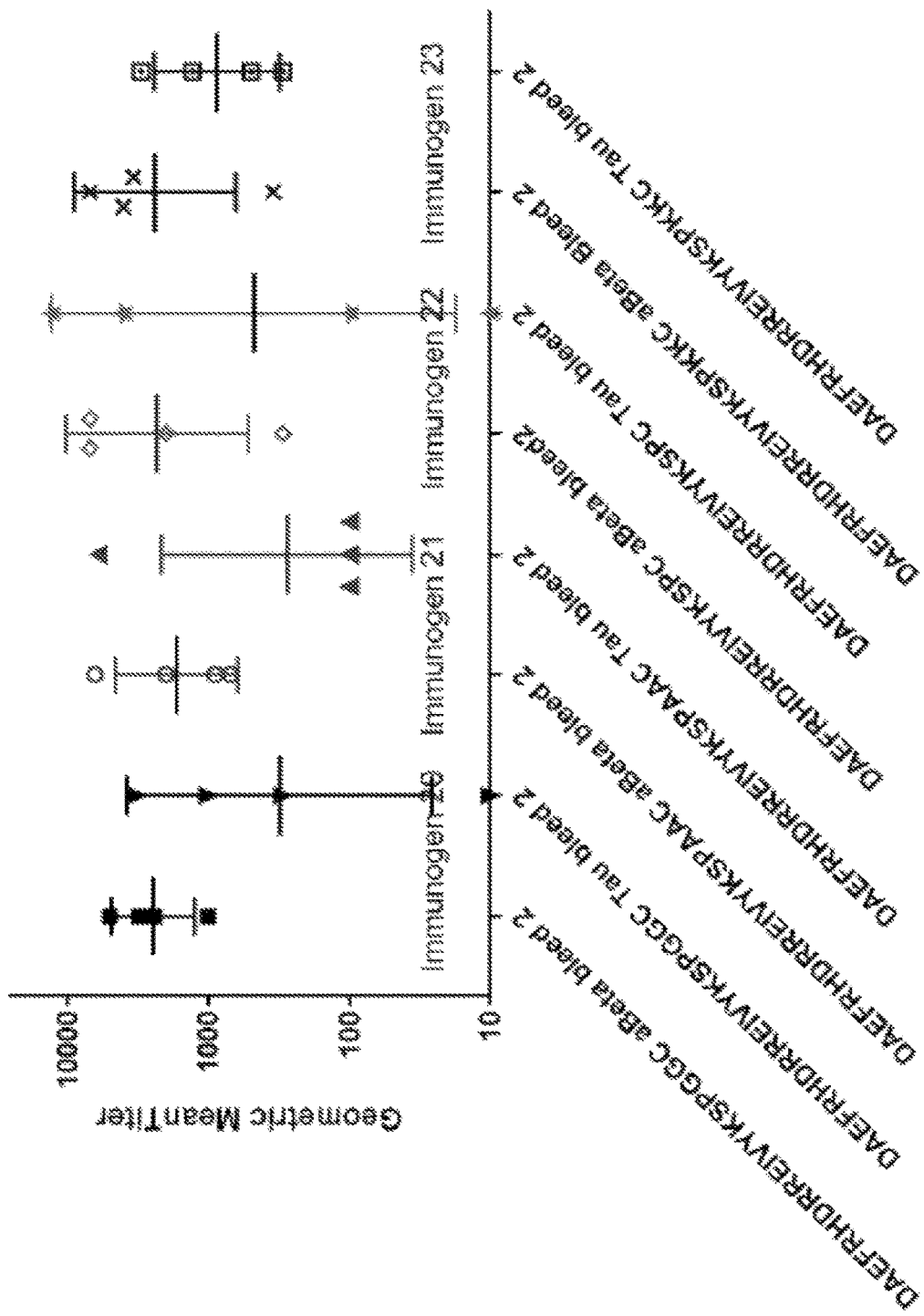

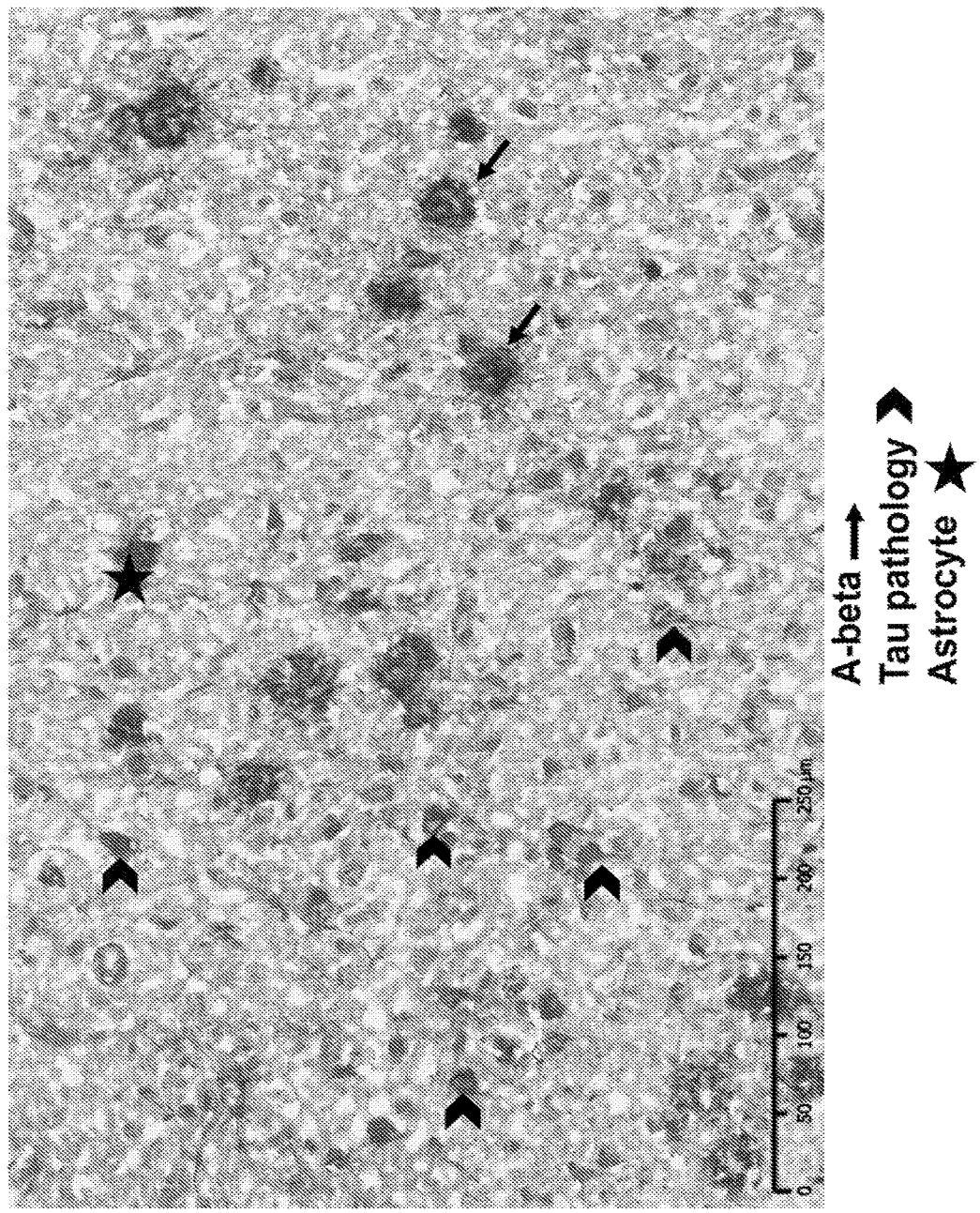
FIG. 6A Immunogen 19 Mouse 1 – 1:1000 dilution
A-beta →
Tau pathology ⟩
Astrocyte ★

Immunogen 19 Mouse 3 – 1:1000 dilution

A-beta →
Tau pathology ›

FIG. 6C
Negative Control - mouse serum – 1:1000 dilution
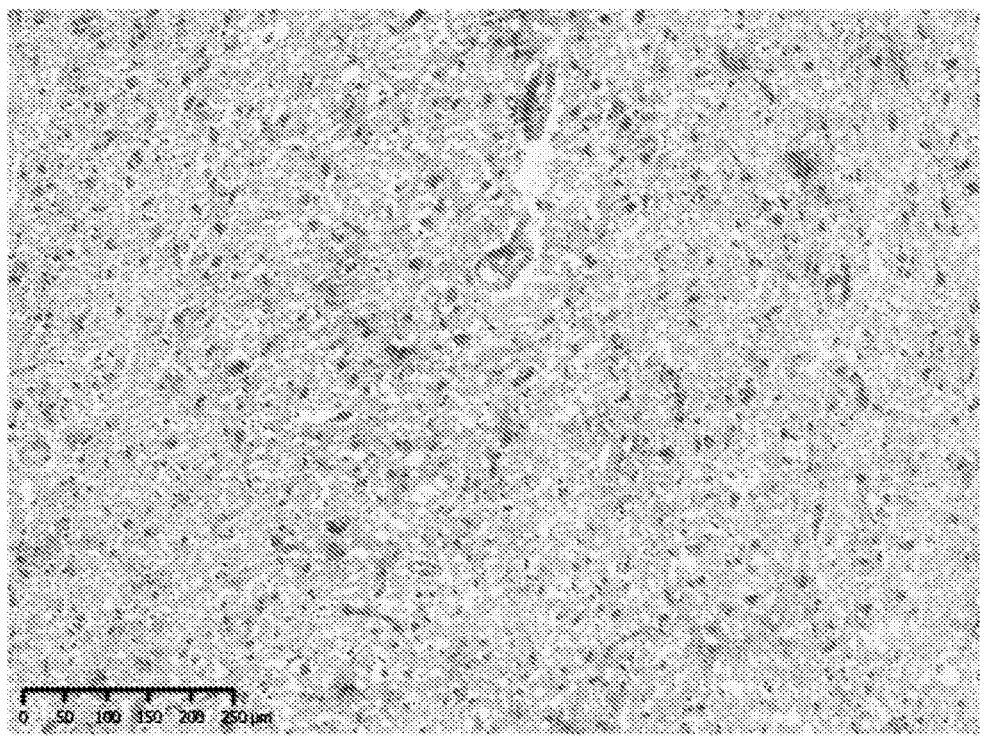
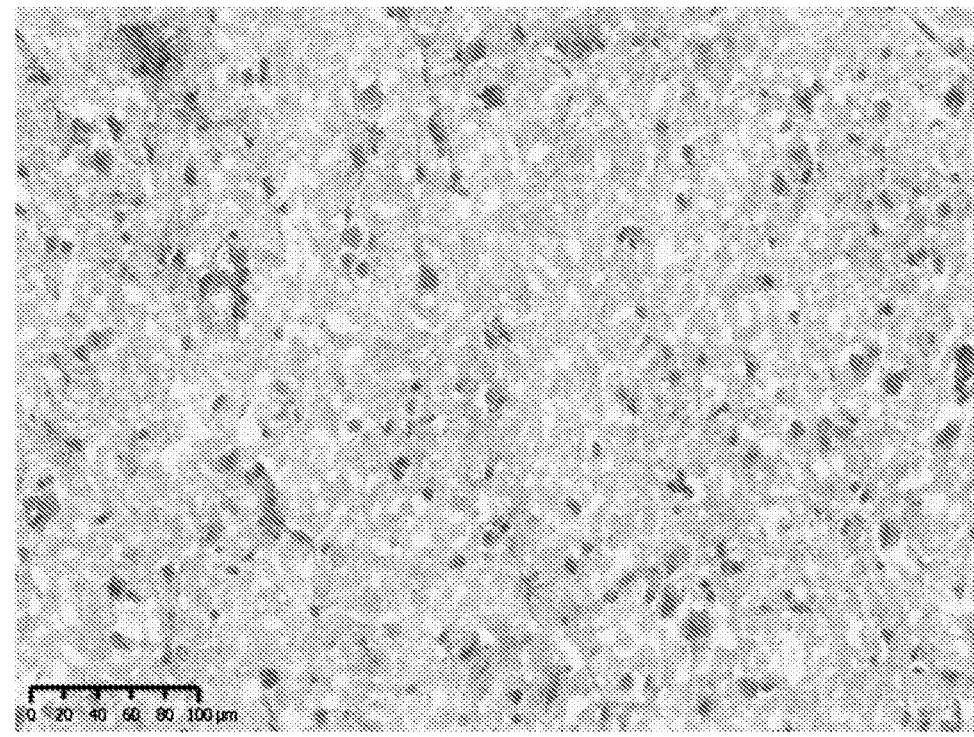

Positive Tau control – m6H3 Ab – 0.1 ug/ml

Tau pathology

REFERENCE: Guinea pig serum Immunogen 9
Vaccine GP # 2 – 1:300 dilution

A-beta →
Tau ▶

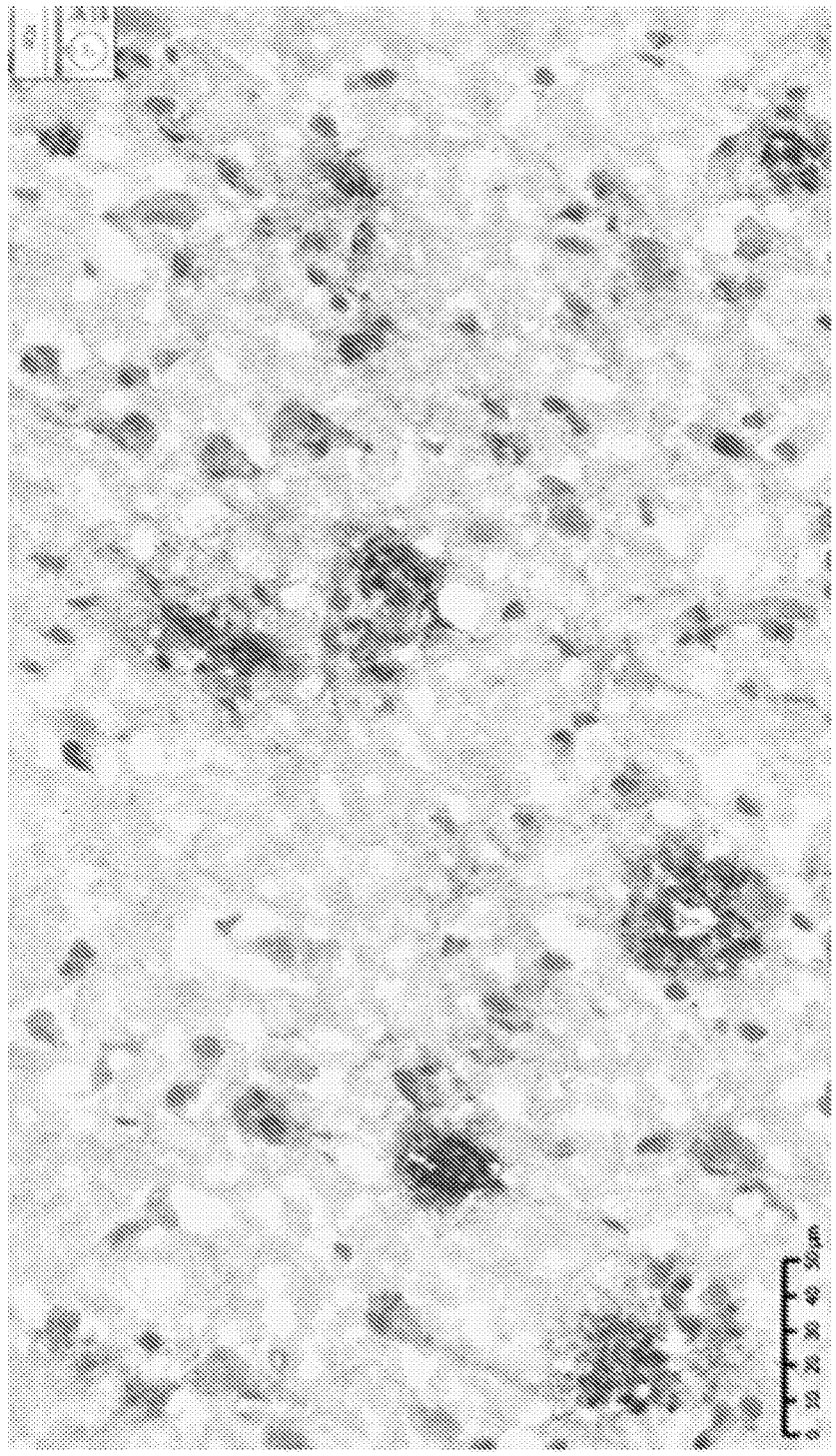
FIG. 10B Weak Tau pathology

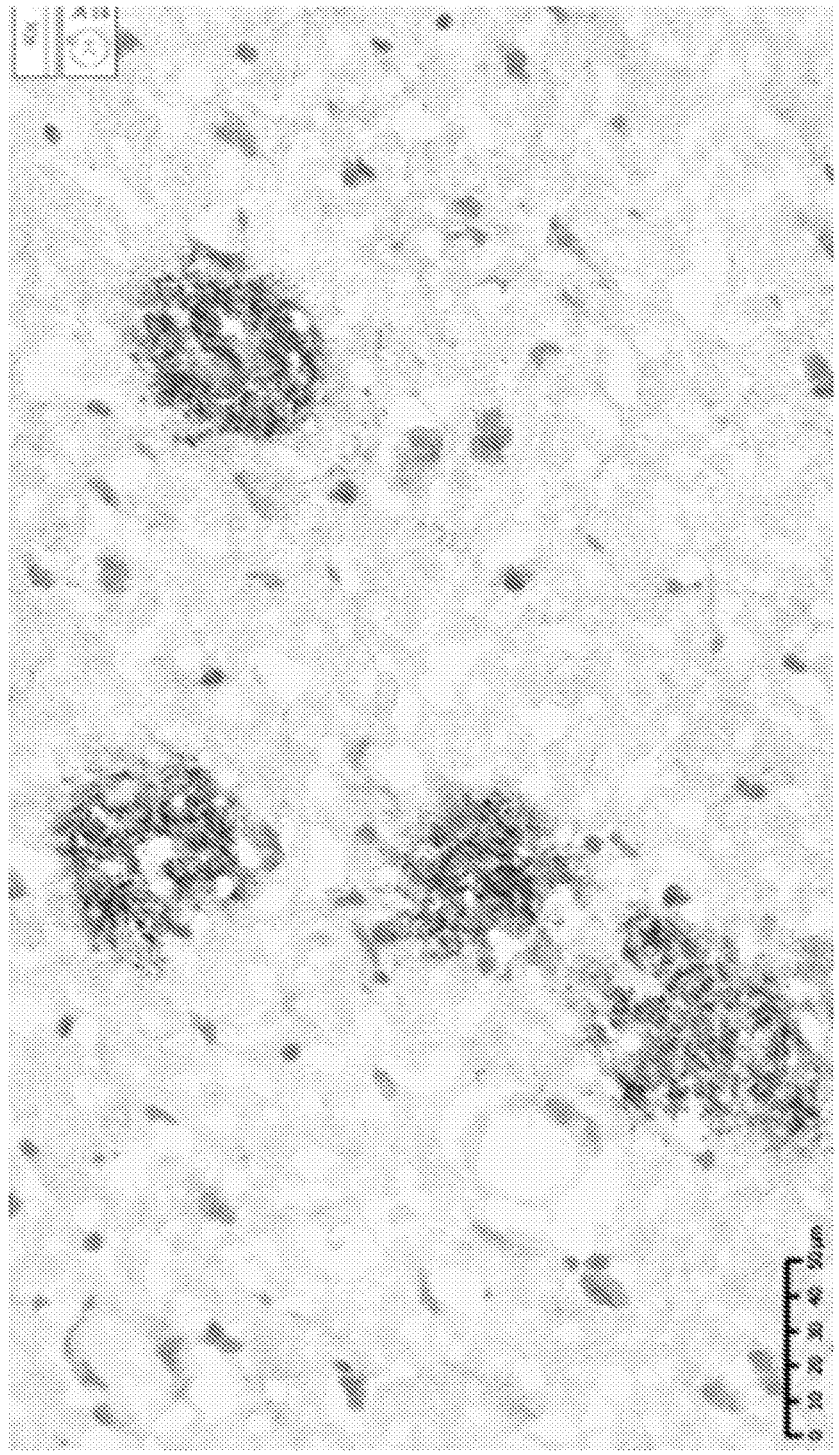
FIG. 12B  No Tau pathology

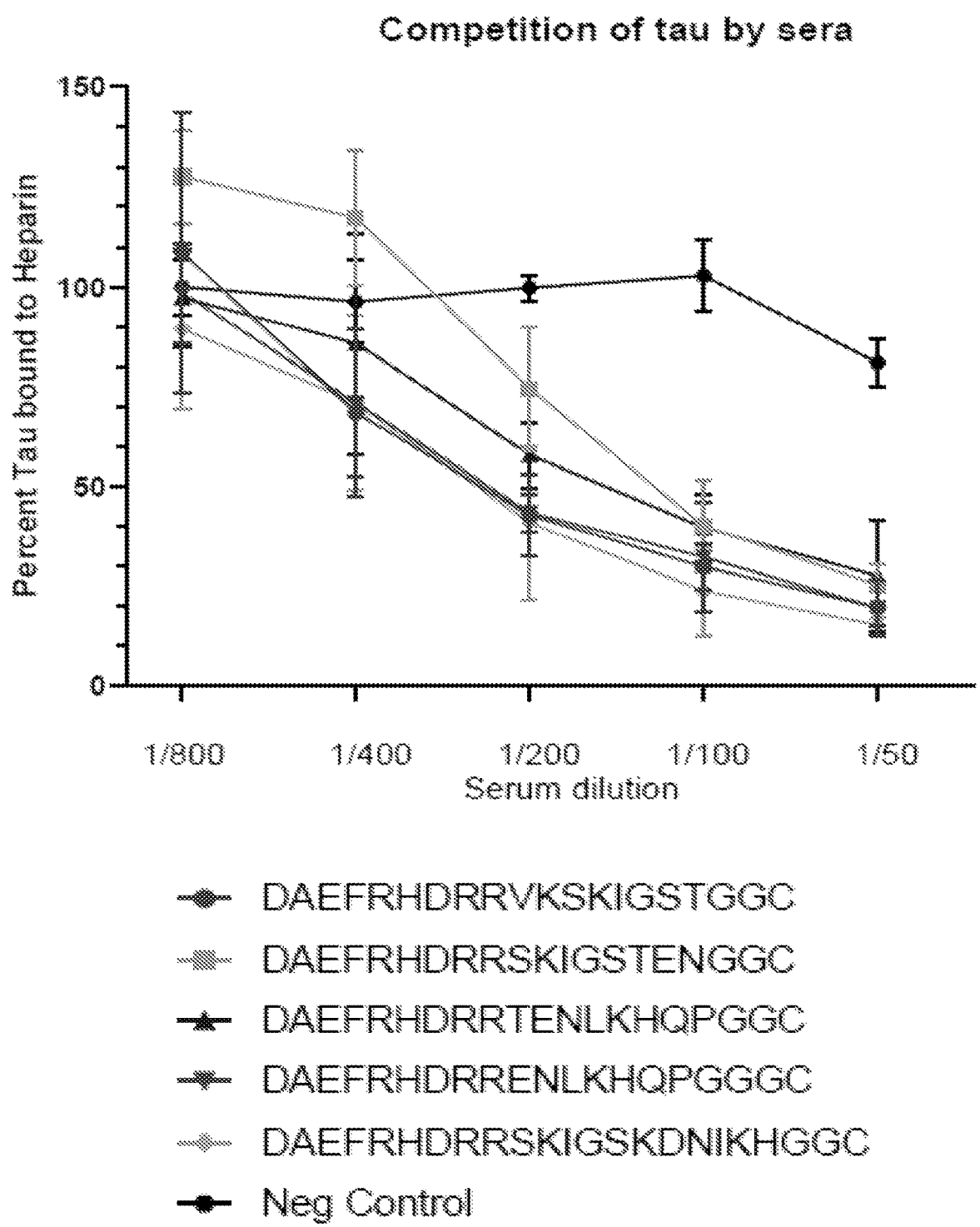

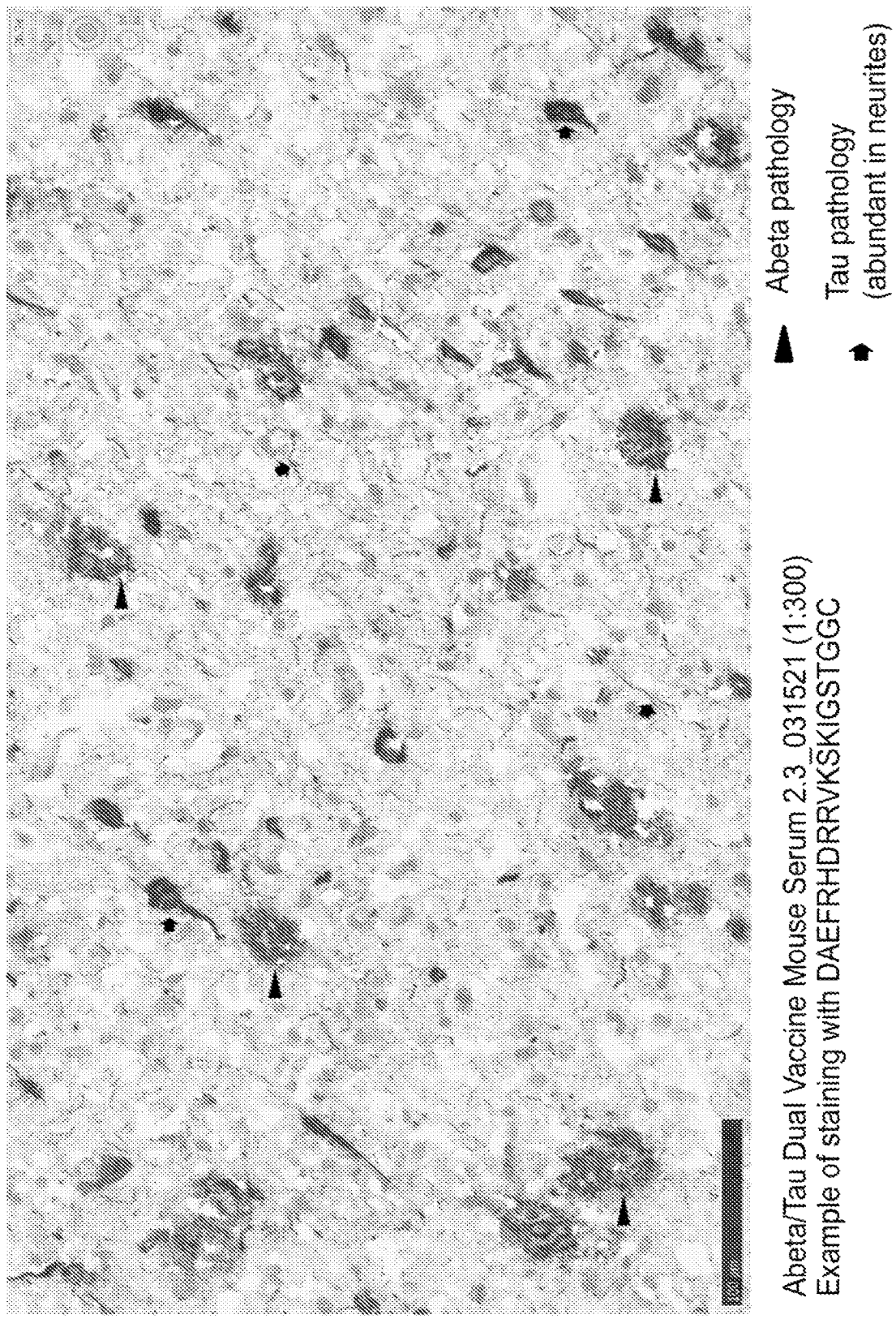

Abeta/Tau Dual Vaccine Mouse Serum 3.1_031521 (1:300)
Example of staining with DAEFRHDRRSKIGSTENGGC ▲ Abeta pathology
◆ Tau pathology (abundant in neurites)

Abeta/Tau Dual Vaccine Mouse Serum 8.4_031521 (1:300)
Example of staining with DAEFRHDRRTENLKHQPGGC ▲ Abeta pathology
♦ Tau pathology (abundant in neurites)

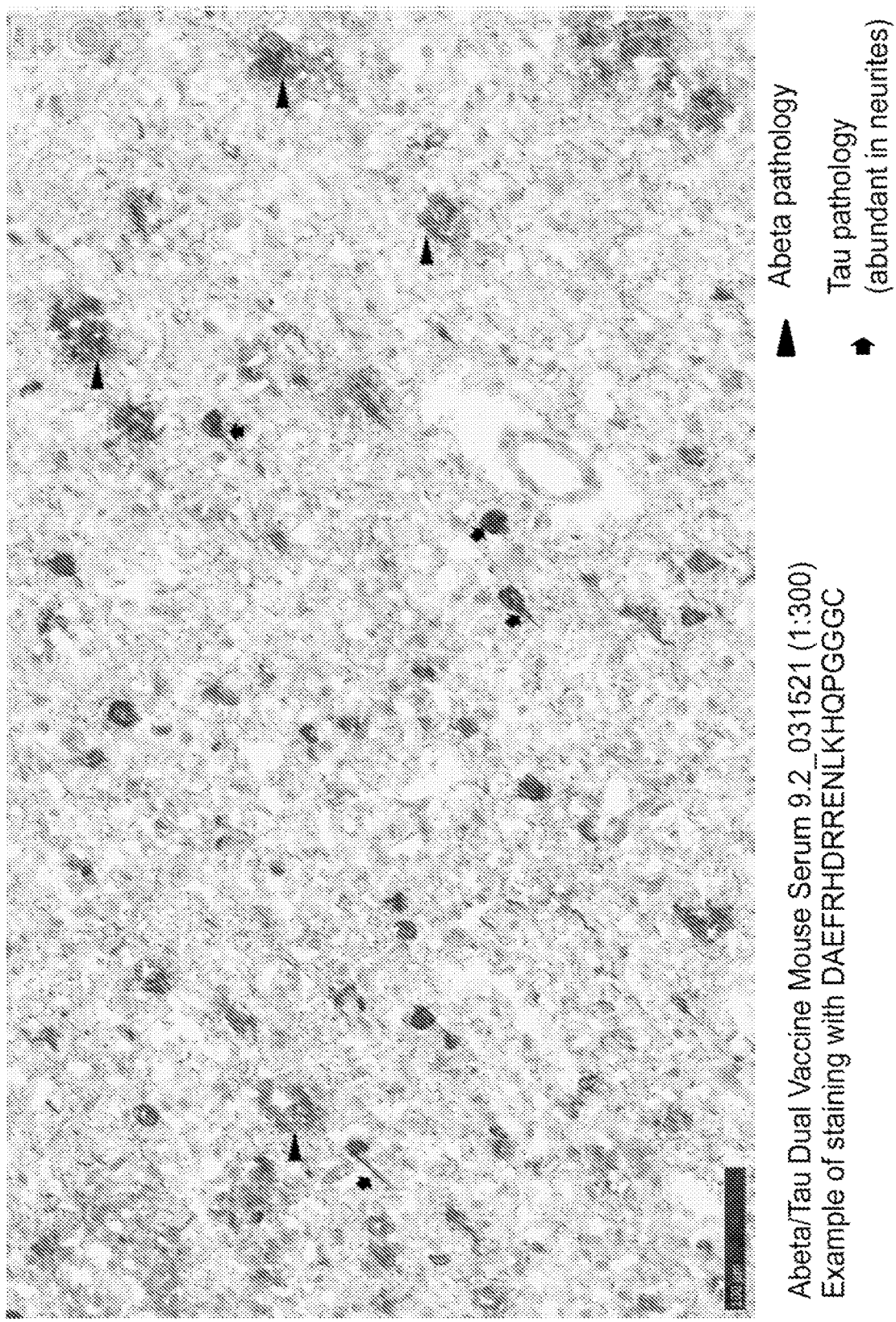

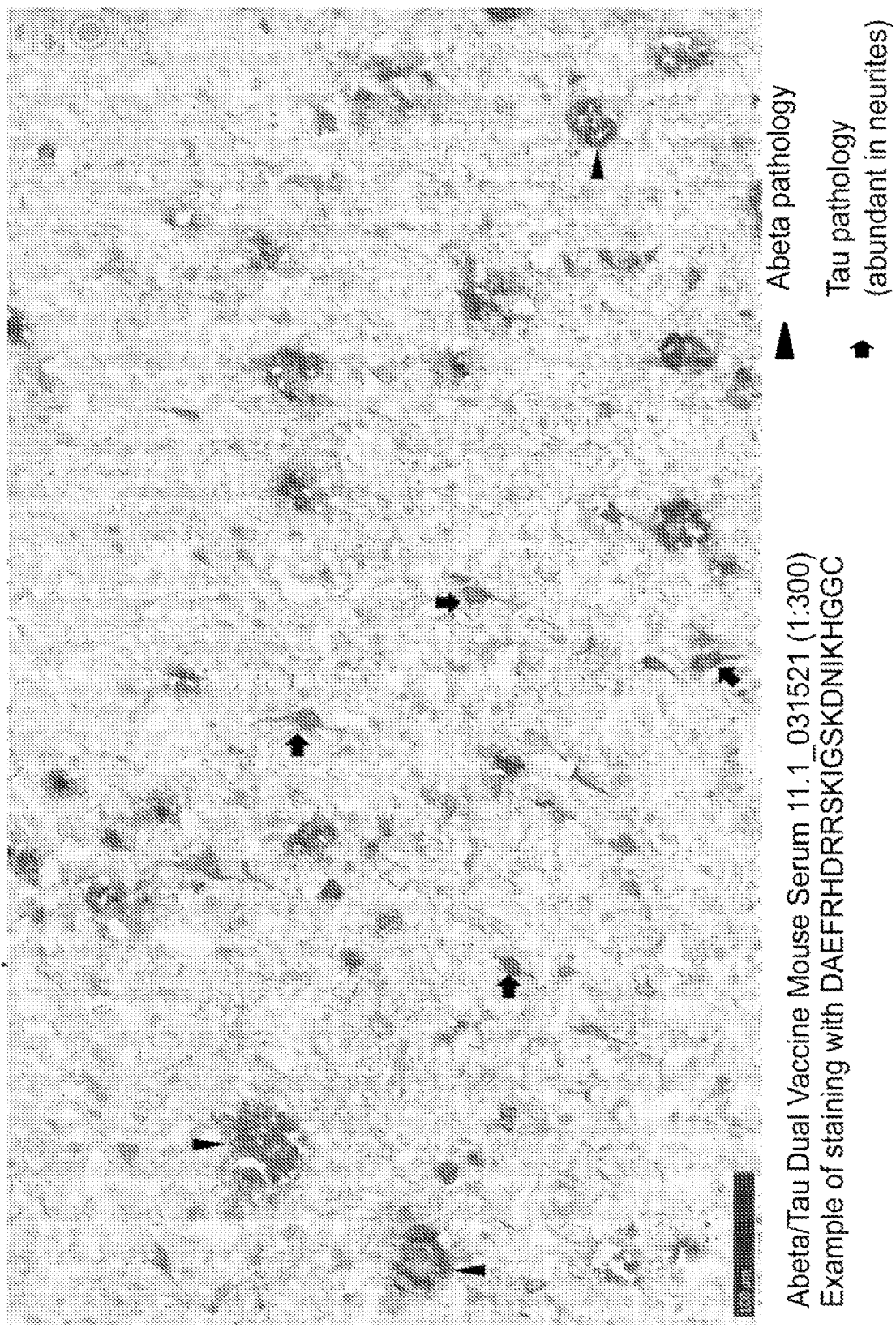

MULTI-EPITOPE VACCINE FOR THE TREATMENT OF ALZHEIMER'S DISEASE

RELATED APPLICATIONS

This application is a divisional application of U.S. application Ser. No. 18/328,528, filed Jun. 2, 2023, which is a divisional application of U.S. application Ser. No. 17/925,813, filed Nov. 16, 2022, which is a U.S. national phase application under 35 U.S.C. § 371 of International Application No. PCT/US2021/033222, filed May 19, 2021, and which claims the benefit of U.S. Provisional Patent Application Ser. No. 63/140,917, filed Jan. 24, 2021, U.S. Provisional Patent Application Ser. No. 63/062,903, filed Aug. 7, 2020, and U.S. Provisional Patent Application Ser. No. 63/027,150, filed May 19, 2020, each of which is incorporated by reference herein in its entirety.

SEQUENCE LISTING STATEMENT

A computer readable form of the Sequence Listing is filed with this application by electronic submission and is incorporated into this application by reference in its entirety. The Sequence Listing is contained in the file created on Jun. 2, 2023, having the file name "20-050-WO-US-DIV_SequenceListing.xml" and is 1,171,456 bytes in size.

FIELD

The disclosure relates to the technical fields of immunology and medicine, and in particular to the treatment of Alzheimer's disease and other diseases of protein misfolding.

BACKGROUND

Alzheimer's disease (AD) is a progressive disease resulting in senile dementia. Broadly speaking, the disease falls into two categories: late onset, which occurs in old age (65+ years) and early onset, which develops well before the senile period, i.e., between 35 and 60 years. In both types of disease, the pathology is the same, but the abnormalities tend to be more severe and widespread in cases beginning at an earlier age. The disease is characterized by at least two types of lesions in the brain, neurofibrillary tangles and senile plaques. Neurofibrillary tangles are intracellular deposits of microtubule associated tau protein consisting of two filaments twisted about each other in pairs. Senile plaques (i.e., amyloid plaques) are areas of disorganized neuropil up to 150 m across with extracellular amyloid deposits at the center which are visible by microscopic analysis of sections of brain tissue. The accumulation of amyloid plaques within the central nervous system is also associated with Down's syndrome and other cognitive disorders, Cerebral amyloid angiopathy (CAA), and the ocular disease Age-Related Macular Degeneration.

A principal constituent of the plaques is a peptide termed Aβ or β-amyloid peptide. Aβ peptide is a 4-kDa internal fragment of 38-43 amino acids of a larger transmembrane glycoprotein named amyloid precursor protein (APP). As a result of proteolytic processing of APP by different secretase enzymes, Aβ is primarily found in both a short form, 40 amino acids in length, and a long form, ranging from 42-43 amino acids in length. Part of the hydrophobic transmembrane domain of APP is found at the carboxy end of Aβ, and may account for the ability of Aβ to aggregate into plaques, particularly in the case of the long form. Accumulation of amyloid plaques in the brain eventually leads to neuronal cell death. The cognitive and physical symptoms associated with this type of neural deterioration characterize Alzheimer's disease.

Another protein reported to occur at increased levels in Alzheimer's patients relative to the general population is tau, the principal constituent of neurofibrillary tangles, which together with amyloid plaques are a hallmark characteristic of Alzheimer's disease. Tau tangles constitute abnormal fibrils measuring 10 nm in diameter occurring in pairs wound in a helical fashion with a regular periodicity of 80 nm. The tau within neurofibrillary tangles is abnormally phosphorylated (hyperphosphorylated) with phosphate groups attached to specific sites on the molecule. Severe involvement of neurofibrillary tangles is seen in the layer II neurons of the entorhinal cortex, the CA1 and subicular regions of the hippocampus, the amygdala, and the deeper layers (layers III, V, and superficial VI) of the neocortex in Alzheimer's disease. Tau pathologies are known to correlate to cognitive decline.

Accordingly, there exists the need for new therapies and reagents for the prevention or treatment of Alzheimer's disease, in particular, therapies and reagents capable of causing an immune response to the Aβ and Tau present in patients.

SUMMARY

In some embodiments, disclosure is directed to a polypeptide including a first peptide comprising 3-10 amino acids from residues 1-10 of SEQ ID NO:01 linked to a second peptide including 3-13 amino acids from residues 244-400 of SEQ ID NO:02. For example, the second peptide may be from the microtubule binding region (MTBR) of tau (residues 244-372 of SEQ ID NO:02). The first peptide may be N-terminal to the second peptide or the first peptide may be C-terminal to the second peptide. In addition, the first peptide may include an amino acid sequence of one of SEQ ID NOS: 3 to 38 or SEQ ID NOS:1002 to 1057 and the second peptide may include an amino acid sequence of one of SEQ ID NOS: 39-56, 83-86, or 146-996. For example, the first polypeptide may be DAEFRHD (SEQ ID NO:06), DAEFR (SEQ ID NO:08), or EFRHD (SEQ ID NO:21), and the second polypeptide may be 5-13 amino acids, for example QIVYKPV (SEQ ID NO:39), EIVYKSV (SEQ ID NO:42), EIVYKSP (SEQ ID NO:43), EIVYKPV (SEQ ID NO:44), NIKHVP (SEQ ID NO:48), VKSKIGST (SEQ ID NO:801), SKIGSTEN (SEQ ID NO:817), TENLKHQP (SEQ ID NO:695), ENLKHQPG (SEQ ID NO:689), SKIGSTDNIKH (SEQ ID NO:985), SKIGSKDNIKH (SEQ ID NO:986), or SKIGSLDNIKH (SEQ ID NO:988).

In other embodiments, the first peptide and second peptide may be linked by a cleavable linker, which may be an amino acid sequence. A cleavable peptide linker, if present, can be 1-10 amino acids in length. In some embodiments, the linker comprises between about 1-10 amino acids, about 1-9 amino acids, about 1-8 amino acids, about 1-7 amino acids, about 1-6 amino acids, about 1-5 amino acids, about 1-4 amino acids, about 1-3 amino acids, about 2 amino acids, or one (1) amino acid. In some embodiments, the cleavable peptide linker is 1 amino acid, 2 amino acids, 3 amino acids, 4 amino acids, 5 amino acids, 6 amino acids, 7 amino acids, 8 amino acids, 9 amino acids, or 10 amino acids. For example, the linker may be arginine-arginine (Arg-Arg), arginine-valine-arginine-arginine (Arg-Val-Arg-Arg (SEQ ID NO:69)), valine-citrulline (Val-Cit), valine-arginine (Val-Arg), valine-lysine (Val-Lys), valine-alanine (Val-Ala), phenylalanine-lysine (Phe-Lys), glycine-alanine-glycine-alanine (Gly-Ala-Gly-Ala; SEQ ID NO:80), Ala-Gly-Ala-Gly (SEQ ID NO:81), or Lys-Gly-Lys-Gly (SEQ ID NO:82). In particular embodiments, the polypeptide may be DAEFRHDRRQIVYKPV (SEQ ID NO:57), DAEFRHDRREIVYKSV (SEQ ID NO:58), DAEFRHDRRVKSKIGSTGGC (SEQ ID NO:997), DAEFRHDRRSKIGSTENGGC (SEQ ID NO:998), DAEFRHDRRTENLKHQPGGC (SEQ ID NO: 999), DAEFRHDRRENLKHQPGGGC (SEQ ID NO:1000), or DAEFRHDRRSKIGSKDNIKHGGC (SEQ ID NO:1001).

In further embodiments, the polypeptide may include a linker to a carrier at a C-terminal portion of the polypeptide, or at a N-terminal portion of the polypeptide. A linker, if present, can be 1-10 amino acids in length. In some embodiments, the linker comprises between about 1-10 amino acids, about 1-9 amino acids, about 1-8 amino acids, about 1-7 amino acids, about 1-6 amino acids, about 1-5 amino acids, about 1-4 amino acids, about 1-3 amino acids, about 2 amino acids, or one (1) amino acid. In some embodiments, the linker is 1 amino acid, 2 amino acids, 3 amino acids, 4 amino acids, 5 amino acids, 6 amino acids, 7 amino acids, 8 amino acids, 9 amino acids, or 10 amino acids. For example, the linker may include an amino acid sequence of GG, GGG, AA, AAA, KK, KKK, SS and SSS. In addition, the linker to the carrier, if present at the C-terminus, may include a C-terminal cysteine (C). Alternatively, the linker to the carrier, if present at the N-terminus, may include a N-terminal cysteine (C). For example, the polypeptide may include the amino acid sequence of DAEFRHDRRQIVYKPVXXC (SEQ ID NO:70), wherein XX and C are independently optional and, if present, XX can be GG, AA, KK, SS, GAGA (SEQ ID NO:80), AGAG (SEQ ID NO:81), or KGKG (SEQ ID NO:82). For example, the polypeptide may include the amino acid sequence of DAEFRHDRREIVYKSVXXC (SEQ ID NO:79), wherein XX and C are independently optional and, if present, XX can be GG, AA, KK, SS, GAGA (SEQ ID NO:80), AGAG (SEQ ID NO:81), and KGKG (SEQ ID NO:82).

In other embodiments, the disclosure is directed to an immunotherapy composition including the polypeptides of the disclosure, wherein the polypeptide may be linked to a carrier. The carrier may include serum albumins, immunoglobulin molecules, thyroglobulin, ovalbumin, tetanus toxoid (TT), diphtheria toxoid (DT), a genetically modified cross-reacting material (CRM) of diphtheria toxin, CRM197, meningococcal outer membrane protein complex (OMPC) and *H. influenzae* protein D (HiD), rEPA (*Pseudomonas aeruginosa* exotoxin A), KLH (keyhole limpet hemocyanin), and flagellin.

Still further, embodiments of the disclosure are directed to a pharmaceutical formulation includes the polypeptides or the immunotherapy compositions of the disclosure, and including at least one adjuvant. The adjuvant may be aluminum hydroxide, aluminum phosphate, aluminum sulfate, 3 De-O-acylated monophosphoryl lipid A (MPL), QS-21, QS-18, QS-17, QS-7, TQL1055, Complete Freund's Adjuvant (CFA), Incomplete Freund's Adjuvant (IFA), oil in water emulsions (such as squalene or peanut oil), CpG, polyglutamic acid, polylysine, AddaVax™, MF59@, and combinations thereof. In addition, the formulation may include a liposomal formulation, a diluent, or a multiple antigen presenting system (MAP). The MAP may include one or more of a Lys-based dendritic scaffold, helper T-cell epitopes, immune stimulating lipophilic moieties, cell penetrating peptides, radical induced polymerization, self-assembling nanoparticles as antigen-presenting platforms and gold nanoparticles.

Still further, embodiments of the disclosure are directed to an immunotherapy composition including a first peptide sequence comprising 3-10 amino acid residues from the first ten N-terminal residues of SEQ ID NO:01 and a second peptide sequence comprising 3-13 amino acids from residues 244-400 of SEQ ID NO:02. The first peptide may include an amino acid sequence of one of SEQ ID NOS: 3 to 38 or SEQ ID NOS:1002 to 1057, and the second peptide may include an amino acid sequence of one of SEQ ID NOS: 39 to 56, SEQ ID NOS:83-86 or SEQ ID NOS:146-996. Each of the first peptide and the second peptide may include a linker to a carrier at a C-terminal portion of the polypeptide, or at a N-terminal portion of the polypeptide. When present, the linker may include an amino acid sequence selected from GG, GGG, AA, AAA, KK, KKK, SS, SSS, GAGA (SEQ ID NO:80), AGAG (SEQ ID NO:81), and KGKG (SEQ ID NO:82), and may include a C-terminal cysteine (C). In some embodiments, where the C-terminal residues in the immunogen are either IVYKPV (SEQ ID NO:194), VYKPV (SEQ ID NO:195), YKPV (SEQ ID NO:196), KPV, or PV the linker is an amino acid linker that does not have a N-terminal glycine (e.g., GG, GAGA (SEQ ID NO:80)). The carrier may include serum albumins, immunoglobulin molecules, thyroglobulin, ovalbumin, tetanus toxoid (TT), diphtheria toxoid (DT), a genetically modified cross-reacting material (CRM) of diphtheria toxin, CRM197, meningococcal outer membrane protein complex (OMPC) and *H. influenzae* protein D (HiD), rEPA (*Pseudomonas aeruginosa* exotoxin A), KLH (keyhole limpet hemocyanin), and flagellin.

In addition, the immunotherapy composition may include at least one pharmaceutically acceptable diluent and/or a multiple antigen presenting system (MAP). The MAP may include one or more of a Lys-based dendritic scaffold, helper T-cell epitopes, immune stimulating lipophilic moieties, cell penetrating peptides, radical induced polymerization, self-assembling nanoparticles as antigen-presenting platforms and gold nanoparticles.

The immunotherapy composition may be included in a pharmaceutical composition including the immunotherapy composition and at least one adjuvant such as aluminum hydroxide, aluminum phosphate, aluminum sulfate, 3 De-O-acylated monophosphoryl lipid A (MPL), QS-21, QS-18, QS-17, QS-7, TQL1055, Complete Freund's Adjuvant (CFA), Incomplete Freund's Adjuvant (IFA), oil in water emulsions (such as squalene or peanut oil), CpG, polyglutamic acid, polylysine, AddaVax™, MF59@, and combinations thereof.

Embodiments of the disclosure are also directed to nucleic acid sequences encoding the polypeptides and the immunotherapy compositions of the disclosure. The nucleic acids may be included in a nucleic acid immunotherapy composition including the nucleic acid and at least one adjuvant.

Still further, embodiments of the disclosure are directed to a methods for treating or effecting prophylaxis of Alzheimer's disease in a subject, and methods for inhibiting or reducing aggregation of at least one of Aβ and tau in a subject having or at risk of developing Alzheimer's disease. The methods include administrating to the subject an immunotherapy composition, a nucleic acids immunotherapy composition, or a pharmaceutical formulation of the disclosure.

The methods of the disclosure may include repeating the administering at least a second time, at least a third time, at least a fourth time, at least a fifth time, or at least a sixth time, and may include repeating the administering at an interval of about 21 to about 28 days.

Still further, methods of the disclosure are directed to inducing an immune response in an animal. The methods include administering to the animal a polypeptide, an immunotherapy composition, a pharmaceutical formulation or a nucleic acid immunotherapy composition of the disclosure in a regimen effective to generate an immune response including antibodies that specifically bind to Aβ, tau, or both Aβ and tau. The immune response may include antibodies that specifically bind to the N-terminal region of Aβ and/or the microtubule region of tau.

In other embodiments, the disclosure is directed to an immunization kit including an immunotherapy composition of the disclosure and may include an adjuvant, wherein the immunotherapy composition may be in a first container and the adjuvant may be a second container.

Still further, the disclosure is directed to a kit including a nucleic acid immunotherapy composition of the disclosure and may include an adjuvant. The nucleic acid may be in a first container and the adjuvant may be in a second container.

BRIEF DESCRIPTION OF THE FIGURES

FIG. 5A shows that mice vaccinated with dual peptide antigens with various linkers produce similar titers to Aβ and Tau.

FIG. 5B shows that mice vaccinated with dual peptide antigens with the Tau sequence EIVYKSP (SEQ ID NO:43) produce titers to Aβ and Tau.

FIG. 6A shows staining of Aβ and Tau pathology in fresh frozen human AD brain tissue using serum (1:1000 dilution) from a mouse vaccinated with Immunogen 19.

FIG. 6C shows lack of staining of Aβ and Tau pathology in fresh frozen human AD brain tissue using serum (1:1000 dilution) from an unvaccinated mouse.

(FIG. 7B) showing 0, 8 and 24 weeks) over the experiment are expressed as mean titer+/−SEM.

FIG. 10B shows modest staining of Tau pathology in fresh frozen human AD brain tissue using serum (1:300 dilution) from cynomolgus monkey #1003.

FIG. 12B shows a lack of staining of Tau pathology in fresh frozen human AD brain tissue using serum (1:300 dilution) from cynomolgus monkey #2501.

FIG. 14 shows blocking of tau binding to Heparin by sera from AP-tau constructs DAEFRHDRRVKSKIGSTGGC (SEQ ID NO:997); DAEFRHDRRSKIGSTENGGC (SEQ ID NO:998); DAEFRHDRRTENLKHQPGGC (SEQ ID NO:999); DAEFRHDRRENLKHQPGGGC (SEQ ID NO:1000); and DAEFRHDRRSKIGSKDNIKHGGC (SEQ ID NO:1001).

FIG. 16A shows Abeta/Tau Dual Vaccine Mouse Serum 2.3_031521 (1:300) Example of staining with DAEFRHDRRVKSKIGSTGGC (SEQ ID NO:997).

FIG. 16D shows Abeta/Tau Dual Vaccine Mouse Serum 9.2_031521 (1:300) Example of staining with DAEFRHDRRENLKHQPGGGC (SEQ ID NO:1000).

FIG. 16E shows Abeta/Tau Dual Vaccine Mouse Serum 11.1_031521 (1:300) Example of staining with DAEFRHDRRSKIGSKDNIKHGGC (SEQ ID NO: 1001).

DESCRIPTION

Figure 1:
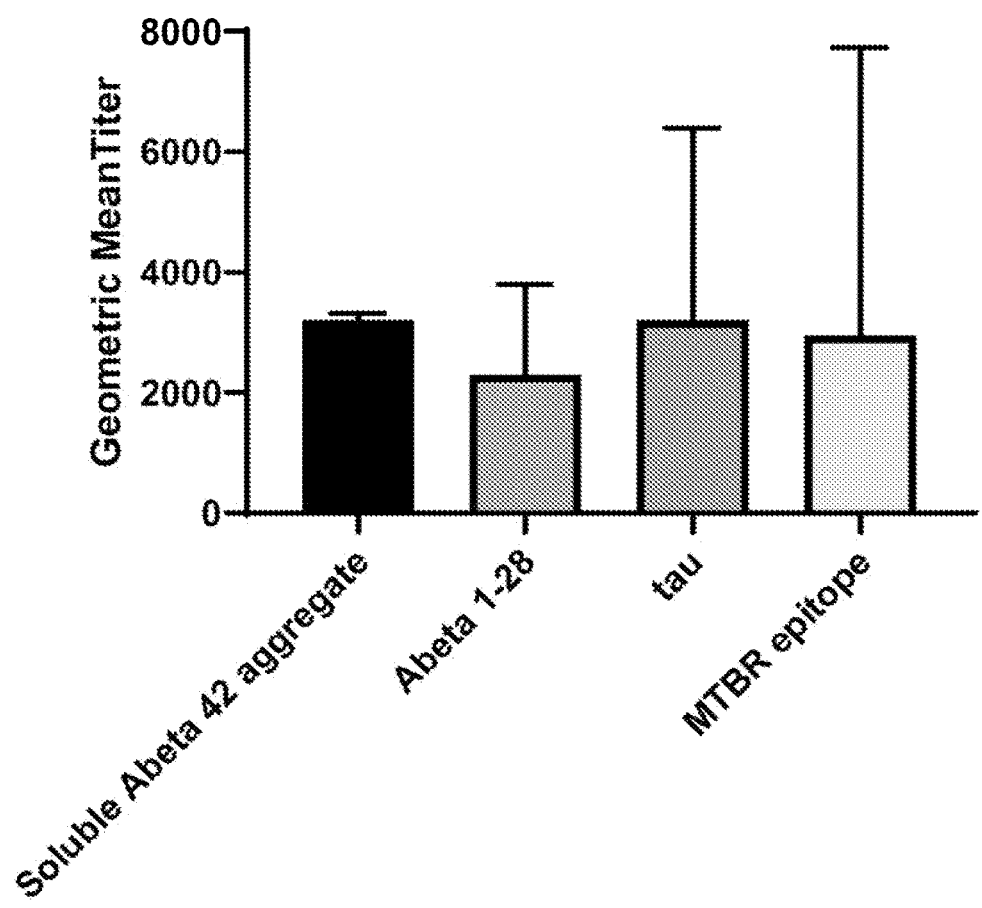
FIG. 1 shows the results of an experiment comparing the geometric mean titers of Guinea Pig serum for immunogen DAEFRHDRRQIVYKPV (SEQ ID NO:57) on monomeric Aβ amino acids 1-28 (DAEFRHDSGYEVHHQKLFFAE-DVGSNKG; SEQ ID NO:67), soluble aggregate species of Aβ (Aβ 42), full length tau, and tau MTBR epitope containing GGGSVQIVYKPVDLS (SEQ ID NO:68) containing an N-terminal biotin.

The disclosure provides peptide compositions and immunotherapy compositions comprising an amyloid-beta (Aβ) peptide and a tau peptide. The disclosure also provides methods of treating or effecting prophylaxis of Alzheimer's disease or other diseases with beta-amyloid deposition in a subject, including methods of clearing and preventing formation of deposits, inhibiting or reducing aggregation of Aβ and/or tau, blocking the binding and/or uptake of Aβ and/or tau by neurons, inhibiting transmission of tau species between cells, and inhibiting propagation of pathology between brain regions in a subject having or at risk of developing Alzheimer's disease or other diseases containing tau and/or amyloid-beta accumulations. The methods include administering to such patients the compositions comprising an amyloid-beta (Aβ) peptide and a tau peptide.

A number of terms are defined below. As used herein, the singular forms "a," "an", and "the" include plural referents unless the context clearly dictates otherwise. For example, the term "a compound" or "at least one compound" can include a plurality of compounds, including mixtures thereof.

Unless otherwise apparent from the context, the term "about" encompasses insubstantial variations, such as values within a standard margin of error of measurement (e.g., SEM) of a stated value. For example the term "about" as used herein when referring to a measurable value such as a parameter, an amount, a temporal duration, can encompass variations of +/−10% or less, +/−5% or less, or +/−1% or less or less of and from the specified value. Designation of a range of values includes all integers within or defining the range, and all subranges defined by integers within the range. As used herein, statistical significance means $p<0.05$.

Compositions or methods "comprising" or "including" one or more recited elements may include other elements not specifically recited. For example, a composition that "comprises" or "includes" a polypeptide sequence may contain the sequence alone or in combination with other sequences or ingredients.

An individual is at increased risk of a disease if the subject has at least one known risk-factor (e.g., age, genetic, biochemical, family history, and situational exposure) placing individuals with that risk factor at a statistically significant greater risk of developing the disease than individuals without the risk factor.

The term "patient" includes human and other mammalian subjects that receive either prophylactic or therapeutic treatment, including treatment naïve subjects. As used herein, the terms "subject" or "patient" refer to any single subject for which treatment is desired, including other mammalian subjects such as, humans, cattle, dogs, guinea pigs, rabbits, and so on. Also intended to be included as a subject are any subjects involved in clinical research trials not showing any clinical sign of disease, or subjects involved in epidemiological studies, or subjects used as controls.

The term "disease" refers to any abnormal condition that impairs physiological function. The term is used broadly to encompass any disorder, illness, abnormality, pathology, sickness, condition, or syndrome in which physiological function is impaired, irrespective of the nature of the etiology.

The term "symptom" refers to a subjective evidence of a disease, such as altered gait, as perceived by the subject. A "sign" refers to objective evidence of a disease as observed by a physician.

As used herein, the terms "treat" and "treatment" refer to the alleviation or amelioration of one or more symptoms or effects associated with the disease, prevention, inhibition or delay of the onset of one or more symptoms or effects of the disease, lessening of the severity or frequency of one or more symptoms or effects of the disease, and/or increasing or trending toward desired outcomes as described herein.

The terms "prevention", "prevent", or "preventing" as used herein refer to contacting (for example, administering) the peptide(s) or immunotherapy compositions of the present disclosure with a subject before the onset of a disease, with or without Aβ and/or tau pathology already present (primary and secondary prevention), thereby delaying the onset of clinical symptoms and/or alleviating symptoms of the disease after the onset of the disease, compared to when the subject is not contacted with the peptide or immunotherapy compositions, and does not refer to completely suppressing the onset of the disease. In some cases, prevention may occur for limited time after administration of the peptide or immunotherapy compositions of the present disclosure. In other cases, prevention may occur for the duration of a treatment regimen comprising administering the peptide or immunotherapy compositions of the present disclosure.

The terms "reduction", "reduce", or "reducing" as used herein refer to decreasing the amount of Aβ and/or tau present in a subject or in tissue of the subject, or suppressing an increase in the amount of Aβ and/or tau present in a subject or in tissue of the subject, which encompasses decreasing or suppressing an increase in (e.g., decreasing the rate of increase) the amount of Aβ and/or tau present, accumulated, aggregated, or deposited in the subject or tissue in the subject. In certain embodiments, the decrease in or suppression of an increase in (e.g., decreasing the rate of increase) the amount of Aβ and/or tau present, accumulated, aggregated, or deposited in the subject refers to an amount of Aβ and/or tau present, accumulated, aggregated, or deposited in the central nervous system (CNS) of the subject. In certain embodiments, the decrease in or suppression of an increase in (e.g., decreasing the rate of increase) the amount of Aβ and/or tau present, accumulated, aggregated, or deposited in the subject refers to an amount of Aβ and/or tau present, accumulated, aggregated, or deposited in the periphery (e.g., peripheral circulatory system) of the subject. In certain embodiments, the decrease in or suppression of an increase in (e.g., decreasing the rate of increase) the amount of Aβ and/or tau present, accumulated, aggregated, or deposited in the subject refers to an amount of Aβ and/or tau present, accumulated, aggregated, or deposited in the brain of the subject. In some embodiments, the Aβ and/or tau reduced is the pathological form(s) of the Aβ (e.g., extracellular plaque deposits of the β-amyloid peptide (Aβ), neuritic amyloid plaques), and/or tau (e.g., neurofibrillary tangles of tau, dystrophic neurites). In yet other embodiments, pathological indicators of neurodegenerative disease are decreased.

The terms "epitope" or "antigenic determinant" refers to a site on an antigen to which B and/or T cells respond, or to a site on an antigen to which an antibody binds. Epitopes can be formed both from contiguous amino acids or from noncontiguous amino acids juxtaposed by tertiary folding of a protein. Epitopes formed from contiguous amino acids are typically retained on exposure to denaturing solvents whereas epitopes formed by tertiary folding are typically lost on treatment with denaturing solvents. An epitope typically includes at least 3, at least 4, at least 5, at least 6, at least 7, at least 8, at least 9, at least 10, at least 11, at least 12, or at least 13 amino acids in a unique spatial conformation. Methods of determining spatial conformation of epitopes include, for example, x-ray crystallography and 2-dimensional nuclear magnetic resonance. See, e.g., Epitope Mapping Protocols in Methods in Molecular Biology, Vol. 66, Glenn E. Morris, Ed. (1996).

An "immunogenic agent" or "immunogen" or "antigen" is capable of inducing an immunological response against itself or modified/processed versions of itself upon administration to an animal, optionally in conjunction with an adjuvant. The terms "immunogenic agent" or "immunogen" or "antigen" refer to a compound or composition comprising a peptide, polypeptide or protein which is "antigenic" or "immunogenic" when administered in an appropriate amount (an "immunogenically effective amount"), i.e., capable of inducing, eliciting, augmenting or boosting a cellular and/or humoral immune response and of being recognized by the products of that response (T cells, antibodies). An immunogen can be a peptide, or a combination of two or more same or different peptides, that includes at least 3, at least 4, at least 5, at least 6, at least 7, at least 8, at least 9, at least 10, at least 11, at least 12, or at least 13 amino acids in a liner or spatial conformation.

An immunogen may be effective when given alone or in combination, or linked to, or fused to, another substance (which can be administered at one time or over several intervals). An immunogenic agent or immunogen may include an antigenic peptide or polypeptide that is linked to a carrier as described herein.

A nucleic acid such as DNA or RNA that encodes an antigenic peptide, or polypeptide is referred to as a "DNA [or RNA] immunogen," as the encoded peptide or polypeptide is expressed in vivo after administration of the DNA or RNA. The peptide or polypeptide can be recombinantly expressed from a vaccine vector, which can be naked DNA or RNA that comprises the peptide or polypeptide coding sequence operably linked to a promoter, e.g., an expression vector or cassette as described herein.

The term "adjuvant" refers to a compound that, when administered in conjunction with an antigen, augments the immune response to the antigen, but when administered alone does not generate an immune response to the antigen. Adjuvants can augment an immune response by several mechanisms including lymphocyte recruitment, stimulation of B and/or T cells, and stimulation of macrophages. An adjuvant may be a natural compound, a modified version of or derivative of a natural compound, or a synthetic compound.

The terms "peptide" and "polypeptide" are used interchangeably herein and refer to a chain of two or more consecutive amino acids. If and when a distinction is made, context makes the meaning clear. For example, if two or more peptides described herein are joined to make a dimeric or multimeric peptide, polypeptide may be used to indicate "poly" or "more than one" peptide.

The term "pharmaceutically acceptable" means that the carrier, diluent, excipient, adjuvant, or auxiliary is compatible with the other ingredients of a pharmaceutical formulation and not substantially deleterious to the recipient thereof.

The terms "immunotherapy" or "immune response" refer to the development of a beneficial humoral (antibody mediated) and/or a cellular (mediated by antigen-specific T cells or their secretion products) response directed against an Aβ and/or tau peptide in a recipient. Such a response can be an active response induced by administration of immunogen (e.g. an Aβ and/or tau peptide). A cellular immune response is elicited by the presentation of polypeptide epitopes in association with Class I or Class II MHC molecules to activate antigen-specific CD4+T helper cells and/or CD8$^+$ cytotoxic T cells. The response may also involve activation of monocytes, macrophages, NK cells, basophils, dendritic cells, astrocytes, microglia cells, eosinophils or other components of innate immunity. The presence of a cell-mediated immunological response can be determined by proliferation assays (CD4$^+$ T cells) or CTL (cytotoxic T lymphocyte) assays. The relative contributions of humoral and cellular responses to the protective or therapeutic effect of an immunogen can be distinguished by separately isolating antibodies and T-cells from an immunized syngeneic animal and measuring protective or therapeutic effect in a second subject.

Amyloid Beta (Aβ)

Aβ (also referred to herein as beta amyloid peptide or Abeta) peptide is about a 4-kDa internal fragment of 38-43 amino acids of APP (Aβ39, Aβ40, Aβ41, Aβ42, and Aβ43). Aβ40, for example, consists of residues 672-711 of APP and Aβ42 consists of residues 673-713 of APP. As a result of proteolytic processing of APP by different secretase enzymes in vivo or in situ, Aβ is found in both a "short form", 40 amino acids in length, and a "long form", ranging from 42-43 amino acids in length. Epitopes or antigenic determinants, as described herein, are located within the N-terminus of the Aβ peptide and include residues within amino acids 1-10 and 12-25 of Aβ, for example from residues 1-3, 1-4, 1-5, 1-6, 1-7, or 3-7, 2-4, 2-5, 2-6, 2-7, or 2-8 of Aβ, residues 3-5, 3-6, 3-7, 3-8, or 3-9 of Aβ, or residues 4-7, 4-8, 4-9, or 4-10 residues 12-24, 12-23, 12-22, 13-25, 13-24, 13-23, 13-22, 14-25, 14-24, 14-23, 14-22, 15-25, 15-24, 15-23, or 15-22 of Aβ. For example, from residues 12-17, 12-18, 12-19, 12-20, 12-21, 13-17, 13-18, 13-19, 13-20, 13-21, 13-22, 14-17, 14-18, 14-19, 14-20, 14-21, 14-22, 14-23, 15-17, 15-18, 15-19, 15-20, 15-21, 15-22, 15-23, or 15-24 of Aβ42. Additional examples of epitopes or antigenic determinants include residues 16-18, 16-19, 16-20, 16-21, 16-22, 16-23, 16-24, 16-25, 17-19, 17-20, 17-21, 17-22, 17-23, 17-24 or 17-25 of Aβ42. Other examples of epitopes or antigenic determinants include residues 18-20, 18-21, 18-22, 18-23, 18-24, 18-25, 19-21, 19-22, 19-23, 19-24, 19-25, 20-22, 20-23, 20-24, 20-25, 21-23, 21-24 or 21-25 of Aβ42.

Aβ (Abeta) is the principal component of characteristic plaques of Alzheimer's disease. Aβ is generated by processing of a larger protein APP by two enzymes, termed beta and gamma secretases. Known mutations in APP associated with Alzheimer's disease occur proximate to the site of beta or gamma secretase, or within Aβ. Part of the hydrophobic transmembrane domain of APP is found at the carboxy end of Aβ, and may account for the ability of Aβ to aggregate into plaques, particularly in the case of the long form. Accumulation of amyloid plaques in the brain eventually leads to neuronal cell death. The physical symptoms associated with this type of neural deterioration characterize Alzheimer's disease.

Tau

Tau is a protein with a molecular weight of about 50,000 that is normally present in nerve axons or the like, and contributes to microtubular stability. The tau proteins (or T proteins) are a group of six highly-soluble protein isoforms produced by alternative splicing from the gene MAPT (microtubule-associated protein tau). They have roles primarily in maintaining the stability of microtubules in axons and are abundant in the neurons of the central nervous system (CNS). They are less common elsewhere but are also expressed at very low levels in CNS astrocytes and oligodendrocytes. Pathologies and dementias of the nervous system such as Alzheimer's disease and Parkinson's disease are associated with tau proteins that have become hyperphosphorylated insoluble aggregates called neurofibrillary tangles. Pathogenic tau species causes toxic effects through direct binding to cells and/or accumulation inside cells and/or initiation of misfolding processes (seeding) and is can be propagated from one cell to another via cell-to-cell transmission. Toxicity could also happen by neurofibrillary tangles (NFTs), which leads to cell death and cognitive decline. Other tauopathies include, for example, progressive supranuclear palsy, corticobasal syndrome, some frontotemporal dementias, and chronic traumatic encephalopathy.

Aβ/Tau Polypeptides of an Immunogen

An agent used for active immunization can induce in a patient an immune response and can serve as an immunotherapy. Agents used for active immunization can be, for example, the same types of immunogens used for generating monoclonal antibodies in laboratory animals, and may include 3, 4, 5, 6, 7, 8, 9, 10, 11, 12, or 13 or more contiguous amino acids from a region of Aβ and/or tau peptide. In each of the embodiments of the peptides described herein, the peptides may comprise, consist, or consist essentially of the recited sequences.

In some embodiments of the disclosure, an Aβ/tau immunogen can include an Aβ peptide comprising 3-10 amino acids from residues 1-10 or 12-25 of the N-terminal sequence of Aβ (SEQ ID NO:01) linked to a tau peptide comprising 3-10 amino acids from residues 244-400 of the long form of tau (SEQ ID NO:02). For example, the tau peptide may comprise 3-13 amino acids from the microtubule binding region of tau (residues 344-372 of SEQ ID NO:02).

In some embodiments of the disclosure, the Aβ peptide can include 3-10 amino acids from residues 1-10 or 12-25 of

```
                                          (SEQ ID NO: 01)
DAEFRHDSGYEVHHQKLVFFAEDVGSNKGAIIGLMVGGVVIA.
```

For example, the Aβ peptide is selected from the following:

```
                            (SEQ ID NO: 03)
            DAEFRHDSGY, (SEQ ID NO: 04)
            DAEFRHDSG, (SEQ ID NO: 05)
            DAEFRHDS, (SEQ ID NO: 06)
            DAEFRHD, (SEQ ID NO: 07)
            DAEFRH, (SEQ ID NO: 08)
            DAEFR, (SEQ ID NO: 09)
            DAEF, (SEQ ID NO: 10)
            DAE, (SEQ ID NO: 11)
            AEFRHDSGY, (SEQ ID NO: 12)
            AEFRHDSG, (SEQ ID NO: 13)
            AEFRHDS, (SEQ ID NO: 14)
            AEFRHD, (SEQ ID NO: 15)
            AEFRH, (SEQ ID NO: 16)
            AEFR, (SEQ ID NO: 17)
            AEF, (SEQ ID NO: 18)
            EFRHDSGY,
```

-continued

EFRHDSG, (SEQ ID NO: 19)

EFRHDS, (SEQ ID NO: 20)

EFRHD, (SEQ ID NO: 21)

EFRH, (SEQ ID NO: 22)

EFR, (SEQ ID NO: 23)

FRHDSGY, (SEQ ID NO: 24)

FRHDSG, (SEQ ID NO: 25)

FRHDS, (SEQ ID NO: 26)

FRHD, (SEQ ID NO: 27)

FRH, (SEQ ID NO: 28)

RHDSGY, (SEQ ID NO: 29)

RHDSG, (SEQ ID NO: 30)

RHDS, (SEQ ID NO: 31)

RHD, (SEQ ID NO: 32)

HDSGY, (SEQ ID NO: 33)

HDSG, (SEQ ID NO: 34)

HDS, (SEQ ID NO: 35)

DSGY, (SEQ ID NO: 36)

DSG, (SEQ ID NO: 37)

SGY, (SEQ ID NO: 38)

VHHQKLVFFA, (SEQ ID NO: 1002)

VHHQKLVFF, (SEQ ID NO: 1003)

VHHQKLVF, (SEQ ID NO: 1004)

VHHQKLV, (SEQ ID NO: 1005)

VHHQKL, (SEQ ID NO: 1006)

HHQKLVFFAE, (SEQ ID NO: 1007)

HHQKLVFFA, (SEQ ID NO: 1008)

HHQKLVFF, (SEQ ID NO: 1009)

HHQKLVF, (SEQ ID NO: 1010)

HHQKLV, (SEQ ID NO: 1011)

HHQKL, (SEQ ID NO: 1012)

HQKLVFFAED, (SEQ ID NO: 1013)

HQKLVFFAE, (SEQ ID NO: 1014)

HQKLVFFA, (SEQ ID NO: 1015)

HQKLVFF, (SEQ ID NO: 1016)

HQKLVF, (SEQ ID NO: 1017)

HQKLV, (SEQ ID NO: 1018)

HQKL, (SEQ ID NO: 1019)

QKLVFFAEDV, (SEQ ID NO: 1020)

QKLVFFAED, (SEQ ID NO: 1021)

QKLVFFAE, (SEQ ID NO: 1022)

QKLVFFA, (SEQ ID NO: 1023)

QKLVFF, (SEQ ID NO: 1024)

QKLVF, (SEQ ID NO: 1025)

QKLV, (SEQ ID NO: 1026)

QKL, (SEQ ID NO: 1027)

KLVFFAEDVG, (SEQ ID NO: 1028)

KLVFFAEDV, (SEQ ID NO: 1029)

KLVFFAED, (SEQ ID NO: 1030)

KLVFFAE, (SEQ ID NO: 1031)

KLVFFA, (SEQ ID NO: 1032)

KLVFF, (SEQ ID NO: 1033)

KLVF, (SEQ ID NO: 1034)

KLV, (SEQ ID NO: 1035)

-continued

LVFFAEDVG, (SEQ ID NO: 1036)

LVFFAEDV, (SEQ ID NO: 1037)

LVFFAED, (SEQ ID NO: 1038)

LVFFAE, (SEQ ID NO: 1039)

LVFFA, (SEQ ID NO: 1040)

LVFF, (SEQ ID NO: 1041)

LVF, (SEQ ID NO: 1042)

VFFAEDVG, (SEQ ID NO: 1043)

VFFAEDV, (SEQ ID NO: 1044)

VFFAED, (SEQ ID NO: 1045)

VFFAE, (SEQ ID NO: 1046)

VFFA, (SEQ ID NO: 1047)

VFF, (SEQ ID NO: 1048)

FFAEDVG, (SEQ ID NO: 1049)

FFAEDV, (SEQ ID NO: 1050)

FFAED, (SEQ ID NO: 1051)

FFAE, (SEQ ID NO: 1052)

FFA, (SEQ ID NO: 1053)

FAEDVG, (SEQ ID NO: 1054)

FAEDV, (SEQ ID NO: 1055)

FAED, (SEQ ID NO: 1056)
and

FAE. (SEQ ID NO: 1057)

In certain embodiments, the Aβ peptide is DAEFRHD (SEQ ID NO:06), DAEFR (SEQ ID NO:08) or EFRHD (SEQ ID NO:21).

The tau peptide can correspond to a peptide comprising 3-13 amino acids from residues 244-400 of SEQ ID NO:02. In some embodiments, the fragment is unphosphorylated. In some embodiments, the fragment is phosphorylated. In some embodiments, the tau peptide comprises an amino acid sequence represented by the consensus motif (Q/E)IVYK(S/P) (SEQ ID NO:996). In some embodiments, the tau peptide comprises an amino acid sequence represented by the consensus motif KXXSXXNX(K/H)H (SEQ ID NO: 995) where X is any amino acid. In some embodiments, the tau peptide is selected from SEQ ID NOS: 146-996. In some embodiments, the tau peptide is selected from the following:

QIVYKPV, (SEQ ID NO: 39)

QIVYKP, (SEQ ID NO: 40)

QIVYKSV, (SEQ ID NO: 41)

EIVYKSV, (SEQ ID NO: 42)

QIVYKS, (SEQ ID NO: 83)

EIVYKSP, (SEQ ID NO: 43)

EIVYKS, (SEQ ID NO: 84)

EIVYKPV, (SEQ ID NO: 44)

EIVYKP, (SEQ ID NO: 85)

IVYKSPV, (SEQ ID NO: 45)

IVYK, (SEQ ID NO: 46)

CNIKHVPG, (SEQ ID NO: 86)

CNIKHVP, (SEQ ID NO: 47)

NIKHVP, (SEQ ID NO: 48)

HVPGGG, (SEQ ID NO: 49)

HVPGG, (SEQ ID NO: 50)

HKPGGG, (SEQ ID NO: 51)

HKPGG, (SEQ ID NO: 52)

KHVPGGG, SEQ ID NO: 53)

KHVPGG, (SEQ ID NO: 54)

HQPGGG, (SEQ ID NO: 55)

HQPGG, (SEQ ID NO: 56)

VKSKIGST, (SEQ ID NO: 801)

SKIGSTEN, (SEQ ID NO: 817)

TENLKHQP, (SEQ ID NO: 695)

-continued

ENLKHQPG, (SEQ ID NO: 689)

SKIGSTDNIKH, (SEQ ID NO: 985)

SKIGSKDNIKH,
and (SEQ ID NO: 986)

SKIGSLDNIKH. (SEQ ID NO: 988)

In each of these embodiments, the peptide may comprise, consist, or consist essentially of the recited sequences.

In some embodiments, the Aβ and tau peptides are linked to form a dual Aβ/Tau polypeptide. The Aβ and tau peptides can be linked by an intra-peptide linker. For example, a polypeptide linker located between the C-terminal of the first peptide and the N terminal of the second peptide. With or without the intra-peptide linker, the Aβ peptide and the tau peptide may be positioned in a dual Aβ/tau polypeptide in any order. For example, the Aβ peptide may be positioned at the N-terminal portion of the dual polypeptide and the tau peptide may be positioned at the C-terminal portion of the dual polypeptide. Or, the tau peptide may be positioned at the N-terminal portion of the dual polypeptide and the Aβ peptide may be positioned at the C-terminal portion of the dual polypeptide side of the tau peptide. Reference to a first peptide or a second peptide herein is not intended to suggest an order of the Aβ or tau peptides in the polypeptide of the immunogens.

In addition, the C-terminal portion of the Aβ peptide, the tau peptide, or the dual Aβ-tau polypeptide can include a linker for conjugating the peptides or the polypeptide to a carrier. Linkers that couple the peptides or dual polypeptide to the carrier may include, for example, GG, GGG, KK, KKK, AA, AAA, SS, SSS, GAGA (SEQ ID NO:80), AGAG (SEQ ID NO:81), KGKG (SEQ ID NO:82), and the like between the peptides or dual polypeptide and the carrier and may further include a C-terminal or a N-terminal cysteine to provide a short peptide linker (e.g., G-G-C-, K-K-C-, A-A-C-, or S—S-C-). In some embodiments, where the C-terminal residues in the immunogen are either IVYKPV (SEQ ID NO:194), VYKPV (SEQ ID NO:195), YKPV (SEQ ID NO:196), KPV, or PV the linker is an amino acid linker that does not have a N-terminal glycine (e.g., GG, GAGA (SEQ ID NO:80)). In some embodiments, the linker comprises an amino acid sequence any one of AA, AAA, KK, KKK, SS, SSS, AGAG (SEQ ID NO:81), GG, GGG, GAGA (SEQ ID NO:80), and KGKG (SEQ ID NO:82). In some embodiments, any of the Aβ peptide, the tau peptide, and the dual Aβ/tau polypeptide may include a C-terminal cysteine without the spacer. In some embodiments, any of the Aβ peptide, the tau peptide, and the dual Aβ/tau polypeptide may include a N-terminal cysteine without the spacer.

When the Aβ and tau polypeptides are linked to form a dual Aβ/tau polypeptide, the linker may be a cleavable linker. As used herein, the term "cleavable linker" refers to any linker between the antigenic peptides that promotes or otherwise renders the Aβ peptide and the tau peptide more susceptible to separation from each other by cleavage (for example, by endopeptidases, proteases, low pH or any other means that may occur within or around the antigen-presenting cell) and, thereby, processing by the antigen-presenting cell, than equivalent peptides lacking such a cleavable linker. In some compositions, the cleavable linker is a protease-sensitive dipeptide or oligopeptide cleavable linker. In certain embodiments, the cleavable linker is sensitive to cleavage by a protease of the trypsin family of proteases. In some compositions, the cleavable linker comprises an amino acid sequence selected from the group consisting of arginine-arginine (Arg-Arg), arginine-valine-arginine-arginine (Arg-Val-Arg-Arg; SEQ ID NO:69), valine-citrulline (Val-Cit), valine-arginine (Val-Arg), valine-lysine (Val-Lys), valine-alanine (Val-Ala), phenylalanine-lysine (Phe-Lys), GAGA (SEQ ID NO:80), AGAG (SEQ ID NO:81), and KGKG (SEQ ID NO:82). In some compositions, the cleavable linker is arginine-arginine (Arg-Arg).

In some embodiments of the disclosure, the dual Aβ/tau polypeptide comprises, consists or consists essentially of an amino acid sequence selected from DAEFRHDRRQIVYKPV (SEQ ID NO:57) or DAEFRHDRREIVYKSV (SEQ ID NO:58), or DAEFRHDRRQIVYKPVXXC (SEQ ID NO:70), wherein XX and the C-terminal cysteine are each independently optional, or DAEFRHDRREIVYKSVXXC (SEQ ID NO:79), wherein XX and C are independently optional and, if present, XX can be GG, AA, KK, SS, GAGA (SEQ ID NO:80), AGAG (SEQ ID NO:81), and KGKG (SEQ ID NO:82).

In some embodiments, the dual Aβ/tau polypeptide is as follows:

[first peptide]-[linker 1]-[second peptide]-[linker 2]-[Cys], wherein, if the [first peptide] is an Aβ peptide then the [second peptide] is a tau peptide, and if the [first peptide] is a tau peptide, then the [second peptide] is an Aβ peptide, each of [linker 1], [linker 2] and [Cys] are optional, and [linker 1] and [linker 2] are the same or different linkers.

In certain embodiments, the dual Aβ/tau polypeptide is as follows:

[Cys]-[linker 2]-[first peptide]-[linker 1]-[second peptide]

wherein, if the [first peptide] is an Aβ peptide then the [second peptide] is a tau peptide, and if the [first peptide] is a tau peptide, then the [second peptide] is an Aβ peptide, and each of [linker 1], [linker 2] and [Cys] are optional, and [linker 1] and [linker 2] are the same or different linkers.

Examples of the Aβ peptide include any one SEQ ID NOS 3-38 or SEQ ID NOS:1002-1057.

Examples of the tau peptide include any one of SEQ ID NOS: 39-56, 83-86, or 146-996.

[Linker 1] is optional, and when present, may be a cleavable linker. A cleavable linker, if present, can be 1-10 amino acids in length. In some embodiments, the linker comprises between about 1-10 amino acids, about 1-9 amino acids, about 1-8 amino acids, about 1-7 amino acids, about 1-6 amino acids, about 1-5 amino acids, about 1-4 amino acids, about 1-3 amino acids, about 2 amino acids, or one (1) amino acid. In some embodiments, the cleavable linker is 1 amino acid, 2 amino acids, 3 amino acids, 4 amino acids, 5 amino acids, 6 amino acids, 7 amino acids, 8 amino acids, 9 amino acids, or 10 amino acids. In some embodiments, the linker may be a cleavable linker having an amino acid sequence selected from the group consisting of arginine-arginine (Arg-Arg), arginine-valine-arginine-arginine (Arg-Val-Arg-Arg; SEQ ID NO:69), valine-citrulline (Val-Cit), valine-arginine (Val-Arg), valine-lysine (Val-Lys), valine-alanine (Val-Ala), phenylalanine-lysine (Phe-Lys), glycine-alanine-glycine-alanine (Gly-Ala-Gly-Ala; SEQ ID NO:80), alanine-glycine-alanine-glycine (Gly-Ala-Gly-Ala; SEQ ID NO:81), and lysine-glycine-lysine-glycine (Lys-Gly-Lys-Gly; SEQ ID NO:82).

[Linker 2] is optional, and when present is a linker that couples the polypeptide to a carrier. A linker, if present, can be 1-10 amino acids in length. In some embodiments, the linker comprises between about 1-10 amino acids, about 1-9 amino acids, about 1-8 amino acids, about 1-7 amino acids, about 1-6 amino acids, about 1-5 amino acids, about 1-4 amino acids, about 1-3 amino acids, about 2 amino acids, or one (1) amino acid. In some embodiments, the linker is 1 amino acid, 2 amino acids, 3 amino acids, 4 amino acids, 5 amino acids, 6 amino acids, 7 amino acids, 8 amino acids, 9 amino acids, or 10 amino acids. In some embodiments, the amino acid composition of a linker can mimic the composition of linkers found in natural multidomain proteins, where certain amino acids are overrepresented, underrepresented or equi-represented in natural linkers as compared to their abundance in whole protein. For example, threonine (Thr), serine (Ser), proline (Pro), glycine (Gly), aspartic acid (Asp), lysine (Lys), glutamine (Gln), asparagine (Asn), arginine (Arg), phenylalanine (Phe), glutamic acid (Glu) and alanine (Ala) are overrepresented in natural linkers. In contrast, isoleucine (Ile), tyrosine (Tyr), tryptophan (Trp), and cysteine (Cys) are underrepresented. In general, overrepresented amino acids were polar uncharged or charged residues, which constitute approximately 50% of naturally encoded amino acids, and Pro, Thr, and Gln were the most preferable amino acids for natural linkers. In some embodiments, the amino acid composition of a linker can mimic the composition of linkers commonly found in recombinant proteins, which can generally by classified as flexible or rigid linkers. For example, flexible linkers found in recombinant proteins are generally composed of small, non-polar (e.g. Gly) or polar (e.g. Ser or Thr) amino acids whose small size provides flexibility and allows for mobility of the connecting functional domains. The incorporation of, e.g., Ser or Thr can maintain the stability of the linker in aqueous solutions by forming hydrogen bonds with the water molecules, and therefore can reduce interactions between the linker and the immunogens. In some embodiments, a linker comprises stretches of Gly and Ser residues ("GS" linker). An example of a widely used flexible linker is (Gly-Gly-Ser)n, (Gly-Gly-Gly-Ser)n (SEQ ID NO:1062) or (Gly-Gly-Gly-Gly-Ser)n (SEQ ID NO:1063), where n=1-3. Adjusting the copy number "n" can optimize a linker to achieve sufficient separation of the functional immunogen domains to, e.g., maximize an immunogenic response. Many other flexible linkers have been designed for recombinant fusion proteins that can be used herein. In some embodiments, linkers can be rich in small or polar amino acids such as Gly and Ser but also contain additional amino acids such as Thr and Ala to maintain flexibility, as well as polar amino acids such as Lys and Glu to improve solubility. See, e.g., Chen, X. et al., "Fusion Protein Linkers: Property, Design and Functionality" Adv Drug Deliv Rev., 15; 65(10): 1357-1369 (203). In certain embodiments, when present, the linker can be an amino acid sequence selected from the group consisting of as GG, GGG, KK, KKK, AA, AAA, SS, SSS, G-A-G-A (SEQ ID NO:80), A-G-A-G (SEQ ID NO:81), and K-G-K-G (SEQ ID NO:82).

[Cys] is optional and can be helpful to conjugate the polypeptide to a carrier. When present, the Cys can be at the C-terminal portion of the polypeptide, or at the N-terminal portion of the polypeptide.

Examples of the [first peptide]-[linker 1]-[second peptide]-[linker 2]-[Cys] dual Aβ/tau polypeptide of the disclosure include the following:

TABLE 1

| Immunogen Lab ID | Abeta Sequence | Abeta SEQ ID NO. | Endo peptidase linker | Tau Sequence | tau SEQ ID NO. | C-Terminal linker | Cys | Immunogen SEQ ID NO |
|---|---|---|---|---|---|---|---|---|
| 9 | DAEFRHD | 06 | RR | QIVYKPV | 39 | GG | C | 59 |
| 10 | DAEFRHD | 06 | RR | QIVYKPV | 39 | None | C | 60 |
| 18 | DAEFRHD | 06 | RR | QIVYKPV | 39 | AA | C | 61 |
| 19 | DAEFRHD | 06 | RR | QIVYKPV | 39 | KK | C | 62 |
| 20 | DAEFRHD | 06 | RR | EIVYKSP | 43 | GG | C | 63 |
| 21 | DAEFRHD | 06 | RR | EIVYKSP | 43 | AA | C | 64 |
| 22 | DAEFRHD | 06 | RR | EIVYKSP | 43 | None | C | 65 |
| 23 | DAEFRHD | 06 | RR | EIVYKSP | 43 | KK | C | 66 |
| 12 | DAEFRHD | 06 | RR | NIKHVP | 48 | GG | C | 78 |

Polypeptide Immunogens

The Aβ peptide, the tau peptide and, the dual Aβ/tau polypeptide are immunogens in accordance with the disclosure. In some embodiments, the peptides and the dual Aβ-tau polypeptide can be linked to a suitable carrier to help elicit an immune response. Accordingly, one or more the peptides and dual Aβ-tau polypeptides of the disclosure can be linked to a carrier. For example, each of the Aβ peptide, tau peptide and the Aβ-tau polypeptide may be linked to the carrier with or without spacer amino acids (e.g., Gly-Gly, Gly-Gly-Gly, Ala-Ala, Ala-Ala-Ala, Lys-Lys, Lys-Lys-Lys, Ser-Ser, Ser-Ser-Ser, Gly-Ala-Gly-Ala (SEQ ID NO:80), Ala-Gly-Ala-Gly (SEQ ID NO:81), or Lys-Gly-Lys-Gly (SEQ ID NO:82)). In certain embodiments, the dual Aβ-tau polypeptide can be linked to a suitable carrier using a C-terminal cysteine to provide a linker between the peptide(s) and the carrier or the dual Aβ/tau polypeptide and the carrier. In certain embodiments, the dual Aβ-tau polypeptide can be linked to a suitable carrier using an N-terminal cysteine to provide a linker between the peptide(s) and the carrier. In some embodiments, where the C-terminal residues in the immunogen are either IVYKPV (SEQ ID NO:194), VYKPV (SEQ ID NO:195), YKPV (SEQ ID NO:196), KPV, or PV the linker is an amino acid linker that does not have a N-terminal glycine (e.g., GG, GAGA (SEQ ID NO:80)).

Suitable carriers include, but are not limited to serum albumins, keyhole limpet hemocyanin, immunoglobulin molecules, thyroglobulin, ovalbumin, tetanus toxoid, or a toxoid from other pathogenic bacteria, such as diphtheria (e.g., CRM197), E. coli, cholera, or H. pylori, or an attenuated toxin derivative. T cell epitopes are also suitable carrier molecules. Some conjugates can be formed by linking peptide immunogens of the invention to an immunostimulatory polymer molecule (e.g., tripalmitoyl-S-glycerine cysteine (Pam3Cys), mannan (a mannose polymer), or glucan (a β 1-2 polymer)), cytokines (e.g., IL-1, IL-1 alpha and β peptides, IL-2, γ-INF, IL-10, GM-CSF), and chemokines (e.g., MIP1-α and β, and RANTES). Additional carriers include virus-like particles. In some compositions, immunogenic peptides can also be linked to carriers by chemical crosslinking. Techniques for linking an immunogen to a carrier include the formation of disulfide linkages using N-succinimidyl 3-(2-pyridylthio)propionate (SPDP), and succinimidyl 4-(N-maleimidomethyl)cyclohexane-1-carboxylate (SMCC) (if the peptide lacks a sulfhydryl group, this can be provided by addition of a cysteine residue). These reagents create a disulfide linkage between themselves and peptide cysteine resides on one protein and an amide linkage through the epsilon-amino on a lysine, or other free amino group in other amino acids. In some embodiments, chemical crosslinking can comprise use of SBAP (succinimidyl 3-(bromoacetamido)propionate), which is a short (6.2 angstrom) cross-linker for amine-to-sulfhydryl conjugation via N-hydroxysuccinimide (NHS) ester and bromoacetyl reactive groups. A variety of such disulfide/amide-forming agents are described by Jansen et al., "Immunotoxins: Hybrid Molecules Combining High Specificity and Potent Cytotoxicity" *Immunological Reviews* 62:185-216 (February 1982). Other bifunctional coupling agents form a thioether rather than a disulfide linkage. Many of these thioether-forming agents are commercially available and include reactive esters of 6-maleimidocaproic acid, 2-bromoacetic acid, and 2-iodoacetic acid, 4-(N-maleimido-methyl)cy-clohexane-1-carboxylic acid. The carboxyl groups can be activated by combining them with succinimide or 1-hydroxyl-2-nitro-4-sulfonic acid, sodium salt. Virus-like particles (VLPs), also called pseudovirions or virus-derived particles, represent subunit structures composed of multiple copies of a viral capsid and/or envelope protein capable of self-assembly into VLPs of defined spherical symmetry in vivo. (Powilleit, et al., (2007) PLoS ONE 2(5):e415.) Alternatively, peptide immunogens can be linked to at least one artificial T-cell epitope capable of binding a large proportion of MHC Class II molecules, such as the pan DR epitope ("PADRE"). Pan DR-binding peptides (PADRE) are described in U.S. Pat. No. 5,736,142, WO 95/07707, and Alexander, et al, *Immunity*, 1:751-761 (1994).

Active immunogens can be presented in multimeric form in which multiple copies of an immunogen (peptide of polypeptide) are presented on a carrier as a single covalent molecule. In some embodiments, the carrier includes various forms of the dual Aβ/tau polypeptide. For instance, the dual Aβ/tau polypeptide of the immunogen can include polypeptides that have the Aβ antigen and the tau antigen in different orders, or may be present with or without an intrapeptide linker and/or a linker to a carrier.

In some compositions, the immunogenic peptides can also be expressed as fusion proteins with carriers. In certain compositions, the immunogenic peptides can be linked at the amino terminus, the carboxyl terminus, or internally to the carrier. In some compositions, the carrier is CRM197. In some compositions, the carrier is diphtheria toxoid.

Nucleic Acids

The disclosure further provides nucleic acids encoding any of the amyloid-beta (Aβ) peptides and the tau peptides as disclosed herein. The nucleic acid immunotherapy compositions, as disclosed herein, comprise, consist of, or consist essentially of, a first nucleic acid sequence encoding an amyloid-beta (Aβ) peptide, and a second nucleic acid sequence encoding a tau peptide as disclosed herein. For example, the Aβ peptide is a sequence that is 3-10 amino acid residues in length and from the first ten N-terminal residues of SEQ ID NO:01, and the tau peptide is a sequence that is 3-13 amino acids in length and from residues 244-400 of SEQ ID NO:02. Accordingly, a nucleic acid encoding any of SEQ ID NOS: 3-38 or SEQ ID NOS:1002-1057 may be combined with a nucleic acid encoding any of SEQ ID NOS: 39-56, 83-86, or 146-996 to provide an immunogen and a component of pharmaceutical composition of the disclosure. Likewise, one or more nucleic acids encoding any of Abeta and tau sequences may include the codons for an RR-N-terminal or -RR C-terminal dipeptide. In certain embodiments, the Aβ and tau peptide sequences may be encoded by the same nucleic acid sequence or by separate nucleic acid sequences. In some embodiments, the nucleic acid sequences may also encode a linker to a carrier and/or a C-terminal cysteine as described herein. In addition, when a single nucleic acid sequence encodes both peptides, the sequence may also encode an intra-peptide linker as described herein. The nucleic acid compositions described herein (pharmaceutical compositions) can be used in methods for treating or effecting prophylaxis and/or prevention of Alzheimer's disease. In another embodiment, the nucleic acid immunotherapy compositions as disclosed herein provide compositions for reducing pathogenic forms of Aβ and/or tau in the subject and/or in the tissue of the subject. In some embodiments, the Aβ and/or tau reduced by the immunotherapy compositions is the pathological form(s) of the Aβ (e.g. extracellular plaque deposits of the β-amyloid peptide (Aβ); neuritic amyloid plaques), and/or tau (e.g. flame-shaped neurofibrillary tangles of tau; neurofibrillary tangles of tau). In yet other embodiment, pathological indicators of neurodegenerative disease are decreased by the nucleic acid immunotherapy compositions. In another embodiment, the nucleic acid immunotherapy compositions as disclosed herein provide compositions for reducing brain Aβ and brain tau.

A nucleic acid such as DNA that encodes an immunogen and is used as a vaccine can be referred to as a "DNA immunogen" or "DNA vaccine" as the encoded polypeptides are expressed in vivo after administration of the DNA. DNA vaccines are intended to induce antibodies against the proteins of interest they encode in a subject by: integrating DNA encoding the proteins of interest into a vector (a plasmid or virus); administering the vector to the subject; and expressing the proteins of interest in the subject in which the vector has been administered to stimulate the immune system of the subject. A DNA vaccine remains in the body of the subject for a long time after the administration, and continues to slowly produce the encoded proteins. Thus, excessive immune responses can be avoided. DNA vaccines can also be modified using a genetic engineering techniques. Optionally, such nucleic acids further encode a signal peptide and can be expressed with the signal peptide linked to peptide. Coding sequences of nucleic acids can be operably linked with regulatory sequences to ensure expression of the coding sequences, such as a promoter, enhancer, ribosome binding site, transcription termination signal, and the like. The nucleic acids encoding Aβ and tau can occur in isolated form or can be cloned into one or more vectors. The nucleic acids can be synthesized by, for example, solid state synthesis or PCR of overlapping oligonucleotides. Nucleic acids encoding Aβ and tau peptides and polypeptides with and without linkers or cleavable linkers and with our without protein based carriers can be joined as one contiguous nucleic acid, e.g., within an expression vector.

DNA is more stable than RNA, but involves some potential safety risks such as induction of anti-DNA antibodies, thus in some embodiments, the nucleic acid can be RNA. RNA nucleic acid that encodes an immunogen and is used as a vaccine can be referred to as a "RNA immunogen" or "RNA vaccine" or "mRNA vaccine" as the encoded polypeptides are expressed in vivo after administration of the RNA. Ribonucleic acid (RNA) vaccines can safely direct a subject's cellular machinery to produce one or more polypeptide(s) of interest. In some embodiments, a RNA vaccine can be a non-replicating mRNA (messenger-RNA) or a virally derived, self-amplifying RNA. mRNA-based vaccines encode the antigens of interest and contain 5' and 3' untranslated regions (UTRs), whereas self-amplifying RNAs encode not only the antigens, but also the viral replication machinery that enables intracellular RNA amplification and abundant protein expression. In vitro transcribed mRNA can be produced from a linear DNA template using a T7, a T3 or an Sp6 phage RNA polymerase. The resulting product can contain an open reading frame that encodes the peptides of interest as disclosed herein, flanking 5'- and 3'-UTR sequences, a 5' cap and a poly(A) tail. In some embodiments, a RNA vaccine can comprise transamplifying RNA (for example, see Beissert et al., Molecular Therapy January 2020 28(1):119-128). In certain embodiments, RNA vaccines encode an Aβ peptide and a tau peptide as disclosed herein, and are capable of expressing the Aβ and a tau peptides, in particular if transferred into a cell such as an immature antigen presenting cell. RNA may also contain sequences which encode other polypeptide sequences such as immune stimulating elements. In some embodiments, the RNA of a RNA vaccine can be modified RNA. The term "modified" in the context of the RNA can include any modification of RNA which is not naturally present in RNA. For example, modified RNA can refer to RNA with a 5'-cap; however, RNA may comprise further modifications. A 5'-cap can be modified to possess the ability to stabilize RNA when attached thereto. In certain embodiments, a further modification may be an extension or truncation of the naturally occurring poly(A) tail or an alteration of the 5'- or 3'-untranslated regions (UTR). In some embodiments, the RNA e.g. or mRNA vaccine is formulated in an effective amount to produce an antigen specific immune response in a subject. For example, the RNA vaccine formulation is administered to a subject in order to stimulate the humoral and/or cellular immune system of the subject against the Aβ and tau antigens, and thus may further comprise one or more adjuvant(s), diluents, carriers, and/or excipients, and is applied to the subject in any suitable route in order to elicit a protective and/or therapeutic immune reaction against the Aβ and tau antigens.

Basic texts disclosing general methods of molecular biology, all of which are incorporated by reference, include: Sambrook, J et al., Molecular Cloning: A Laboratory Manual, 2$^{nd}$ Edition, Cold Spring Harbor Press, Cold Spring Harbor, N.Y., 1989; Ausubel, F M et al. Current Protocols in Molecular Biology, Vol. 2, Wiley-Interscience, New York, (current edition); Kriegler, Gene Transfer and Expression: A Laboratory Manual (1990); Glover, D M, ed, DNA Cloning: A Practical Approach, vol. I & II, IRL Press, 1985; Albers, B. et al., Molecular Biology of the Cell, 2$^{nd}$ Ed., Garland Publishing, Inc., New York, N.Y. (1989); Watson, J D et al., Recombinant DNA, 2$^{nd}$ Ed., Scientific American Books, New York, 1992; and Old, R W et al., Principles of Gene Manipulation: An Introduction to Genetic Engineering, 2$^{nd}$ Ed., University of California Press, Berkeley, Calif. (1981).

Techniques for the manipulation of nucleic acids, such as, e.g., generating mutations in sequences, sub-cloning, labeling probes, sequencing, hybridization and the like are well described in the scientific and patent literature. See, e.g., Sambrook, ed., MOLECULAR CLONING: A LABORATORY MANUAL (2ND ED.), Vols. 1-3, Cold Spring Harbor Laboratory, (1989); CURRENT PROTOCOLS IN MOLECULAR BIOLOGY, Ausubel, ed. John Wiley & Sons, Inc., New York (1997); LABORATORY TECHNIQUES IN BIOCHEMISTRY AND MOLECULAR BIOLOGY: HYBRIDIZATION WITH NUCLEIC ACID PROBES, Part I. Tijssen, ed. Elsevier, N.Y. (1993).

Nucleic acids, vectors, capsids, polypeptides, and the like can be analyzed and quantified by any of a number of general means well known to those of skill in the art. These include, e.g., analytical biochemical methods such as NMR, spectrophotometry, radiography, electrophoresis, capillary electrophoresis, high performance liquid chromatography (HPLC), thin layer chromatography (TLC), and hyperdiffusion chromatography, various immunological methods, e.g. fluid or gel precipitin reactions, immunodiffusion, immunoelectrophoresis, radioimmunoassays (RIAs), enzyme-linked immunosorbent assays (ELISAs), immunofluorescence assays, Southern analysis, Northern analysis, dot-blot analysis, gel electrophoresis (e.g., SDS-PAGE), RT-PCR, quantitative PCR, other nucleic acid or target or signal amplification methods, radiolabeling, scintillation counting, and affinity chromatography.

Pharmaceutical Compositions

Each of the peptides and immunogens described herein can be presented in a pharmaceutical composition that is administered with pharmaceutically acceptable adjuvants and pharmaceutically acceptable excipients. The adjuvant increases the titer of induced antibodies and/or the binding affinity of induced antibodies relative to the situation if the peptide were used alone. A variety of adjuvants can be used in combination with an immunogen of the disclosure to elicit an immune response. Some adjuvants augment the intrinsic response to an immunogen without causing conformational changes in the immunogen that affect the qualitative form of the response. An adjuvant may be a natural compound, a modified version of or derivative of a natural compound, or a synthetic compound.

Some adjuvants include aluminum salts, such as aluminum hydroxide and aluminum phosphate, 3 De-O-acylated monophosphoryl lipid A (MPL™) (see GB 2220211 (RIBI ImmunoChem Research Inc., Hamilton, Montana, now part of Corixa). As used herein, MPL refers to natural and synthetic versions of MPL. Examples of synthetic versions include PHAD®, 3D-PHAD® and 3D(6A)-PHAD® (Avanti Polar Lipids, Alabaster, Alabama).

QS-21 is a triterpene glycoside or saponin isolated from the bark of the Quillaja *saponaria* Molina tree found in South America (see Kensil et al., in Vaccine Design: The Subunit and Adjuvant Approach (eds. Powell & Newman, Plenum Press, NY, 1995)) QS-21 products include Stimulon® (Antigenics, Inc., New York, NY; now Agenus, Inc. Lexington, MA) and QS-21 Vaccine Adjuvant (Desert King, San Diego, CA). QS-21 has been disclosed, characterized, and evaluated in U.S. Pat. Nos. 5,057,540, and 8,034,348, the disclosures of which are herein incorporated by reference. Additionally, QS-21 has been evaluated in numerous clinical trials in various dosages. See, NCT00960531 (clinicaltrials.gov/ct2/show/study/NCT00960531), Hull et al., Curr Alzheimer Res. 2017 July; 14(7): 696-708 (evaluated 50 mcg of QS-21 in with various doses of vaccine ACC-001); Gilman et al., "Clinical effects of Abeta immunization (AN1792) in patients with AD in an interrupted trial" Neurology. 2005 May 10; 64(9):1553-62; Wald et al., "Safety and immunogenicity of long HSV-2 peptides complexed with rhHsc70 in HSV-2 seropositive persons" Vaccine 2011; 29(47):8520-8529; and Cunningham et al., "Efficacy of the Herpes Zoster Subunit Vaccine in Adults 70 Years of Age or Older." NEJM. 2016 Sep. 15; 375(11):1019-32. QS-21 is used in FDA approved vaccines including SHINGRIX. SHINGRIX contains 50 mcg of QS-21. In certain embodiments, the amount of QS-21 is from about 10 µg to about 500 µg.

TQL1055 is an analogue of QS-21 (Adjuvance Technologies, Lincoln, NE). The semi-synthetic TQL1055 has been characterized in comparison to QS-21 as having high purity, increased stability, decreased local tolerability, decreased systemic tolerability. TQL1055 has been disclosed, characterized, and evaluated in US20180327436 A1, WO2018191598 A1, WO2018200656 A1, and WO2019079160 A1, the disclosures of which are herein incorporated by reference. US20180327436 A1 teaches that 2.5 fold more TQ1055 was superior to 20 µg QS-21 but there was not an improvement over 50 µg TQL1055. However, unlike QS-21 there was no increase in either weight loss or hemolysis of RBC as the TQL1055 dose increased. WO2018200656 A1 teaches that with an optimal amount of TQ1055, one can lower the amount of antigen and achieve superior titers. In certain embodiments, the amount of TQL1055 is from about 10 µg to about 500 µg.

Other adjuvants are oil in water emulsions (such as squalene or peanut oil), optionally in combination with immune stimulants, such as monophosphoryl lipid A (see Stoute et al., N. Engl. J. Med. 336, 86-91 (1997)), pluronic polymers, and killed mycobacteria. Ribi adjuvants are oil-in-water emulsions. Ribi contains a metabolizable oil (squalene) emulsified with saline containing Tween 80. Ribi also contains refined mycobacterial products which act as immunostimulants and bacterial monophosphoryl lipid A. Other adjuvants can be CpG oligonucleotides (see WO 98/40100), cytokines (e.g., IL-1, IL-1 alpha and β peptides, IL-2, γ-INF, IL-10, GM-CSF), chemokines (e.g., MIP1-α and β, and RANTES), saponins, RNA, and/or TLR agonists (for example, TLR4 agonists such as MPL and synthetic MPL molecules), aminoalkyl glucosaminide phosphate and other TLR agonists. Adjuvants can be administered as a component of a therapeutic composition with an active agent or can be administered separately, before, concurrently with, or after administration of the therapeutic agent.

In various embodiments of the disclosure, the adjuvant is QS-21 (Stimulon™) In some compositions, the adjuvant is MPL. In certain embodiments, the amount of MPL is from about 10 µg to about 500 µg. In some compositions, the adjuvant is TQL1055. In certain embodiments, the amount of TQL1055 is from about 10 µg to about 500 µg. In some compositions, the adjuvant is QS21. In certain embodiments, the amount of QS21 is from about g to about 500 µg. In some compositions, the adjuvant is a combination of MPL and QS-21. In some compositions, the adjuvant is a combination of MPL and TQL1055. In some compositions, the adjuvant can be in a liposomal formulation.

In addition, some embodiments of the disclosure can comprise a multiple antigen presenting system (MAP). Multiple antigen-presenting peptide vaccine systems have been developed to avoid the adverse effects associated with conventional vaccines (i.e., live-attenuated, killed or inactivated pathogens), carrier proteins and cytotoxic adjuvants. Two main approaches have been used to develop multiple antigen presenting peptide vaccine systems: (1) the addition of functional components, e.g., T-cell epitopes, cell-penetrating peptides, and lipophilic moieties; and (2) synthetic approaches using size-defined nanomaterials, e.g., self-assembling peptides, non-peptidic dendrimers, and gold nanoparticles, as antigen-displaying platforms. Use of a multiple antigenic peptide (MAP) system can improve the sometimes poor immunogenicity of subunit peptide vaccines. In a MAP system, multiple copies of antigenic peptides are simultaneously bound to the a- and ε-amino groups of a non-immunogenic Lys-based dendritic scaffold, helping to confer stability from degradation, thus enhancing molecular recognition by immune cells, and induction of stronger immune responses compared with small antigenic peptides alone. In some compositions, the MAP comprises one or more of a Lys-based dendritic scaffold, helper T-cell epitopes, immune stimulating lipophilic moieties, cell penetrating peptides, radical induced polymerization, self-assembling nanoparticles as antigen-presenting platforms and gold nanoparticles.

Pharmaceutical compositions for parenteral administration are preferably sterile and substantially isotonic and manufactured under GMP conditions. Pharmaceutical compositions can be provided in unit dosage form (i.e., the dosage for a single administration). Pharmaceutical compositions can be formulated using one or more physiologically acceptable carriers, diluents, excipients or auxiliaries. The formulation depends on the route of administration chosen. For injection, the peptides of the disclosure can be formulated in aqueous solutions, preferably in physiologically compatible buffers such as Hank's solution, Ringer's solution, or physiological saline or acetate buffer (to reduce discomfort at the site of injection). The solution can contain formulatory agents such as suspending, stabilizing and/or dispersing agents. Alternatively, peptide compositions can be in lyophilized form for constitution with a suitable vehicle, e.g., sterile pyrogen-free water, before use.

Peptides (and optionally a carrier fused to the peptide(s)) can also be administered in the form of a nucleic acid encoding the peptide(s) and expressed in situ in a subject. A nucleic acid segment encoding an immunogen is typically linked to regulatory elements, such as a promoter and enhancer that allow expression of the DNA segment in the intended target cells of a subject. For expression in blood cells, as is desirable for induction of an immune response, promoter and enhancer elements from, for example, light or heavy chain immunoglobulin genes or the CMV major intermediate early promoter and enhancer are suitable to direct expression. The linked regulatory elements and coding sequences are often cloned into a vector.

DNA and RNA can be delivered in naked form (i.e., without colloidal or encapsulating materials). Alternatively a number of viral vector systems can be used including retroviral systems (see, e.g., Boris-Lawrie and Teumin, Cur. Opin. Genet. Develop. 3(1):102-109 (1993)); adenoviral vectors (see, e.g., Bett et al, J. Virol. 67(10); 5911-21 (1993)); adeno-associated virus vectors (see, e.g., Zhou et al., J. Exp. Med. 179(6):1867-75 (1994)), viral vectors from the pox family including vaccinia virus and the avian pox viruses, viral vectors from the alpha virus genus such as those derived from Sindbis and Semliki Forest Viruses (see, e.g., Dubensky et al., *J. Virol.* 70(1):508-519 (1996)), Venezuelan equine encephalitis virus (see U.S. Pat. No. 5,643, 576) and rhabdoviruses, such as vesicular stomatitis virus (see WO 96/34625) and papillomaviruses (WO 94/12629; Ohe et al., *Human Gene Therapy* 6(3):325-333 (1995); and Xiao & Brandsma, *Nucleic Acids. Res.* 24(13):2620-2622 (1996)).

DNA and RNA encoding an immunogen, or a vector containing the same, can be packaged into liposomes, nanoparticles or lipoproteins complexes. Suitable other polymers, include, for example, protamine liposomes, polysaccharide particles, cationic nanoemulsion, cationic polymer, cationic polymer liposome, cationic lipid nanoparticles, cationic lipid, cholesterol nanoparticles, cationic lipid-cholesterol, PEG nanoparticle, or dendrimer nanoparticles. Additional suitable lipids and related analogs are described by U.S. Pat. Nos. 5,208,036, 5,264,618, 5,279,833, and 5,283, 185, each of which are herein incorporated by reference in their entirety. Vectors and DNA encoding an immunogen can also be adsorbed to or associated with particulate carriers, examples of which include polymethyl methacrylate polymers and polylactides and poly(lactide-co-glycolides), (see, e.g., McGee et al., *J. Micro Encap.* March-April 1997; 14(2):197-210).

Pharmaceutically acceptable carrier compositions can also include additives, including, but not limited to, water, pharmaceutically acceptable organic solvents, collagen, polyvinyl alcohol, polyvinylpyrrolidone, carboxyvinyl polymers, carboxymethylcellulose sodium, sodium polyacrylate, sodium alginate, water-soluble dextran, carboxymethyl starch sodium, pectin, methylcellulose, ethylcellulose, xanthan gum, gum arabic, casein, agar, polyethylene glycol, diglycerine, glycerine, propylene glycol, petrolatum, paraffin, stearyl alcohol, stearic acid, human serum albumin, mannitol, sorbitol, lactose, and surfactants acceptable as pharmaceutical additives.

Subjects Amenable to Treatment

The presence of Aβ plaques and/or neurofibrillary tangles has been found in several diseases including Alzheimer's disease, Down's syndrome, mild cognitive impairment, cerebral amyloid angiopathy, primary age-related tauopathy, postencephalitic parkinsonism, posttraumatic dementia or dementia pugilistica, Pick's disease, type C Niemann-Pick disease, supranuclear palsy, frontotemporal dementia, frontotemporal lobar degeneration, argyrophilic grain disease, globular glial tauopathy, amyotrophic lateral sclerosis/parkinsonism dementia complex of Guam, corticobasal degeneration (CBD), dementia with Lewy bodies, Lewy body variant of Alzheimer's disease (LBVAD), chronic traumatic encephalopathy (CTE), globular glial tauopathy (GGT), Parkinson's disease, progressive supranuclear palsy (PSP), dry age-related macular degeneration (AMD), and inclusion-body myositis.

The compositions and methods of the disclosure can be used in treatment or prophylaxis of any of these diseases. Because of the widespread association between neurological diseases and Aβ and/or tau, the compositions and methods of the disclosure can be used in treatment or prophylaxis of any subject showing elevated levels of Aβ and/or tau (e.g., in the CSF) compared with a mean value in individuals without neurological disease. The compositions and methods of the disclosure can also be used in treatment or prophylaxis of neurological disease in individuals having a mutation in Aβ and/or tau associated with neurological disease. The methods are particularly suitable for treatment or prophylaxis of Alzheimer's disease.

Subjects amenable to treatment include individuals at risk of disease but not showing symptoms, as well as patients presently showing symptoms, including treatment naïve subjects that have not been previous treated for disease. Subjects at risk of disease include those in an aging population, asymptomatic subjects with Aβ and/or tau pathologies and having a known genetic risk of disease. Such individuals include those having relatives who have experienced this disease, and those whose risk is determined by analysis of genetic or biochemical markers. Genetic markers of risk include mutations in Aβ and/or tau, as well as mutations in other genes associated with neurological disease. For example, the ApoE4 allele in heterozygous and even more so in homozygous form is associated with risk of Alzheimer's disease (AD). Other markers of risk of Alzheimer's disease include mutations in the APP gene, particularly mutations at position 717 and positions 670 and 671 referred to as the Hardy and Swedish mutations respectively, mutations in the presenilin genes, PS1 and PS2, a family history of AD, hypercholesterolemia or atherosclerosis. Individuals presently suffering from Alzheimer's disease can be recognized by PET imaging, from characteristic dementia, as well as the presence of risk factors described above. In addition, a number of diagnostic tests are available for identifying individuals who have AD. These include measurement of CSF or blood tau or phospho-tau and Aβ42 levels. Elevated tau or phospho-tau and decreased Aβ42 levels signify the presence of AD. Some mutations associated with Parkinson's disease, for example, Ala30Pro or Ala53Thr, or mutations in other genes associated with Parkinson's disease such as leucine-rich repeat kinase (LRRK2 or PARK8). Subjects can also be diagnosed with any of the neurological diseases mentioned above by the criteria of the DSM IV TR.

In asymptomatic subjects, treatment can begin at any age (e.g., 10, 20, 30, or more). Usually, however, it is not necessary to begin treatment until a subject reaches 20, 30, 40, 50, 60, 70, 80, or 90 years of age. Treatment typically entails multiple dosages over a period of time. Treatment can be monitored by assaying antibody levels over time. If the response falls, a booster dosage is indicated. In the case of potential Down's syndrome patients, treatment can begin antenatally by administering therapeutic agent to the mother or shortly after birth.

Methods of Treatments and Uses

The disclosure provides methods of inhibiting or reducing aggregation of Abeta and/or tau in a subject having or at risk of developing a neurodegenerative disease (e.g., Alzheimer's disease). The methods include administering to the subject the compositions as disclosed herein. A therapeutically effective amount is a dosage that, when given for an effective period of time, achieves the desired immunological or clinical effect. Dosage regimens may be adjusted to provide the optimum therapeutic response. For example, several divided doses may be administered at set intervals (e.g., weekly, monthly) or the dose may be proportionally reduced as indicated by the exigencies of the therapeutic situation.

In prophylactic applications, the compositions described herein can be administered to a subject susceptible to, or otherwise at risk of a disease (e.g., Alzheimer's disease) in a regimen (dose, frequency and route of administration) effective to reduce the risk, lessen the severity, or delay the onset of at least one sign or symptom of the disease. In particular, the regimen is effective to inhibit or delay Aβ plaque formation and/or inhibit or delay tau or phospho-tau and paired filaments formed from it in the brain, and/or inhibit or delay its toxic effects and/or inhibit/or delay development of behavioral deficits. In therapeutic applications, the compositions described herein are administered to a subject suspected of, or a patient already suffering from a disease (e.g., Alzheimer's disease) in a regimen (dose, frequency and route of administration) effective to ameliorate or at least inhibit further deterioration of at least one sign or symptom of the disease. In particular, the regimen is preferably effective to reduce or at least inhibit further increase of levels of Aβ plaques and/or tau, phosphor-tau, or paired filaments formed from it, associated toxicities and/or behavioral deficits.

A regimen is considered therapeutically or prophylactically effective if an individual treated achieves an outcome more favorable than the mean outcome in a control population of comparable subjects not treated by methods of the invention, or if a more favorable outcome is demonstrated in treated subjects versus control subjects in a controlled clinical trial (e.g., a phase II, phase II/III or phase III trial) at the p<0.05 or 0.01 or even 0.001 level.

Effective doses of vary depending on many different factors, such as means of administration, target site, physiological state of the patient, whether the patient is an ApoE carrier, whether the patient is human or an animal, other medications administered, and whether treatment is prophylactic or therapeutic.

In some embodiments, the effective amount is a total dose of 25 μg to 1000 g, or 50 μg to 1000 μg. In some embodiments, the effective amount is a total dose of 100 μg. In some embodiments, the effective amount is a dose of 25 μg administered to the subject a total of two times. In some embodiments, the effective amount is a dose of 100 μg administered to the subject a total of two times. In some embodiments, the effective amount is a dose of 400 μg administered to the subject a total of two times. In some embodiments, the effective amount is a dose of 500 μg administered to the subject a total of two times. In some embodiments, a RNA (e.g., mRNA) vaccine is administered to a subject by intradermal, intramuscular injection, or by intranasal administration.

In some embodiments, the amount of an agent for active immunotherapy varies from 1 to 1,000 micrograms (g), or from 0.1-500 g, or from 10 to 500 g, or from 50 to 250 g per patient and can be from 1-100 or 1-10 μg per injection for human administration. The timing of injections can vary significantly from once a day, to once a week, to once a month, to once a year, to once a decade. A typical regimen consists of an immunization followed by booster injections at time intervals, such as 6 week intervals or two months. Another regimen consists of an immunization followed by one or more booster injections 1, 2, 3, 4, 5, 6, 7, 8, 9, 10, 11, or 12 months later. Another regimen entails an injection every two months for life. Alternatively, booster injections can be on an irregular basis as indicated by monitoring of immune response. The frequency of administration may be once or more as long as the side effects are within a clinically acceptable range.

In some embodiments, the compositions or methods as disclosed herein comprise administering to a subject a nucleic acid vaccine comprising one or more DNA or RNA polynucleotides having an open reading frame encoding a first peptide and a second peptide wherein a dosage of between 10 μg/kg and 400 μg/kg of the nucleic acid vaccine is administered to the subject. In some embodiments the dosage of the RNA polynucleotide is 1-5 ag, 5-10 ag, 10-15 μg, 15-20 ag, 10-25 μg, 20-25 ag, 20-50 ag, 30-50 ag, 40-50 ag, 40-60 ag, 60-80 ag, 60-100 ag, 50-100 ag, 80-120 ag, 40-120 ag, 40-150 ag, 50-150 ag, 50-200 ag, 80-200 ag, 100-200 ag, 120-250 ag, 150-250 ag, 180-280 ag, 200-300 ag, 50-300 ag, 80-300 ag, 100-300 ag, 40-300 ag, 50-350 ag, 100-350 ag, 200-350 ag, 300-350 ag, 320-400 ag, 40-380 ag, 40-100 ag, 100-400 ag, 200-400 ag, or 300-400 ag per dose. In some embodiments, the nucleic acid is administered to the subject by intradermal or intramuscular injection. In some embodiments, the nucleic acid is administered to the subject on day zero. In some embodiments, a second dose of the nucleic acid is administered to the subject on day seven, or fourteen, or twenty one.

The compositions described herein are preferably administered via a peripheral route (i.e., one in which the administered composition results in a robust immune response and/or the induced antibody population crosses the blood brain barrier to reach an intended site in the brain, spinal cord, or eye). For peripheral diseases, the induced antibodies leave the vasculature to reach the intended peripheral organs. Routes of administration include oral, subcutaneous, intranasal, intradermal, or intramuscular. Some routes for active immunization are subcutaneous and intramuscular. Intramuscular administration and subcutaneous administration can be made at a single site or multiple sites. Intramuscular injection is most typically performed in the arm or leg muscles. In some methods, agents are injected directly into a particular tissue where deposits have accumulated.

The number of dosages administered can be adjusted to result in a more robust immune response (for example, higher titers). For acute disorders or acute exacerbations of a chronic disorder, between 1 and 10 doses are often sufficient. Sometimes a single bolus dose, optionally in divided form, is sufficient for an acute disorder or acute exacerbation of a chronic disorder. For chronic disorders, a vaccine/immunotherapy as disclosed herein can be administered at regular intervals, e.g., weekly, fortnightly, monthly, quarterly, every six months for at least 1, 5 or 10 years, or the life of the patient.

An effective amount of a DNA or RNA encoded immunogen can be between about 1 nanogram and about 1 gram per kilogram of body weight of the recipient, or about between about 0.1 g/kg and about 10 mg/kg, or about between about 1 g/kg and about 1 mg/kg. Dosage forms suitable for internal administration preferably contain (for the latter dose range) from about 0.1 μg to 100 μg of active ingredient per unit. The active ingredient may vary from 0.5 to 95% by weight based on the total weight of the composition. Alternatively, an effective dose of dendritic cells loaded with the antigen is between about $10^4$ and $10^8$ cells. Those skilled in the art of immunotherapy will be able to adjust these doses without undue experimentation.

The nucleic acid compositions may be administered in a convenient manner, e.g., injection by a convenient and effective route. Routes can include, but are not limited to, intradermal "gene gun" delivery or intramuscular injection. The modified dendritic cells are administered by subcutaneous, intravenous or intramuscular routes. Other possible routes include oral administration, intrathecal, inhalation, transdermal application, or rectal administration.

Depending on the route of administration, the composition may be coated in a material to protect the compound from the action of enzymes, acids and other natural conditions which may inactivate the compound. Thus, it may be necessary to coat the composition with, or co-administer the composition with, a material to prevent its inactivation. For example, an enzyme inhibitors of nucleases or proteases (e.g., pancreatic trypsin inhibitor, diisopropylfluorophosphate and trasylol) or in an appropriate carrier such as liposomes (including water-in-oil-in-water emulsions) as well as conventional liposomes (Strejan et al., J. Neuroimmunol 7(1):27-41, 1984).

The immunotherapeutic compositions disclosed herein may also be used in combination with other treatments for diseases associated with the accumulation of Aβ or tau, for example, anti-Aβ antibodies such as antibodies that specifically bind to any of the Aβ epitopes disclosed herein. For example, aducanumab or any of the antibodies disclosed in, for example, U.S. Patent Publication No. 20100202968 and U.S. Pat. No. 8,906,367, and/or anti-tau antibodies such as antibodies that specifically bind to any of the tau epitopes disclosed herein, ABBV-8E12, gosuranemab, zagotenemab, RG-6100, BIIB076 or any of the antibodies disclosed in WO2014/165271, U.S. Pat. No. 10,501,531, WO2017/191559, WO2017/191560, WO2017/191561, US 20190330314, US 20190330316, and WO2018/204546. In some combination therapy methods, the patient receives passive immunotherapy prior to the active immunotherapy methods disclosed herein. In other methods, the patient receives passive and active immunotherapy during the same period of treatment. Alternatively, patients may receive active immunotherapy prior to passive immunotherapy. Combinations may also include small molecule therapies and non-immunogenic therapies such as RAZADYNE® (galantamine), EXELON® (rivastigmine), and ARICEPT© (donepezil) and other compositions that improve the function of nerve cells in the brain.

The compositions of the disclosure may be used in the manufacture of medicaments for the treatment regimens described herein.

Treatment Regimens

Desired outcomes of the methods of treatment as disclosed herein vary according to the disease and patient profile and are determinable to those skilled in the art. Desired outcomes include an improvement in the patient's health status. Generally, desired outcomes include measurable indices such as reduction or clearance of pathologic amyloid fibrils, decreased or inhibited amyloid aggregation and/or deposition of amyloid fibrils, and increased immune response to pathologic and/or aggregated amyloid fibrils. Desired outcomes also include amelioration of amyloid disease-specific symptoms. As used herein, relative terms such as "improve," "increase," or "reduce" indicate values relative to a control, such as a measurement in the same individual prior to initiation of treatment described herein, or a measurement in a control individual or group. A control individual is an individual afflicted with the same amyloid disease as the individual being treated, who is about the same age as the individual being treated (to ensure that the stages of the disease in the treated individual and the control individual are comparable), but who has not received treatment using the disclosed immunotherapy/vaccine formulations. Alternatively, a control individual is a healthy individual, who is about the same age as the individual being treated. Changes or improvements in response to therapy are generally statistically significant and described by a p-value less than or equal to 0.1, less than 0.05, less than 0.01, less than 0.005, or less than 0.001 may be regarded as significant.

Effective doses of the compositions as disclosed herein, for the treatment of a subject vary depending upon many different factors, including means of administration, target site, physiological state of the patient, whether the patient is human or an animal, other medications administered, if any, and whether treatment is prophylactic or therapeutic. Treatment dosages can be titrated to optimize safety and efficacy. The amount of immunogen can also depend on whether adjuvant is also administered, with higher dosages being required in the absence of adjuvant. The amount of an immunogen for administration sometimes varies from 1-500 μg per patient and more usually from 5-500 μg per injection for human administration. Occasionally, a higher dose of 1-2 mg per dosage is used. Typically, about 10, 20, 50 or 100 μg is used for each human dosage. The timing of dosages can vary significantly from once a day, to once a year, to once a decade. On any given day that a dosage of immunogen is given, the dosage is greater than 1 g/patient and usually greater than 10 g/patient if adjuvant is also administered, and greater than 10 g/patient and usually greater than 100 g/patient in the absence of adjuvant. A typical regimen consists of an immunization followed by booster dosage(s) at 6-week intervals. Another regimen consists of an immunization followed by booster dosage(s) 1, 2, 3, 4, 5, 6, 7, 8, 9, 10, 11, or 12 months later. Another regimen entails dosage(s) every two months for life. Alternatively, booster dosage(s) can be on an irregular basis as indicated by monitoring of immune response.

When administered in combination with a second treatment for Alzheimer's disease, such as, Razadyne® (galantamine), Exelon® (rivastigmine), and Aricept® (donepezil), the second treatment can be administered according the product label or as necessary in view of the treatment with the compositions of the disclosure.

Kits

The disclosure further provides kits (e.g., containers) comprising the compositions disclosed herein and related materials, such as instructions for use (e.g., package insert). The instructions for use may contain, for example, instructions for administration of the compositions and optionally one or more additional agents. The containers of peptide and/or nucleic acid compositions may be unit doses, bulk packages (e.g., multi-dose packages), or sub-unit doses.

Package insert refers to instructions customarily included in commercial packages of therapeutic products that contain information about the indications, usage, dosage, administration, contraindications and/or warnings concerning the use of such therapeutic products. Kits can also include a second container comprising a pharmaceutically acceptable buffer, such as bacteriostatic water for injection (BWFI), phosphate-buffered saline, Ringer's solution and dextrose solution. It can also include other materials desirable from a commercial and user standpoint, including other buffers, diluents, filters, needles, and syringes.

Uses

Each of the peptides, polypeptides, immunogens, and pharmaceutical compositions described herein may be for use in treating one or more of the diseases as described herein. In addition, each of the peptides, polypeptides, immunogens, and pharmaceutical compositions described herein may be for use in methods for treating one or more of the diseases as described herein. Each of the peptides, polypeptides, immunogens, and pharmaceutical compositions described herein may be used in a method for manufacturing a medicament for treating or use in treating one or more of the diseases as described herein.

The following are provided for exemplification purposes only and are not intended to limit the scope of the invention described in broad terms above.

All U.S. and international patent applications identified herein are incorporated by reference in their entirety.

Examples

Example 1: Immunization of Guinea Pigs

Guinea pigs were injected intramuscularly with 50 µg of a test immunogen, 25 µg QS21 in 200 µl of Addavax on day 0, 21, 49 and 77. Bleeds were done 7 days post immunization. The peptides tested included DAEFRHD (SEQ ID NO:06), QIVYKPV (SEQ ID NO:39), and DAEFRHDRRQIVYKPV (SEQ ID NO:57). The specific immunogens were DAEFRHDC (SEQ ID NO:71), QIVYKPVGGC (SEQ ID NO:72), and DAEFRHDRRQIVYKPVGGC (SEQ ID NO:59). The peptides were coupled through the C-terminal cysteine to CRM-197 with a maleimide linkage.

Female Guinea Pigs were at least 5 weeks old at the start of the study having an approximate body weight of 350-500 g. Appropriate animal housing and research procedures for animal husbandry and care were conducted in an accredited facility in accordance with the guidelines of the U.S. Department of Agriculture's (USDA) and the Assessment and Accreditation of Laboratory Animal Care (AAALAC) International.

The immunogen concentration was 0.5 mg/ml. Prior to each administration of the test immunogen, approximately a 3 cm$^2$ area on each hind limb was shaved and wiped with ethanol for visualization of the injection site. Each animal received a test immunogen dose of 200 microliters (0.25 micrograms/microliter) divided into two separate sites each of 100 microliter per injection (i.e., animals received 50 µg of immunogen in 100 µl PBS+25 µg of QS21 in 100 µl MF59). A 25G-27G needle was inserted intramuscularly into the hind limb, approximately 0.25-0.5 cm deep, and injected at 100 microliters per site. Injection sites were rotated each administration between four separate sites per hind limb and separated by at least 2 cm.

Example 2: Measurement of Antibody Titers

Whole blood samples were collected into clot activator tubes via jugular vein at 250-350 microliters per collection at weeks 1, 4, and 8. The maximum volume of whole blood was collected into clot activator tubes via cardiac puncture at termination on week 12. All blood samples were allowed to clot at room temperature for greater than 30 minutes, centrifuged at ambient temperature (approximately 20-25° C.) at 3,000 RPM for 10-15 minutes, and serum supernatant was transferred individually into clean cryovials. Serum supernatant was stored frozen at −80° C. (±12° C.).

Titer Guinea Pig Bleed on Soluble Aβ Aggregates

[00171] 2.5 g/ml of a soluble aggregate Aβ prep (HFIP film of Aβ 42 was resuspended and incubated overnight with shaking, then spun to remove insoluble aggregate) was coated on to the plate at 100 µl per well in PBS and incubated overnight at room temperature. Plates were blocked for 1 hour with 1% BSA in PBS. Plates were aspirated and to row A, 200 µl of 0.1% BSA in PBS Tween was added to 1-4. In 1 neg. GP serum was added at 1/100 while 2-4 contained 1/100 test serum. Rows B-H contained 100 µl of 0.1% BSA in PBS Tween. Rows were serially diluted 12 down the plate giving dilution of 1/100 to 1/12800. Wells were incubated 2 hours at room temperature, then were washed and a 1/5000 dilution of anti Guinea Pig IgG HRP in 0.1% BSA in PBS Tween was prepared and then 100 µl added to the washed well. This incubated for 1 hour and was washed. OPD substrate was prepared using Thermo-Fisher OPD tablets at 1 tablet per 10 mls. Thermo fisher substrate buffer was added at 1/10 and each well had 100 µl added and incubated for 15 minutes. 50 µl of 2N H$_2$SO$_4$ was added to stop the reaction and plates were read on a molecular devices spectromax at 490 nM. Titer defined as the dilution giving 50% maximum OD and was extrapolated if it fell between dilutions Titer Guinea Pig bleeds on Tau 2 g/ml recombinant WT Tau 4R2N was coated on to the plate using 100 µl per well in PBS and incubated overnight at room temperature. Plates were blocked for 1 hour with 1% BSA in PBS. Plates were aspirated and to row A 200 µl of 0.1% BSA in PBS Tween was added. In column 1 neg. GP serum was added at 1/100 while the rest of the row contained 1/100 test serums. Rows were serially diluted 12 down the plate giving dilution of 1/100 to 1/12800. Wells incubated 2 hours at room temperature then were washed and a 1/5000 dilution of anti-Guinea Pig IgG HRP in 0.1% BSA in PBS Tween was prepared and then 100 µl added to the washed well. This incubated for 1 hour and was washed. OPD substrate was prepared using Thermo-Fisher OPD tablets at 1 tablet per 10 mls. Thermo fisher substrate buffer was added at 1/10 and each well had 100 µl added and was incubated for 15 minutes. 50 µl of 2N H$_2$SO$_4$ was added to stop the reaction and plates were read on a molecular devices spectromax at 490 nM. Titer was defined as the dilution giving 50% maximum OD and was extrapolated if it fell between dilutions.

Titer Guinea Pig Bleed on Aβ 1-28 or Aβ 1-15

Aβ 1-15 and Aβ 1-28 were both used at different parts of the study. Both of these will not form aggregates. 2 g/ml Aβ monomers were coated at coated on to the plate 100 µl per well in PBS and incubated overnight at room temperature. Plates were blocked for 1 hour with 1% BSA in PBS. Plates were aspirated and to row A 200 µl of 0.1% BSA in PBS Tween was added. In column 1 neg. GP serum was added at 1/100 while the rest of the row contained 1/100 test serums. Rows were serially diluted 12 down the plate giving dilution of 1/100 to 1/12800. Wells incubated 2 hours at room temperature then were washed and a 1/5000 dilution of anti Guinea Pig IgG HRP in 0.1% BSA in PBS Tween was prepared and then 100 µl added to the washed well. This incubated for 1 hour and was washed. OPD substrate was prepared using Thermo-Fisher OPD tablets at 1 tablet per 10 mls. Thermo fisher substrate buffer was added at 1/10 and each well had 100 µl added and was incubated for 15 minutes. 50 µl of 2N H$_2$SO$_4$ was added to stop the reaction and plates were read on a molecular devices spectromax at 490 nM. Titer was defined as the dilution giving 50% maximum OD and was extrapolated if it fell between dilutions.

Titering the Tau Against a Peptide Containing its Epitope

Thermofisher neutavidin plates were rehydrated with 0.05% Tween in TBS and aspirated. Peptide GGGSVQIVYKPVDLS (SEQ ID NO:68) containing a biotin was made up in a 1/500 dilution in 0.1% BSA in PBS tween. Adding 100 µl per well for 1 hour and then washed. To row A of the plate 200 µl of 0.1% BSA in PBS Tween was added. In column 1 neg. GP serum was added at 1/100 while the rest of the rows contained 1/100 test serums. Rows were serially diluted 12 down the plate giving dilution of 1/100 to 1/12800. Wells incubated 2 hours at room temperature then were washed and a 1/5000 dilution of anti Guinea Pig IgG HRP in 0.1% BSA in PBS Tween was prepared and then 100 µl added to the washed well. This incubated for 1 hour and was washed. OPD substrate was prepared using Thermo-Fisher OPD tablets at 1 tablet per 10 mls. Thermo fisher substrate buffer was added at 1/10 and each well had 100 µl added and was incubated for 15 minutes. 50 μl of 2N H$_2$SO$_4$ was added to stop the reaction and plates were read on a molecular devices spectromax at 490 nM. Titer defined as the dilution giving 50% maximum OD and was extrapolated if it fell between dilutions.

FIG. 1 shows the results comparing the geometric mean titers of Guinea Pig serum for immunogen DAEFRHDRRQIVYKPV (SEQ ID NO:57) titered on monomeric Aβ 1-28, soluble aggregates of Aβ, full length tau, and tau MTBR epitope containing GGGSVQIVYKPVDLS (SEQ ID NO:68).

Figure 2A:
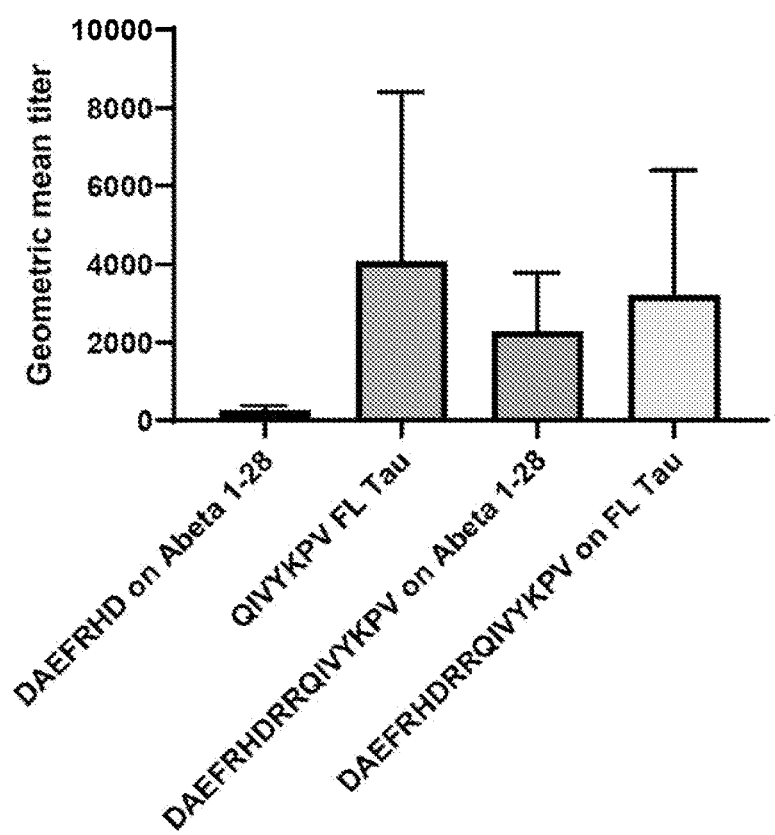
FIG. 2A shows the results of an experiment comparing the titers of Guinea pig serum for a single peptide immunogen versus dual peptide immunogens of the disclosure on all forms of Aβ and full-length tau protein (DAEFRHD is SEQ ID NO:6; QIVYKPV is SEQ ID NO: 39; DAEFRHDRRQI-VYKPV is SEQ ID NO:57).
Figure 2B:
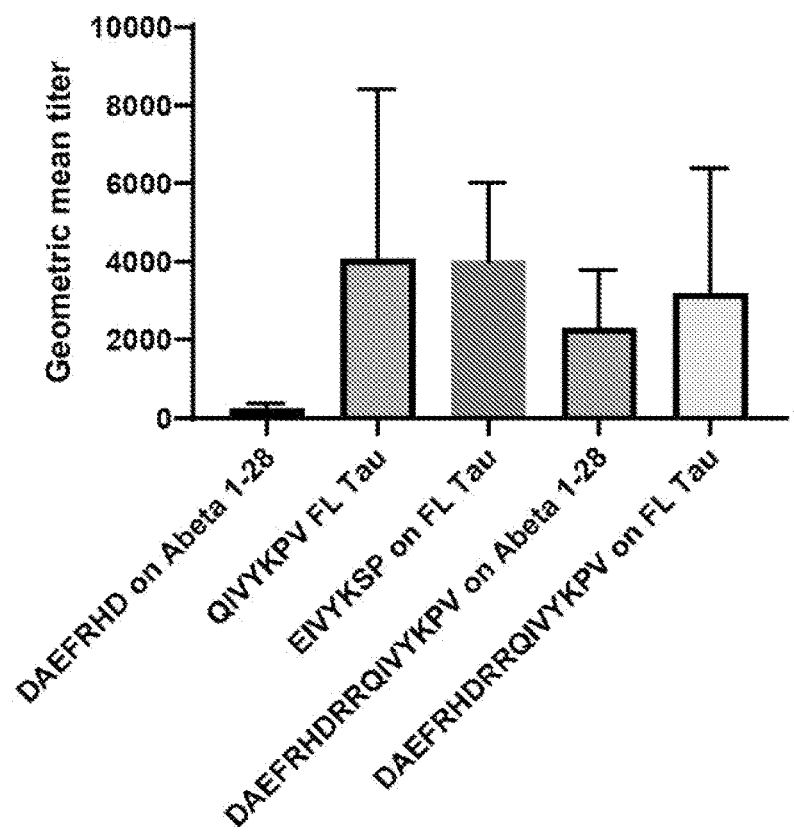
FIG. 2B shows the results of an experiment comparing the titers of Guinea pig serum for a single peptide immunogen versus dual peptide immunogens of the disclosure on all forms of Aβ and full-length tau protein (DAEFRHD is SEQ ID NO:6; QIVYKPV is SEQ ID NO:39; EIVYKSP is SEQ ID NO:43; DAEFRHDRRQIVYKPV is SEQ ID NO:57).
Figure 3A:
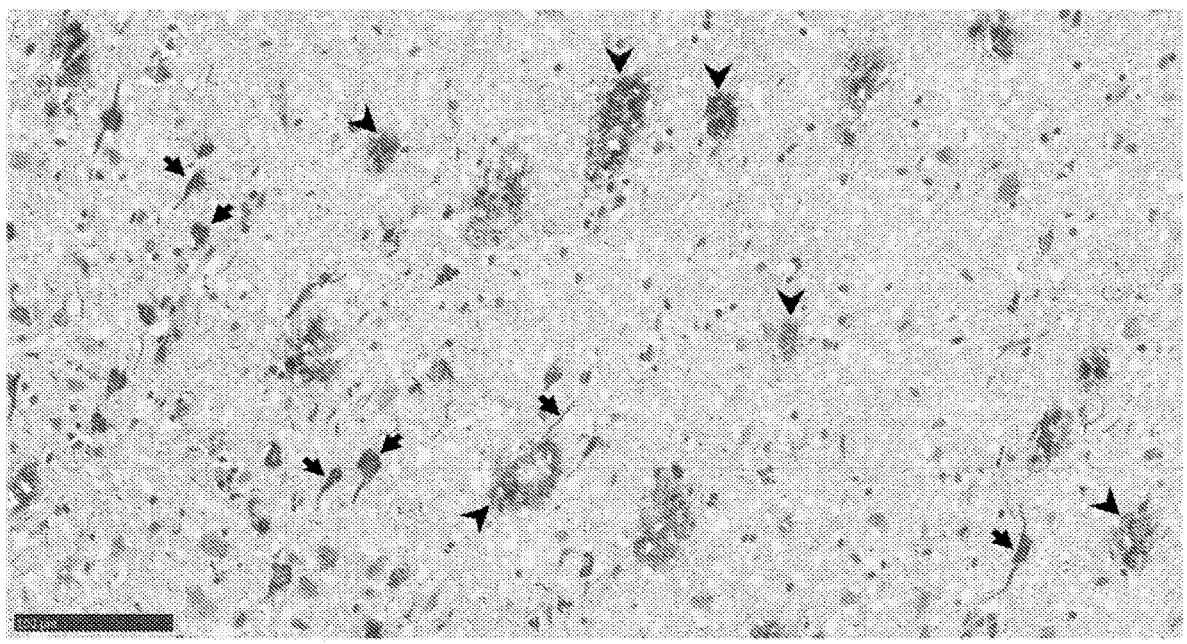
FIG. 3A shows staining of Aβ and Tau pathology in fresh frozen human AD brain tissue using serum (1:300 dilution) from a Guinea pig vaccinated with Immunogen 9 (DAE-FRHDRRQIVYKPVGGC; SEQ ID NO:59).
Figure 3B:
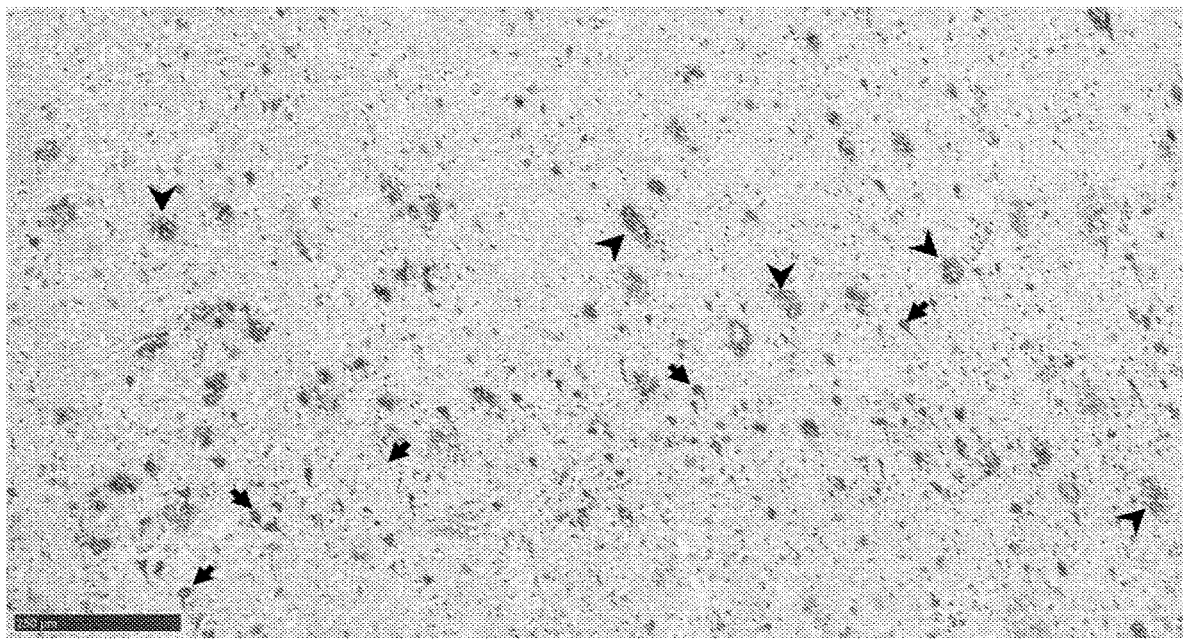
FIG. 3B shows staining of Aβ and Tau pathology in fresh frozen human AD brain tissue using serum (1:300 dilution) from a Guinea pig vaccinated with Immunogen 9 (DAE-FRHDRRQIVYKPVGGC; SEQ ID NO:59).
Figure 3C:
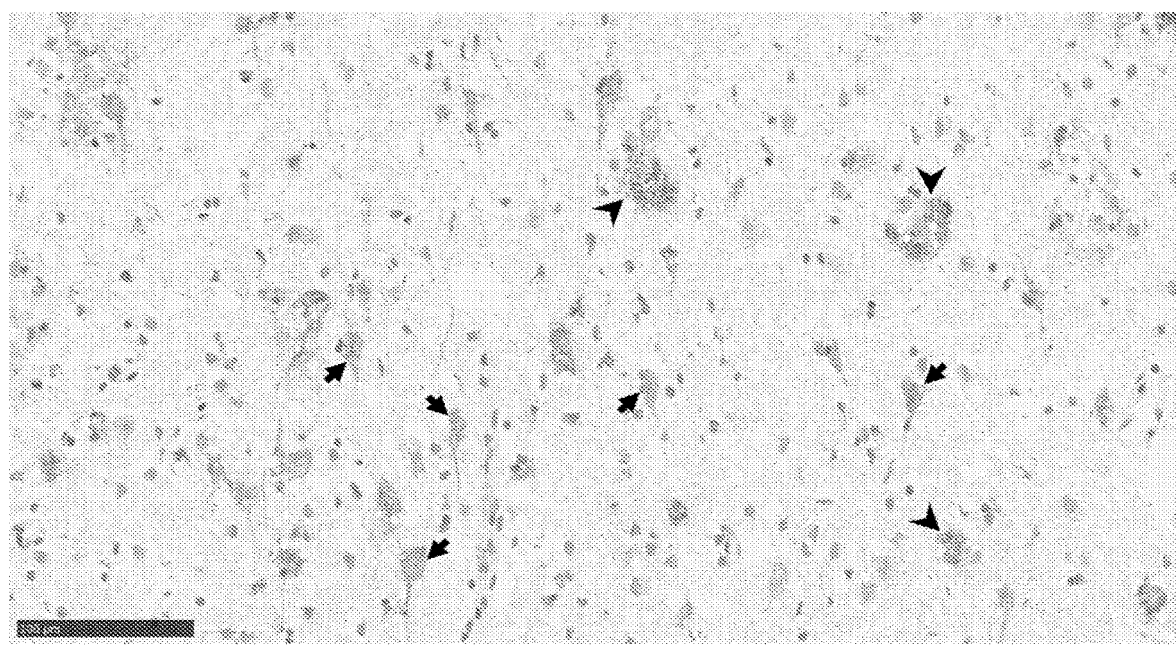
FIG. 3C shows staining of Aβ and Tau pathology in fresh frozen human AD brain tissue using serum (1:1500 dilution) from a Guinea pig vaccinated with Immunogen 9 (DAE-FRHDRRQIVYKPVGGC; SEQ ID NO:59).
Figure 3D:
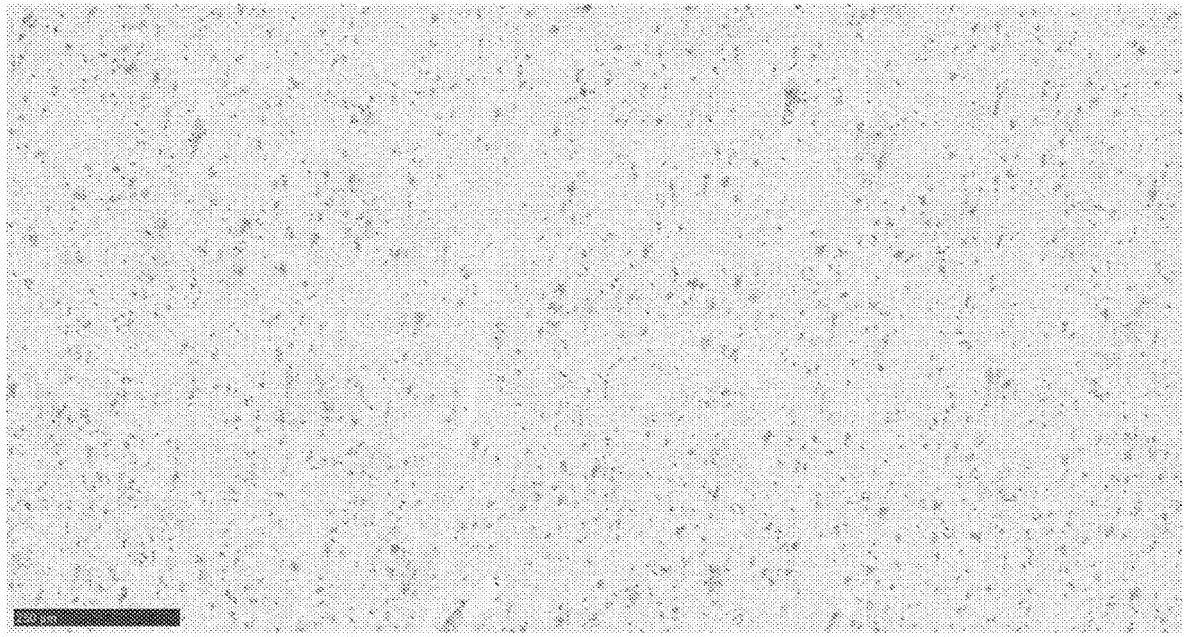
FIG. 3D shows lack of staining of Aβ and Tau pathology in fresh frozen human AD brain tissue using serum (1:300 dilution) from an unvaccinated Guinea pig.
Figure 3E:
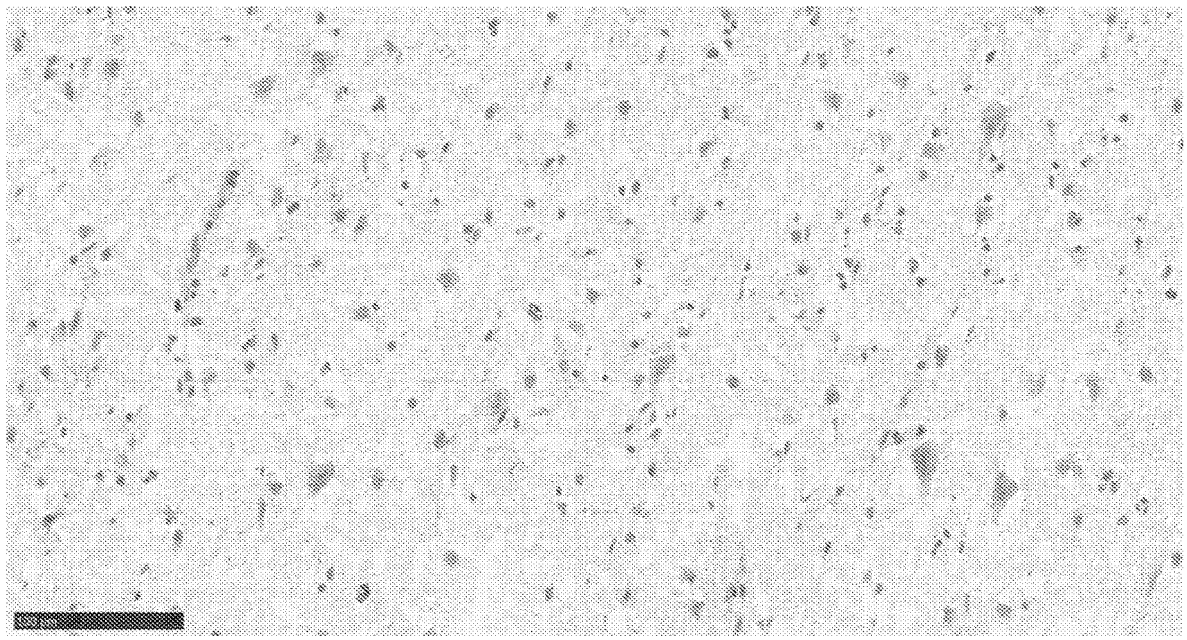
FIG. 3E shows lack of staining of Aβ and Tau pathology in fresh frozen human AD brain tissue using serum (1:300 dilution) from an unvaccinated Guinea pig.
Figure 3F:
FIG. 3F shows lack of staining of Aβ and Tau pathology in fresh frozen human AD brain tissue using serum (1:1500 dilution) from an unvaccinated Guinea pig.

FIG. 2 shows the results for a single peptide immunogen Aβ and tau peptides (DAEFRHD (SEQ ID NO:06) and QIVYKPV (SEQ ID NO:39)) versus dual peptide immunogen DAEFRHDRRQIVYKPV (SEQ ID NO:57) on Aβ 1-28 and full-length tau.

Example 3: Staining of Alzheimer's Brain Tissue with Sera from Guinea Pigs Immunized with a Vaccine as Disclosed Herein Autopsy blocks of fresh frozen human brain tissue (~0.5 g) were embedded in optimal cutting temperature compound (OCT compound) and cut using a cryostat to generate 10 m sections. The sections were placed into a solution of glucose oxidase and beta D-glucose, in the presence of sodium azide, to block endogenous peroxidase. Once tissue sections were prepared, the staining with the specified Guinea pig sera from Guinea pigs immunized with a vaccine as disclosed herein was carried out at two dilutions (1:300 and 1:1500), using a rabbit anti-guinea pig secondary antibody and a DAKO DAB Detection Kit as per the manufacturer's instructions. The staining was processed using an automated Leica Bond Stainer. The results indicate that sera from Guinea pigs immunized with a vaccine as disclosed herein comprises antibodies specific to Aβ and tau in human brain tissue of Alzheimer's patients (see FIG. 3A-3F).

Example 4: Serum from Vaccinated Animals Blocks Soluble Aβ Aggregates from Binding to Neurons E18 primary rat hippocampal neurons were cultured as described previously (Zago, et al. "Neutralization of Soluble, Synaptotoxic Amyloid β Species by Antibodies Is Epitope Specific," *J Neurosci.* 2012 Feb. 22; 32(8): 2696-2702). Soluble Aβ aggregate was pre-incubated with or without guinea pig vaccine serum on culture DIV14-21 to block soluble Aβ aggregate from neuritic binding. Guinea pig serum was isolated from animals vaccinated with dual immunogen peptide: DAEFRHDRRQIVYKPVGGC (SEQ ID NO:59; Immunogen 9). Fresh unlabeled, biotinylated or (9:1) soluble Aβ was prepared one day prior and incubated overnight at 4° C. Each diluted serum sample (1:1000, 1:300, and 1:100) and soluble Aβ solution was prepared at 2× the final concentration in one-half of final treatment volume using NeuroBasal-no phenol red (NB-NPR) medium. This was combined with one-half final volume of 2× soluble Aβ and with one-half final volume of 2× diluted guinea pig vaccine serum to make up a 1× final concentration in total final treatment volume, which was mixed well and then pre-incubated for 30 minutes at 37° C. E18 neurons were rinsed with NB-NPR at 150 μL/well before adding binding treatment. Guinea pig serum from vaccinated animals/Aβ treatment was added to E18 neurons at 60 μL/well, and then incubated for 30 minutes at 37° C. under normal incubator conditions (5% CO$_2$; 9% O$_2$). Cells were rinsed twice using 150p/well of NB-NPR, and then fixed in 4% paraformaldehyde in 1×DPBS for 20 minutes. Cells were permeabilized using 0.1 TX-100 for 5 minutes, and blocked using 10% normal goat serum (NGS) for 1 hour at room temperature (RT). Cells were incubated with MAP2 & NeuN primary antibodies in 100 μL/well, 1×DPBS containing 1% BSA+1% NGS overnight at 4° C. The next day, cells were rinsed twice in 150p/well 1×DPBS for 5 minutes each wash. Secondary antibodies were added for 1 hour at RT in 100 μL/well 1×DPBS+1% BSA+1% NGS. High-content imaging (HCI) analysis was performed to quantify soluble aggregate Aβ neuritic binding using Operetta HCI CLS instrument (Perkin Elmer; modified Neurite Outgrowth algorithm: 40× H$_2$O objective; 40 fields per well; (n=3) per condition; data shown as mean (+/−) SD); MAP2 & NeuN (Abcam) neuronal markers used to each trace neurite tree and count cell body number per optical field; Neuritic Aβ souble aggregate spots detected using streptavidin-488 or polyclonal Aβ antibody (Thermo; Millipore); and data reported as Aβ soluble aggregate spots/neuron (or as Integrated Intensity)).

Figure 4A:
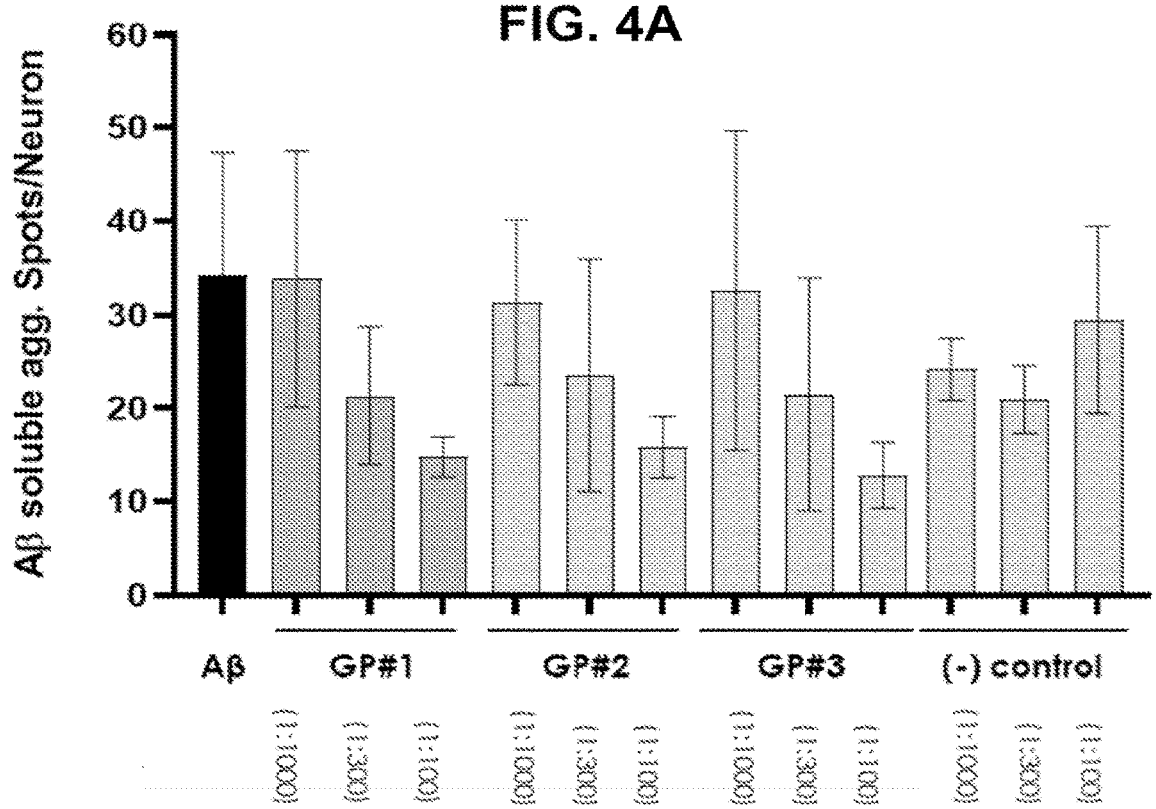
FIG. 4A shows that Guinea pig serum from animals vaccinated with a dual immunogen peptide, DAE-FRHDRRQIVYKPVGGC (SEQ ID NO:59; Immunogen 9), inhibited Abeta soluble aggregates binding to primary neurons in a dose-dependent manner.
Figure 4B:
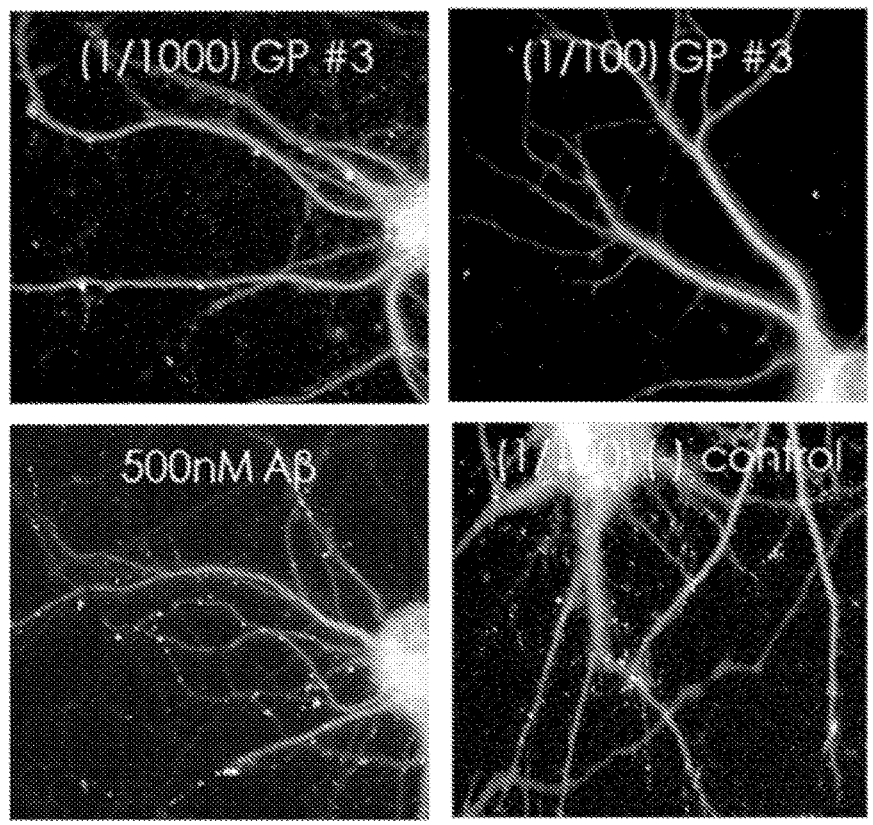
FIG. 4B shows examples of Ab staining on primary neurons in the presence or absence of Guinea pig serum from animals vaccinated with a dual immunogen peptide, DAEFRHDRRQIVYKPVGGC (SEQ ID NO:59; Immunogen 9).
Figure 6B:
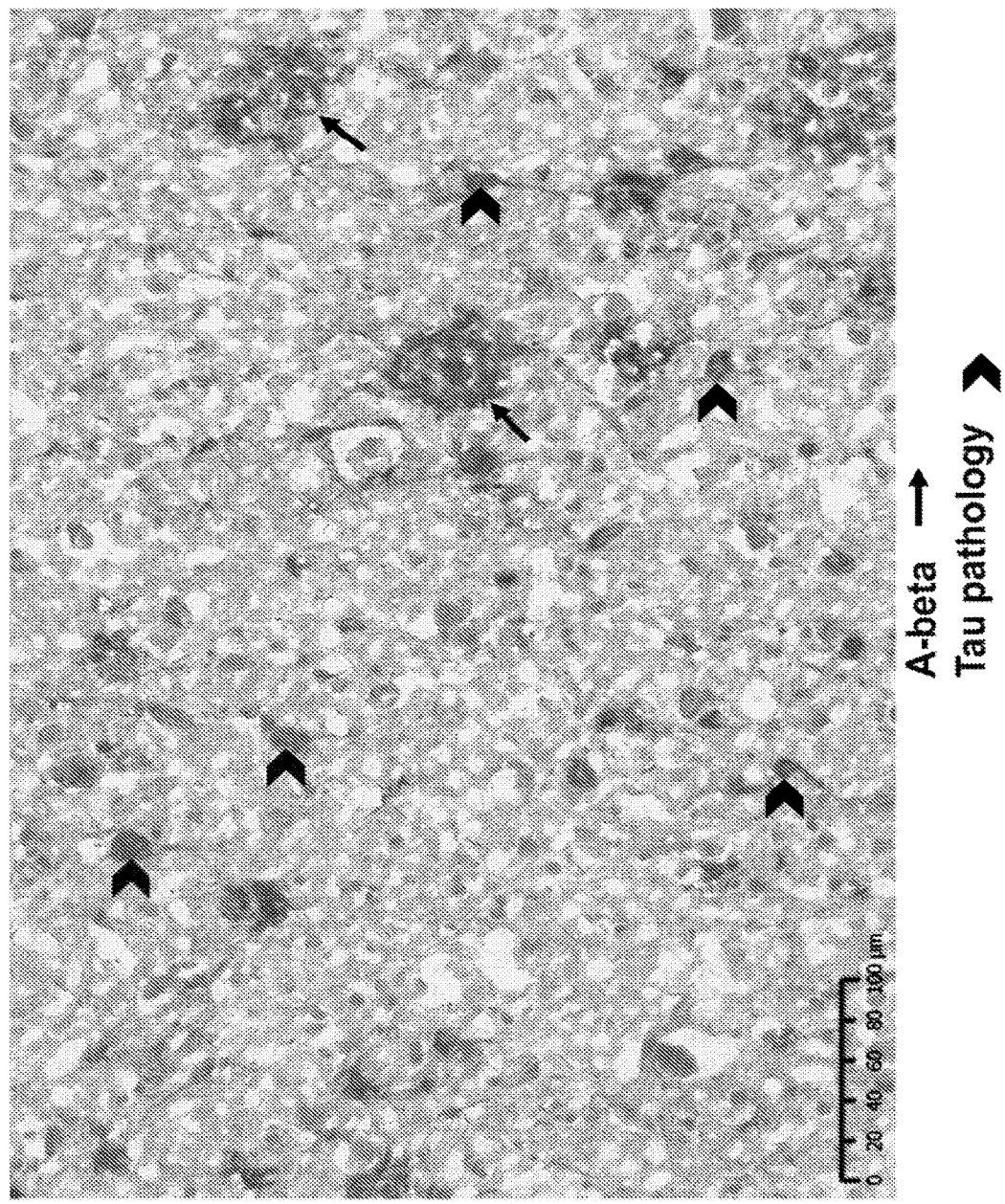
FIG. 6B shows staining of Aβ and Tau pathology in fresh frozen human AD brain tissue using serum (1:1000 dilution) from a mouse vaccinated with Immunogen 19.
Figure 6D:
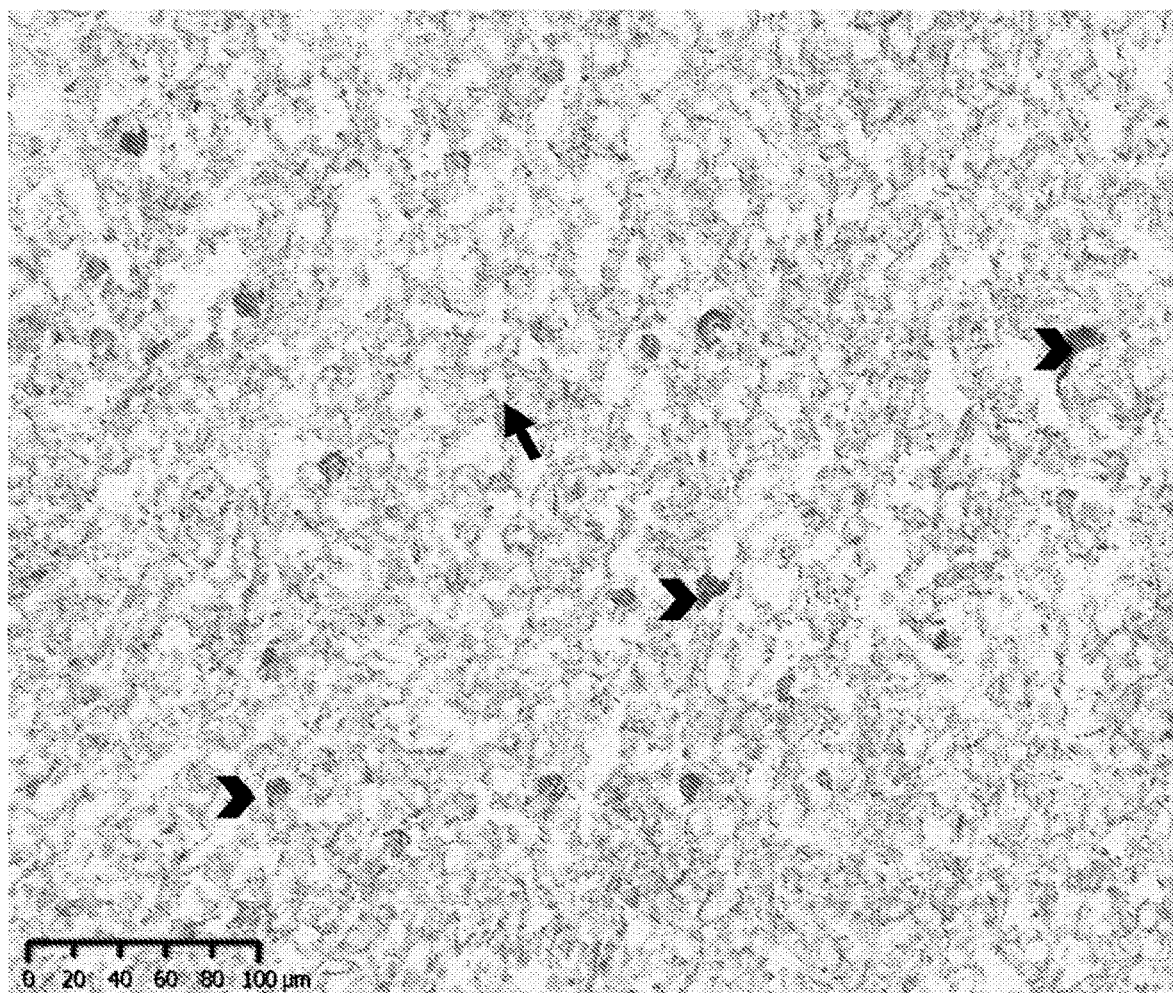
FIG. 6D shows staining of Tau pathology in fresh frozen human AD brain tissue using anti-Tau antibody m6H3 (0.1 g/ml).
Figure 6E:
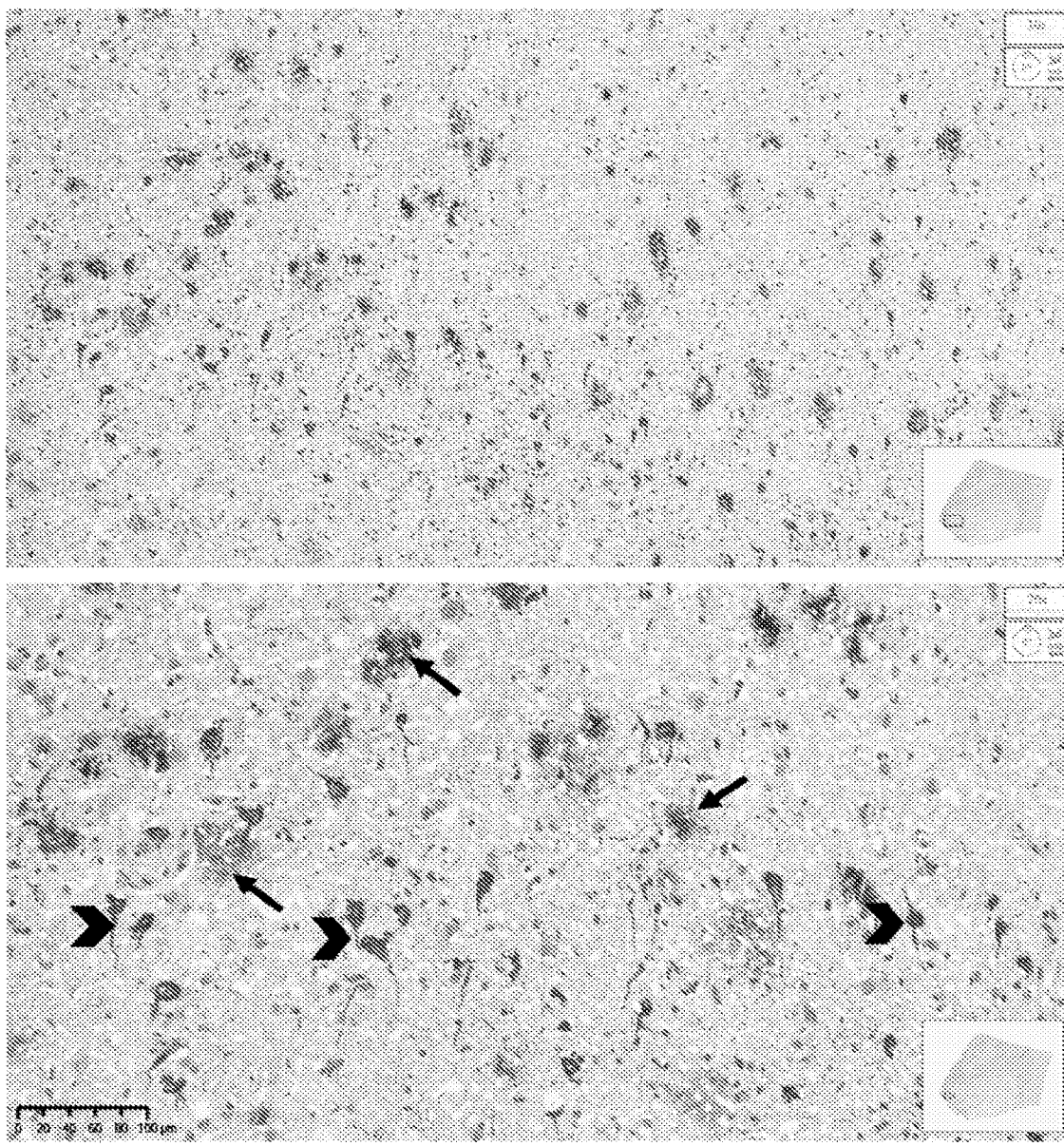
FIG. 6E shows comparable staining of Tau pathology in fresh frozen human AD brain tissue using serum (1:1500 dilution) from a Guinea pig vaccinated with Immunogen 9 (DAEFRHDRRQIVYKPVGGC; SEQ ID NO:59).

Approximately 80-150 neurons were observed per well for each condition tested. The results demonstrate that Guinea pig serum from animals vaccinated with a dual immunogen peptide, DAEFRHDRRQIVYKPVGGC (SEQ ID NO:59; Immunogen 9), inhibited Abeta binding to neurons in a dose dependent manner (see FIG. 4).

Example 5: Mice Vaccinated with Dual Peptide Antigens Produce Titers to AP and Tau Swiss Webster Female mice were injected on day 0, 14 and 28 with 25 μg of a dual peptide immunogen (Table 2) and 25 μg QS21 (Desert King) in PBS total 200 l/injection. Each mouse received 200 μl subcutaneously. Mice were bled on day 21 and 35.

TABLE 2

| Immunogen | Dual peptide immunogen sequence (SEQ ID NO.) |
|---|---|
| 9 | DAEFRHDRRQIVYKPVGGC (SEQ ID NO: 59) |
| 10 | DAEFRHDRRQIVYKPVC (SEQ ID NO: 60) |
| 18 | DAEFRHDRRQIVYKPVAAC (SEQ ID NO: 61) |
| 19 | DAEFRHDRRQIVYKPVKKC (SEQ ID NO: 62) |
| 20 | DAEFRHDRREIVYKSPGGC (SEQ ID NO: 63) |
| 21 | DAEFRHDRREIVYKSPAAC (SEQ ID NO: 64) |
| 22 | DAEFRHDRREIVYKSPC (SEQ ID NO: 65) |
| 23 | DAEFRHDRREIVYKSPKKC (SEQ ID NO: 66) |

The immunogens containing Tau peptide EIVYKSP (SEQ ID No:43); see FIG. 5B) showed greater variability overall in tau titers (with the exception of immunogen 23) than those with the tau MTBR sequence QIVYKPV (SEQ ID NO:39); therefore the base microtubule binding region (MTBR) peptide containing DAEFRHDRRQIVYKPV (SEQ ID NO:57) was also tested (FIG. 5A). Titers of three immunogens with different linkers (no linker, AA and KK) compared to the GGC linker are shown in FIG. 5.

Titers observed from the second bleed are set forth in Tables 3 and 4:

TABLE 3

Titer Against Abeta 1-28 (at 50% Max OD)

| Immunogen number | mouse # 1 | 2 | 3 | 4 | geometric mean | geometric mean SD factor |
|---|---|---|---|---|---|---|
| 9 | 4000 | 2000 | 6000 | 1000 | 2632.15 | 2.20 |
| 10 | 13000 | 2000 | 4000 | 1000 | 3193.44 | 2.98 |
| 18 | 2000 | 2800 | 1200 | 5000 | 2407.6 | 1.80 |
| 19 | 7200 | 2500 | 1500 | 1800 | 2640.34 | 2.02 |
| 20 | 4000 | 2000 | 6000 | 1000 | 2470 | 1.96 |
| 21 | 13000 | 2000 | 4000 | 1000 | 1665 | 2.71 |
| 22 | 300 | 7000 | 2000 | 7000 | 2329 | 4.43 |
| 23 | 350 | 3400 | 4000 | 7000 | 2403 | 3.74 |

TABLE 4

Titer Against Tau (at 50% Max OD)

| Immunogen number | mouse # 1 | 2 | 3 | 4 | geometric mean | geometric mean SD factor |
|---|---|---|---|---|---|---|
| 9 | 400 | 800 | 200 | 800 | 475.7 | 1.94 |
| 10 | 400 | 3200 | 3200 | 1500 | 1574.4 | 2.67 |
| 18 | 1500 | 100 | 6000 | 100 | 547.7 | 7.72 |
| 19 | 10000 | 1000 | 13000 | 1500 | 3738.9 | 3.68 |
| 20 | 300 | 3200 | No titer | 1000 | 313 | 12.07 |
| 21 | 1500 | 100 | 6000 | 100 | 278.3 | 7.75 |
| 22 | 100 | 4000 | No titer | 13000 | 477.5 | 27.33 |
| 23 | 300 | 3000 | 1300 | 500 | 874.8 | 2.78 |

Titers observed in guinea pigs immunized with Immunogen 9 DAEFRHDRRQIVYKPVGGC (SEQ ID NO:59) are set forth in Table 5 below.

TABLE 5

| Guinea Pig | Titer Against Abeta 1-28 | Titer Against Abeta soluble aggregate | Titer Against Tau | Titer Against bio-GGSQIVYKPVDLS (SEQ ID NO: 73) |
|---|---|---|---|---|
| 1 | 3100 | 1500 | 1600 | 1000 |
| 2 | 3200 | 4000 | 6400 | 6400 |
| 3 | 3300 | 2000 | 3200 | 4000 |

Example 6: Serum from Vaccinated Animals Stains Aβ Plaques and Tau Pathologies in Human Brain Tissue Fresh frozen human brain tissues from autopsied Alzheimer's disease donors or non-diseased controls was embedded in OCT, and cut in a cryostat to generate 10 m frozen sections. The tissue sections were incubated in a solution of glucose oxidase and beta D-glucose, in the presence of sodium azide, to block endogenous peroxidase. The staining with sera from vaccinated mice. Mice were vaccinated with the following dual antigen peptides: DAEFRHDRRQIVYKPVGGC (SEQ ID NO:59, Immunogen 9); DAEFRHDRRQIVYKPVC (SEQ ID NO:60, Immunogen 10); DAEFRHDRRQIVYKPVAAC (SEQ ID NO:61, Immunogen 18); and DAEFRHDRRQIVYKPVKKC (SEQ ID NO:62, Immunogen 19) or control mice. Staining was then carried out at 1:1000 dilution, in an automated Leica Bond Rx Stainer (Leica Biosystems). Antibody binding was detected using the Bond Polymer Refine Detection Kit (DS9800, Leica Biosystems), which is based on an anti-mouse polymer detection, DAB visualization and hematoxylin nuclear counter-staining. After cover-slipping, the stained tissue slides were digitally imaged with a Hamamatsu NanoZoomer 2.0HT slide scanner (Hamamatsu Corporation) with an NDP.scan, 2.5.85 software. The digitized images were viewed and analyzed using the NDP.view, 2.7.43.0 software.

Results demonstrate Aβ plaques and tau neurofibrillary tangles were identified based on their typical histopathological characteristics. Such pathologies were absent from tissues incubated with control mouse serum. Also, non-diseased tissue had no such pathological staining after incubation with the sera from vaccinated mice. FIGS. 6A-E and Table 6 summarize the results of Aβ and Tau staining using mouse sera from animals vaccinated with dual antigen peptides (1:1000 dilution of sera used to stain human brain tissue from AD patients).

TABLE 6

| Serum ID | Aß staining | Tau pathology | Background |
|---|---|---|---|
| 9-1 | + | | Clear |
| 9-2 | + | | Dark |
| 9-3 | +++++ | | Clear |
| 9-4 | ++ | | Clear |
| 10-1 | +++++ | | OK |
| 10-2 | +++ | | Clear |
| 10-3 | ++++ | * | OK |
| 10-4 | ++++ | * | Dark |
| 18-1 | ++ | | Dark |
| 18-3 | + | | Clear |
| 19-1 | +++++ | +++ | OK |
| 19-2 | ++ | * | OK |
| 19-3 | + | ++ | Dark |
| 19-4 | ++ | | OK |

9: DAEFRHDRRQIVYKPVGGC (SEQ ID NO: 59)
10: DAEFRHDRRQIVYKPVC (SEQ ID NO: 60)
18: DAEFRHDRRQIVYKPVAAC (SEQ ID NO: 61)
19: DAEFRHDRRQIVYKPVKKC (SEQ ID NO: 62)
* possible tau pathology, too weak to clearly identify staining as tau Example 7: Immunization and Determination of Titers in Cynomolgus Monkeys The study described in this example was designed to assess the development of titers to Aβ and tau in cynomolgus monkeys using the dual antigen peptide DAEFRHDRRQIVYKPVGGC (SEQ ID NO:59). We also assessed two injection schedules and persistence of titers.

Immunizations

Several dual Aβ-tau linear immunogens with a dendritic cell cleavage site were screened in mice for balanced titer on Aβ and tau proteins (see Example 5, above). A subset of immunogens were further evaluated in guinea-pig (see Examples 1-5, above) and cynomolgus monkey (this example). Two groups of four monkeys were immunized intramuscularly with 50 g of immunogen (SEQ ID NO:59; DAEFRHDRRQIVYKPVGGC) coupled to CRM197 carrier protein, and 50 µg of the adjuvant QS21. Group 1 was injected on week 0, 4, 12 and 24 with bleeds taken every 2 weeks through week 38. Group 2 was injected at week 0, 8, 24 with bleeds taken every 2 weeks through week 38. Serum titer levels were determined against Aβ and full-length tau. Fresh frozen human AD or control brain sections were stained with sera from immunized and control animals. The activity of the guinea-pig immune sera was also assessed on soluble Aβ oligomer binding in primary rat hippocampal neurons.

Titer Protocol

Measurement of Antibody Titer to Aβ 1-28 in Cynomolgus Monkey

Cynomolgus monkey bleeds were titered by enzyme-linked immunosorbent assay (ELISA). Plates were coated overnight at 2 g/mL with Aβ 1-28 (SEQ ID NO:67) in phosphate-buffered saline (PBS) and then blocked 1 hour with 1% bovine serum albumin (BSA) in PBS. Pre-bleed cynomolgus monkey was used as a negative control while known positive anti-serum from previous mouse studies was used as a positive control at the same dilutions of test serum. Bleeds were diluted in PBS/0.1% BSA/0/1% Tween 20 (PBS/BSA/T) starting at 1/100 and serially diluted 1:2 down the plate. Plates were washed with TBS/Tween 20 and goat anti-monkey immunoglobulin G (IgG) (heavy+light chains) horseradish peroxidase (HRP) (IgG [H+L] HRP; Invitrogen) was added and incubated 1 hour at room temperature. Plates were washed in TBS/Tween 20, and antibody binding was detected with o-phenylenediamine dihydrochloride (OPD) substrate (Thermo Fisher Scientific, Waltham, MA) following manufacturer's instructions. Plates were read at 490 nM on a Molecular Devices Spectromax. Titer was defined as the dilution giving 50% Maximum OD or 4× background (defined in graphs and tables) extrapolation was used if it fell in between dilutions.

Measurement of Antibody Titer to Tau in Cynomolgus Monkey

Cynomolgus monkey bleeds were titered by enzyme-linked immunosorbent assay (ELISA) against full-length recombinant tau (Proteos, Kalamazoo, MI; SEQ ID NO:02). Plates were coated overnight at 2 g/mL tau in phosphate-buffered saline (PBS) and then blocked 1 hour with 1% bovine serum albumin (BSA) in PBS. Pre-bleed guinea pig serum was used as a negative control while known positive anti-serum from previous mouse studies was used as a positive control at the same dilutions of test serum. Bleeds were diluted in PBS/0.1% BSA/0/1% Tween 20 (PBS/BSA/T) starting at 1/100 and serially diluted 1:2 down the plate. Plates were washed with TBS/Tween 20 and goat anti-monkey immunoglobulin G (IgG) (heavy+light chains) horseradish peroxidase (HRP) (IgG [H+L] HRP; Invitrogen) was added and incubated 1 hour at room temperature. Plates were washed in TBS/Tween 20, and antibody binding was detected with o-phenylenediamine dihydrochloride (OPD) substrate (Thermo Fisher Scientific, Waltham, MA) following manufacturer's instructions. Plates were read at 490 nM on a Molecular Devices Spectromax. Titer was defined as the dilution giving 50% Maximum OD or 4× background (defined in graphs and tables) extrapolation was used if it fell in between dilutions.

Titer Cynomolgus Monkey Bleeds on the Carrier Protein CRM197

Cynomolgus monkey bleeds were titered by enzyme-linked immunosorbent assay (ELISA) against CRM197 (FinaBio, Maryland) carrier protein. Plates were coated overnight at 2 g/mL tau in phosphate-buffered saline (PBS) and then blocked 1 hour with 1% bovine serum albumin (BSA) in PBS. Pre-bleed guinea pig serum was used as a negative control while known positive anti-serum from previous mouse studies was used as a positive control at the same dilutions of test serum. Bleeds were diluted in PBS/0.1% BSA/0/1% Tween 20 (PBS/BSA/T) starting at 1/100 and serially diluted 1:2 down the plate. Plates were washed with TBS/Tween 20 and goat anti-monkey immunoglobulin G (IgG) (heavy+light chains) horseradish peroxidase (HRP) (IgG [H+L] HRP; Invitrogen) was added and incubated 1 hour at room temperature. Plates were washed in TBS/Tween 20, and antibody binding was detected with o-phenylenediamine dihydrochloride (OPD) substrate (Thermo Fisher Scientific, Waltham, MA) following manufacturer's instructions. Plates were read at 490 nM on a Molecular Devices Spectromax. Titer was defined as the dilution giving 50% Maximum OD or 4× background (defined in graphs and tables) extrapolation was used if it fell in between dilutions.

Results

Figure 7A:
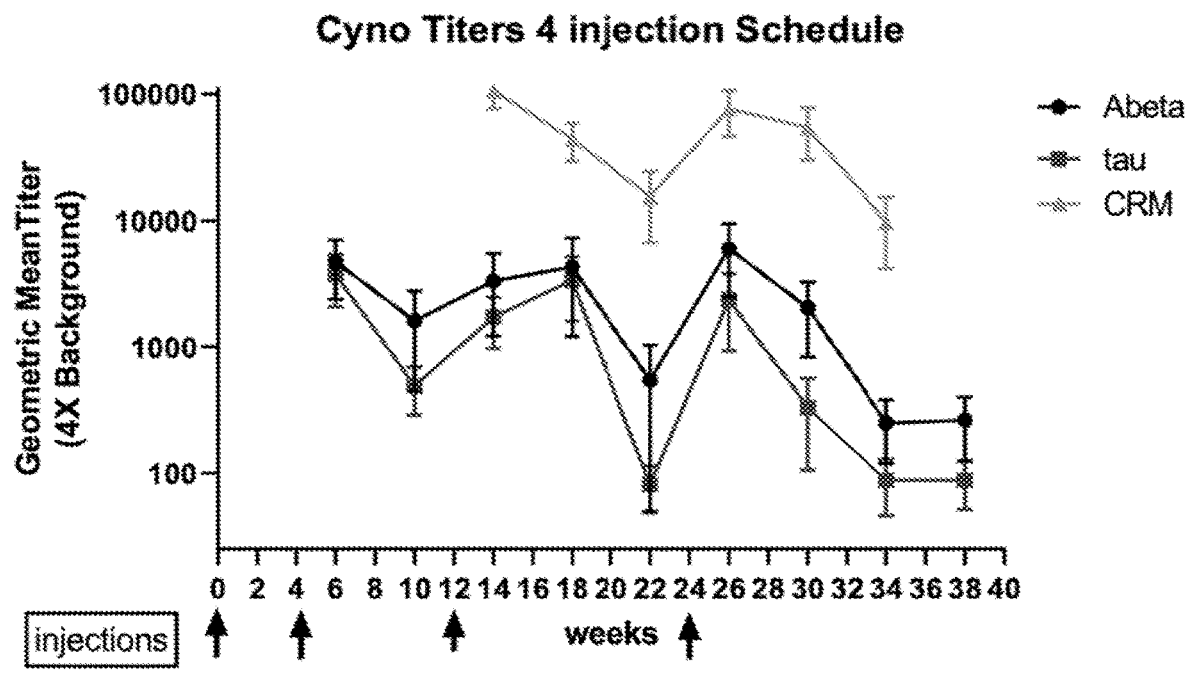
FIGS. 7A and 7B show titers of dual Aβ-tau immunogen in two injection paradigms. Titers to Aβ31-28, full-length tau and the carrier CRM protein of the two injection schedules ((FIG. 7A) showing 0, 4, 12 and 24 weeks.
Figure 7B:
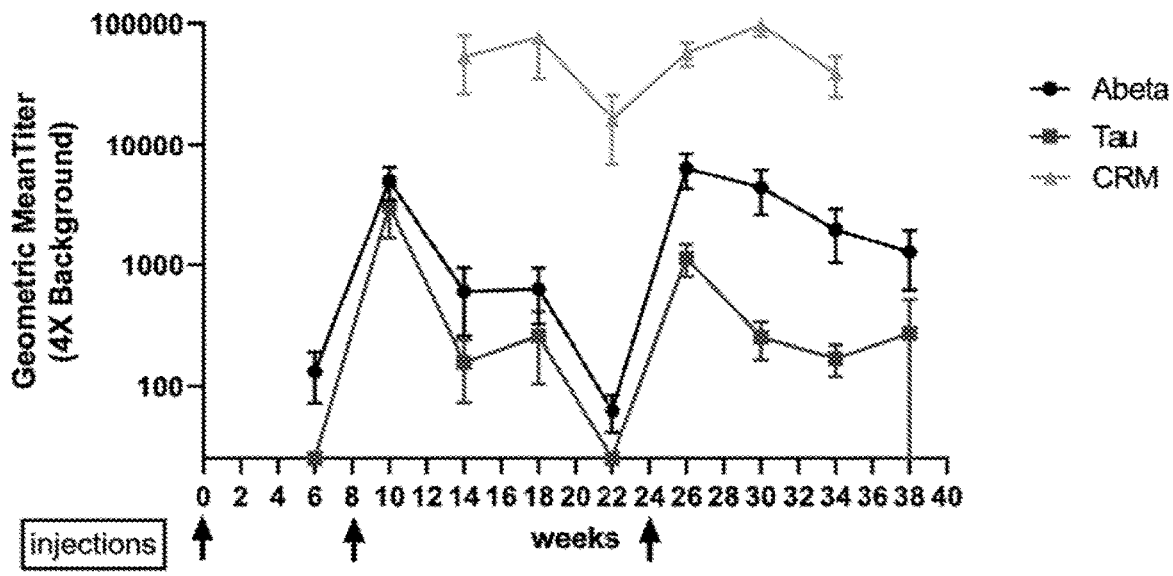
Figure 8A:
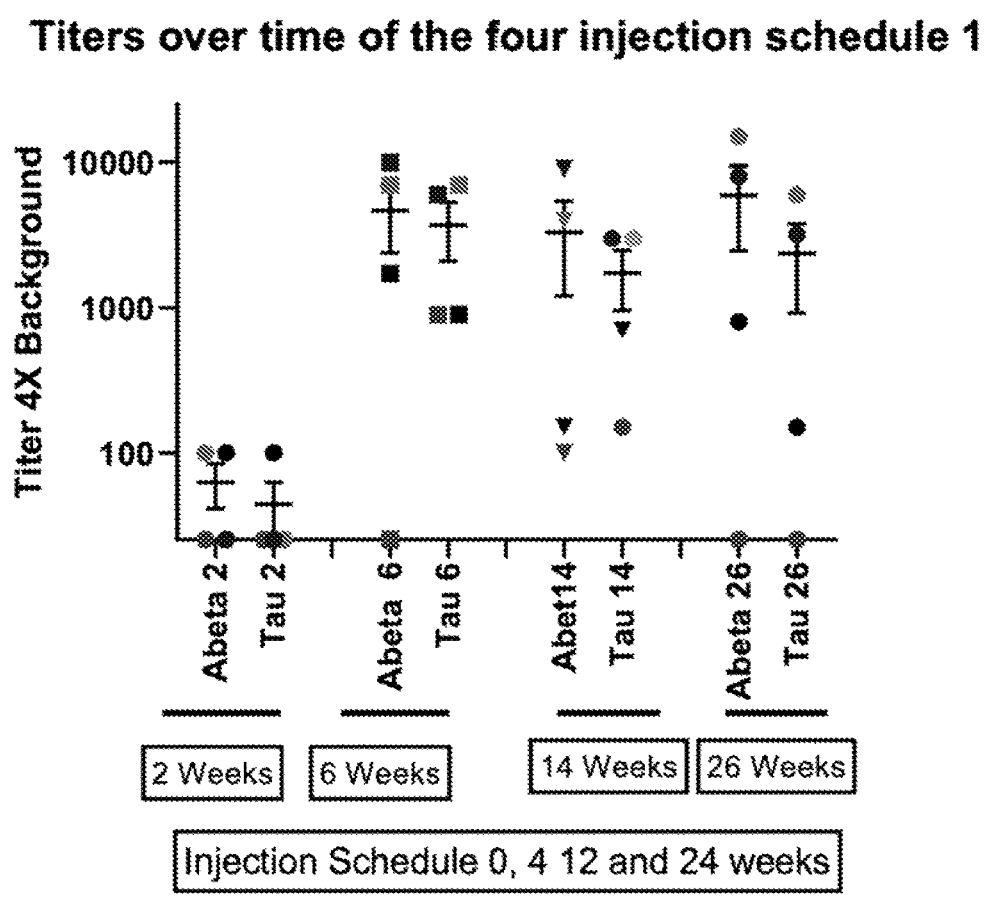
FIG. 8A shows individual animal titers to Aβ and tau two weeks post each injection for the injection schedule of FIG. 7A, i.e., at weeks 2, 6, 14 and 26.
Figure 8B:
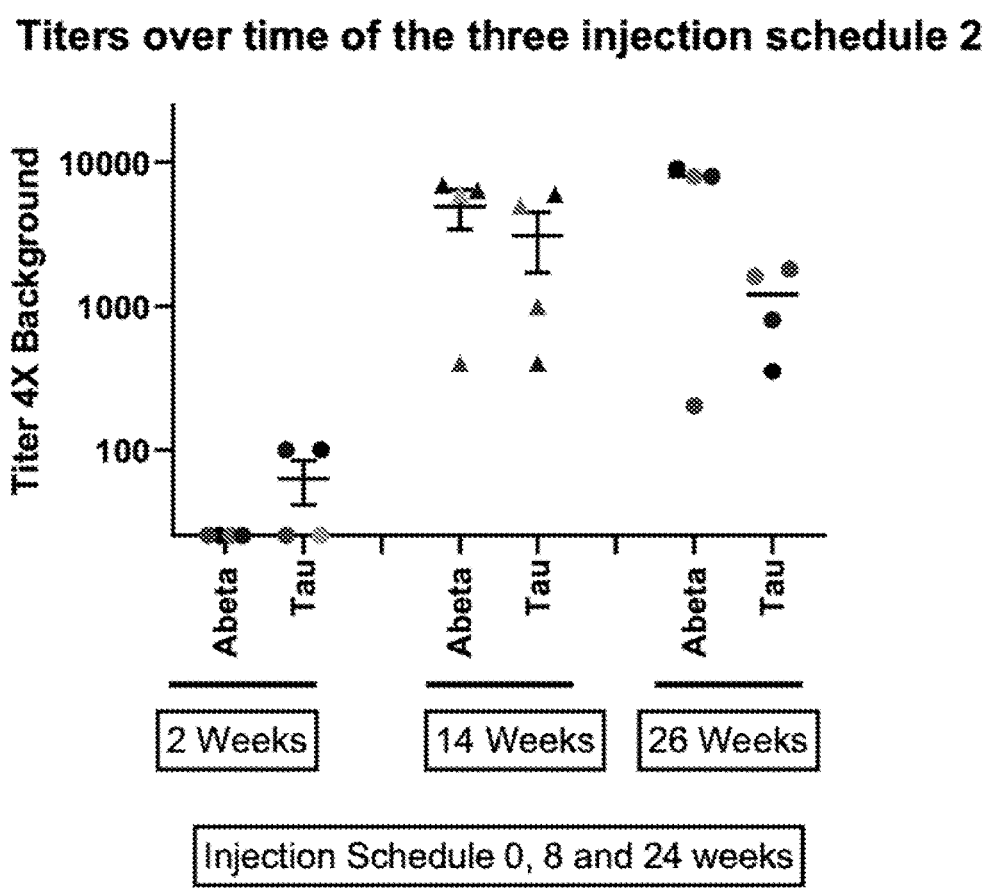
FIG. 8B shows individual animal titers to Aβ and tau two weeks post each injection for the injection schedule of FIG. 7B, i.e., at weeks 2, 14 and 26.

Titers levels were similar for Aβ and tau. Monkeys subject to the group 1 vaccination schedule had titers with a greater area under the curve than those of group 2 but did not show a significant improvement in maximum titer under these conditions (FIG. 7A, FIG. 7B). Overall titer levels were lower than the guinea pig study described above. This change may be attributable to a change of adjuvant from QS21 in ADDVAX in the Guinea pig to QS21 in phosphate buffered saline (PBS) in cynomolgus monkeys to match approved vaccines. Persistence of titer was modest for both four injection and three injection vaccination schedules (FIG. 8A, FIG. 8B). These results demonstrate that these immunogens can generate a balanced immune response to Aβ and tau in primates. Optimization of dosing schedule and/or formulation may improve titer levels and persistence.

Example 8: Immunohistochemistry on AD and Control Brain Sections

Sera from immunized monkeys were evaluated for the ability to bind pathological Aβ plaques and tau tangles in human brain tissue from subjects with AD. Binding both Aβ plaques and tau tangles is expected reduce plaque burden and reduce tau transmission which in turn should reduce the signs and symptoms of AD.

Autopsy blocks of fresh frozen human brain tissue were embedded in optimal cutting temperature compound (OCT compound) and cut using a cryostat to generate 10 micron sections. The sections were placed into a solution of glucose oxidase and beta D-glucose, in the presence of sodium azide, to block endogenous peroxidase. Once tissue sections were prepared, the staining with the specified cynomolgus immune sera was carried out at two dilutions (1:300 in 5% goat serum with 0.25% Triton for 1 hour at RT). Binding was detected with a mouse anti-monkey IgG secondary antibody purified unlabeled (Mybiosource 3 mg/mL) for 1 hour at RT, and a goat anti-mouse IgG secondary antibody (Jackson, 1:200) for 1 hour at RT, avidin-biotin complex (ABC; Vector PK-4000) and a DAKO DAB Detection Kit according to manufacturer instructions. The staining was processed using an automated Leica Bond Stainer.

Figure 9A:
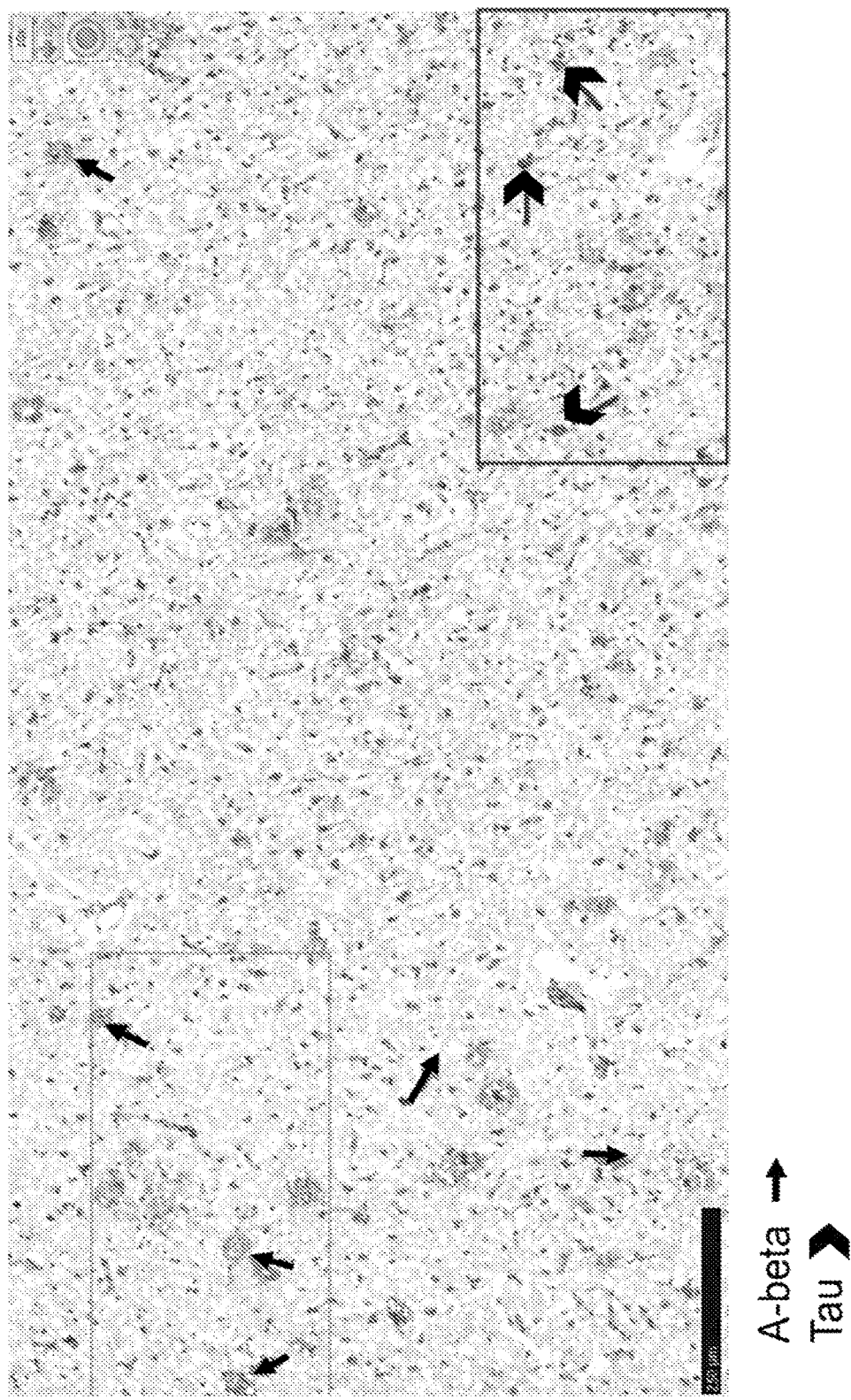
FIG. 9A shows staining of Aβ and Tau pathology in fresh frozen human AD brain tissue using week 26 serum (1:300 dilution) from cynomolgus monkey #1001 vaccinated with Immunogen 15 (DAEFRHDRRQIVYKPVGGC; SEQ ID NO:59) on a four injection vaccination schedule.
Figure 9B:
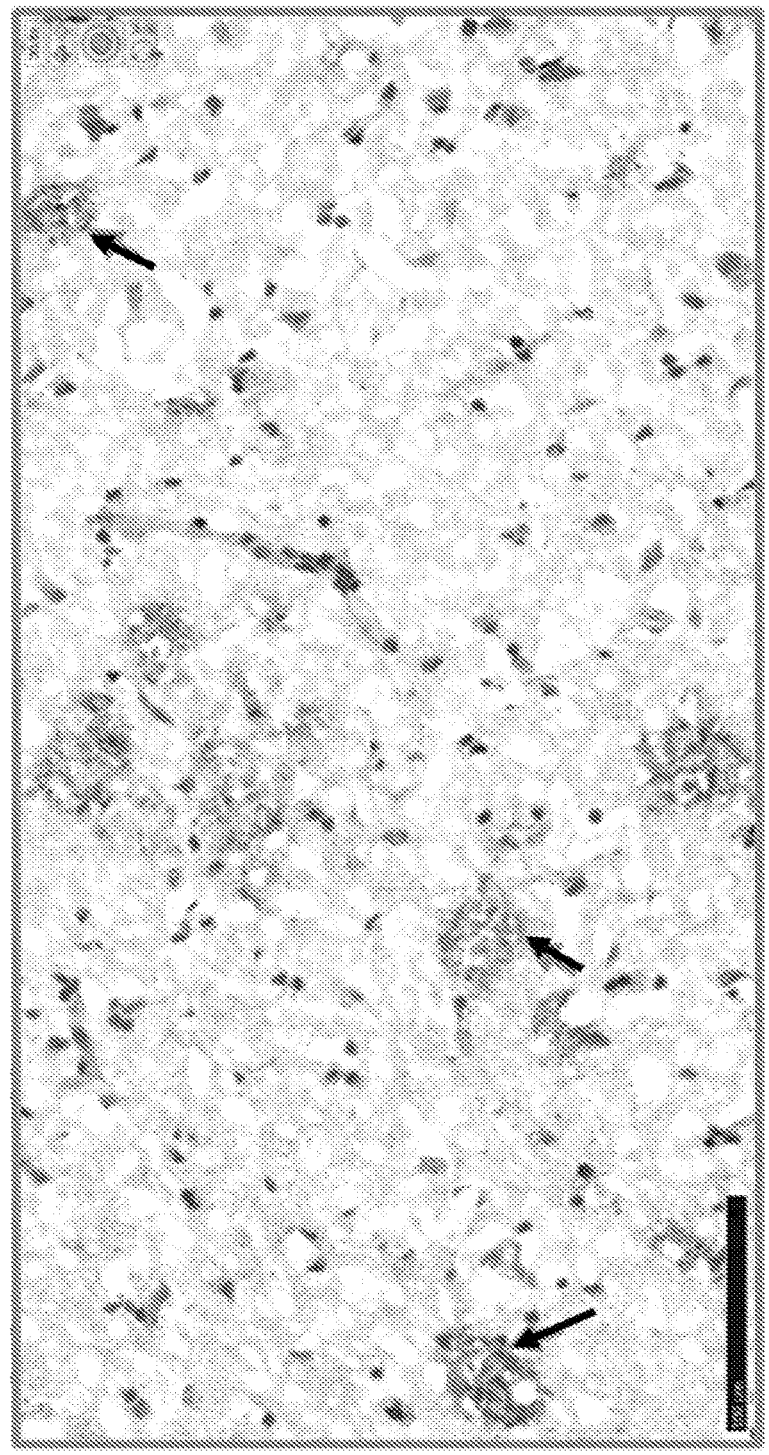
FIG. 9B shows a zoomed view of the rectangle indicating staining of Aβ pathology in FIG. 9A.
Figure 9C:
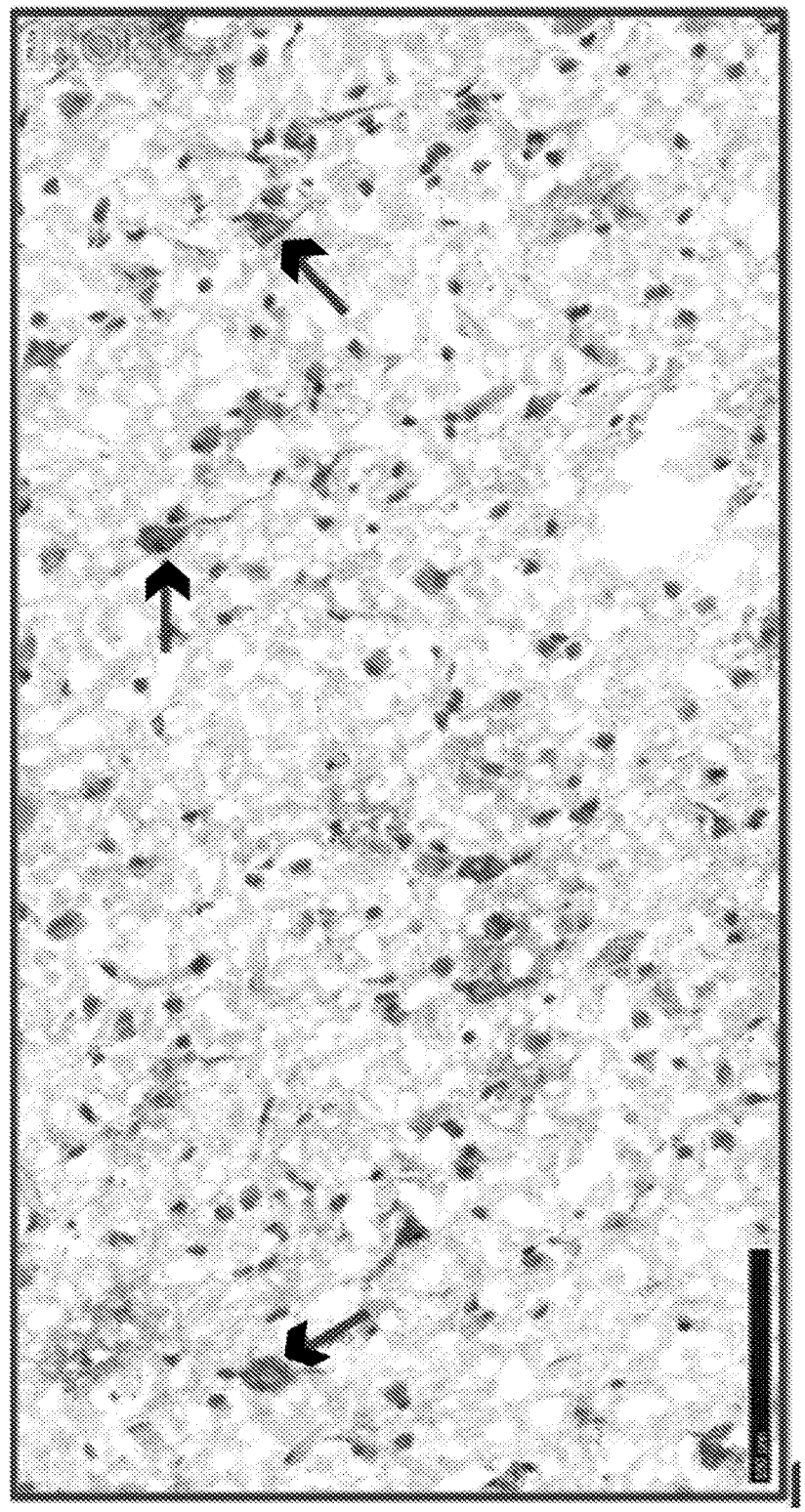
FIG. 9C shows a shows a zoomed view of the rectangle indicating staining of Tau pathology in FIG. 9A.
Figure 10A:
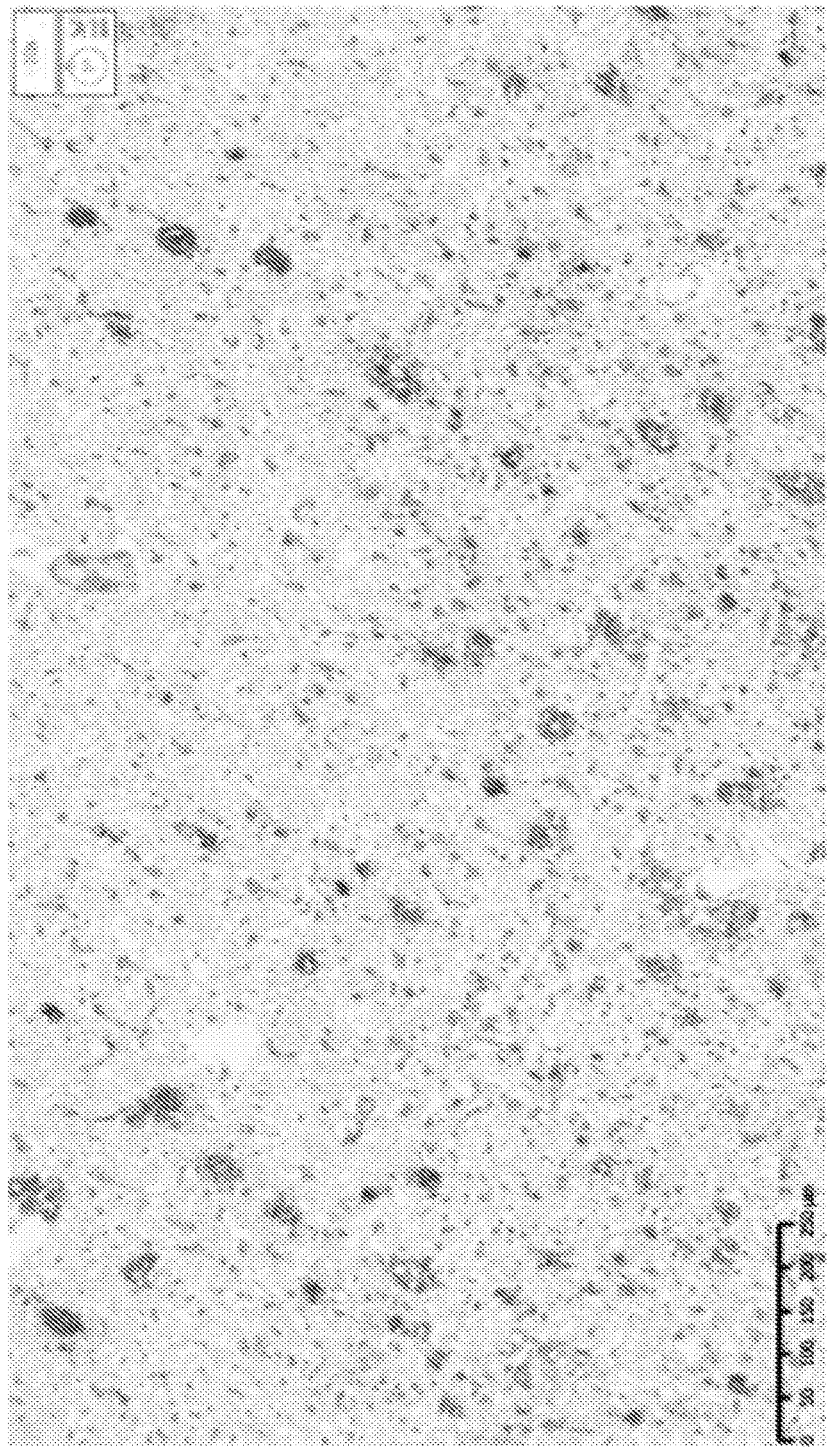
FIG. 10A shows staining of Aβ pathology in fresh frozen human AD brain tissue using serum (1:300 dilution) from cynomolgus monkey #1003 vaccinated with Immunogen 15 (DAEFRHDRRQIVYKPVGGC; SEQ ID NO:59).
Figure 11A:
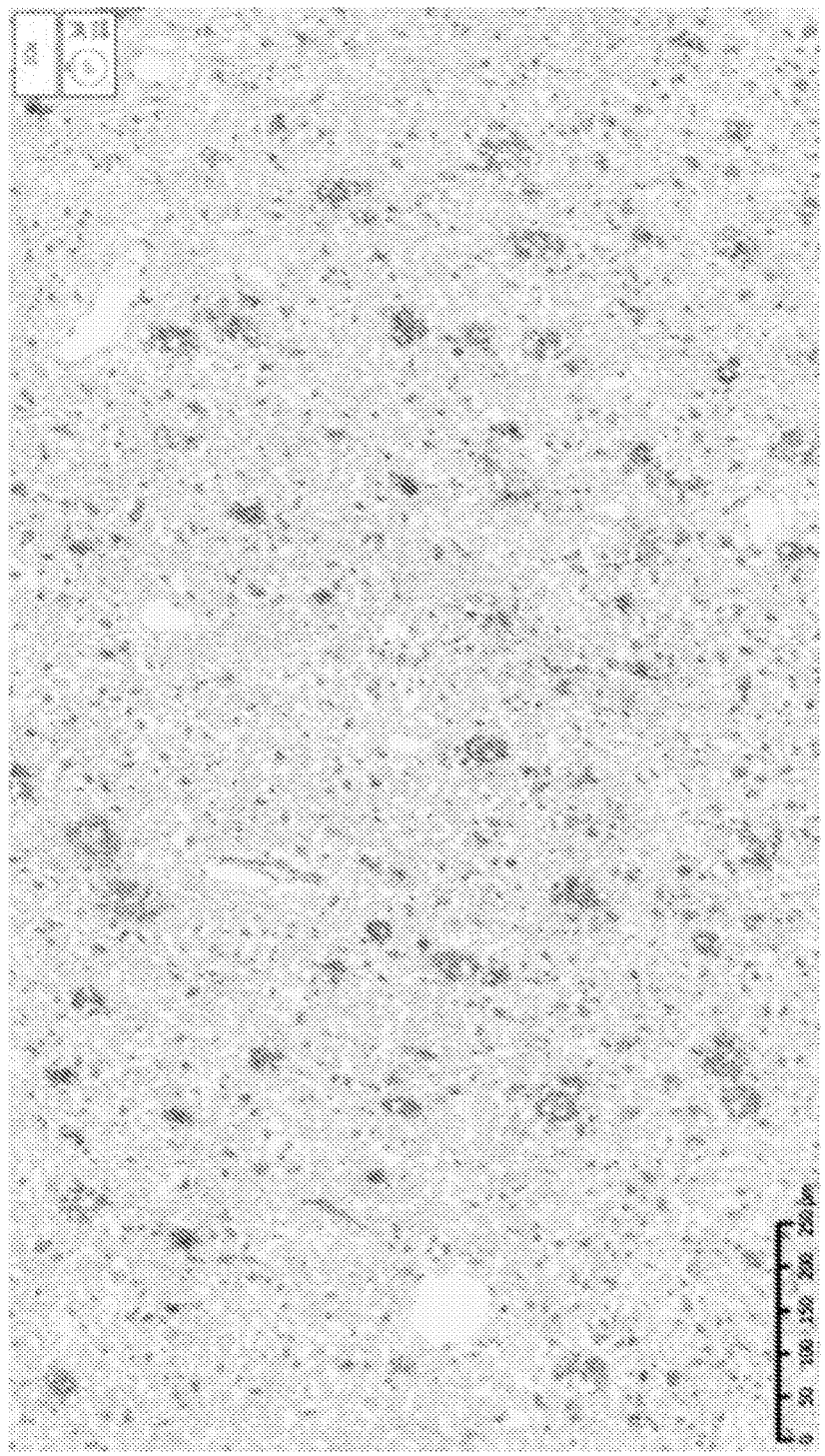
FIG. 11A shows staining of Aβ pathology in fresh frozen human AD brain tissue using serum (1:300 dilution) from cynomolgus monkey #1501 vaccinated with Immunogen 15 (DAEFRHDRRQIVYKPVGGC; SEQ ID NO:59).
Figure 11B:
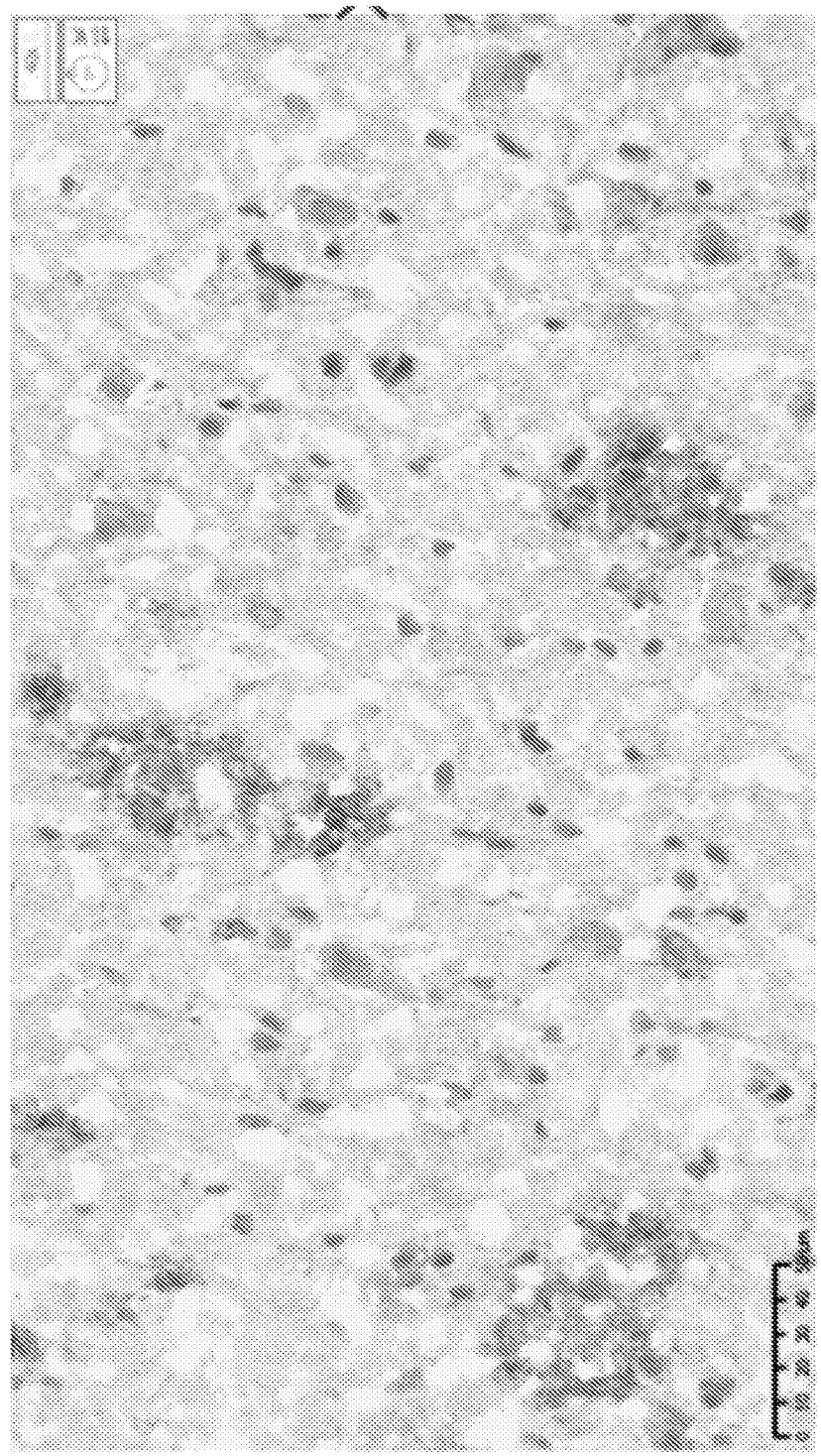
FIG. 11B shows minimal staining of Tau pathology in fresh frozen human AD brain tissue using serum (1:300 dilution) from cynomolgus monkey #1501.
Figure 12A:
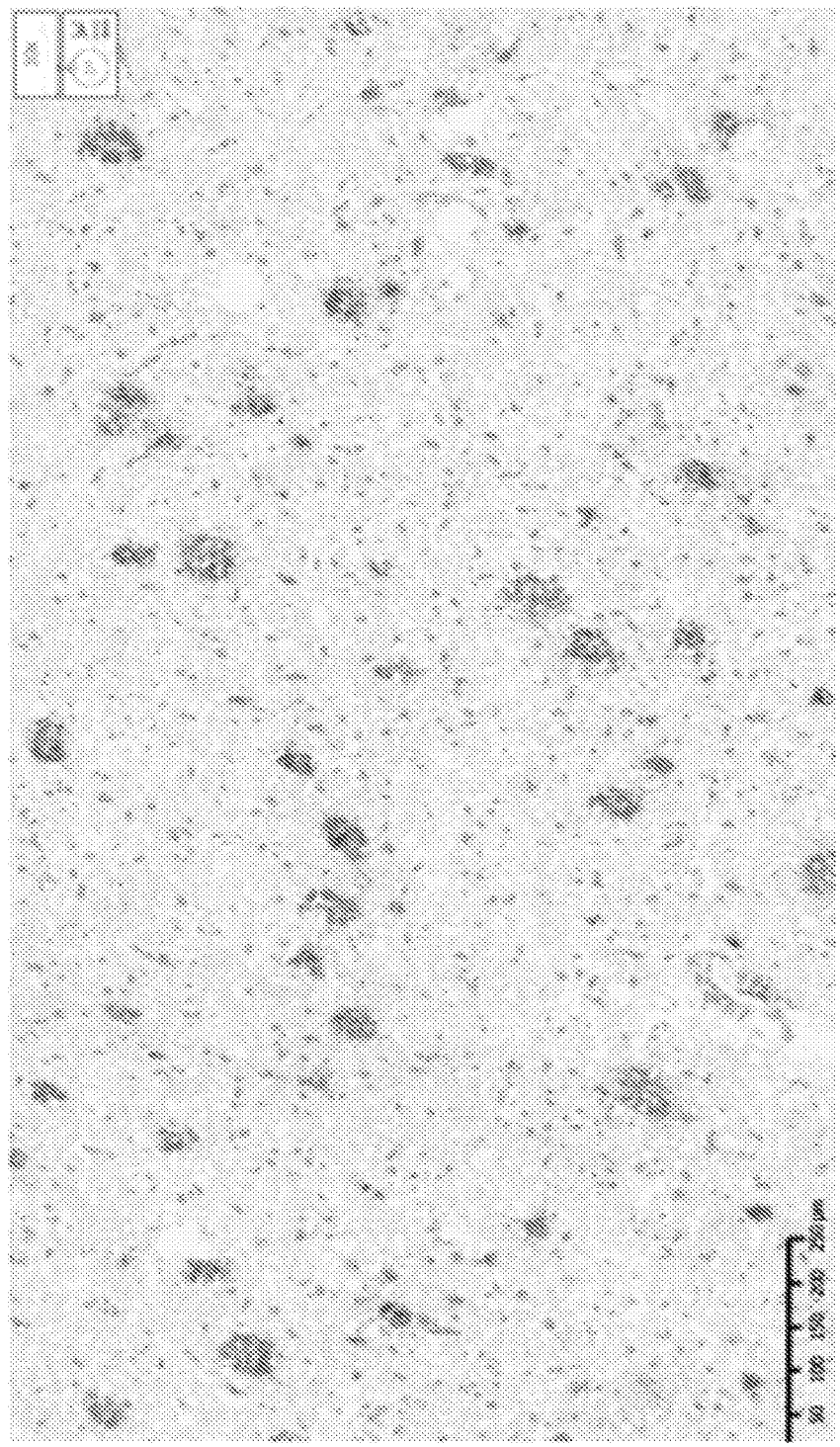
FIG. 12A shows staining of Aβ pathology in fresh frozen human AD brain tissue using serum (1:300 dilution) from cynomolgus monkey #2501 vaccinated with Immunogen 15 (DAEFRHDRRQIVYKPVGGC; SEQ ID NO:59).

Table 7 shows a summary of the staining in the cynomolgus monkey study. All animal except 1002 had positive staining for Aβ. Only animal 1001 had strong tau staining (FIG. 9A-FIG. 9C), with 1003 (FIG. 10A-FIG. 10B) and 1501 (FIG. 11A-FIG. 11B) demonstrating modest staining. Animal 2501, for example, did not demonstrate significant tau staining (FIG. 12A-FIG. 12B). There did not appear to be a correlation with tau staining and tau titers as evidenced by animal 1001, which did not have a strong tau titer but stained tau strongly.

TABLE 7

| Animal Number | Aβ Staining | Tau Staining | Aβ Titer | Tau Titer |
|---|---|---|---|---|
| 1001 | + | ++ | 800 | 150 |
| 1002 | − | − | 25 | 25 |
| 1003 | +++ | + | 15000 | 6000 |
| 1501 | +++ | +/− | 8000 | 3200 |
| 2001 | +++ | − | 9000 | 350 |
| 2003 | ++ | − | 200 | 1500 |
| 2102 | +++ | − | 8000 | 800 |
| 2501 | +++ | − | 8000 | 1600 |

Immune sera bound avidly to Aβ plaques and tau tangles in human AD brain sections at concentrations expected to be achieved in CNS under in vivo conditions. Monkeys with the strongest titers at week 26 stained Aβ, and one monkey with low to moderate tau titers stained both Aβ and tau.

These results demonstrate that the serum antibody binding of the cynomolgus monkey antibody response to be balanced and bind to pathological Aβ plaques and tau tangles.

Example 9: Serum Blocking of Soluble Aβ Aggregates from Binding to Neurons and T-Cell Activity Primary hippocampal neurons isolated from E18 rat were cultured as described above. Fresh unlabeled, biotinylated or (9:1) soluble Aβ was prepared one day prior to assay and incubated overnight at 4° C. Neurons were rinsed with NB-NPR at 150p/well before adding Aβ/serum treatment. An IgG cut of cynomolgus monkey bleeds from vaccinated animals was added to E18 neurons at 60 µL/well, and then incubated for 30 minutes at 37° C. under normal incubator conditions (5% CO2; 9% O2). Cells were rinsed twice using 150 µL/well of NB-NPR, and then fixed in 4% paraformaldehyde in 1×DPBS for 20 minutes. Cells were permeabilized using 0.1 TX-100 for 5 minutes, and blocked using 10% normal goat serum (NGS; Thermofisher) for 1 hour at room temperature (RT). Cells were incubated with MAP2 & NeuN primary antibodies in 100 µL/well, in 1×DPBS containing 1% BSA+1% NGS overnight at 4° C.

The next day, cells were rinsed twice in 150 µL/well 1×DPBS for 5 minutes each wash. Secondary antibodies were added for 1 hour at RT in 100 µL/well 1×DPBS+1% BSA+1% NGS. Aβ soluble aggregate spots were detected using streptavidin-488 or polyclonal Aβ antibody (Thermofisher; Millipore); High-content imaging (HCI) analysis was performed to quantify soluble aggregate Aβ neuritic binding using Operetta HCI CLS instrument (Perkin Elmer; modified Neurite Outgrowth algorithm: 40× $H_2O$ objective; 40 fields per well; (n=3) per condition; data shown as mean (+/−) SD); MAP2 & NeuN (Abcam) neuronal markers were used to each trace neurite tree and count cell body number per optical field; Neuritic data were reported as Aβ soluble aggregate spots/neuron (or as Integrated Intensity)). Approximately 80-150 neurons were observed per well for each condition tested (Zago, et al., 2012).

T-cell reactivity was also investigated. Immune sera inhibited the binding of soluble Aβ aggregates to hippocampal neurons. Immunogens did not elicit cytotoxic T-cell responses to Aβ or tau.

Example 10: Animals Vaccinated with Dual Peptide Antigens Produce Titers to Aβ and Tau The study described in this example was designed to assess dual Aβ and tau antigen peptides in mice. The dual Aβ-tau constructs in this example effectively demonstrated: high titers for both antigens; blocking of tau binding to heparin; and staining/binding to Aβ and tau peptides in brain tissue from human Alzheimer's patients. Furthermore, titers against tau for an engineered tau immunogen (Dual #11) were comparable, and in some cases, better than other tau immunogens despite including a non-native tau sequence. This demonstrates that engineered immunogens are useful in vaccine constructs.

TABLE 8

| Dual Construct ID # | Abeta Sequence | Abeta SEQ ID NO. | Endo peptidase linker | Tau Sequence | tau SEQ ID NO. | C-Terminal linker | Cys |
|---|---|---|---|---|---|---|---|
| 2 | DAEFRHD | 06 | RR | VKSKIGST | 801 | GG | C |
| 3 | DAEFRHD | 06 | RR | SKIGSTEN | 817 | GG | C |
| 8 | DAEFRHD | 06 | RR | TENLKHQP | 695 | GG | C |
| 9 | DAEFRHD | 06 | RR | ENLKHQPG | 689 | GG | C |
| 11 | DAEFRHD | 06 | RR | SKIGSKDNIKH | 986 | GG | C |

TABLE 9

| Dual Construct ID # | Sequence | SEQ ID NO: |
|---|---|---|
| 2 | DAEFRHDRRVKSKIGSTGGC | 997 |
| 3 | DAEFRHDRRSKIGSTENGGC | 998 |
| 8 | DAEFRHDRRTENLKHQPGGC | 999 |
| 9 | DAEFRHDRRENLKHQPGGGC | 1000 |
| 11 | DAEFRHDRRSKIGSKDNIKHGGC | 1001 |

Conjugation-Peptides were made by Biopeptide (San Diego, CA) CRM-bromoacetate was received from Fina Biosolutions (Rockville, MD) peptides were coupled to CRM following the below protocol.

1M Tris HCL pH 8.0, MilliQ DI Water and 50 mM Borate, 100 mM NaCl, 5 mM EDTA pH 8.5 were sterile filtered and degassed. 1 mg of each peptide was dissolved in 0.2 mls of degassed water, then 0.1 mls degassed Tris_HCL was added. This was followed by 0.2 mls of the stock CRM-Bromoacetate (1 mg total), finally 0.5 mls of the Borate buffer was added. This incubated 24 hours at 4 degrees C. on a nutator to provide mixing. Samples were desalted into PBS and 5 μl was run on a 10% Tris gel to confirm conjugation.

Injection of animals: Four (4) female Swiss webster mice were used in each group. Immunogen preparation was 25 μg Immunogen, 25 μg QS21 and 150 μl of 0.02% Tween 80/PBS per injection. Each mouse received 200 μl subcutaneously. Mice were injected at day 0, at 4 weeks from day 0, and at 8 weeks from day 0, with bleeds taken for titer at 5 weeks from day 0 and animals sacrificed and terminal bleed collected at 9 weeks from day 0 (see FIG. 13).

Titer Assay: Mouse serum was titered by enzyme-linked immunosorbent assay (ELISA). Plates were coated overnight at 2 g/mL with either Abeta 1-28 (Anaspec, San Jose, CA), or recombinant tau (Proteos, Kalamazoo, MI in phosphate-buffered saline (PBS), and then blocked 1 hour with 1% bovine serum albumin (BSA) in PBS. Normal mouse serum was used as a negative control while known positive anti-serum from previous mouse studies was used as a positive control at the same dilutions as test serum. Bleeds were diluted in PBS/0.1% BSA/0.1% Tween 20 (PBS/BSA/T) starting at 1/100 and serially diluted 1:2 down the plate. Plates were washed with TBS/Tween 20 and goat anti-mouse immunoglobulin G (IgG) (heavy+light chains) horseradish peroxidase (HRP) (ThermoFisher) 1/5000 was added and incubated 1 hour at room temperature. Plates were washed in TBS/Tween 20, and antibody binding was detected with o-phenylenediamine dihydrochloride (OPD) substrate (Thermo Fisher Scientific, Waltham, MA) following manufacturer's instructions. Plates were read at 490 nM on a Molecular Devices Spectromax. Titer was defined as the dilution giving 4× background (defined in graphs and tables); extrapolation was used if it fell in between dilutions.

MTBR Binding

Certain antibodies that bind to MTBR can bind to more than one MTBR region due to the homology of the various MTBR regions. Antiserum is titered on four MTBR regions using peptides of MTBR 1-4 purchased from Anaspec (San Jose, CA)

```
MTBR peptide 1
                                  (SEQ ID NO: 1058)
QTAPVPMPDLKNVKSKIGSTENLKHQPGGGK MTBR peptide 2
                                  (SEQ ID NO: 1059)
VQIINKKLDLSNVQSKCGSKDNIKHVPGGGS MTBR peptide 3
                                  (SEQ ID NO: 1060)
VQIVYKPVDLSKVTSKCGSLGNIHHKPGGGQ MTBR peptide 4
                                  (SEQ ID NO: 1061)
VEVKSEKLDFKDRVQSKIGSLDNITHVPGGGN
```

Mouse serum is titered by enzyme-linked immunosorbent assay (ELISA). Plates are coated overnight at 2 g/mL with each the various MTBR peptides in phosphate-buffered saline (PBS) and then blocked 1 hour with 1% bovine serum albumin (BSA) in PBS. Normal mouse serum is used as a negative control. Bleeds are diluted in PBS/0.1% BSA/0.1% Tween 20 (PBS/BSA/T) starting at 1/100 and serially diluted 1:2 down the plate. Plates are washed with TBS/Tween 20 and goat anti-mouse immunoglobulin G (IgG) (heavy+light chains) horseradish peroxidase (HRP) (ThermoFisher) 1/5000 is added and incubated 1 hour at room temperature. Plates are washed in TBS/Tween 20, and antibody binding is detected with o-phenylenediamine dihydrochloride (OPD) substrate (Thermo Fisher Scientific, Waltham, MA) following manufacturer's instructions. Plates are read at 490 nM on a Molecular Devices Spectromax. Titer is defined as the dilution giving 4× background (defined in graphs and tables); extrapolation is used if it falls in between dilutions.

Blocking of Tau Binding to Heparin

As a potential surrogate marker for the ability of the serum to block uptake of tau into cells an ELISA measuring the blocking of tau binding to Heparin plates was developed. Recombinant tau was biotinylated in-house. Heparin coated plates (Bioworld, Dublin, OH) were blocked with 2% BSA/PBS for 1 hour. In a separate deep well polypropylene 96 well plate (ThermoFisher) Serum was diluted from 1/25-1/3200 in 2% BSA/PBS, 60 μl total, to this 60 μl 200 ng/ml biotinylated tau in 2% BSA/PBS was added for a final concentration of serum 1/50-1/6400 and tau at 100 ng/ml. The mixture of serum and tau incubated for 2 hours then 100 l/well was transferred to the blocked heparin plates and incubated 1 hour. Plates were washed in 0.1% Tween 20/TBS and goat anti-mouse immunoglobulin G (IgG) (heavy+light chains) horseradish peroxidase (HRP) (ThermoFisher) 1/5000 was added and incubated 1 hour at room temperature. Plates were washed in TBS/Tween 20 and 100 μl ThermoFisher TIB added and incubated 8 minutes stopped H2SO4 and read at 450.

IHC Binding of Serum

Autopsy blocks of fresh frozen human brain tissue were embedded in optimal cutting temperature compound (OCT compound) and cut using a cryostat to generate 10 m sections. The sections were placed into a solution of glucose oxidase and beta D-glucose, in the presence of sodium azide, to block endogenous peroxidase. Once tissue sections were prepared, the staining with the specified mouse immune sera was carried out at 1:500 in 5% goat serum with 0.25% triton for 1 hour at RT. To image the binding to plagues and tangles, Biotin-SP-Conjugated Goat anti mouse IgG from Jackson (Lot #115-065-166) at 1:200 dilution were incubated with the sections. DAKO DAB Detection Kit as per the manufacturer's instructions. The staining was processed using an automated Leica Bond Stainer. The results indicate that sera from Guinea pigs immunized with a vaccine as disclosed herein comprises antibodies specific to Abeta and tau in human brain tissue of Alzheimer's patients Serum Blocking of Abeta Binding to Neurons E18 primary rat hippocampal neurons are cultured as described previously (Zago, et al. "Neutralization of Soluble, Synaptotoxic Amyloid β Species by Antibodies Is Epitope Specific," *J Neurosci.* 2012 Feb. 22; 32(8): 2696-2702). Soluble Aβ aggregate is pre-incubated with or without vaccine serum on culture DIV14-21 to block soluble Aβ aggregate from neuritic binding. Fresh unlabeled, biotinylated or (9:1) soluble Aβ is prepared one day prior and incubated overnight at 4° C. Each diluted serum sample and soluble Aβ solution is prepared at 2× the final concentration in one-half of final treatment volume using NeuroBasal-no phenol red (NB-NPR) medium. This is combined with one-half final volume of 2× soluble Aβ and with one-half final volume of 2× diluted vaccine serum to make up a 1× final concentration in total final treatment volume, which is mixed well and then pre-incubated for 30 minutes at 37° C. E18 neurons are rinsed with NB-NPR at 150 μL/well before adding binding treatment. Serum from vaccinated animals/Aβ treatment to is added to E18 neurons at 60 μL/well, and then incubated for 30 minutes at 37° C. under normal incubator conditions (5% CO2; 9% $O_2$). Cells are rinsed twice using 150 μL/well of NB-NPR, and then fixed in 4% paraformaldehyde in 1×DPBS for 20 minutes. Cells are permeabilized using 0.1 TX-100 for 5 minutes, and blocked using 10% normal goat serum (NGS) for 1 hour at room temperature (RT). Cells are incubated with MAP2 & NeuN primary antibodies in 100 μL/well, 1×DPBS containing 1% BSA+1% NGS overnight at 4° C. The next day, cells are rinsed twice in 150 μL/well 1×DPBS for 5 minutes each wash. Secondary antibodies are added for 1 hour at RT in 100 μL/well 1×DPBS+1% BSA+1% NGS. High-content imaging (HCl) analysis is performed to quantify soluble aggregate Aβ neuritic binding using Operetta HCl CLS instrument (Perkin Elmer; modified Neurite Outgrowth algorithm: 40× $H_2O$ objective; 40 fields per well; (n=3) per condition; data shown as mean (+/−) SD); MAP2 & NeuN (Abcam) neuronal markers is used to each trace neurite tree and count cell body number per optical field; Neuritic Aβ souble aggregate spots detected using streptavidin-488 or polyclonal Aβ antibody (Thermo; Millipore); and data reported as Aβ soluble aggregate spots/neuron (or as Integrated Intensity)). Approximately 80-150 neurons are observed per well for each condition tested.

Results

Data for Abeta and tau titers and staining is summarized in Table 10 and Table 11.

TABLE 10

| | Animal | Titer Abeta | Titer Tau | 50% blocking tau binding | IHC Abeta | IHC Tau |
|---|---|---|---|---|---|---|
| Dual Construct 2 | 2.1 | 35,000 | 35,000 | 1:300 | ++++ | + |
| | 2.2 | 21,000 | 75,000 | 1:225 | ++++ | + |
| | 2.3 | 12,000 | 21,000 | 1:550 | +++ | +++++ |
| | 2.4 | 20,000 | 7,000 | 1:200 | ++ | +++++ |
| Dual Construct 3 | 3.1 | 22,000 | 12,000 | 1:275 | +++ | ++++ |
| | 3.2 | 20,000 | 2,000 | 1:200 | ~ | ++++ |
| | 3.3 | 7,000 | 40,000 | 1:125 | ++++ | ++ |
| | 3.4 | 1,000 | 25,000 | 1:200 | + | ++++ |

TABLE 10-continued

| | Animal | Titer Abeta | Titer Tau | 50% blocking tau binding | IHC Abeta | IHC Tau |
|---|---|---|---|---|---|---|
| Dual Construct 8 | 8.1 | 15,000 | 100,000 | 1:275 | ++ (or +½) | ++++½ |
| | 8.2 | 7,000 | 6,800 | 1:675 | ++ (or +½) | +++ |
| | 8.3 | 60,000 | 10,000 | 1:200 | +++ | − |
| | 8.4 | 30,000 | 20,000 | 1:200 | ++++ | ++++ |
| Dual Construct 9 | 9.1 | 150,000 | 50,000 | 1:525 | + | ++++½ |
| | 9.2 | 30,000 | 21,000 | 1:325 | ++ | ++++ |
| | 9.3 | 13,000 | 30,000 | 1:325 | +++ | ++++ |
| | 9.4 | 72,000 | 30,000 | 1:625 | +++ | +++ |
| Dual Construct 11 | 11.1 | 30,000 | 6,000 | 1:375 | ++++ | ++½ |
| | 11.2 | 10,000 | 40,000 | 1:875 | ~ | ++++ |
| | 11.3 | 11,000 | 20,000 | 1:325 | ++++½ | ++ |
| | 11.4 | 10,000 | 10,000 | 1:275 | ++++ | + |

TABLE 11

| Dual Abeta/Tau Mouse Sera | A-beta | Tau Cell bodies | Neurites | Notes |
|---|---|---|---|---|
| 2.1 | ++++ | + | + | |
| 2.2 | ++++ | ++ | + | Presence of nuclear staining |
| 2.3 | +++ | +++++ | +++ | |
| 2.4 | ++ | +++++ | ++++ | |
| 3.1 | +++ | ++++ | +++++ | |
| 3.2 | − | ++++ | +++++ | |
| 3.3 | ++++ | ++ | +++ | Strong nuclear staining |
| 3.4 | + | ++++ | ++ | |
| 8.1 | ++ | ++++ | ++++ | |
| 8.2 | ++ | +++ | +++ | |
| 8.3 | +++ | − | − | |
| 8.4 | ++++ | ++++ | +++++ | |
| 9.1 | + | ++++ | ++++ | |
| 9.2 | ++ | ++++ | +++ | |
| 9.3 | +++ | ++++ | ++++ | |
| 9.4 | +++ | +++ | ++++ | |
| 11.1 | ++++ | ++ | +++ | |
| 11.2 | + | ++++ | + | |
| 11.3 | +++++ | ++ | − | |
| 11.4 | ++++ | + | − | Some nuclear staining |

Titers

Figure 13:
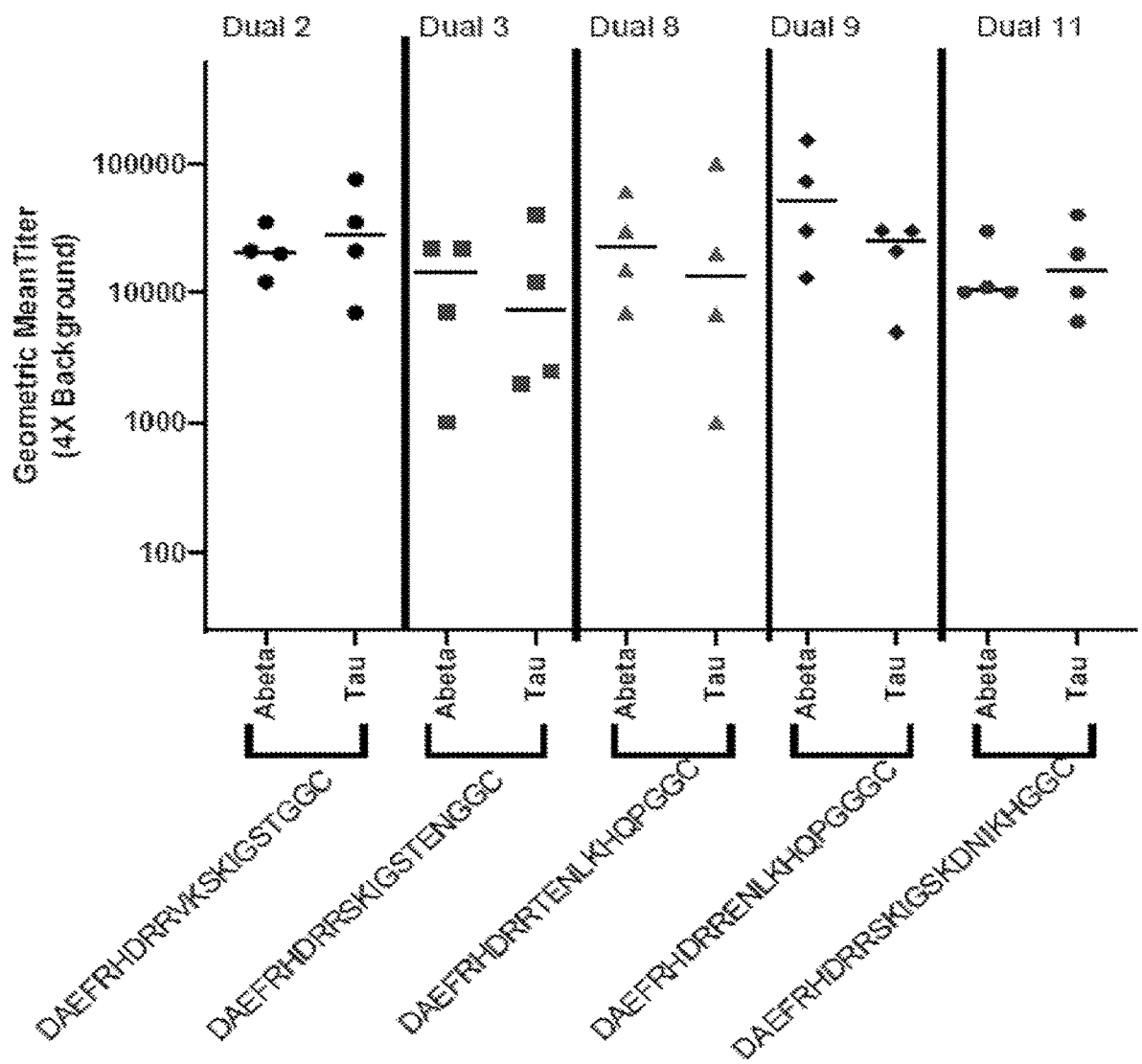
FIG. 13 shows animal titers to Aβ and tau 9 weeks post injection at day 0, at 4 weeks and at 8 weeks for the dual Abeta-tau constructs DAEFRHDRRVKSKIGSTGGC (SEQ ID NO:997); DAEFRHDRRSKIGSTENGGC (SEQ ID NO:998); DAEFRHDRRTENLKHQPGGC (SEQ ID NO:999); DAEFRHDRRENLKHQPGGGC (SEQ ID NO:1000); and DAEFRHDRRSKIGSKDNIKHGGC (SEQ ID NO:1001).

As seen in FIG. 13 and Tables 10-13, all groups most animals produced high and balanced Abeta and tau titers, though some had a less variable titer response.

TABLE 12

Titers for the dual Abeta/tau constructs.

| | Abeta | | | | tau | | | |
|---|---|---|---|---|---|---|---|---|
| | Mouse 1 | Mouse 2 | Mouse 3 | Mouse 4 | Mouse 1 | Mouse 2 | Mouse 3 | Mouse 4 |
| Dual Construct 2 | | | | | | | | |
| Bleed 1 | 30000 | 25000 | 25000 | 12000 | 150 | 5000 | 3000 | 4000 |
| Bleed 2 | 35000 | 21000 | 12000 | 20000 | 35000 | 75000 | 21000 | 7000 |
| Dual Construct 3 | | | | | | | | |
| Bleed 1 | 6400 | 800 | 15000 | 100 | 4000 | 6400 | 5000 | 2000 |
| Bleed 2 | 22000 | 22000 | 7000 | 1000 | 12000 | 2000 | 40000 | 2500 |
| Dual Construct 8 | | | | | | | | |
| Bleed 1 | 1500 | 2000 | 20000 | 18000 | 10000 | 25000 | 200 | 8000 |
| Bleed 2 | 15000 | 7000 | 60000 | 30000 | 100000 | 6800 | 1000 | 20000 |

TABLE 12-continued

Titers for the dual Abeta/tau constructs.

|  | Abeta | | | | tau | | | |
|---|---|---|---|---|---|---|---|---|
|  | Mouse 1 | Mouse 2 | Mouse 3 | Mouse 4 | Mouse 1 | Mouse 2 | Mouse 3 | Mouse 4 |
| Dual Construct 9 | | | | | | | | |
| Bleed 1 | 2000 | 12000 | 13000 | 6400 | 800 | 6000 | 7000 | 2000 |
| Bleed 2 | 150000 | 30000 | 13000 | 72000 | 5000 | 21000 | 30000 | 30000 |
| Dual Construct 11 | | | | | | | | |
| Bleed 1 | 6000 | 2000 | 5000 | 7000 | 6400 | 7000 | 2500 | 4000 |
|  | 30000 | 10000 | 11000 | 10000 | 6000 | 40000 | 20000 | 10000 |

TABLE 13

Remaining tau bound after serum incubation

DAEFRHDRRVKSKIGSTGGC
(SEQ ID NO: 997)

| dilution | Mouse 1 | Mouse 2 | Mouse 3 | Mouse 4 |
|---|---|---|---|---|
| 50 | 19.57 | 29.12 | 16.66 | 12.70 |
| 100 | 28.93 | 38.25 | 26.51 | 25.21 |
| 200 | 41.16 | 53.48 | 29.64 | 46.53 |
| 400 | 59.88 | 89.43 | 43.15 | 81.31 |
| 800 | 95.14 | 139.21 | 65.00 | 134.97 |

DAEFRHDRRENLKHQPGGGC
(SEQ ID NO: 1000)

| dilution | Mouse 1 | Mouse 2 | Mouse 3 | Mouse 4 |
|---|---|---|---|---|
| 50 | 16.44 | 21.90 | 24.26 | 15.35 |
| 100 | 22.07 | 47.55 | 39.93 | 19.39 |
| 200 | 37.10 | 44.06 | 48.36 | 43.65 |
| 400 | 58.32 | 86.61 | 86.41 | 51.98 |
| 800 | 93.54 | 98.76 | 115.50 | 86.00 |

DAEFRHDRRSKIGSTENGGC
(SEQ ID NO: 998)

| dilution | Mouse 1 | Mouse 2 | Mouse 3 | Mouse 4 |
|---|---|---|---|---|
| 50 | 16.84 | 27.29 | 28.01 | 28.56 |
| 100 | 25.18 | 39.02 | 53.18 | 42.60 |
| 200 | 55.66 | 73.61 | 93.32 | 75.38 |
| 400 | 92.87 | 120.00 | 131.15 | 125.27 |
| 800 | 110.16 | 132.77 | 130.90 | 135.93 |

DAEFRHDRRSKIGSKDNIKHGGC
(SEQ ID NO: 1001)

| dilution | Mouse 1 | Mouse 2 | Mouse 3 | Mouse 4 |
|---|---|---|---|---|
| 50 | 15.25 | 13.15 | 14.73 | 17.81 |
| 100 | 19.45 | 11.20 | 26.64 | 37.79 |
| 200 | 37.65 | 14.59 | 56.17 | 54.57 |
| 400 | 74.17 | 39.69 | 78.69 | 91.10 |
| 800 | 90.35 | 62.16 | 96.30 | 109.00 |

DAEFRHDRRTENLKHQPGGC
(SEQ ID NO: 999)

| dilution | Mouse 1 | Mouse 2 | Mouse 3 | Mouse 4 |
|---|---|---|---|---|
| 50 | 20.01 | 12.36 | 35.04 | 42.63 |
| 100 | 37.62 | 28.44 | 44.45 | 47.62 |
| 200 | 54.86 | 47.97 | 66.72 | 61.84 |
| 400 | 114.93 | 48.51 | 91.94 | 87.67 |
| 800 | 110.60 | 81.25 | 100.01 | 97.15 |

TABLE 13-continued

Remaining tau bound after serum incubation

Negative Control

| dilution | Mouse 1 | Mouse 2 | Mouse 3 | Mouse 4 |
|---|---|---|---|---|
| 50 | 83.35 | 71.98 | 84.30 | 83.96 |
| 100 | 114.78 | 94.03 | 103.43 | 98.98 |
| 200 | 104.03 | 100.60 | 97.80 | 96.83 |
| 400 | 86.73 | 111.16 | 95.31 | 91.72 |
| 800 | 96.20 | 110.05 | 99.38 | 94.45 |

Blocking of Tau Binding to Heparin

All constructs showed the ability to block the binding of tau to heparin, in particular, construct DAEFRHDRRVKSKIGSTGGC (SEQ ID NO:997) and construct DAEFRHDRRENLKHQPGGGC (SEQ ID NO:1000) showing the most robust blocking. See FIG. 15, Table 10 and Table 11.

IHC on Alzheimer Brain

Figure 16B:
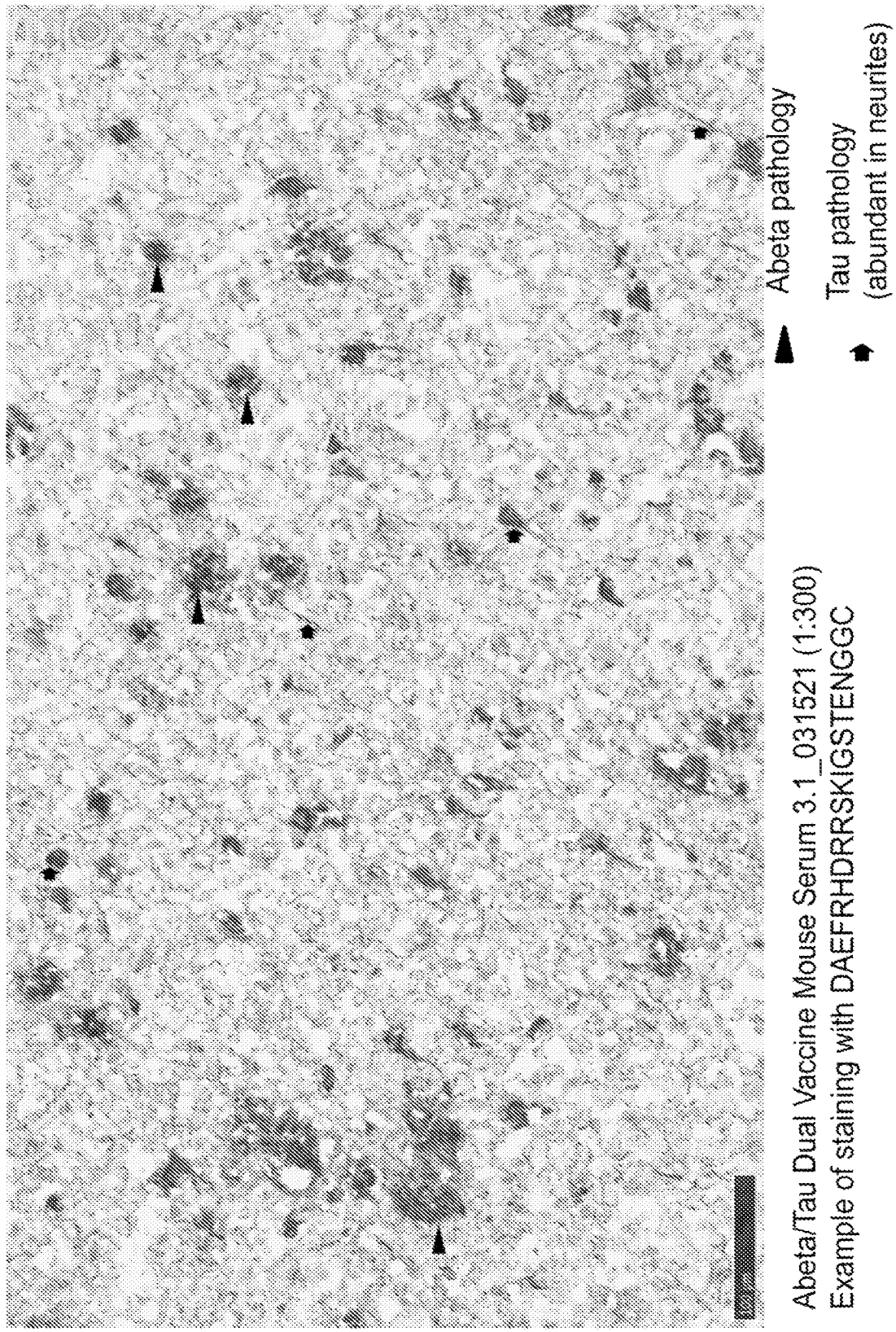
FIG. 16B shows Abeta/Tau Dual Vaccine Mouse Serum 3.1_031521 (1:300) Example of staining with DAEFRHDRRSKIGSTENGGC (SEQ ID NO:998).
Figure 16C:
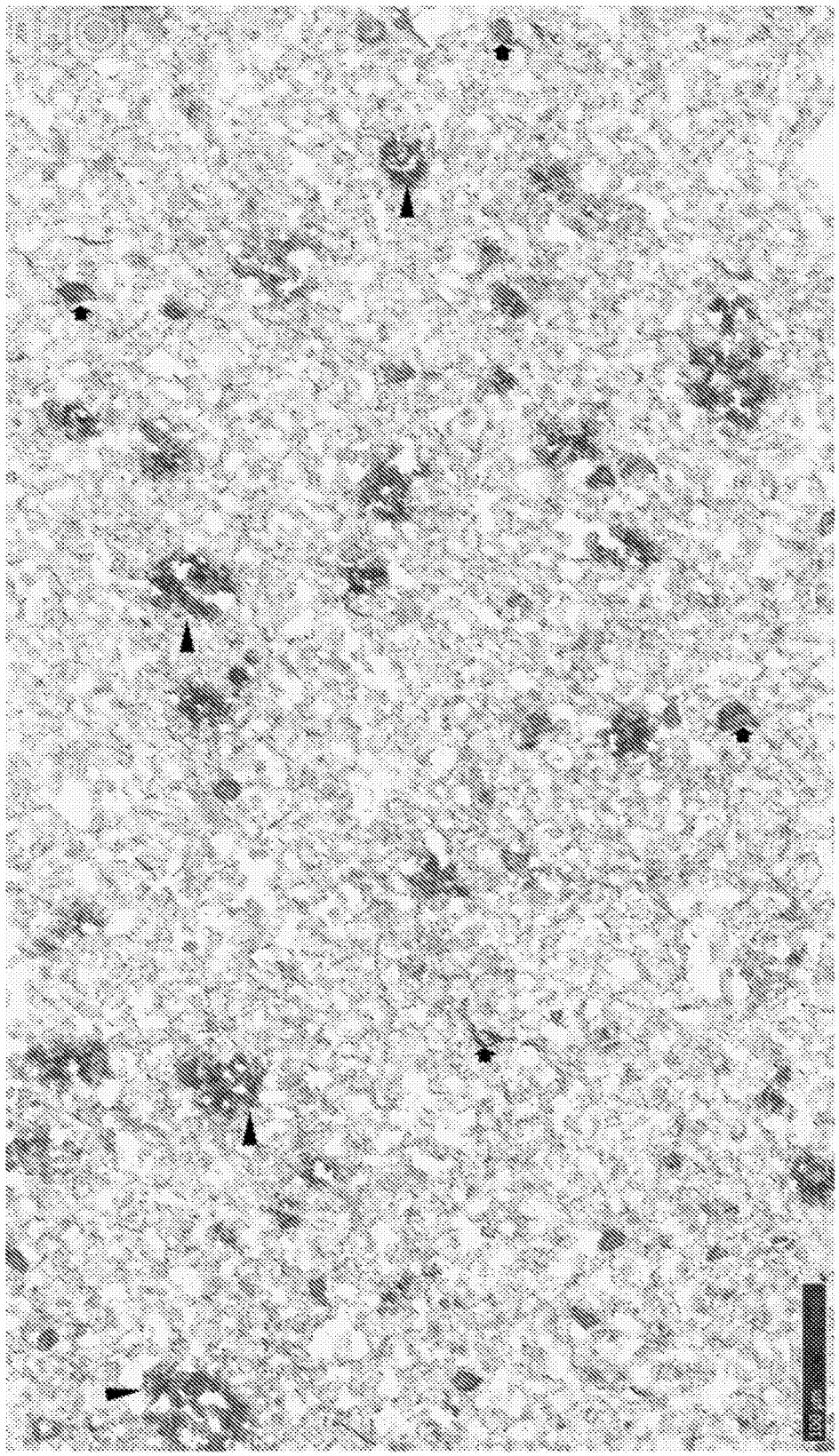
FIG. 16C shows Abeta/Tau Dual Vaccine Mouse Serum 8.4_031521 (1:300) Example of staining with DAEFRHDRRTENLKHQPGGC (SEQ ID NO:999).

Most animals had staining of pathological Abeta and tau, see FIG. 16.

Example 11: Immunogens

Immunogens were selected for evaluation in vaccine peptide constructs. Constructs comprise Aβ immunogens and tau immunogens. Some immunogens comprise a tau peptide comprising 3-10 amino acids from tau. Other immunogens comprise an engineered tau immunogen.

Engineered Tau Immunogens

Certain immunogenic peptides were designed and selected to (i) raise antibodies that bind within the within microtubule binding repeats (MTBRs) of human Tau protein, (ii) be less likely to generate an unwanted T cell-mediated autoimmune response, and (iii) be less likely to raise antibodies that would cross-react with other human proteins.

First, sequence analysis and 3D modeling of Tau MTBRs was conducted to identify amino acid residues that may be important for raising antibodies that bind MTBR. The results of these analyses were used to design synthetic Tau immunogenic peptides with conserved residues and shuffled interspersed residues. Resulting engineered synthetic peptides are listed in Table 14.

TABLE 14

Engineered Tau immunogenic peptides

| Engineered tau immunogenic peptides sequence | SEQ ID NO: |
|---|---|
| SKIGSTENLKH | 978 |
| SKIGSTENIKH | 979 |
| SKIGSKDNLKH | 980 |
| SKIGSKENIKH | 981 |
| SKIGSLENLKH | 982 |
| SKIGSLENIKH | 983 |
| SKIGSTDNLKH | 984 |
| SKIGSTDNIKH | 985 |
| SKIGSKDNIKH | 986 |
| SKIGSLDNLKH | 987 |
| SKIGSLDNIKH | 988 |
| SKIGSTGNLKH | 989 |
| SKIGSTGNIKH | 990 |
| SKIGSKGNLKH | 991 |
| SKIGSKGNIKH | 992 |
| SKIGSLGNLKH | 993 |
| SKIGSLGNIKH | 994 |

Next, to assess the potential of an unwanted T cell-mediated autoimmune response, the engineered peptides were subjected to in silico analysis to predict MHC II binding using the IEDB (Immune Epitope Database) from National Institute of Allergy and Infectious Diseases/La Jolla Immunology Institute. MHC class II binding is considered a good indicator of a sequence containing a T-cell epitope. A panel of alleles were used for MHC II binding prediction. Engineered peptides with a predicted half maximal inhibitory concentration (IC50) above a specified cutoff were considered to have a low probability of MHC II binding and were selected for further analysis.

Finally, the engineered peptides with low predicted MHC II binding were evaluated to predict if the anti-Tau MTBR antibodies that would be raised by the peptides could have unwanted cross-reactivity with other human proteins. Sequences of the engineered peptides were subjected to bioinformatic analysis against a non-redundant human proteome database to determine homology with human proteins. Engineered peptide sequences with low homology to secreted or cell-surface proteins were selected as top candidates to be used as antigens. Top candidate engineered Tau immunogenic peptides are listed in Table 15.

TABLE 15

Top candidate engineered Tau immunogenic peptides.

| Engineered tau immunogenic peptides sequence | SEQ ID NO: |
|---|---|
| SKIGSTDNIKH | 985 |
| SKIGSKDNIKH | 986 |
| SKIGSLDNIKH | 988 |

Figure 15A:
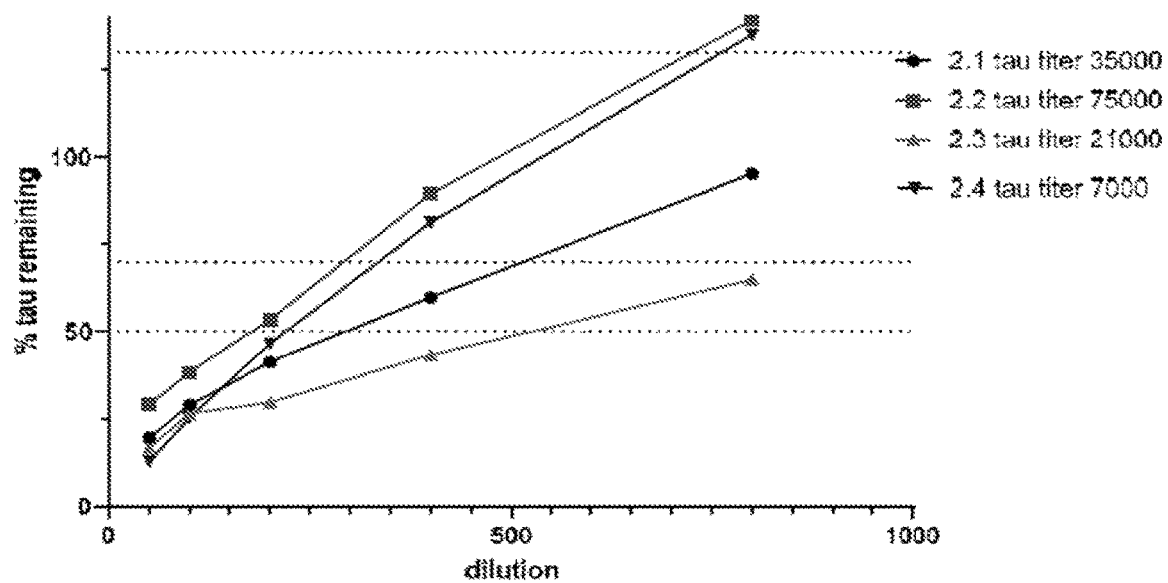
FIG. 15A shows competition of tau by sera from DAEFRHDRRVKSKIGSTGGC construct (SEQ ID NO:997).
Figure 15B:
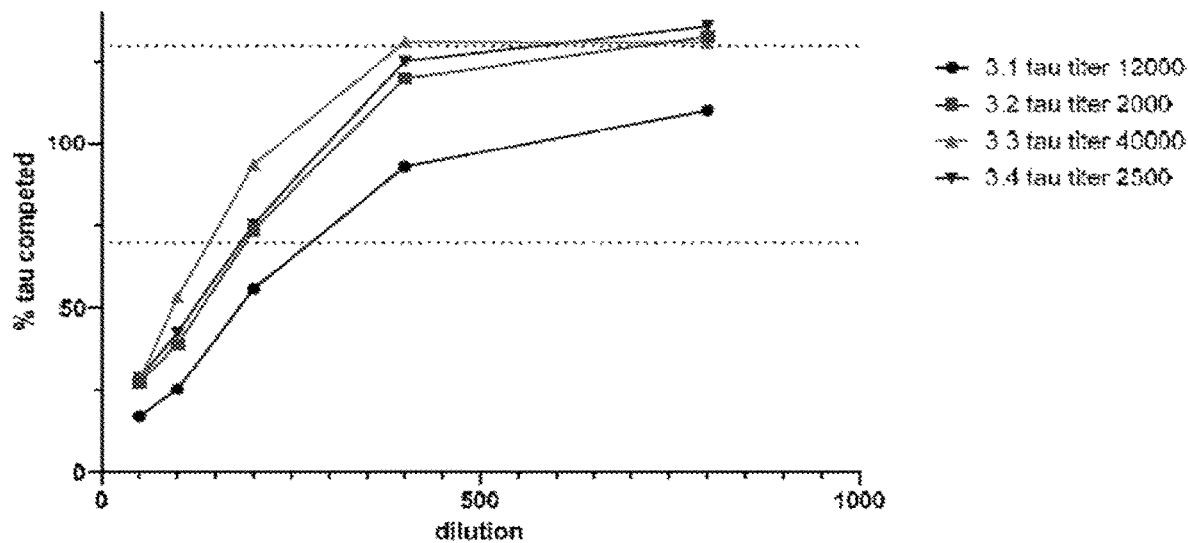
FIG. 15B shows competition of tau by sera from DAEFRHDRRSKIGSTENGGC construct (SEQ ID NO:998).
Figure 15C:
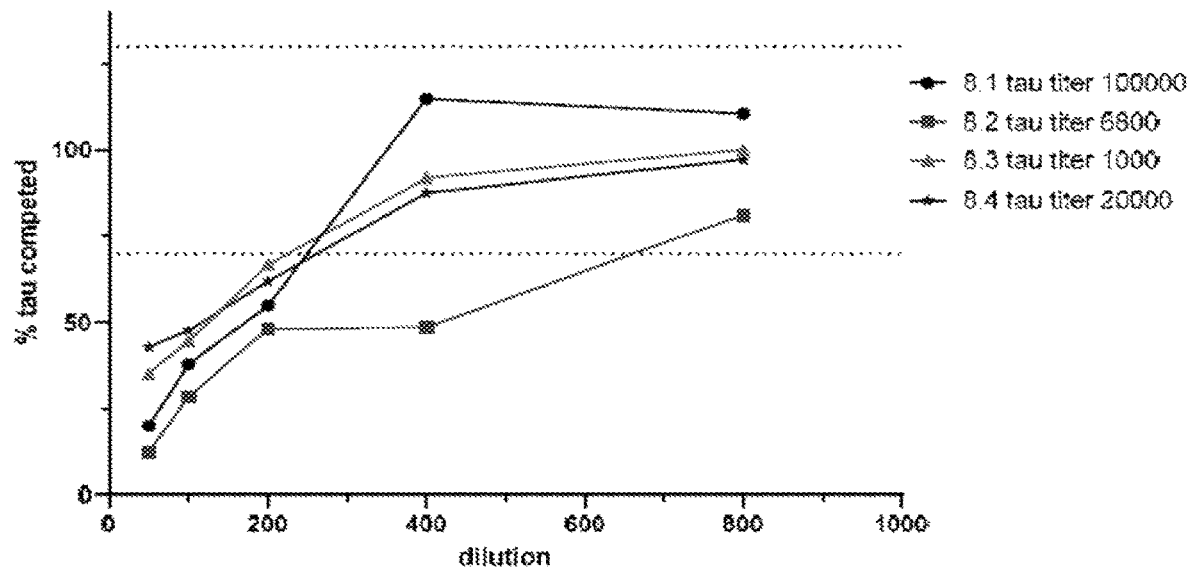
FIG. 15C shows competition of tau by sera from DAEFRHDRRTENLKHQPGGC construct (SEQ ID NO:999).
Figure 15D:
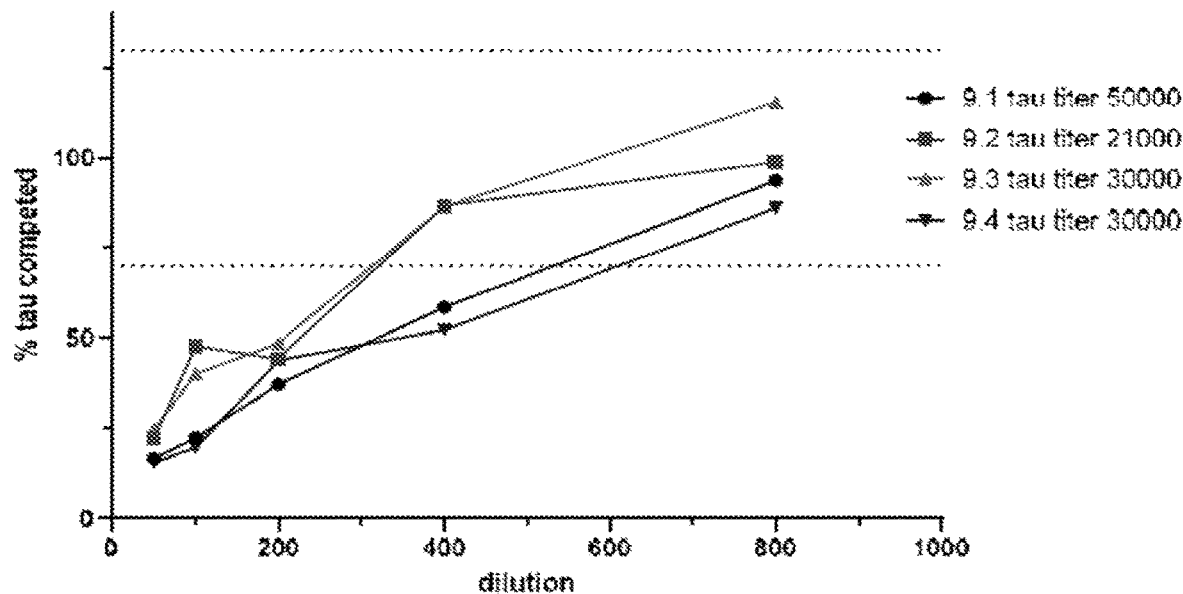
FIG. 15D shows competition of tau by sera from DAEFRHDRRENLKHQPGGGC construct (SEQ ID NO:1000).
Figure 15E:
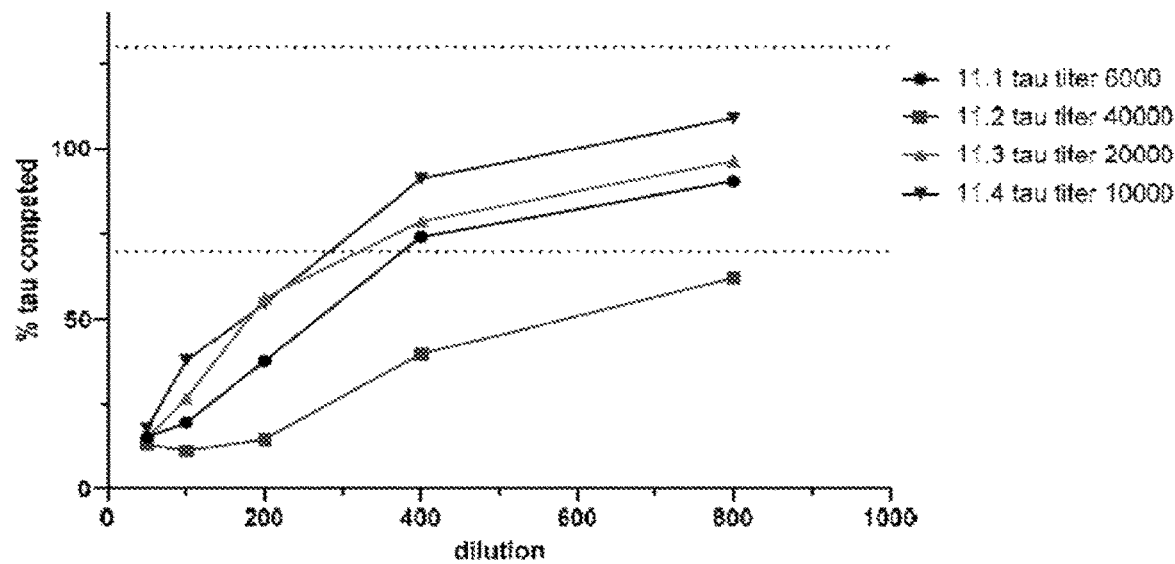
FIG. 15E shows competition of tau by sera from DAEFRHDRRSKIGSKDNIKHGGC construct (SEQ ID NO:1001).
Figure 15F:
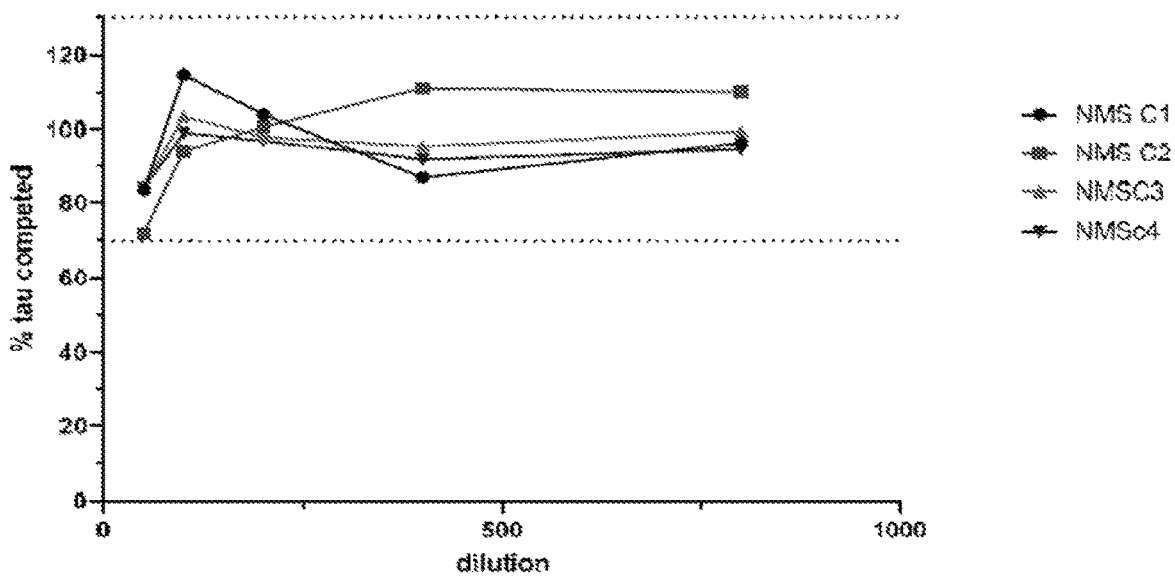
FIG. 15F shows competition of tau by sera from controls.
Figure 15G:
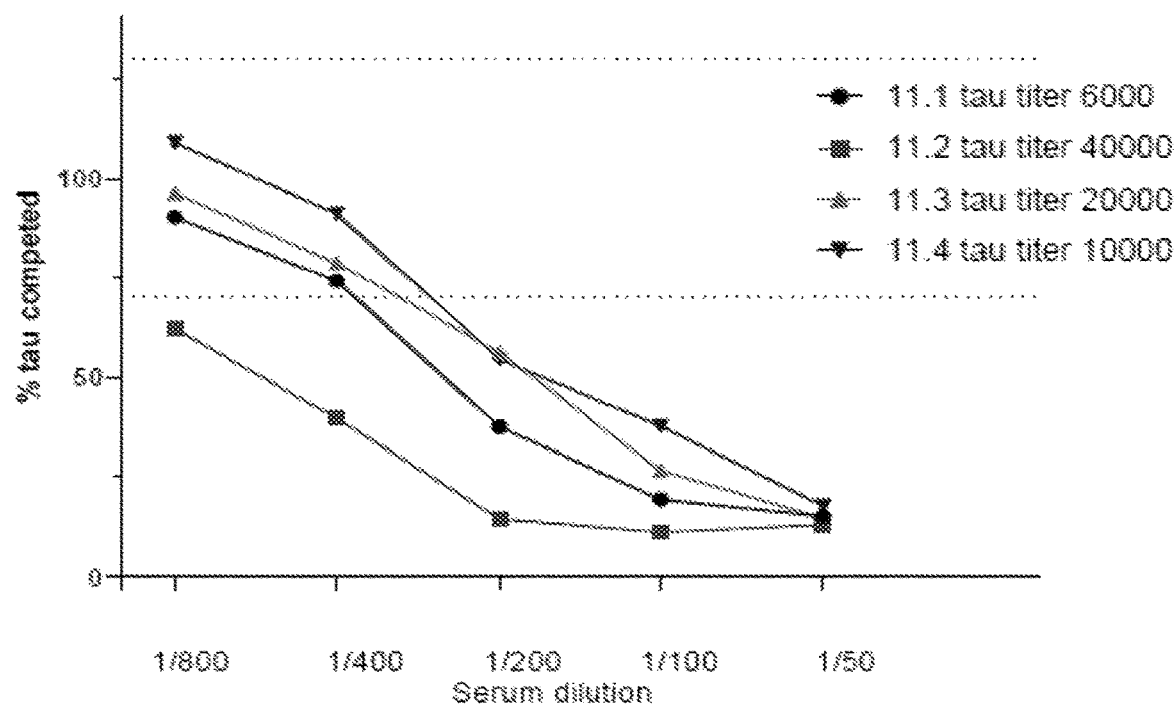
FIG. 15G shows competition of tau by sera from DAEFRHDRRSKIGSKDNIKHGGC construct (SEQ ID NO:1001).

The dual Aβ-tau constructs comprising an engineered tau immunogen (e.g., Dual #11) demonstrated results that were comparable, and in some cases, better than other tau immunogens despite including a non-native tau sequence. FIG. 13 shows high titers for both Abeta and tau antigens, including an engineered tau sequence. FIG. 14 shows blocking of tau binding to heparin. FIG. 15G shows resulting tau antibody binding to MTBR region peptides. FIG. 16 E shows staining/binding to Aβ and tau peptides in brain tissue from human Alzheimer's patients. This demonstrates that engineered immunogens are useful in vaccine constructs

CONCLUSION

Dual immunogen Aβ-tau vaccine constructs were developed and it was shown that these constructs raised balanced titers to Aβ and tau in mice, guinea-pigs, and cynomolgus monkeys. The antibodies were immunoreactive with both Aβ plaques and neurofibrillary tau tangles in human AD brain sections and blocked the binding of soluble Aβ aggregates (oligomers) to neurons without eliciting T-cell responses for Aβ or tau. These results support the development of a single-agent, dual-immunogen vaccine with the ability to target the pathogenic forms of Aβ and tau. These results support the development of a dual Aβ-tau vaccine with the ability to target pathogenic Aβ and tau for the prevention and/or treatment of AD.

Although various specific embodiments of the present invention have been described herein, it is to be understood that the invention is not limited to those precise embodiments and that various changes or modifications can be affected therein by one skilled in the art without departing from the scope and spirit of the invention.

In each of the embodiments of the peptide described herein, the peptide may comprise, consist, or consist essentially of the recited sequences. Thus, incorporated in this disclosure (see Table 16) are the following sequences that can be part of the compositions comprising an amyloid-beta (Aβ) peptide and a tau peptide as disclosed herein.

TABLE 16

SEQUENCES

SEQ ID NO: 01 - Abeta 1-42
DAEFRHDSGYEVHHQKLVFFAEDVGSNKGAIIGLMVGGVVIA

SEQ ID NO: 02 - TAU (UNIPROTKB - P10636
(Homo sapiens)

>P10636-8 (Isoform Tau-F)
```
           10         20         30         40
MAEPROEFEV MEDHAGTYGL GDRKDQGGYT MHQDQEGDTD 50         60         70         80
AGLKESPLQT PTEDGSEEPG SETSDAKSTP TAEDVTAPLV 90        100        110        120
DEGAPGKQAA AQPHTEIPEG TTAEEAGIGD TPSLEDEAAG 130        140        150        160
```

TABLE 16-continued

SEQUENCES

```
              HVTQARMVSK SKDGTGSDDK KAKGADGKTK IATPRGAAPP
         170        180        190        200
       GQKGQANATR IPAKTPPAPK TPPSSGEPPK SGDRSGYSSP
         210        220        230        240
       GSPGTPGSRS RTPSLPTPPT REPKKVAVVR TPPKSPSSAK
         250        260        270        280
       SRLQTAPVPM PDLKNVKSKI GSTENLKHQP GGGKVQIINK
         290        300        310        320
       KLDLSNVQSK CGSKDNIKHV PGGGSVQIVY KPVDLSKVTS
         330        340        350        360
       KCGSLGNIHH KPGGGQVEVK SEKLDFKDRV QSKIGSLDNI
         370        380        390        400
       THVPGGGNKK IETHKLTFRE NAKAKTDHGA EIVYKSPVVS
         410        420        430        440
       GDTSPRHLSN VSSTGSIDMV DSPQLATLAD EVSASLAKQG L
```

A-beta immunogens:

| Sequence | ID |
|---|---|
| DAEFRHDSGY | (SEQ ID NO: 03) |
| DAEFRHDSG | (SEQ ID NO: 04) |
| DAEFRHDS | (SEQ ID NO: 05) |
| DAEFRHD | (SEQ ID NO: 06) |
| DAEFRH | (SEQ ID NO: 07) |
| DAEFR | (SEQ ID NO: 08) |
| DAEF | (SEQ ID NO: 09) |
| DAE | (SEQ ID NO: 10) |
| AEFRHDSGY | (SEQ ID NO: 11) |
| AEFRHDSG | (SEQ ID NO: 12) |
| AEFRHDS | (SEQ ID NO: 13) |
| AEFRHD | (SEQ ID NO: 14) |
| AEFRH | (SEQ ID NO: 15) |
| AEFR | (SEQ ID NO: 16) |
| AEF | (SEQ ID NO: 17) |
| EFRHDSGY | (SEQ ID NO: 18) |
| EFRHDSG | (SEQ ID NO: 19) |
| EFRHDS | (SEQ ID NO: 20) |
| EFRHD | (SEQ ID NO: 21) |
| EFRH | (SEQ ID NO: 22) |
| EFR | (SEQ ID NO: 23) |
| FRHDSGY | (SEQ ID NO: 24) |
| FRHDSG | (SEQ ID NO: 25) |
| FRHDS | (SEQ ID NO: 26) |
| FRHD | (SEQ ID NO: 27) |
| FRH | (SEQ ID NO: 28) |
| RHDSGY | (SEQ ID NO: 29) |
| RHDSG | (SEQ ID NO: 30) |
| RHDS | (SEQ ID NO: 31) |
| RHD | (SEQ ID NO: 32) |
| HDSGY | (SEQ ID NO: 33) |
| HDSG | (SEQ ID NO: 34) |
| HDS | (SEQ ID NO: 35) |
| DSGY | (SEQ ID NO: 36) |
| DSG | (SEQ ID NO: 37) |
| SGY | (SEQ ID NO: 38) |
| VHHQKLVFFA | (SEQ ID NO: 1002) |
| VHHQKLVFF | (SEQ ID NO: 1003) |
| VHHQKLVF | (SEQ ID NO: 1004) |
| VHHQKLV | (SEQ ID NO: 1005) |
| VHHQKL | (SEQ ID NO: 1006) |
| HHQKLVFFAE | (SEQ ID NO: 1007) |
| HHQKLVFFA | (SEQ ID NO: 1008) |
| HHQKLVFF | (SEQ ID NO: 1009) |
| HHQKLVF | (SEQ ID NO: 1010) |
| HHQKLV | (SEQ ID NO: 1011) |
| HHQKL | (SEQ ID NO: 1012) |
| HQKLVFFAED | (SEQ ID NO: 1013) |
| HQKLVFFAE | (SEQ ID NO: 1014) |
| HQKLVFFA | (SEQ ID NO: 1015) |
| HQKLVFF | (SEQ ID NO: 1016) |
| HQKLVF | (SEQ ID NO: 1017) |
| HQKLV | (SEQ ID NO: 1018) |
| HQKL | (SEQ ID NO: 1019) |
| QKLVFFAEDV | (SEQ ID NO: 1020) |
| QKLVFFAED | (SEQ ID NO: 1021) |
| QKLVFFAE | (SEQ ID NO: 1022) |
| QKLVFFA | (SEQ ID NO: 1023) |
| QKLVFF | (SEQ ID NO: 1024) |
| QKLVF | (SEQ ID NO: 1025) |
| QKLV | (SEQ ID NO: 1026) |
| QKL | (SEQ ID NO: 1027) |
| KLVFFAEDVG | (SEQ ID NO: 1028) |
| KLVFFAEDV | (SEQ ID NO: 1029) |
| KLVFFAED | (SEQ ID NO: 1030) |
| KLVFFAE | (SEQ ID NO: 1031) |

TABLE 16-continued

SEQUENCES

| Sequence | ID |
|---|---|
| KLVFFA | (SEQ ID NO: 1032) |
| KLVFF | (SEQ ID NO: 1033) |
| KLVE | (SEQ ID NO: 1034) |
| KLV | (SEQ ID NO: 1035) |
| LVFFAEDVG | (SEQ ID NO: 1036) |
| LVFFAEDV | (SEQ ID NO: 1037) |
| LVFFAED | (SEQ ID NO: 1038) |
| LVFFAE | (SEQ ID NO: 1039) |
| LVFFA | (SEQ ID NO: 1040) |
| LVFF | (SEQ ID NO: 1041) |
| LVF | (SEQ ID NO: 1042) |
| VFFAEDVG | (SEQ ID NO: 1043) |
| VFFAEDV | (SEQ ID NO: 1044) |
| VFFAED | (SEQ ID NO: 1045) |
| VFFAE | (SEQ ID NO: 1046) |
| VFFA | (SEQ ID NO: 1047) |
| VFF | (SEQ ID NO: 1048) |
| FFAEDVG | (SEQ ID NO: 1049) |
| FFAEDV | (SEQ ID NO: 1050) |
| FFAED | (SEQ ID NO: 1051) |
| FFAE | (SEQ ID NO: 1052) |
| FFA | (SEQ ID NO: 1053) |
| FAEDVG | (SEQ ID NO: 1054) |
| FAEDV | (SEQ ID NO: 1055) |
| FAED | (SEQ ID NO: 1056) |
| FAE | (SEQ ID NO: 1057) |
| Tau immunogens: | |
| QIVYKPV | (SEQ ID NO: 39) |
| QIVYKP | (SEQ ID NO: 40) |
| QIVYKSV | (SEQ ID NO: 41) |
| EIVYKSV | (SEQ ID NO: 42) |
| QIVYKS | (SEQ ID NO: 83) |
| EIVYKSP | (SEQ ID NO: 43) |
| EIVYKS | (SEQ ID NO: 84) |
| EIVYKPV | (SEQ ID NO: 44) |
| EIVYKP | (SEQ ID NO: 85) |
| IVYKSPV | (SEQ ID NO: 45) |
| IVYK | (SEQ ID NO: 46) |
| CNIKHVPG | (SEQ ID NO: 86) |
| CNIKHVP | (SEQ ID NO: 47) |
| NIKHVP | (SEQ ID NO: 48) |
| HVPGGG | (SEQ ID NO: 49) |
| HVPGG | (SEQ ID NO: 50) |
| HKPGGG | (SEQ ID NO: 51) |
| HKPGG | (SEQ ID NO: 52) |
| KHVPGGG | (SEQ ID NO: 53) |
| KHVPGG | (SEQ ID NO: 54) |
| HQPGGG | (SEQ ID NO: 55) |
| HQPGG | (SEQ ID NO: 56) |
| VQIINK | (SEQ ID NO: 146) |
| VQIINKK | (SEQ ID NO: 147) |
| VQIINKKL | (SEQ ID NO: 148) |
| QIINK | (SEQ ID NO: 149) |
| QIINKK | (SEQ ID NO: 150) |
| QIINKKL | (SEQ ID NO: 151) |
| EAAGHVTQC | (SEQ ID NO: 152) |
| EAAGHVTQAR | (SEQ ID NO: 153) |
| AAGHVTQAC | (SEQ ID NO: 154) |
| AGHVTQARC | (SEQ ID NO: 155) |
| AGHVTQAR | (SEQ ID NO: 156) |
| GYTMHQD | (SEQ ID NO: 157) |
| QGGYTMHC | (SEQ ID NO: 158) |
| QGGYTMHQD | (SEQ ID NO: 159) |
| GGYTMHQC | (SEQ ID NO: 160) |
| VPGGGSVQIV | (SEQ ID NO: 161) |
| PGGGSVQIV | (SEQ ID NO: 162) |
| GGGSVQIV | (SEQ ID NO: 163) |
| GGSVQIV | (SEQ ID NO: 164) |
| GSVQIV | (SEQ ID NO: 165) |
| SVQIV | (SEQ ID NO: 166) |
| VQIV | (SEQ ID NO: 167) |
| QIV | (SEQ ID NO: 168) |
| PGGGSVQIVY | (SEQ ID NO: 169) |
| GGGSVQIVY | (SEQ ID NO: 170) |
| GGSVQIVY | (SEQ ID NO: 171) |
| GSVQIVY | (SEQ ID NO: 172) |
| SVQIVY | (SEQ ID NO: 173) |
| VQIVY | (SEQ ID NO: 174) |

TABLE 16-continued

SEQUENCES

| Sequence | SEQ ID NO |
|---|---|
| QIVY | (SEQ ID NO: 175) |
| IVY | (SEQ ID NO: 176) |
| GGGSVQIVYK | (SEQ ID NO: 177) |
| GGSVQIVYK | (SEQ ID NO: 178) |
| GSVQIVYK | (SEQ ID NO: 179) |
| SVQIVYK | (SEQ ID NO: 180) |
| VQIVYK | (SEQ ID NO: 181) |
| QIVYK | (SEQ ID NO: 182) |
| VYK | (SEQ ID NO: 183) |
| GGSVQIVYKP | (SEQ ID NO: 184) |
| GSVQIVYKP | (SEQ ID NO: 185) |
| SVQIVYKP | (SEQ ID NO: 186) |
| VQIVYKP | (SEQ ID NO: 187) |
| IVYKP | (SEQ ID NO: 188) |
| VYKP | (SEQ ID NO: 189) |
| YKP | (SEQ ID NO: 190) |
| GSVQIVYKPV | (SEQ ID NO: 191) |
| SVQIVYKPV | (SEQ ID NO: 192) |
| VQIVYKPV | (SEQ ID NO: 193) |
| IVYKPV | (SEQ ID NO: 194) |
| VYKPV | (SEQ ID NO: 195) |
| YKPV | (SEQ ID NO: 196) |
| KPV | (SEQ ID NO: 197) |
| SVQIVYKPVD | (SEQ ID NO: 198) |
| VQIVYKPVD | (SEQ ID NO: 199) |
| QIVYKPVD | (SEQ ID NO: 200) |
| IVYKPVD | (SEQ ID NO: 201) |
| VYKPVD | (SEQ ID NO: 203) |
| YKPVD | (SEQ ID NO: 204) |
| KPVD | (SEQ ID NO: 205) |
| PVD | (SEQ ID NO: 206) |
| VQIVYKPVDL | (SEQ ID NO: 207) |
| QIVYKPVDL | (SEQ ID NO: 208) |
| IVYKPVDL | (SEQ ID NO: 209) |
| VYKPVDL | (SEQ ID NO: 210) |
| YKPVDL | (SEQ ID NO: 211) |
| KPVDL | (SEQ ID NO: 212) |
| PVDL | (SEQ ID NO: 213) |
| VDL | (SEQ ID NO: 214) |
| QIVYKPVDLS | (SEQ ID NO: 215) |
| IVYKPVDLS | (SEQ ID NO: 216) |
| VYKPVDLS | (SEQ ID NO: 217) |
| YKPVDLS | (SEQ ID NO: 218) |
| KPVDLS | (SEQ ID NO: 219) |
| PVDLS | (SEQ ID NO: 220) |
| VDLS | (SEQ ID NO: 221) |
| DLS | (SEQ ID NO: 222) |
| IVYKPVDLSK | (SEQ ID NO: 223) |
| VYKPVDLSK | (SEQ ID NO: 224) |
| YKPVDLSK | (SEQ ID NO: 225) |
| KPVDLSK | (SEQ ID NO: 226) |
| PVDLSK | (SEQ ID NO: 227) |
| VDLSK | (SEQ ID NO: 228) |
| DLSK | (SEQ ID NO: 229) |
| LSK | (SEQ ID NO: 230) |
| VYKPVDLSKV | (SEQ ID NO: 231) |
| YKPVDLSKV | (SEQ ID NO: 232) |
| KPVDLSKV | (SEQ ID NO: 233) |
| PVDLSKV | (SEQ ID NO: 234) |
| VDLSKV | (SEQ ID NO: 235) |
| DLSKV | (SEQ ID NO: 236) |
| LSKV | (SEQ ID NO: 237) |
| SKV | (SEQ ID NO: 238) |
| YKPVDLSKVT | (SEQ ID NO: 239) |
| KPVDLSKVT | (SEQ ID NO: 240) |
| PVDLSKVT | (SEQ ID NO: 241) |
| VDLSKVT | (SEQ ID NO: 242) |
| AKTDHGAEIV | (SEQ ID NO: 243) |
| KTDHGAEIV | (SEQ ID NO: 244) |
| TDHGAEIV | (SEQ ID NO: 245) |
| DHGAEIV | (SEQ ID NO: 246) |
| HGAEIV | (SEQ ID NO: 247) |
| GAEIV | (SEQ ID NO: 248) |
| AEIV | (SEQ ID NO: 249) |
| EIV | (SEQ ID NO: 250) |
| KTDHGAEIVY | (SEQ ID NO: 251) |
| TDHGAEIVY | (SEQ ID NO: 252) |
| DHGAEIVY | (SEQ ID NO: 253) |

TABLE 16-continued

SEQUENCES

| | |
|---|---|
| HGAEIVY | (SEQ ID NO: 254) |
| GAEIVY | (SEQ ID NO: 255) |
| AEIVY | (SEQ ID NO: 256) |
| EIVY | (SEQ ID NO: 257) |
| IVY | (SEQ ID NO: 258) |
| TDHGAEIVYK | (SEQ ID NO: 259) |
| DHGAEIVYK | (SEQ ID NO: 260) |
| HGAEIVYK | (SEQ ID NO: 261) |
| GAEIVYK | (SEQ ID NO: 262) |
| AEIVYK | (SEQ ID NO: 263) |
| EIVYK | (SEQ ID NO: 264) |
| IVYK | (SEQ ID NO: 265) |
| DHGAEIVYKS | (SEQ ID NO: 266) |
| HGAEIVYKS | (SEQ ID NO: 267) |
| GAEIVYKS | (SEQ ID NO: 268) |
| AEIVYKS | (SEQ ID NO: 269) |
| EIVYKS | (SEQ ID NO: 270) |
| IVYKS | (SEQ ID NO: 271) |
| VYKS | (SEQ ID NO: 272) |
| YKS | (SEQ ID NO: 273) |
| HGAEIVYKSP | (SEQ ID NO: 274) |
| GAEIVYKSP | (SEQ ID NO: 275) |
| AEIVYKSP | (SEQ ID NO: 276) |
| EIVYKSP | (SEQ ID NO: 277) |
| IVYKSP | (SEQ ID NO: 278) |
| VYKSP | (SEQ ID NO: 279) |
| YKSP | (SEQ ID NO: 280) |
| KSP | (SEQ ID NO: 281) |
| GAEIVYKSPV | (SEQ ID NO: 282) |
| AEIVYKSPV | (SEQ ID NO: 283) |
| EIVYKSPV | (SEQ ID NO: 284) |
| IVYKSPV | (SEQ ID NO: 285) |
| VYKSPV | (SEQ ID NO: 286) |
| YKSPV | (SEQ ID NO: 287) |
| KSPV | (SEQ ID NO: 288) |
| SPV | (SEQ ID NO: 289) |
| AEIVYKSPVV | (SEQ ID NO: 290) |
| EIVYKSPVV | (SEQ ID NO: 291) |
| IVYKSPVV | (SEQ ID NO: 292) |
| VYKSPVV | (SEQ ID NO: 293) |
| YKS PVV | (SEQ ID NO: 294) |
| KSPVV | (SEQ ID NO: 295) |
| SPVV | (SEQ ID NO: 296) |
| PVV | (SEQ ID NO: 297) |
| EIVYKSPVVS | (SEQ ID NO: 298) |
| IVYKSPVVS | (SEQ ID NO: 299) |
| VYKSPVVS | (SEQ ID NO: 300) |
| YKSPVVS | (SEQ ID NO: 301) |
| KSPVVS | (SEQ ID NO: 302) |
| SPVVS | (SEQ ID NO: 303) |
| PVVS | (SEQ ID NO: 304) |
| VVS | (SEQ ID NO: 305) |
| IVYKSPVVSG | (SEQ ID NO: 306) |
| VYKSPVVSG | (SEQ ID NO: 307) |
| YKSPVVSG | (SEQ ID NO: 308) |
| KSPVVSG | (SEQ ID NO: 309) |
| SPVVSG | (SEQ ID NO: 310) |
| PVVSG | (SEQ ID NO: 311) |
| VVSG | (SEQ ID NO: 312) |
| VSG | (SEQ ID NO: 313) |
| VYKSPVVSGD | (SEQ ID NO: 314) |
| YKSPVVSGD | (SEQ ID NO: 315) |
| KSPVVSGD | (SEQ ID NO: 316) |
| SPVVSGD | (SEQ ID NO: 317) |
| PVVSGD | (SEQ ID NO: 318) |
| VVSGD | (SEQ ID NO: 319) |
| VSGD | (SEQ ID NO: 320) |
| SGD | (SEQ ID NO: 321) |
| YKSPVVSGDT | (SEQ ID NO: 322) |
| KSPVVSGDT | (SEQ ID NO: 323) |
| SPVVSGDT | (SEQ ID NO: 324) |
| PVVSGDT | (SEQ ID NO: 325) |
| VVSGDT | (SEQ ID NO: 326) |
| VSGDT | (SEQ ID NO: 327) |
| SGDT | (SEQ ID NO: 328) |
| GDT | (SEQ ID NO: 329) |
| KSPVVSGDTS | (SEQ ID NO: 330) |
| SPVVSGDTS | (SEQ ID NO: 331) |

TABLE 16-continued

SEQUENCES

| Sequence | SEQ ID NO |
|---|---|
| PVVSGDTS | (SEQ ID NO: 332) |
| VVSGDTS | (SEQ ID NO: 333) |
| VSGDTS | (SEQ ID NO: 334) |
| SGDTS | (SEQ ID NO: 335) |
| GDTS | (SEQ ID NO: 336) |
| DTS | (SEQ ID NO: 337) |
| SPVVSGDTSP | (SEQ ID NO: 338) |
| PVVSGDTSP | (SEQ ID NO: 339) |
| VVSGDTSP | (SEQ ID NO: 340) |
| VSGDTSP | (SEQ ID NO: 341) |
| SGDTSP | (SEQ ID NO: 342) |
| GDTSP | (SEQ ID NO: 343) |
| DTSP | (SEQ ID NO: 344) |
| TSP | (SEQ ID NO: 345) |
| PVVSGDTSPR | (SEQ ID NO: 346) |
| VVSGDTSPR | (SEQ ID NO: 347) |
| VSGDTSPR | (SEQ ID NO: 348) |
| SGDTSPR | (SEQ ID NO: 349) |
| GDTSPR | (SEQ ID NO: 350) |
| DTSPR | (SEQ ID NO: 351) |
| TSPR | (SEQ ID NO: 352) |
| SPR | (SEQ ID NO: 353) |
| HQPGGGKVQI | (SEQ ID NO: 354) |
| QPGGGKVQI | (SEQ ID NO: 355) |
| PGGGKVQI | (SEQ ID NO: 356) |
| GGGKVQI | (SEQ ID NO: 357) |
| GGKVQI | (SEQ ID NO: 358) |
| GKVQI | (SEQ ID NO: 359) |
| KVQI | (SEQ ID NO: 360) |
| VQI | (SEQ ID NO: 361) |
| QPGGGKVQII | (SEQ ID NO: 362) |
| PGGGKVQII | (SEQ ID NO: 363) |
| GGGKVQII | (SEQ ID NO: 365) |
| GGKVQII | (SEQ ID NO: 366) |
| GKVQII | (SEQ ID NO: 367) |
| KVQII | (SEQ ID NO: 368) |
| VQII | (SEQ ID NO: 369) |
| QII | (SEQ ID NO: 370) |
| PGGGKVQIIN | (SEQ ID NO: 371) |
| GGGKVQIIN | (SEQ ID NO: 372) |
| GGKVQIIN | (SEQ ID NO: 373) |
| GKVQIIN | (SEQ ID NO: 374) |
| KVQIIN | (SEQ ID NO: 375) |
| VQIIN | (SEQ ID NO: 376) |
| QIIN | (SEQ ID NO: 377) |
| IIN | (SEQ ID NO: 378) |
| GGGKVQIINK | (SEQ ID NO: 379) |
| GGKVQIINK | (SEQ ID NO: 380) |
| GKVQIINK | (SEQ ID NO: 381) |
| KVQIINK | (SEQ ID NO: 382) |
| IINK | (SEQ ID NO: 383) |
| INK | (SEQ ID NO: 384) |
| GGKVQIINKK | (SEQ ID NO: 385) |
| GKVQIINKK | (SEQ ID NO: 386) |
| KVQIINKK | (SEQ ID NO: 387) |
| IINKK | (SEQ ID NO: 388) |
| INKK | (SEQ ID NO: 389) |
| NKK | (SEQ ID NO: 390) |
| GKVQIINKKL | (SEQ ID NO: 391) |
| KVQIINKKL | (SEQ ID NO: 392) |
| IINKKL | (SEQ ID NO: 393) |
| INKKL | (SEQ ID NO: 394) |
| NKKL | (SEQ ID NO: 395) |
| KKL | (SEQ ID NO: 396) |
| KVQIINKKLD | (SEQ ID NO: 397) |
| VQIINKKLD | (SEQ ID NO: 398) |
| QIINKKLD | (SEQ ID NO: 399) |
| IINKKLD | (SEQ ID NO: 400) |
| INKKLD | (SEQ ID NO: 401) |
| NKKLD | (SEQ ID NO: 402) |
| KKLD | (SEQ ID NO: 403) |
| KLD | (SEQ ID NO: 404) |
| VQIINKKLDL | (SEQ ID NO: 405) |
| QIINKKLDL | (SEQ ID NO: 406) |
| IINKKLDL | (SEQ ID NO: 407) |
| INKKLDL | (SEQ ID NO: 408) |
| NKKLDL | (SEQ ID NO: 409) |
| KKLDL | (SEQ ID NO: 410) |

TABLE 16-continued

SEQUENCES

| | |
|---|---|
| KLDL | (SEQ ID NO: 411) |
| LDL | (SEQ ID NO: 412) |
| QIINKKLDLS | (SEQ ID NO: 413) |
| IINKKLDLS | (SEQ ID NO: 414) |
| INKKLDLS | (SEQ ID NO: 415) |
| NKKLDLS | (SEQ ID NO: 416) |
| KKLDLS | (SEQ ID NO: 417) |
| KLDLS | (SEQ ID NO: 418) |
| LDLS | (SEQ ID NO: 419) |
| IINKKLDLSN | (SEQ ID NO: 420) |
| INKKLDLSN | (SEQ ID NO: 421) |
| NKKLDLSN | (SEQ ID NO: 422) |
| KKLDLSN | (SEQ ID NO: 423) |
| KLDLSN | (SEQ ID NO: 424) |
| LDLSN | (SEQ ID NO: 425) |
| DLSN | (SEQ ID NO: 426) |
| LSN | (SEQ ID NO: 427) |
| INKKLDLSNV | (SEQ ID NO: 428) |
| NKKLDLSNV | (SEQ ID NO: 429) |
| KKLDLSNV | (SEQ ID NO: 430) |
| KLDLSNV | (SEQ ID NO: 431) |
| LDLSNV | (SEQ ID NO: 432) |
| DLSNV | (SEQ ID NO: 433) |
| LSNV | (SEQ ID NO: 434) |
| SNV | (SEQ ID NO: 435) |
| NKKLDLSNVQ | (SEQ ID NO: 436) |
| KKLDLSNVQ | (SEQ ID NO: 437) |
| KLDLSNVQ | (SEQ ID NO: 438) |
| LDLSNVQ | (SEQ ID NO: 439) |
| DLSNVQ | (SEQ ID NO: 440) |
| LSNVQ | (SEQ ID NO: 441) |
| SNVQ | (SEQ ID NO: 442) |
| NVQ | (SEQ ID NO: 443) |
| KKLDLSNVQS | (SEQ ID NO: 444) |
| KLDLSNVQS | (SEQ ID NO: 445) |
| LDLSNVQS | (SEQ ID NO: 446) |
| DLSNVQS | (SEQ ID NO: 447) |
| LSNVQS | (SEQ ID NO: 448) |
| SNVQS | (SEQ ID NO: 449) |
| NVQS | (SEQ ID NO: 450) |
| VQS | (SEQ ID NO: 451) |
| SKCGSKDNIK | (SEQ ID NO: 452) |
| KCGSKDNIK | (SEQ ID NO: 453) |
| CGSKDNIK | (SEQ ID NO: 454) |
| GSKDNIK | (SEQ ID NO: 455) |
| SKDNIK | (SEQ ID NO: 456) |
| KDNIK | (SEQ ID NO: 457) |
| DNIK | (SEQ ID NO: 458) |
| NIK | (SEQ ID NO: 459) |
| KCGSKDNIKH | (SEQ ID NO: 460) |
| CGSKDNIKH | (SEQ ID NO: 461) |
| GSKDNIKH | (SEQ ID NO: 462) |
| SKDNIKH | (SEQ ID NO: 463) |
| KDNIKH | (SEQ ID NO: 464) |
| DNIKH | (SEQ ID NO: 465) |
| NIKH | (SEQ ID NO: 466) |
| IKH | (SEQ ID NO: 467) |
| CGSKDNIKHV | (SEQ ID NO: 468) |
| GSKDNIKHV | (SEQ ID NO: 469) |
| SKDNIKHV | (SEQ ID NO: 470) |
| KDNIKHV | (SEQ ID NO: 471) |
| DNIKHV | (SEQ ID NO: 472) |
| NIKHV | (SEQ ID NO: 473) |
| IKHV | (SEQ ID NO: 474) |
| KHV | (SEQ ID NO: 475) |
| GSKDNIKHVP | (SEQ ID NO: 476) |
| SKDNIKHVP | (SEQ ID NO: 477) |
| KDNIKHVP | (SEQ ID NO: 478) |
| DNIKHVP | (SEQ ID NO: 479) |
| IKHVP | (SEQ ID NO: 480) |
| KHVP | (SEQ ID NO: 481) |
| HVP | (SEQ ID NO: 482) |
| SKDNIKHVPG | (SEQ ID NO: 483) |
| KDNIKHVPG | (SEQ ID NO: 484) |
| DNIKHVPG | (SEQ ID NO: 485) |
| NIKHVPG | (SEQ ID NO: 486) |
| IKHVPG | (SEQ ID NO: 487) |
| KHVPG | (SEQ ID NO: 488) |

TABLE 16-continued

SEQUENCES

| | |
|---|---|
| HVPG | (SEQ ID NO: 489) |
| VPG | (SEQ ID NO: 490) |
| KDNIKHVPGG | (SEQ ID NO: 491) |
| DNIKHVPGG | (SEQ ID NO: 492) |
| NIKHVPGG | (SEQ ID NO: 493) |
| IKHVPGG | (SEQ ID NO: 494) |
| KHVPGG | (SEQ ID NO: 495) |
| VPGG | (SEQ ID NO: 496) |
| PGG | (SEQ ID NO: 497) |
| DNIKHVPGGG | (SEQ ID NO: 498) |
| NIKHVPGGG | (SEQ ID NO: 499) |
| IKHVPGGG | (SEQ ID NO: 500) |
| VPGGG | (SEQ ID NO: 501) |
| PGGG | (SEQ ID NO: 502) |
| GGG | (SEQ ID NO: 503) |
| NIKHVPGGGS | (SEQ ID NO: 504) |
| IKHVPGGGS | (SEQ ID NO: 505) |
| KHVPGGGS | (SEQ ID NO: 506) |
| HVPGGGS | (SEQ ID NO: 507) |
| VPGGGS | (SEQ ID NO: 508) |
| PGGGS | (SEQ ID NO: 509) |
| GGGS | (SEQ ID NO: 510) |
| GGS | (SEQ ID NO: 511) |
| IKHVPGGGSV | (SEQ ID NO: 512) |
| KHVPGGGSV | (SEQ ID NO: 513) |
| HVPGGGSV | (SEQ ID NO: 514) |
| VPGGGSV | (SEQ ID NO: 515) |
| PGGGSV | (SEQ ID NO: 516) |
| GGGSV | (SEQ ID NO: 517) |
| GGSV | (SEQ ID NO: 518) |
| GSV | (SEQ ID NO: 519) |
| KHVPGGGSVQ | (SEQ ID NO: 520) |
| HVPGGGSVQ | (SEQ ID NO: 521) |
| VPGGGSVQ | (SEQ ID NO: 522) |
| PGGGSVQ | (SEQ ID NO: 523) |
| GGGSVQ | (SEQ ID NO: 524) |
| GGSVQ | (SEQ ID NO: 525) |
| GSVQ | (SEQ ID NO: 526) |
| SVQ | (SEQ ID NO: 527) |
| HVPGGGSVQI | (SEQ ID NO: 528) |
| VPGGGSVQI | (SEQ ID NO: 529) |
| PGGGSVQI | (SEQ ID NO: 530) |
| GGGSVQI | (SEQ ID NO: 531) |
| GGSVQI | (SEQ ID NO: 532) |
| GSVQI | (SEQ ID NO: 533) |
| SVQI | (SEQ ID NO: 534) |
| GGSVQIVYKS | (SEQ ID NO: 535) |
| GSVQIVYKS | (SEQ ID NO: 536) |
| SVQIVYKS | (SEQ ID NO: 537) |
| VQIVYKS | (SEQ ID NO: 538) |
| QIVYKS | (SEQ ID NO: 539) |
| IVYKS | (SEQ ID NO: 540) |
| VYKS | (SEQ ID NO: 541) |
| YKS | (SEQ ID NO: 542) |
| GSVQIVYKSV | (SEQ ID NO: 543) |
| SVQIVYKSV | (SEQ ID NO: 544) |
| VQIVYKSV | (SEQ ID NO: 545) |
| QIVYKSV | (SEQ ID NO: 546) |
| IVYKSV | (SEQ ID NO: 547) |
| VYKSV | (SEQ ID NO: 548) |
| YKSV | (SEQ ID NO: 549) |
| SVQIVYKSVD | (SEQ ID NO: 550) |
| VQIVYKSVD | (SEQ ID NO: 551) |
| QIVYKSVD | (SEQ ID NO: 552) |
| IVYKSVD | (SEQ ID NO: 553) |
| VYKSVD | (SEQ ID NO: 554) |
| YKSVD | (SEQ ID NO: 555) |
| KSVD | (SEQ ID NO: 556) |
| SVD | (SEQ ID NO: 557) |
| VQIVYKSVDL | (SEQ ID NO: 558) |
| QIVYKSVDL | (SEQ ID NO: 559) |
| IVYKSVDL | (SEQ ID NO: 560) |
| VYKSVDL | (SEQ ID NO: 561) |
| YKSVDL | (SEQ ID NO: 562) |
| KSVDL | (SEQ ID NO: 563) |
| SVDL | (SEQ ID NO: 564) |
| QIVYKSVDLS | (SEQ ID NO: 565) |
| IVYKSVDLS | (SEQ ID NO: 566) |

TABLE 16-continued

SEQUENCES

| Sequence | SEQ ID NO |
|---|---|
| VYKSVDLS | (SEQ ID NO: 567) |
| YKSVDLS | (SEQ ID NO: 568) |
| KSVDLS | (SEQ ID NO: 569) |
| SVDLS | (SEQ ID NO: 570) |
| IVYKSVDLSK | (SEQ ID NO: 571) |
| VYKSVDLSK | (SEQ ID NO: 572) |
| YKSVDLSK | (SEQ ID NO: 573) |
| KSVDLSK | (SEQ ID NO: 574) |
| SVDLSK | (SEQ ID NO: 364) |
| VYKSVDLSKV | (SEQ ID NO: 575) |
| YKSVDLSKV | (SEQ ID NO: 576) |
| KSVDLSKV | (SEQ ID NO: 577) |
| SVDLSKV | (SEQ ID NO: 578) |
| YKSVDLSKVT | (SEQ ID NO: 579) |
| KSVDLSKVT | (SEQ ID NO: 580) |
| SVDLSKVT | (SEQ ID NO: 581) |
| DLSKVT | (SEQ ID NO: 582) |
| LSKVT | (SEQ ID NO: 583) |
| SKVT | (SEQ ID NO: 584) |
| KVT | (SEQ ID NO: 585) |
| HGAEIVYKSV | (SEQ ID NO: 586) |
| GAEIVYKSV | (SEQ ID NO: 587) |
| AEIVYKSV | (SEQ ID NO: 588) |
| GAEIVYKSVV | (SEQ ID NO: 589) |
| AEIVYKSVV | (SEQ ID NO: 590) |
| EIVYKSVV | (SEQ ID NO: 591) |
| IVYKSVV | (SEQ ID NO: 592) |
| VYKSVV | (SEQ ID NO: 593) |
| YKSVV | (SEQ ID NO: 594) |
| KSVV | (SEQ ID NO: 595) |
| SVV | (SEQ ID NO: 596) |
| AEIVYKSVVS | (SEQ ID NO: 597) |
| EIVYKSVVS | (SEQ ID NO: 598) |
| IVYKSVVS | (SEQ ID NO: 599) |
| VYKSVVS | (SEQ ID NO: 600) |
| YKSVVS | (SEQ ID NO: 601) |
| KSVVS | (SEQ ID NO: 602) |
| SVVS | (SEQ ID NO: 603) |
| EIVYKSVVSG | (SEQ ID NO: 604) |
| IVYKSVVSG | (SEQ ID NO: 605) |
| VYKSVVSG | (SEQ ID NO: 606) |
| YKSVVSG | (SEQ ID NO: 607) |
| KSVVSG | (SEQ ID NO: 608) |
| SVVSG | (SEQ ID NO: 609) |
| VVSG | (SEQ ID NO: 610) |
| VSG | (SEQ ID NO: 611) |
| IVYKSVVSGD | (SEQ ID NO: 612) |
| VYKSVVSGD | (SEQ ID NO: 613) |
| YKSVVSGD | (SEQ ID NO: 614) |
| KSVVSGD | (SEQ ID NO: 615) |
| SVVSGD | (SEQ ID NO: 616) |
| VVSGD | (SEQ ID NO: 617) |
| VYKSVVSGDT | (SEQ ID NO: 618) |
| YKSVVSGDT | (SEQ ID NO: 619) |
| KSVVSGDT | (SEQ ID NO: 620) |
| SVVSGDT | (SEQ ID NO: 621) |
| YKSVVSGDTS | (SEQ ID NO: 622) |
| KSVVSGDTS | (SEQ ID NO: 623) |
| SVVSGDTS | (SEQ ID NO: 624) |
| YKSVVSGDTS | (SEQ ID NO: 625) |
| KSVVSGDTS | (SEQ ID NO: 626) |
| SVVSGDTS | (SEQ ID NO: 627) |
| VVSGDTS | (SEQ ID NO: 628) |
| KSVVSGDTSP | (SEQ ID NO: 629) |
| SVVSGDTSP | (SEQ ID NO: 630) |
| SVVSGDTSPR | (SEQ ID NO: 631) |
| DHGAEIVYKP | (SEQ ID NO: 632) |
| HGAEIVYKP | (SEQ ID NO: 633) |
| GAEIVYKP | (SEQ ID NO: 634) |
| AEIVYKP | (SEQ ID NO: 635) |
| HGAEIVYKPV | (SEQ ID NO: 636) |
| GAEIVYKPV | (SEQ ID NO: 637) |
| AEIVYKPV | (SEQ ID NO: 638) |
| GAEIVYKPVV | (SEQ ID NO: 639) |
| AEIVYKPVV | (SEQ ID NO: 640) |
| EIVYKPVV | (SEQ ID NO: 641) |
| IVYKPVV | (SEQ ID NO: 642) |
| VYKPVV | (SEQ ID NO: 643) |

TABLE 16-continued

SEQUENCES

| Sequence | SEQ ID NO |
|---|---|
| YKPVV | (SEQ ID NO: 644) |
| KPVV | (SEQ ID NO: 645) |
| AEIVYKPVVS | (SEQ ID NO: 646) |
| EIVYKPVVS | (SEQ ID NO: 647) |
| IVYKPVVS | (SEQ ID NO: 648) |
| VYKPVVS | (SEQ ID NO: 649) |
| YKPVVS | (SEQ ID NO: 650) |
| KPVVS | (SEQ ID NO: 651) |
| EIVYKPVVSG | (SEQ ID NO: 652) |
| IVYKPVVSG | (SEQ ID NO: 653) |
| VYKPVVSG | (SEQ ID NO: 654) |
| YKPVVSG | (SEQ ID NO: 655) |
| KPVVSG | (SEQ ID NO: 656) |
| IVYKPVVSGD | (SEQ ID NO: 657) |
| VYKPVVSGD | (SEQ ID NO: 658) |
| YKPVVSGD | (SEQ ID NO: 659) |
| KPVVSGD | (SEQ ID NO: 660) |
| VYKPVVSGDT | (SEQ ID NO: 661) |
| YKPVVSGDT | (SEQ ID NO: 662) |
| KPVVSGDT | (SEQ ID NO: 663) |
| YKPVVSGDTS | (SEQ ID NO: 664) |
| KPVVSGDTS | (SEQ ID NO: 665) |
| PVVSGDTS | (SEQ ID NO: 666) |
| VVSGDTS | (SEQ ID NO: 667) |
| KPVVSGDTSP | (SEQ ID NO: 668) |
| CNIK | (SEQ ID NO: 669) |
| CNIKH | (SEQ ID NO: 670) |
| CNIKHV | (SEQ ID NO: 671) |
| CNIKHVPGG | (SEQ ID NO: 672) |
| CNIKHVPGGG | (SEQ ID NO: 673) |
| CNIKHVPGGGS | (SEQ ID NO: 674) |
| ENLKHQPGGG | (SEQ ID NO: 675) |
| NLKHQPGGG | (SEQ ID NO: 676) |
| LKHQPGGG | (SEQ ID NO: 677) |
| KHQPGGG | (SEQ ID NO: 678) |
| HQPGGG | (SEQ ID NO: 679) |
| QPGGG | (SEQ ID NO: 680) |
| TENLKHQPGG | (SEQ ID NO: 681) |
| ENLKHQPGG | (SEQ ID NO: 682) |
| NLKHQPGG | (SEQ ID NO: 683) |
| LKHQPGG | (SEQ ID NO: 684) |
| KHQPGG | (SEQ ID NO: 685) |
| HQPGG | (SEQ ID NO: 686) |
| QPGG | (SEQ ID NO: 687) |
| TENLKHQPG | (SEQ ID NO: 688) |
| ENLKHQPG | (SEQ ID NO: 689) |
| NLKHQPG | (SEQ ID NO: 690) |
| LKHQPG | (SEQ ID NO: 691) |
| KHQPG | (SEQ ID NO: 692) |
| HQPG | (SEQ ID NO: 693) |
| QPG | (SEQ ID NO: 694) |
| TENLKHQP | (SEQ ID NO: 695) |
| ENLKHQP | (SEQ ID NO: 696) |
| NLKHQP | (SEQ ID NO: 697) |
| LKHQP | (SEQ ID NO: 698) |
| KHQP | (SEQ ID NO: 699) |
| HQP | (SEQ ID NO: 700) |
| TENLKHQ | (SEQ ID NO: 701) |
| ENLKHQ | (SEQ ID NO: 702) |
| NLKHQ | (SEQ ID NO: 703) |
| LKHQ | (SEQ ID NO: 704) |
| KHQ | (SEQ ID NO: 705) |
| TENLKH | (SEQ ID NO: 706) |
| ENLKH | (SEQ ID NO: 707) |
| NLKH | (SEQ ID NO: 708) |
| LKH | (SEQ ID NO: 709) |
| TENLK | (SEQ ID NO: 710) |
| ENLK | (SEQ ID NO: 711) |
| NLK | (SEQ ID NO: 712) |
| TENL | (SEQ ID NO: 713) |
| ENI | (SEQ ID NO: 714) |
| TEN | (SEQ ID NO: 715) |
| KDNIKHVPGGG | (SEQ ID NO: 716) |
| KDNI | (SEQ ID NO: 717) |
| KDN | (SEQ ID NO: 718) |
| IKHVGGG | (SEQ ID NO: 719) |
| IKHVGG | (SEQ ID NO: 720) |
| IKHVG | (SEQ ID NO: 721) |

TABLE 16-continued

SEQUENCES

| Sequence | SEQ ID NO |
|---|---|
| KHVGGG | 722 |
| KHVGG | 723 |
| KHVG | 724 |
| LGNIHHKPGGG | 725 |
| GNIHHKPGGG | 726 |
| NIHHKPGGG | 727 |
| IHHKPGGG | 728 |
| HHKPGGG | 729 |
| KPGGG | 730 |
| LGNIHHKPGG | 731 |
| GNIHHKPGG | 732 |
| NIHHKPGG | 733 |
| IHHKPGG | 734 |
| HHKPGG | 735 |
| KPGG | 736 |
| LGNIHHKPG | 737 |
| GNIHHKPG | 738 |
| NIHHKPG | 739 |
| IHHKPG | 740 |
| HHKPG | 741 |
| HKPG | 742 |
| KPG | 743 |
| LGNIHHKP | 744 |
| GNIHHKP | 745 |
| NIHHKP | 746 |
| IHHKP | 747 |
| HHKP | 748 |
| HKP | 749 |
| LGNIHHK | 750 |
| GNIHHK | 751 |
| NIHHK | 752 |
| IHHK | 753 |
| HHK | 754 |
| LGNIHH | 755 |
| GNIHH | 756 |
| NIHH | 757 |
| IHH | 758 |
| LGNIH | 759 |
| GNIH | 760 |
| NIH | 761 |
| LGNI | 762 |
| GNI | 763 |
| LGN | 764 |
| LDNITHVPGGG | 765 |
| DNITHVPGGG | 766 |
| NITHVPGGG | 767 |
| ITHVPGGG | 768 |
| THVPGGG | 769 |
| LDNITHVPGG | 770 |
| DNITHVPGG | 771 |
| NITHVPGG | 772 |
| ITHVPGG | 773 |
| THVPGG | 774 |
| LDNITHVPG | 775 |
| DNITHVPG | 776 |
| NITHVPG | 777 |
| ITHVPG | 778 |
| THVPG | 779 |
| LDNITHVP | 780 |
| DNITHVP | 781 |
| NITHVP | 782 |
| ITHVP | 783 |
| THVP | 784 |
| LDNITHV | 785 |
| DNITHV | 786 |
| NITHV | 787 |
| ITHV | 788 |
| THV | 789 |
| LDNITH | 790 |
| DNITH | 791 |
| NITH | 792 |
| ITH | 793 |
| LDNIT | 794 |
| DNIT | 795 |
| NIT | 796 |
| LDNI | 797 |
| LDN | 798 |
| KNVKSKIGST | 799 |

TABLE 16-continued

| SEQUENCES | |
|---|---|
| NVKSKIGST | (SEQ ID NO: 800) |
| VKSKIGST | (SEQ ID NO: 801) |
| KSKIGST | (SEQ ID NO: 802) |
| SKIGST | (SEQ ID NO: 803) |
| KIGST | (SEQ ID NO: 804) |
| IGST | (SEQ ID NO: 805) |
| GST | (SEQ ID NO: 806) |
| NVKSKIGSTE | (SEQ ID NO: 807) |
| VKSKIGSTE | (SEQ ID NO: 808) |
| KSKIGSTE | (SEQ ID NO: 809) |
| SKIGSTE | (SEQ ID NO: 810) |
| KIGSTE | (SEQ ID NO: 811) |
| IGSTE | (SEQ ID NO: 812) |
| GSTE | (SEQ ID NO: 813) |
| STE | (SEQ ID NO: 814) |
| VKSKIGSTEN | (SEQ ID NO: 815) |
| KSKIGSTEN | (SEQ ID NO: 816) |
| SKIGSTEN | (SEQ ID NO: 817) |
| KIGSTEN | (SEQ ID NO: 818) |
| IGSTEN | (SEQ ID NO: 819) |
| GSTEN | (SEQ ID NO: 820) |
| STEN | (SEQ ID NO: 821) |
| KSKIGSTENL | (SEQ ID NO: 822) |
| SKIGSTENL | (SEQ ID NO: 823) |
| KIGSTENL | (SEQ ID NO: 824) |
| IGSTENL | (SEQ ID NO: 825) |
| GSTENL | (SEQ ID NO: 826) |
| STENL | (SEQ ID NO: 827) |
| SKIGSTENLK | (SEQ ID NO: 828) |
| KIGSTENLK | (SEQ ID NO: 829) |
| IGSTENLK | (SEQ ID NO: 830) |
| GSTENLK | (SEQ ID NO: 831) |
| STENLK | (SEQ ID NO: 832) |
| KIGSTENLKH | (SEQ ID NO: 833) |
| IGSTENLKH | (SEQ ID NO: 834) |
| GSTENLKH | (SEQ ID NO: 835) |
| STENLKH | (SEQ ID NO: 836) |
| IGSTENLKHQ | (SEQ ID NO: 837) |
| GSTENLKHQ | (SEQ ID NO: 838) |
| STENLKHQ | (SEQ ID NO: 839) |
| GSTENLKHQP | (SEQ ID NO: 840) |
| STENLKHQP | (SEQ ID NO: 841) |
| STENLKHQPG | (SEQ ID NO: 842) |
| SNVQSKCGSK | (SEQ ID NO: 843) |
| NVQSKCGSK | (SEQ ID NO: 844) |
| VQSKCGSK | (SEQ ID NO: 845) |
| QSKCGSK | (SEQ ID NO: 846) |
| SKCGSK | (SEQ ID NO: 847) |
| KCGSK | (SEQ ID NO: 848) |
| CGSK | (SEQ ID NO: 849) |
| GSK | (SEQ ID NO: 850) |
| NVQSKCGSKD | (SEQ ID NO: 851) |
| VQSKCGSKD | (SEQ ID NO: 852) |
| QSKCGSKD | (SEQ ID NO: 853) |
| SKCGSKD | (SEQ ID NO: 854) |
| KCGSKD | (SEQ ID NO: 855) |
| CGSKD | (SEQ ID NO: 856) |
| GSKD | (SEQ ID NO: 857) |
| SKD | (SEQ ID NO: 858) |
| VQSKCGSKDN | (SEQ ID NO: 859) |
| QSKCGSKDN | (SEQ ID NO: 860) |
| SKCGSKDN | (SEQ ID NO: 861) |
| KCGSKDN | (SEQ ID NO: 862) |
| CGSKDN | (SEQ ID NO: 863) |
| GSKDN | (SEQ ID NO: 864) |
| SKDN | (SEQ ID NO: 865) |
| QSKCGSKDNI | (SEQ ID NO: 866) |
| SKCGSKDNI | (SEQ ID NO: 867) |
| KCGSKDNI | (SEQ ID NO: 868) |
| CGSKDNI | (SEQ ID NO: 869) |
| GSKDNI | (SEQ ID NO: 870) |
| SKDNI | (SEQ ID NO: 871) |
| SKVTSKCGSL | (SEQ ID NO: 872) |
| KVTSKCGSL | (SEQ ID NO: 873) |
| VTSKCGSL | (SEQ ID NO: 874) |
| TSKCGSL | (SEQ ID NO: 875) |
| SKCGSL | (SEQ ID NO: 876) |
| KCGSL | (SEQ ID NO: 877) |

TABLE 16-continued

| SEQUENCES | |
|---|---|
| CGSL | (SEQ ID NO: 878) |
| GSL | (SEQ ID NO: 879) |
| KVTSKCGSLG | (SEQ ID NO: 880) |
| VTSKCGSLG | (SEQ ID NO: 881) |
| TSKCGSLG | (SEQ ID NO: 882) |
| SKCGSLG | (SEQ ID NO: 883) |
| KCGSLG | (SEQ ID NO: 884) |
| CGSLG | (SEQ ID NO: 885) |
| GSLG | (SEQ ID NO: 886) |
| SLG | (SEQ ID NO: 887) |
| VTSKCGSLGN | (SEQ ID NO: 888) |
| TSKCGSLGN | (SEQ ID NO: 889) |
| SKCGSLGN | (SEQ ID NO: 890) |
| KCGSLGN | (SEQ ID NO: 891) |
| CGSLGN | (SEQ ID NO: 892) |
| GSLGN | (SEQ ID NO: 893) |
| SLGN | (SEQ ID NO: 894) |
| TSKCGSLGNI | (SEQ ID NO: 895) |
| SKCGSLGNI | (SEQ ID NO: 896) |
| KCGSLGNI | (SEQ ID NO: 897) |
| CGSLGNI | (SEQ ID NO: 898) |
| GSLGNI | (SEQ ID NO: 899) |
| SLGNI | (SEQ ID NO: 900) |
| SKCGSLGNIH | (SEQ ID NO: 901) |
| KCGSLGNIH | (SEQ ID NO: 902) |
| CGSLGNIH | (SEQ ID NO: 903) |
| GSLGNIH | (SEQ ID NO: 904) |
| SLGNIH | (SEQ ID NO: 905) |
| KCGSLGNIHH | (SEQ ID NO: 906) |
| CGSLGNIHH | (SEQ ID NO: 907) |
| GSLGNIHH | (SEQ ID NO: 908) |
| SLGNIHH | (SEQ ID NO: 909) |
| CGSLGNIHHK | (SEQ ID NO: 910) |
| GSLGNIHHK | (SEQ ID NO: 911) |
| SLGNIHHK | (SEQ ID NO: 912) |
| GSLGNIHHKP | (SEQ ID NO: 913) |
| SLGNIHHKP | (SEQ ID NO: 914) |
| SLGNIHHKPG | (SEQ ID NO: 915) |
| DRVQSKIGSL | (SEQ ID NO: 916) |
| RVQSKIGSL | (SEQ ID NO: 917) |
| VQSKIGSL | (SEQ ID NO: 918) |
| QSKIGSL | (SEQ ID NO: 919) |
| SKIGSL | (SEQ ID NO: 920) |
| KIGSL | (SEQ ID NO: 921) |
| IGSL | (SEQ ID NO: 922) |
| RVQSKIGSLD | (SEQ ID NO: 923) |
| VQSKIGSLD | (SEQ ID NO: 924) |
| QSKIGSLD | (SEQ ID NO: 925) |
| SKIGSLD | (SEQ ID NO: 926) |
| KIGSLD | (SEQ ID NO: 927) |
| IGSLD | (SEQ ID NO: 928) |
| GSLD | (SEQ ID NO: 929) |
| SLD | (SEQ ID NO: 930) |
| VQSKIGSLDN | (SEQ ID NO: 931) |
| QSKIGSLDN | (SEQ ID NO: 932) |
| SKIGSLDN | (SEQ ID NO: 933) |
| KIGSLDN | (SEQ ID NO: 934) |
| IGSLDN | (SEQ ID NO: 935) |
| GSLDN | (SEQ ID NO: 936) |
| SLDN | (SEQ ID NO: 937) |
| QSKIGSLDNI | (SEQ ID NO: 938) |
| SKIGSLDNI | (SEQ ID NO: 939) |
| KIGSLDNI | (SEQ ID NO: 940) |
| IGSLDNI | (SEQ ID NO: 941) |
| GSLDNI | (SEQ ID NO: 942) |
| SKIGSLDNIT | (SEQ ID NO: 943) |
| KIGSLDNIT | (SEQ ID NO: 944) |
| IGSLDNIT | (SEQ ID NO: 945) |
| GSLDNIT | (SEQ ID NO: 946) |
| SLDNIT | (SEQ ID NO: 947) |
| KIGSLDNITH | (SEQ ID NO: 948) |
| IGSLDNITH | (SEQ ID NO: 949) |
| GSLDNITH | (SEQ ID NO: 950) |
| SLDNITH | (SEQ ID NO: 951) |
| IGSLDNITHV | (SEQ ID NO: 952) |
| GSLDNITHV | (SEQ ID NO: 953) |
| SLDNITHV | (SEQ ID NO: 954) |
| GSLDNITHVP | (SEQ ID NO: 955) |

TABLE 16-continued

SEQUENCES

| Sequence | SEQ ID NO |
|---|---|
| SLDNITHVP | 956 |
| SLDNITHVPG | 957 |
| PDLKNVKS | 958 |
| DLKNVKSK | 959 |
| LKNVKSKI | 960 |
| KNVKSKIG | 961 |
| NVKSKIGS | 962 |
| DLSNVQSK | 963 |
| LSNVQSKC | 964 |
| SNVQSKCG | 965 |
| NVQSKCGS | 966 |
| VDLSKVTS | 967 |
| DLSKVTSK | 968 |
| LSKVTSKC | 969 |
| SKVTSKCG | 970 |
| KVTSKCGS | 971 |
| LDFKDRVQ | 972 |
| DFKDRVQS | 973 |
| FKDRVQSK | 974 |
| KDRVQSKI | 975 |
| DRVQSKIG | 976 |
| RVQSKIGS | 977 |
| SKIGSTENLKH | 978 |
| SKIGSTENIKH | 979 |
| SKIGSKDNLKH | 980 |
| SKIGSKENIKH | 981 |
| SKIGSLENLKH | 982 |
| SKIGSLENIKH | 983 |
| SKIGSTDNLKH | 984 |
| SKIGSTDNIKH | 985 |
| SKIGSKDNIKH | 986 |
| SKIGSLDNLKH | 987 |
| SKIGSLDNIKH | 988 |
| SKIGSTGNLKH | 989 |
| SKIGSTGNIKH | 990 |
| SKIGSKGNLKH | 991 |
| SKIGSKGNIKH | 992 |
| SKIGSLGNLKH | 993 |
| SKIGSLGNIKH | 994 |

Lys Xaa$_1$ Xaa$_2$ Ser Xaa$_3$ Xaa$_4$ Asn Xaa$_5$ Xaa$_6$ His (SEQ ID NO:995), wherein
Xaa$_1$ is I or C;
Xaa$_2$ is G;
Xaa$_3$ is T, K or L;
Xaa$_4$ is E, D or G;
Xaa$_5$ is L or I;
Xaa$_6$ is K, H or T.

| Sequence | SEQ ID NO |
|---|---|
| (Q/E) IVYK (S/P) | 996 |
| DAEFRHDRRQIVYKPV | 57 |
| DAEFRHDRREIVYKSV | 58 |
| DAEFRHDRRQIVYKPVGGC | 59 |
| DAEFRHDRRQIVYKPVC | 60 |
| DAEFRHDRRQIVYKPVAAC | 61 |
| DAEFRHDRRQIVYKPVKKC | 62 |
| DAEFRHDRREIVYKSPGGC | 63 |
| DAEFRHDRREIVYKSPAAC | 64 |
| DAEFRHDRREIVYKSPC | 65 |
| DAEFRHDRREIVYKSPKKC | 66 |
| DAEFRHDSGYEVHHQKLFFAEDVGSNKG | 67 |
| GGGSVQIVYKPVDLS | 68 |
| Arg-Val-Arg-Arg (RVRR) | 69 |
| Gly-Ala-Gly-Ala (GAGA) | 80 |
| Ala-Gly-Ala-Gly (AGAG) | 81 |
| Lys-Gly-Lys-Gly (KGKG) | 82 |
| DAEFRHDRRQIVYKPVXXC If present, XX can be GG or AA or KK or SS. | 70 |
| DAEFRHDRREIVYKSVXXC If present, XX can be GG or AA or KK or SS. | 79 |
| DAEFRHDC | 71 |
| QIVYKPVGGC | 72 |

-continued

GGSQIVYKPVDLS (SEQ ID NO: 73)

DAEFRHDRREIVYKSVGGC (SEQ ID NO: 74)

DAEFRHDRREIVYKSVAAC (SEQ ID NO: 75)

DAEFRHDRREIVYKSVC (SEQ ID NO: 76)

DAEFRHDRREIVYKSVKKC (SEQ ID NO: 77)

DAEFRHDRRNIKHVPGGC (SEQ ID NO: 78)

DAEFRHDRRVKSKIGSTGGC (SEQ ID NO: 997)

DAEFRHDRRSKIGSTENGGC (SEQ ID NO: 998)

DAEFRHDRRTENLKHQPGGC (SEQ ID NO: 999)

DAEFRHDRRENLKHQPGGGC (SEQ ID NO: 1000)

DAEFRHDRRSKIGSKDNIKHGGC (SEQ ID NO: 1001)

MTBR peptide 1
QTAPVPMPDLKNVKSKIGSTENLKHQPGGGK (SEQ ID NO: 1058)

MTBR peptide 2
VQIINKKLDLSNVQSKCGSKDNIKHVPGGGS (SEQ ID NO: 1059)

MTBR peptide 3
VQIVYKPVDLSKVTSKCGSLGNIHHKPGGGQ (SEQ ID NO: 1060)

MTBR peptide 4
VEVKSEKLDFKDRVQSKIGSLDNITHVPGGGN (SEQ ID NO: 1061)

GGGS (SEQ ID NO: 1062)

GGGGS (SEQ ID NO: 1063)

---

SEQUENCE LISTING

```
Sequence total quantity: 1063
SEQ ID NO: 1                   moltype = AA   length = 42
FEATURE                        Location/Qualifiers
REGION                         1..42
                               note = Synthetic peptide
source                         1..42
                               mol_type = protein
                               organism = synthetic construct
SEQUENCE: 1
DAEFRHDSGY EVHHQKLVFF AEDVGSNKGA IIGLMVGGVV IA                    42

SEQ ID NO: 2                   moltype = AA   length = 441
FEATURE                        Location/Qualifiers
REGION                         1..441
                               note = Synthetic peptide
source                         1..441
                               mol_type = protein
                               organism = synthetic construct
SEQUENCE: 2
MAEPRQEFEV MEDHAGTYGL GDRKDQGGYT MHQDQEGDTD AGLKESPLQT PTEDGSEEPG   60
SETSDAKSTP TAEDVTAPLV DEGAPGKQAA AQPHTEIPEG TTAEEAGIGD TPSLEDEAAG  120
HVTQARMVSK SKDGTGSDDK KAKGADGKTK IATPRGAAPP GQKGQANATR IPAKTPPAPK  180
TPPSSGEPPK SGDRSGYSSP GSPGTPGSRS RTPSLPTPPT REPKKVAVVR TPPKSPSSAK  240
SRLQTAPVPM PDLKNVKSKI GSTENLKHQP GGKVQIINK KLDLSNVQSK CGSKDNIKHV  300
PGGGSVQIVY KPVDLSKVTS KCGSLGNIHH KPGGGQVEVK SEKLDFKDRV QSKIGSLDNI  360
THVPGGGNKK IETHKLTFRE NAKAKTDHGA EIVYKSPVVS GDTSPRHLSN VSSTGSIDMV  420
DSPQLATLAD EVSASLAKQG L                                            441

SEQ ID NO: 3                   moltype = AA   length = 10
FEATURE                        Location/Qualifiers
REGION                         1..10
                               note = Synthetic peptide
source                         1..10
                               mol_type = protein
                               organism = synthetic construct
SEQUENCE: 3
DAEFRHDSGY                                                         10

SEQ ID NO: 4                   moltype = AA   length = 9
FEATURE                        Location/Qualifiers
REGION                         1..9
                               note = Synthetic peptide
source                         1..9
                               mol_type = protein
                               organism = synthetic construct
```

```
SEQUENCE: 4
DAEFRHDSG                                                                  9

SEQ ID NO: 5               moltype = AA  length = 8
FEATURE                    Location/Qualifiers
REGION                     1..8
                           note = Synthetic peptide
source                     1..8
                           mol_type = protein
                           organism = synthetic construct
SEQUENCE: 5
DAEFRHDS                                                                   8

SEQ ID NO: 6               moltype = AA  length = 7
FEATURE                    Location/Qualifiers
REGION                     1..7
                           note = Synthetic peptide
source                     1..7
                           mol_type = protein
                           organism = synthetic construct
SEQUENCE: 6
DAEFRHD                                                                    7

SEQ ID NO: 7               moltype = AA  length = 6
FEATURE                    Location/Qualifiers
REGION                     1..6
                           note = Synthetic peptide
source                     1..6
                           mol_type = protein
                           organism = synthetic construct
SEQUENCE: 7
DAEFRH                                                                     6

SEQ ID NO: 8               moltype = AA  length = 5
FEATURE                    Location/Qualifiers
REGION                     1..5
                           note = Synthetic peptide
source                     1..5
                           mol_type = protein
                           organism = synthetic construct
SEQUENCE: 8
DAEFR                                                                      5

SEQ ID NO: 9               moltype = AA  length = 4
FEATURE                    Location/Qualifiers
REGION                     1..4
                           note = Synthetic peptide
source                     1..4
                           mol_type = protein
                           organism = synthetic construct
SEQUENCE: 9
DAEF                                                                       4

SEQ ID NO: 10              moltype =    length =
SEQUENCE: 10
000

SEQ ID NO: 11              moltype = AA  length = 9
FEATURE                    Location/Qualifiers
REGION                     1..9
                           note = Synthetic peptide
source                     1..9
                           mol_type = protein
                           organism = synthetic construct
SEQUENCE: 11
AEFRHDSGY                                                                  9

SEQ ID NO: 12              moltype = AA  length = 8
FEATURE                    Location/Qualifiers
REGION                     1..8
                           note = Synthetic peptide
source                     1..8
                           mol_type = protein
                           organism = synthetic construct
SEQUENCE: 12
AEFRHDSG                                                                   8

SEQ ID NO: 13              moltype = AA  length = 7
FEATURE                    Location/Qualifiers
```

```
REGION                    1..7
                          note = Synthetic peptide
source                    1..7
                          mol_type = protein
                          organism = synthetic construct
SEQUENCE: 13
AEFRHDS                                                                  7

SEQ ID NO: 14             moltype = AA  length = 6
FEATURE                   Location/Qualifiers
REGION                    1..6
                          note = Synthetic peptide
source                    1..6
                          mol_type = protein
                          organism = synthetic construct
SEQUENCE: 14
AEFRHD                                                                   6

SEQ ID NO: 15             moltype = AA  length = 5
FEATURE                   Location/Qualifiers
REGION                    1..5
                          note = Synthetic peptide
source                    1..5
                          mol_type = protein
                          organism = synthetic construct
SEQUENCE: 15
AEFRH                                                                    5

SEQ ID NO: 16             moltype = AA  length = 4
FEATURE                   Location/Qualifiers
REGION                    1..4
                          note = Synthetic peptide
source                    1..4
                          mol_type = protein
                          organism = synthetic construct
SEQUENCE: 16
AEFR                                                                     4

SEQ ID NO: 17             moltype =     length =
SEQUENCE: 17
000

SEQ ID NO: 18             moltype = AA  length = 8
FEATURE                   Location/Qualifiers
REGION                    1..8
                          note = Synthetic peptide
source                    1..8
                          mol_type = protein
                          organism = synthetic construct
SEQUENCE: 18
EFRHDSGY                                                                 8

SEQ ID NO: 19             moltype = AA  length = 7
FEATURE                   Location/Qualifiers
REGION                    1..7
                          note = Synthetic peptide
source                    1..7
                          mol_type = protein
                          organism = synthetic construct
SEQUENCE: 19
EFRHDSG                                                                  7

SEQ ID NO: 20             moltype = AA  length = 6
FEATURE                   Location/Qualifiers
REGION                    1..6
                          note = Synthetic peptide
source                    1..6
                          mol_type = protein
                          organism = synthetic construct
SEQUENCE: 20
EFRHDS                                                                   6

SEQ ID NO: 21             moltype = AA  length = 5
FEATURE                   Location/Qualifiers
REGION                    1..5
                          note = Synthetic peptide
source                    1..5
                          mol_type = protein
                          organism = synthetic construct
```

```
SEQUENCE: 21
EFRHD                                                                    5

SEQ ID NO: 22           moltype = AA  length = 4
FEATURE                 Location/Qualifiers
REGION                  1..4
                        note = Synthetic peptide
source                  1..4
                        mol_type = protein
                        organism = synthetic construct
SEQUENCE: 22
EFRH                                                                     4

SEQ ID NO: 23           moltype =   length =
SEQUENCE: 23
000

SEQ ID NO: 24           moltype = AA  length = 7
FEATURE                 Location/Qualifiers
REGION                  1..7
                        note = Synthetic peptide
source                  1..7
                        mol_type = protein
                        organism = synthetic construct
SEQUENCE: 24
FRHDSGY                                                                  7

SEQ ID NO: 25           moltype = AA  length = 6
FEATURE                 Location/Qualifiers
REGION                  1..6
                        note = Synthetic peptide
source                  1..6
                        mol_type = protein
                        organism = synthetic construct
SEQUENCE: 25
FRHDSG                                                                   6

SEQ ID NO: 26           moltype = AA  length = 5
FEATURE                 Location/Qualifiers
REGION                  1..5
                        note = Synthetic peptide
source                  1..5
                        mol_type = protein
                        organism = synthetic construct
SEQUENCE: 26
FRHDS                                                                    5

SEQ ID NO: 27           moltype = AA  length = 4
FEATURE                 Location/Qualifiers
REGION                  1..4
                        note = Synthetic peptide
source                  1..4
                        mol_type = protein
                        organism = synthetic construct
SEQUENCE: 27
FRHD                                                                     4

SEQ ID NO: 28           moltype =   length =
SEQUENCE: 28
000

SEQ ID NO: 29           moltype = AA  length = 6
FEATURE                 Location/Qualifiers
REGION                  1..6
                        note = Synthetic peptide
source                  1..6
                        mol_type = protein
                        organism = synthetic construct
SEQUENCE: 29
RHDSGY                                                                   6

SEQ ID NO: 30           moltype = AA  length = 5
FEATURE                 Location/Qualifiers
REGION                  1..5
                        note = Synthetic peptide
source                  1..5
                        mol_type = protein
                        organism = synthetic construct
SEQUENCE: 30
```

```
RHDSG                                                                   5

SEQ ID NO: 31          moltype = AA  length = 4
FEATURE                Location/Qualifiers
REGION                 1..4
                       note = Synthetic peptide
source                 1..4
                       mol_type = protein
                       organism = synthetic construct
SEQUENCE: 31
RHDS                                                                    4

SEQ ID NO: 32          moltype =   length =
SEQUENCE: 32
000

SEQ ID NO: 33          moltype = AA  length = 5
FEATURE                Location/Qualifiers
REGION                 1..5
                       note = Synthetic peptide
source                 1..5
                       mol_type = protein
                       organism = synthetic construct
SEQUENCE: 33
HDSGY                                                                   5

SEQ ID NO: 34          moltype = AA  length = 4
FEATURE                Location/Qualifiers
REGION                 1..4
                       note = Synthetic peptide
source                 1..4
                       mol_type = protein
                       organism = synthetic construct
SEQUENCE: 34
HDSG                                                                    4

SEQ ID NO: 35          moltype =   length =
SEQUENCE: 35
000

SEQ ID NO: 36          moltype = AA  length = 4
FEATURE                Location/Qualifiers
REGION                 1..4
                       note = Synthetic peptide
source                 1..4
                       mol_type = protein
                       organism = synthetic construct
SEQUENCE: 36
DSGY                                                                    4

SEQ ID NO: 37          moltype =   length =
SEQUENCE: 37
000

SEQ ID NO: 38          moltype =   length =
SEQUENCE: 38
000

SEQ ID NO: 39          moltype = AA  length = 7
FEATURE                Location/Qualifiers
REGION                 1..7
                       note = Synthetic peptide
source                 1..7
                       mol_type = protein
                       organism = synthetic construct
SEQUENCE: 39
QIVYKPV                                                                 7

SEQ ID NO: 40          moltype = AA  length = 6
FEATURE                Location/Qualifiers
REGION                 1..6
                       note = Synthetic peptide
source                 1..6
                       mol_type = protein
                       organism = synthetic construct
SEQUENCE: 40
QIVYKP                                                                  6

SEQ ID NO: 41          moltype = AA  length = 7
```

```
                        -continued

FEATURE                 Location/Qualifiers
REGION                  1..7
                        note = Synthetic peptide
source                  1..7
                        mol_type = protein
                        organism = synthetic construct
SEQUENCE: 41
QIVYKSV                                                             7

SEQ ID NO: 42           moltype = AA   length = 7
FEATURE                 Location/Qualifiers
REGION                  1..7
                        note = Synthetic peptide
source                  1..7
                        mol_type = protein
                        organism = synthetic construct
SEQUENCE: 42
EIVYKSV                                                             7

SEQ ID NO: 43           moltype = AA   length = 7
FEATURE                 Location/Qualifiers
REGION                  1..7
                        note = Synthetic peptide
source                  1..7
                        mol_type = protein
                        organism = synthetic construct
SEQUENCE: 43
EIVYKSP                                                             7

SEQ ID NO: 44           moltype = AA   length = 7
FEATURE                 Location/Qualifiers
REGION                  1..7
                        note = Synthetic peptide
source                  1..7
                        mol_type = protein
                        organism = synthetic construct
SEQUENCE: 44
EIVYKPV                                                             7

SEQ ID NO: 45           moltype = AA   length = 7
FEATURE                 Location/Qualifiers
REGION                  1..7
                        note = Synthetic peptide
source                  1..7
                        mol_type = protein
                        organism = synthetic construct
SEQUENCE: 45
IVYKSPV                                                             7

SEQ ID NO: 46           moltype = AA   length = 4
FEATURE                 Location/Qualifiers
REGION                  1..4
                        note = Synthetic peptide
source                  1..4
                        mol_type = protein
                        organism = synthetic construct
SEQUENCE: 46
IVYK                                                                4

SEQ ID NO: 47           moltype = AA   length = 7
FEATURE                 Location/Qualifiers
REGION                  1..7
                        note = Synthetic peptide
source                  1..7
                        mol_type = protein
                        organism = synthetic construct
SEQUENCE: 47
CNIKHVP                                                             7

SEQ ID NO: 48           moltype = AA   length = 6
FEATURE                 Location/Qualifiers
REGION                  1..6
                        note = Synthetic peptide
source                  1..6
                        mol_type = protein
                        organism = synthetic construct
SEQUENCE: 48
NIKHVP                                                              6
```

```
SEQ ID NO: 49          moltype = AA   length = 6
FEATURE                Location/Qualifiers
REGION                 1..6
                       note = Synthetic peptide
source                 1..6
                       mol_type = protein
                       organism = synthetic construct
SEQUENCE: 49
HVPGGG                                                                   6

SEQ ID NO: 50          moltype = AA   length = 5
FEATURE                Location/Qualifiers
REGION                 1..5
                       note = Synthetic peptide
source                 1..5
                       mol_type = protein
                       organism = synthetic construct
SEQUENCE: 50
HVPGG                                                                    5

SEQ ID NO: 51          moltype = AA   length = 6
FEATURE                Location/Qualifiers
REGION                 1..6
                       note = Synthetic peptide
source                 1..6
                       mol_type = protein
                       organism = synthetic construct
SEQUENCE: 51
HKPGGG                                                                   6

SEQ ID NO: 52          moltype = AA   length = 5
FEATURE                Location/Qualifiers
REGION                 1..5
                       note = Synthetic peptide
source                 1..5
                       mol_type = protein
                       organism = synthetic construct
SEQUENCE: 52
HKPGG                                                                    5

SEQ ID NO: 53          moltype = AA   length = 7
FEATURE                Location/Qualifiers
REGION                 1..7
                       note = Synthetic peptide
source                 1..7
                       mol_type = protein
                       organism = synthetic construct
SEQUENCE: 53
KHVPGGG                                                                  7

SEQ ID NO: 54          moltype = AA   length = 6
FEATURE                Location/Qualifiers
REGION                 1..6
                       note = Synthetic peptide
source                 1..6
                       mol_type = protein
                       organism = synthetic construct
SEQUENCE: 54
KHVPGG                                                                   6

SEQ ID NO: 55          moltype = AA   length = 6
FEATURE                Location/Qualifiers
REGION                 1..6
                       note = Synthetic peptide
source                 1..6
                       mol_type = protein
                       organism = synthetic construct
SEQUENCE: 55
HQPGGG                                                                   6

SEQ ID NO: 56          moltype = AA   length = 5
FEATURE                Location/Qualifiers
REGION                 1..5
                       note = Synthetic peptide
source                 1..5
                       mol_type = protein
                       organism = synthetic construct
SEQUENCE: 56
HQPGG                                                                    5
```

```
SEQ ID NO: 57          moltype = AA   length = 16
FEATURE                Location/Qualifiers
REGION                 1..16
                       note = Synthetic peptide
source                 1..16
                       mol_type = protein
                       organism = synthetic construct
SEQUENCE: 57
DAEFRHDRRQ IVYKPV                                                    16

SEQ ID NO: 58          moltype = AA   length = 16
FEATURE                Location/Qualifiers
REGION                 1..16
                       note = Synthetic peptide
source                 1..16
                       mol_type = protein
                       organism = synthetic construct
SEQUENCE: 58
DAEFRHDRRE IVYKSV                                                    16

SEQ ID NO: 59          moltype = AA   length = 19
FEATURE                Location/Qualifiers
REGION                 1..19
                       note = Synthetic peptide
source                 1..19
                       mol_type = protein
                       organism = synthetic construct
SEQUENCE: 59
DAEFRHDRRQ IVYKPVGGC                                                 19

SEQ ID NO: 60          moltype = AA   length = 17
FEATURE                Location/Qualifiers
REGION                 1..17
                       note = Synthetic peptide
source                 1..17
                       mol_type = protein
                       organism = synthetic construct
SEQUENCE: 60
DAEFRHDRRQ IVYKPVC                                                   17

SEQ ID NO: 61          moltype = AA   length = 19
FEATURE                Location/Qualifiers
REGION                 1..19
                       note = Synthetic peptide
source                 1..19
                       mol_type = protein
                       organism = synthetic construct
SEQUENCE: 61
DAEFRHDRRQ IVYKPVAAC                                                 19

SEQ ID NO: 62          moltype = AA   length = 19
FEATURE                Location/Qualifiers
REGION                 1..19
                       note = Synthetic peptide
source                 1..19
                       mol_type = protein
                       organism = synthetic construct
SEQUENCE: 62
DAEFRHDRRQ IVYKPVKKC                                                 19

SEQ ID NO: 63          moltype = AA   length = 19
FEATURE                Location/Qualifiers
REGION                 1..19
                       note = Synthetic peptide
source                 1..19
                       mol_type = protein
                       organism = synthetic construct
SEQUENCE: 63
DAEFRHDRRE IVYKSPGGC                                                 19

SEQ ID NO: 64          moltype = AA   length = 19
FEATURE                Location/Qualifiers
REGION                 1..19
                       note = Synthetic peptide
source                 1..19
                       mol_type = protein
                       organism = synthetic construct
SEQUENCE: 64
```

```
DAEFRHDRRE IVYKSPAAC                                                     19

SEQ ID NO: 65           moltype = AA   length = 17
FEATURE                 Location/Qualifiers
REGION                  1..17
                        note = Synthetic peptide
source                  1..17
                        mol_type = protein
                        organism = synthetic construct
SEQUENCE: 65
DAEFRHDRRE IVYKSPC                                                       17

SEQ ID NO: 66           moltype = AA   length = 19
FEATURE                 Location/Qualifiers
REGION                  1..19
                        note = Synthetic peptide
source                  1..19
                        mol_type = protein
                        organism = synthetic construct
SEQUENCE: 66
DAEFRHDRRE IVYKSPKKC                                                     19

SEQ ID NO: 67           moltype = AA   length = 28
FEATURE                 Location/Qualifiers
REGION                  1..28
                        note = Synthetic peptide
source                  1..28
                        mol_type = protein
                        organism = synthetic construct
SEQUENCE: 67
DAEFRHDSGY EVHHQKLFFA EDVGSNKG                                           28

SEQ ID NO: 68           moltype = AA   length = 15
FEATURE                 Location/Qualifiers
REGION                  1..15
                        note = Synthetic peptide
source                  1..15
                        mol_type = protein
                        organism = synthetic construct
SEQUENCE: 68
GGGSVQIVYK PVDLS                                                         15

SEQ ID NO: 69           moltype = AA   length = 4
FEATURE                 Location/Qualifiers
REGION                  1..4
                        note = Synthetic peptide
source                  1..4
                        mol_type = protein
                        organism = synthetic construct
SEQUENCE: 69
RVRR                                                                     4

SEQ ID NO: 70           moltype = AA   length = 19
FEATURE                 Location/Qualifiers
REGION                  1..19
                        note = Synthetic peptide
VAR_SEQ                 17
                        note = MISC_FEATURE - Xaa can be GG or AA or KK or SS
source                  1..19
                        mol_type = protein
                        organism = synthetic construct
VAR_SEQ                 18
                        note = MISC_FEATURE - Xaacan be GG or AA or KK or SS
SEQUENCE: 70
DAEFRHDRRQ IVYKPVXXC                                                     19

SEQ ID NO: 71           moltype = AA   length = 8
FEATURE                 Location/Qualifiers
REGION                  1..8
                        note = Synthetic peptide
source                  1..8
                        mol_type = protein
                        organism = synthetic construct
SEQUENCE: 71
DAEFRHDC                                                                 8

SEQ ID NO: 72           moltype = AA   length = 10
FEATURE                 Location/Qualifiers
REGION                  1..10
```

```
                            note = Synthetic peptide
source                      1..10
                            mol_type = protein
                            organism = synthetic construct
SEQUENCE: 72
QIVYKPVGGC                                                                      10

SEQ ID NO: 73               moltype = AA  length = 13
FEATURE                     Location/Qualifiers
REGION                      1..13
                            note = Synthetic peptide
source                      1..13
                            mol_type = protein
                            organism = synthetic construct
SEQUENCE: 73
GGSQIVYKPV DLS                                                                  13

SEQ ID NO: 74               moltype = AA  length = 19
FEATURE                     Location/Qualifiers
REGION                      1..19
                            note = Synthetic peptide
source                      1..19
                            mol_type = protein
                            organism = synthetic construct
SEQUENCE: 74
DAEFRHDRRE IVYKSVGGC                                                            19

SEQ ID NO: 75               moltype = AA  length = 19
FEATURE                     Location/Qualifiers
REGION                      1..19
                            note = Synthetic peptide
source                      1..19
                            mol_type = protein
                            organism = synthetic construct
SEQUENCE: 75
DAEFRHDRRE IVYKSVAAC                                                            19

SEQ ID NO: 76               moltype = AA  length = 17
FEATURE                     Location/Qualifiers
REGION                      1..17
                            note = Synthetic peptide
source                      1..17
                            mol_type = protein
                            organism = synthetic construct
SEQUENCE: 76
DAEFRHDRRE IVYKSVC                                                              17

SEQ ID NO: 77               moltype = AA  length = 19
FEATURE                     Location/Qualifiers
REGION                      1..19
                            note = Synthetic peptide
source                      1..19
                            mol_type = protein
                            organism = synthetic construct
SEQUENCE: 77
DAEFRHDRRE IVYKSVKKC                                                            19

SEQ ID NO: 78               moltype = AA  length = 18
FEATURE                     Location/Qualifiers
REGION                      1..18
                            note = Synthetic peptide
source                      1..18
                            mol_type = protein
                            organism = synthetic construct
SEQUENCE: 78
DAEFRHDRRN IKHVPGGC                                                             18

SEQ ID NO: 79               moltype = AA  length = 19
FEATURE                     Location/Qualifiers
REGION                      1..19
                            note = Synthetic peptide
VAR_SEQ                     17
                            note = MISC_FEATURE - Xaa can be GG or AA or KK or SS
source                      1..19
                            mol_type = protein
                            organism = synthetic construct
VAR_SEQ                     18
                            note = MISC_FEATURE - Xaa can be GG or AA or KK or SS
SEQUENCE: 79
```

DAEFRHDRRE IVYKSVXXC                                                     19

```
SEQ ID NO: 80          moltype = AA  length = 4
FEATURE                Location/Qualifiers
REGION                 1..4
                       note = Synthetic peptide
source                 1..4
                       mol_type = protein
                       organism = synthetic construct
SEQUENCE: 80
GAGA                                                                      4

SEQ ID NO: 81          moltype = AA  length = 4
FEATURE                Location/Qualifiers
REGION                 1..4
                       note = Synthetic peptide
source                 1..4
                       mol_type = protein
                       organism = synthetic construct
SEQUENCE: 81
AGAG                                                                      4

SEQ ID NO: 82          moltype = AA  length = 4
FEATURE                Location/Qualifiers
REGION                 1..4
                       note = Synthetic peptide
source                 1..4
                       mol_type = protein
                       organism = synthetic construct
SEQUENCE: 82
KGKG                                                                      4

SEQ ID NO: 83          moltype = AA  length = 6
FEATURE                Location/Qualifiers
REGION                 1..6
                       note = Synthetic peptide
source                 1..6
                       mol_type = protein
                       organism = synthetic construct
SEQUENCE: 83
QIVYKS                                                                    6

SEQ ID NO: 84          moltype = AA  length = 6
FEATURE                Location/Qualifiers
REGION                 1..6
                       note = Synthetic peptide
source                 1..6
                       mol_type = protein
                       organism = synthetic construct
SEQUENCE: 84
EIVYKS                                                                    6

SEQ ID NO: 85          moltype = AA  length = 6
FEATURE                Location/Qualifiers
REGION                 1..6
                       note = Synthetic peptide
source                 1..6
                       mol_type = protein
                       organism = synthetic construct
SEQUENCE: 85
EIVYKP                                                                    6

SEQ ID NO: 86          moltype = AA  length = 8
FEATURE                Location/Qualifiers
REGION                 1..8
                       note = Synthetic peptide
source                 1..8
                       mol_type = protein
                       organism = synthetic construct
SEQUENCE: 86
CNIKHVPG                                                                  8

SEQ ID NO: 87          moltype =    length =
SEQUENCE: 87
000

SEQ ID NO: 88          moltype =    length =
SEQUENCE: 88
000
```

| | | |
|---|---|---|
| SEQ ID NO: 89  SEQUENCE: 89 | moltype = | length = 000 |
| SEQ ID NO: 90  SEQUENCE: 90 | moltype = | length = 000 |
| SEQ ID NO: 91  SEQUENCE: 91 | moltype = | length = 000 |
| SEQ ID NO: 92  SEQUENCE: 92 | moltype = | length = 000 |
| SEQ ID NO: 93  SEQUENCE: 93 | moltype = | length = 000 |
| SEQ ID NO: 94  SEQUENCE: 94 | moltype = | length = 000 |
| SEQ ID NO: 95  SEQUENCE: 95 | moltype = | length = 000 |
| SEQ ID NO: 96  SEQUENCE: 96 | moltype = | length = 000 |
| SEQ ID NO: 97  SEQUENCE: 97 | moltype = | length = 000 |
| SEQ ID NO: 98  SEQUENCE: 98 | moltype = | length = 000 |
| SEQ ID NO: 99  SEQUENCE: 99 | moltype = | length = 000 |
| SEQ ID NO: 100  SEQUENCE: 100 | moltype = | length = 000 |
| SEQ ID NO: 101  SEQUENCE: 101 | moltype = | length = 000 |
| SEQ ID NO: 102  SEQUENCE: 102 | moltype = | length = 000 |
| SEQ ID NO: 103  SEQUENCE: 103 | moltype = | length = 000 |
| SEQ ID NO: 104  SEQUENCE: 104 | moltype = | length = 000 |
| SEQ ID NO: 105  SEQUENCE: 105 | moltype = | length = 000 |
| SEQ ID NO: 106  SEQUENCE: 106 | moltype = | length = 000 |
| SEQ ID NO: 107  SEQUENCE: 107 | moltype = | length = 000 |
| SEQ ID NO: 108  SEQUENCE: 108 | moltype = | length = |

```
SEQ ID NO: 109           moltype =     length =
SEQUENCE: 109
000

SEQ ID NO: 110           moltype =     length =
SEQUENCE: 110
000

SEQ ID NO: 111           moltype =     length =
SEQUENCE: 111
000

SEQ ID NO: 112           moltype =     length =
SEQUENCE: 112
000

SEQ ID NO: 113           moltype =     length =
SEQUENCE: 113
000

SEQ ID NO: 114           moltype =     length =
SEQUENCE: 114
000

SEQ ID NO: 115           moltype =     length =
SEQUENCE: 115
000

SEQ ID NO: 116           moltype =     length =
SEQUENCE: 116
000

SEQ ID NO: 117           moltype =     length =
SEQUENCE: 117
000

SEQ ID NO: 118           moltype =     length =
SEQUENCE: 118
000

SEQ ID NO: 119           moltype =     length =
SEQUENCE: 119
000

SEQ ID NO: 120           moltype =     length =
SEQUENCE: 120
000

SEQ ID NO: 121           moltype =     length =
SEQUENCE: 121
000

SEQ ID NO: 122           moltype =     length =
SEQUENCE: 122
000

SEQ ID NO: 123           moltype =     length =
SEQUENCE: 123
000

SEQ ID NO: 124           moltype =     length =
SEQUENCE: 124
000

SEQ ID NO: 125           moltype =     length =
SEQUENCE: 125
000

SEQ ID NO: 126           moltype =     length =
SEQUENCE: 126
000

SEQ ID NO: 127           moltype =     length =
SEQUENCE: 127
000

SEQ ID NO: 128           moltype =     length =
```

```
SEQUENCE: 128
000

SEQ ID NO: 129          moltype =    length =
SEQUENCE: 129
000

SEQ ID NO: 130          moltype =    length =
SEQUENCE: 130
000

SEQ ID NO: 131          moltype =    length =
SEQUENCE: 131
000

SEQ ID NO: 132          moltype =    length =
SEQUENCE: 132
000

SEQ ID NO: 133          moltype =    length =
SEQUENCE: 133
000

SEQ ID NO: 134          moltype =    length =
SEQUENCE: 134
000

SEQ ID NO: 135          moltype =    length =
SEQUENCE: 135
000

SEQ ID NO: 136          moltype =    length =
SEQUENCE: 136
000

SEQ ID NO: 137          moltype =    length =
SEQUENCE: 137
000

SEQ ID NO: 138          moltype =    length =
SEQUENCE: 138
000

SEQ ID NO: 139          moltype =    length =
SEQUENCE: 139
000

SEQ ID NO: 140          moltype =    length =
SEQUENCE: 140
000

SEQ ID NO: 141          moltype =    length =
SEQUENCE: 141
000

SEQ ID NO: 142          moltype =    length =
SEQUENCE: 142
000

SEQ ID NO: 143          moltype =    length =
SEQUENCE: 143
000

SEQ ID NO: 144          moltype =    length =
SEQUENCE: 144
000

SEQ ID NO: 145          moltype =    length =
SEQUENCE: 145
000

SEQ ID NO: 146          moltype = AA  length = 6
FEATURE                 Location/Qualifiers
REGION                  1..6
                        note = Synthetic peptide
source                  1..6
                        mol_type = protein
                        organism = synthetic construct
SEQUENCE: 146
```

```
VQIINK                                                                          6

SEQ ID NO: 147          moltype = AA   length = 7
FEATURE                 Location/Qualifiers
REGION                  1..7
                        note = Synthetic peptide
source                  1..7
                        mol_type = protein
                        organism = synthetic construct
SEQUENCE: 147
VQIINKK                                                                         7

SEQ ID NO: 148          moltype = AA   length = 8
FEATURE                 Location/Qualifiers
REGION                  1..8
                        note = Synthetic peptide
source                  1..8
                        mol_type = protein
                        organism = synthetic construct
SEQUENCE: 148
VQIINKKL                                                                        8

SEQ ID NO: 149          moltype = AA   length = 5
FEATURE                 Location/Qualifiers
REGION                  1..5
                        note = Synthetic peptide
source                  1..5
                        mol_type = protein
                        organism = synthetic construct
SEQUENCE: 149
QIINK                                                                           5

SEQ ID NO: 150          moltype = AA   length = 6
FEATURE                 Location/Qualifiers
REGION                  1..6
                        note = Synthetic peptide
source                  1..6
                        mol_type = protein
                        organism = synthetic construct
SEQUENCE: 150
QIINKK                                                                          6

SEQ ID NO: 151          moltype = AA   length = 7
FEATURE                 Location/Qualifiers
REGION                  1..7
                        note = Synthetic peptide
source                  1..7
                        mol_type = protein
                        organism = synthetic construct
SEQUENCE: 151
QIINKKL                                                                         7

SEQ ID NO: 152          moltype = AA   length = 9
FEATURE                 Location/Qualifiers
REGION                  1..9
                        note = Synthetic peptide
source                  1..9
                        mol_type = protein
                        organism = synthetic construct
SEQUENCE: 152
EAAGHVTQC                                                                       9

SEQ ID NO: 153          moltype = AA   length = 10
FEATURE                 Location/Qualifiers
REGION                  1..10
                        note = Synthetic peptide
source                  1..10
                        mol_type = protein
                        organism = synthetic construct
SEQUENCE: 153
EAAGHVTQAR                                                                      10

SEQ ID NO: 154          moltype = AA   length = 9
FEATURE                 Location/Qualifiers
REGION                  1..9
                        note = Synthetic peptide
source                  1..9
                        mol_type = protein
                        organism = synthetic construct
```

-continued

```
SEQUENCE: 154
AAGHVTQAC                                                                    9

SEQ ID NO: 155          moltype = AA  length = 9
FEATURE                 Location/Qualifiers
REGION                  1..9
                        note = Synthetic peptide
source                  1..9
                        mol_type = protein
                        organism = synthetic construct
SEQUENCE: 155
AGHVTQARC                                                                    9

SEQ ID NO: 156          moltype = AA  length = 8
FEATURE                 Location/Qualifiers
REGION                  1..8
                        note = Synthetic peptide
source                  1..8
                        mol_type = protein
                        organism = synthetic construct
SEQUENCE: 156
AGHVTQAR                                                                     8

SEQ ID NO: 157          moltype = AA  length = 7
FEATURE                 Location/Qualifiers
REGION                  1..7
                        note = Synthetic peptide
source                  1..7
                        mol_type = protein
                        organism = synthetic construct
SEQUENCE: 157
GYTMHQD                                                                      7

SEQ ID NO: 158          moltype = AA  length = 8
FEATURE                 Location/Qualifiers
REGION                  1..8
                        note = Synthetic peptide
source                  1..8
                        mol_type = protein
                        organism = synthetic construct
SEQUENCE: 158
QGGYTMHC                                                                     8

SEQ ID NO: 159          moltype = AA  length = 9
FEATURE                 Location/Qualifiers
REGION                  1..9
                        note = Synthetic peptide
source                  1..9
                        mol_type = protein
                        organism = synthetic construct
SEQUENCE: 159
QGGYTMHQD                                                                    9

SEQ ID NO: 160          moltype = AA  length = 8
FEATURE                 Location/Qualifiers
REGION                  1..8
                        note = Synthetic peptide
source                  1..8
                        mol_type = protein
                        organism = synthetic construct
SEQUENCE: 160
GGYTMHQC                                                                     8

SEQ ID NO: 161          moltype = AA  length = 10
FEATURE                 Location/Qualifiers
REGION                  1..10
                        note = Synthetic peptide
source                  1..10
                        mol_type = protein
                        organism = synthetic construct
SEQUENCE: 161
VPGGGSVQIV                                                                  10

SEQ ID NO: 162          moltype = AA  length = 9
FEATURE                 Location/Qualifiers
REGION                  1..9
                        note = Synthetic peptide
source                  1..9
                        mol_type = protein
```

```
                                    -continued
                   organism = synthetic construct
SEQUENCE: 162
PGGGSVQIV                                                                9

SEQ ID NO: 163     moltype = AA   length = 8
FEATURE            Location/Qualifiers
REGION             1..8
                   note = Synthetic peptide
source             1..8
                   mol_type = protein
                   organism = synthetic construct
SEQUENCE: 163
GGGSVQIV                                                                 8

SEQ ID NO: 164     moltype = AA   length = 7
FEATURE            Location/Qualifiers
REGION             1..7
                   note = Synthetic peptide
source             1..7
                   mol_type = protein
                   organism = synthetic construct
SEQUENCE: 164
GGSVQIV                                                                  7

SEQ ID NO: 165     moltype = AA   length = 6
FEATURE            Location/Qualifiers
REGION             1..6
                   note = Synthetic peptide
source             1..6
                   mol_type = protein
                   organism = synthetic construct
SEQUENCE: 165
GSVQIV                                                                   6

SEQ ID NO: 166     moltype = AA   length = 5
FEATURE            Location/Qualifiers
REGION             1..5
                   note = Synthetic peptide
source             1..5
                   mol_type = protein
                   organism = synthetic construct
SEQUENCE: 166
SVQIV                                                                    5

SEQ ID NO: 167     moltype = AA   length = 4
FEATURE            Location/Qualifiers
REGION             1..4
                   note = Synthetic peptide
source             1..4
                   mol_type = protein
                   organism = synthetic construct
SEQUENCE: 167
VQIV                                                                     4

SEQ ID NO: 168     moltype =    length =
SEQUENCE: 168
000

SEQ ID NO: 169     moltype = AA   length = 10
FEATURE            Location/Qualifiers
REGION             1..10
                   note = Synthetic peptide
source             1..10
                   mol_type = protein
                   organism = synthetic construct
SEQUENCE: 169
PGGGSVQIVY                                                              10

SEQ ID NO: 170     moltype = AA   length = 9
FEATURE            Location/Qualifiers
REGION             1..9
                   note = Synthetic peptide
source             1..9
                   mol_type = protein
                   organism = synthetic construct
SEQUENCE: 170
GGGSVQIVY                                                                9

SEQ ID NO: 171     moltype = AA   length = 8
```

```
FEATURE              Location/Qualifiers
REGION               1..8
                     note = Synthetic peptide
source               1..8
                     mol_type = protein
                     organism = synthetic construct
SEQUENCE: 171
GGSVQIVY                                                                  8

SEQ ID NO: 172       moltype = AA  length = 7
FEATURE              Location/Qualifiers
REGION               1..7
                     note = Synthetic peptide
source               1..7
                     mol_type = protein
                     organism = synthetic construct
SEQUENCE: 172
GSVQIVY                                                                   7

SEQ ID NO: 173       moltype = AA  length = 6
FEATURE              Location/Qualifiers
REGION               1..6
                     note = Synthetic peptide
source               1..6
                     mol_type = protein
                     organism = synthetic construct
SEQUENCE: 173
SVQIVY                                                                    6

SEQ ID NO: 174       moltype = AA  length = 5
FEATURE              Location/Qualifiers
REGION               1..5
                     note = Synthetic peptide
source               1..5
                     mol_type = protein
                     organism = synthetic construct
SEQUENCE: 174
VQIVY                                                                     5

SEQ ID NO: 175       moltype = AA  length = 4
FEATURE              Location/Qualifiers
REGION               1..4
                     note = Synthetic peptide
source               1..4
                     mol_type = protein
                     organism = synthetic construct
SEQUENCE: 175
QIVY                                                                      4

SEQ ID NO: 176       moltype =    length =
SEQUENCE: 176
000

SEQ ID NO: 177       moltype = AA  length = 10
FEATURE              Location/Qualifiers
REGION               1..10
                     note = Synthetic peptide
source               1..10
                     mol_type = protein
                     organism = synthetic construct
SEQUENCE: 177
GGGSVQIVYK                                                               10

SEQ ID NO: 178       moltype = AA  length = 9
FEATURE              Location/Qualifiers
REGION               1..9
                     note = Synthetic peptide
source               1..9
                     mol_type = protein
                     organism = synthetic construct
SEQUENCE: 178
GGSVQIVYK                                                                 9

SEQ ID NO: 179       moltype = AA  length = 8
FEATURE              Location/Qualifiers
REGION               1..8
                     note = Synthetic peptide
source               1..8
                     mol_type = protein
```

```
SEQUENCE: 179
GSVQIVYK                                                               8

SEQ ID NO: 180          moltype = AA   length = 7
FEATURE                 Location/Qualifiers
REGION                  1..7
                        note = Synthetic peptide
source                  1..7
                        mol_type = protein
                        organism = synthetic construct
SEQUENCE: 180
SVQIVYK                                                                7

SEQ ID NO: 181          moltype = AA   length = 6
FEATURE                 Location/Qualifiers
REGION                  1..6
                        note = Synthetic peptide
source                  1..6
                        mol_type = protein
                        organism = synthetic construct
SEQUENCE: 181
VQIVYK                                                                 6

SEQ ID NO: 182          moltype = AA   length = 5
FEATURE                 Location/Qualifiers
REGION                  1..5
                        note = Synthetic peptide
source                  1..5
                        mol_type = protein
                        organism = synthetic construct
SEQUENCE: 182
QIVYK                                                                  5

SEQ ID NO: 183          moltype =    length =
SEQUENCE: 183
000

SEQ ID NO: 184          moltype = AA   length = 10
FEATURE                 Location/Qualifiers
REGION                  1..10
                        note = Synthetic peptide
source                  1..10
                        mol_type = protein
                        organism = synthetic construct
SEQUENCE: 184
GGSVQIVYKP                                                             10

SEQ ID NO: 185          moltype = AA   length = 9
FEATURE                 Location/Qualifiers
REGION                  1..9
                        note = Synthetic peptide
source                  1..9
                        mol_type = protein
                        organism = synthetic construct
SEQUENCE: 185
GSVQIVYKP                                                              9

SEQ ID NO: 186          moltype = AA   length = 8
FEATURE                 Location/Qualifiers
REGION                  1..8
                        note = Synthetic peptide
source                  1..8
                        mol_type = protein
                        organism = synthetic construct
SEQUENCE: 186
SVQIVYKP                                                               8

SEQ ID NO: 187          moltype = AA   length = 7
FEATURE                 Location/Qualifiers
REGION                  1..7
                        note = Synthetic peptide
source                  1..7
                        mol_type = protein
                        organism = synthetic construct
SEQUENCE: 187
VQIVYKP                                                                7

SEQ ID NO: 188          moltype = AA   length = 5
```

```
FEATURE             Location/Qualifiers
REGION              1..5
                    note = Synthetic peptide
source              1..5
                    mol_type = protein
                    organism = synthetic construct
SEQUENCE: 188
IVYKP                                                                        5

SEQ ID NO: 189      moltype = AA  length = 4
FEATURE             Location/Qualifiers
REGION              1..4
                    note = Synthetic peptide
source              1..4
                    mol_type = protein
                    organism = synthetic construct
SEQUENCE: 189
VYKP                                                                         4

SEQ ID NO: 190      moltype =    length =
SEQUENCE: 190
000

SEQ ID NO: 191      moltype = AA  length = 10
FEATURE             Location/Qualifiers
REGION              1..10
                    note = Synthetic peptide
source              1..10
                    mol_type = protein
                    organism = synthetic construct
SEQUENCE: 191
GSVQIVYKPV                                                                  10

SEQ ID NO: 192      moltype = AA  length = 9
FEATURE             Location/Qualifiers
REGION              1..9
                    note = Synthetic peptide
source              1..9
                    mol_type = protein
                    organism = synthetic construct
SEQUENCE: 192
SVQIVYKPV                                                                    9

SEQ ID NO: 193      moltype = AA  length = 8
FEATURE             Location/Qualifiers
REGION              1..8
                    note = Synthetic peptide
source              1..8
                    mol_type = protein
                    organism = synthetic construct
SEQUENCE: 193
VQIVYKPV                                                                     8

SEQ ID NO: 194      moltype = AA  length = 6
FEATURE             Location/Qualifiers
REGION              1..6
                    note = Synthetic peptide
source              1..6
                    mol_type = protein
                    organism = synthetic construct
SEQUENCE: 194
IVYKPV                                                                       6

SEQ ID NO: 195      moltype = AA  length = 5
FEATURE             Location/Qualifiers
REGION              1..5
                    note = Synthetic peptide
source              1..5
                    mol_type = protein
                    organism = synthetic construct
SEQUENCE: 195
VYKPV                                                                        5

SEQ ID NO: 196      moltype = AA  length = 4
FEATURE             Location/Qualifiers
REGION              1..4
                    note = Synthetic peptide
source              1..4
                    mol_type = protein
```

```
                                organism = synthetic construct
SEQUENCE: 196
YKPV                                                                          4

SEQ ID NO: 197          moltype =    length =
SEQUENCE: 197
000

SEQ ID NO: 198          moltype = AA   length = 10
FEATURE                 Location/Qualifiers
REGION                  1..10
                        note = Synthetic peptide
source                  1..10
                        mol_type = protein
                        organism = synthetic construct
SEQUENCE: 198
SVQIVYKPVD                                                                   10

SEQ ID NO: 199          moltype = AA   length = 9
FEATURE                 Location/Qualifiers
REGION                  1..9
                        note = Synthetic peptide
source                  1..9
                        mol_type = protein
                        organism = synthetic construct
SEQUENCE: 199
VQIVYKPVD                                                                     9

SEQ ID NO: 200          moltype = AA   length = 8
FEATURE                 Location/Qualifiers
REGION                  1..8
                        note = Synthetic peptide
source                  1..8
                        mol_type = protein
                        organism = synthetic construct
SEQUENCE: 200
QIVYKPVD                                                                      8

SEQ ID NO: 201          moltype = AA   length = 7
FEATURE                 Location/Qualifiers
REGION                  1..7
                        note = Synthetic peptide
source                  1..7
                        mol_type = protein
                        organism = synthetic construct
SEQUENCE: 201
IVYKPVD                                                                       7

SEQ ID NO: 202          moltype =    length =
SEQUENCE: 202
000

SEQ ID NO: 203          moltype = AA   length = 6
FEATURE                 Location/Qualifiers
REGION                  1..6
                        note = Synthetic peptide
source                  1..6
                        mol_type = protein
                        organism = synthetic construct
SEQUENCE: 203
VYKPVD                                                                        6

SEQ ID NO: 204          moltype = AA   length = 5
FEATURE                 Location/Qualifiers
REGION                  1..5
                        note = Synthetic peptide
source                  1..5
                        mol_type = protein
                        organism = synthetic construct
SEQUENCE: 204
YKPVD                                                                         5

SEQ ID NO: 205          moltype = AA   length = 4
FEATURE                 Location/Qualifiers
REGION                  1..4
                        note = Synthetic peptide
source                  1..4
                        mol_type = protein
                        organism = synthetic construct
```

```
SEQUENCE: 205
KPVD                                                                       4

SEQ ID NO: 206         moltype =   length =
SEQUENCE: 206
000

SEQ ID NO: 207         moltype = AA  length = 10
FEATURE                Location/Qualifiers
REGION                 1..10
                       note = Synthetic peptide
source                 1..10
                       mol_type = protein
                       organism = synthetic construct
SEQUENCE: 207
VQIVYKPVDL                                                                10

SEQ ID NO: 208         moltype = AA  length = 9
FEATURE                Location/Qualifiers
REGION                 1..9
                       note = Synthetic peptide
source                 1..9
                       mol_type = protein
                       organism = synthetic construct
SEQUENCE: 208
QIVYKPVDL                                                                  9

SEQ ID NO: 209         moltype = AA  length = 8
FEATURE                Location/Qualifiers
REGION                 1..8
                       note = Synthetic peptide
source                 1..8
                       mol_type = protein
                       organism = synthetic construct
SEQUENCE: 209
IVYKPVDL                                                                   8

SEQ ID NO: 210         moltype = AA  length = 7
FEATURE                Location/Qualifiers
REGION                 1..7
                       note = Synthetic peptide
source                 1..7
                       mol_type = protein
                       organism = synthetic construct
SEQUENCE: 210
VYKPVDL                                                                    7

SEQ ID NO: 211         moltype = AA  length = 6
FEATURE                Location/Qualifiers
REGION                 1..6
                       note = Synthetic peptide
source                 1..6
                       mol_type = protein
                       organism = synthetic construct
SEQUENCE: 211
YKPVDL                                                                     6

SEQ ID NO: 212         moltype = AA  length = 5
FEATURE                Location/Qualifiers
REGION                 1..5
                       note = Synthetic peptide
source                 1..5
                       mol_type = protein
                       organism = synthetic construct
SEQUENCE: 212
KPVDL                                                                      5

SEQ ID NO: 213         moltype = AA  length = 4
FEATURE                Location/Qualifiers
REGION                 1..4
                       note = Synthetic peptide
source                 1..4
                       mol_type = protein
                       organism = synthetic construct
SEQUENCE: 213
PVDL                                                                       4

SEQ ID NO: 214         moltype =   length =
SEQUENCE: 214
```

```
000

SEQ ID NO: 215            moltype = AA   length = 10
FEATURE                   Location/Qualifiers
REGION                    1..10
                          note = Synthetic peptide
source                    1..10
                          mol_type = protein
                          organism = synthetic construct
SEQUENCE: 215
QIVYKPVDLS                                                         10

SEQ ID NO: 216            moltype = AA   length = 9
FEATURE                   Location/Qualifiers
REGION                    1..9
                          note = Synthetic peptide
source                    1..9
                          mol_type = protein
                          organism = synthetic construct
SEQUENCE: 216
IVYKPVDLS                                                           9

SEQ ID NO: 217            moltype = AA   length = 8
FEATURE                   Location/Qualifiers
REGION                    1..8
                          note = Synthetic peptide
source                    1..8
                          mol_type = protein
                          organism = synthetic construct
SEQUENCE: 217
VYKPVDLS                                                            8

SEQ ID NO: 218            moltype = AA   length = 7
FEATURE                   Location/Qualifiers
REGION                    1..7
                          note = Synthetic peptide
source                    1..7
                          mol_type = protein
                          organism = synthetic construct
SEQUENCE: 218
YKPVDLS                                                             7

SEQ ID NO: 219            moltype = AA   length = 6
FEATURE                   Location/Qualifiers
REGION                    1..6
                          note = Synthetic peptide
source                    1..6
                          mol_type = protein
                          organism = synthetic construct
SEQUENCE: 219
KPVDLS                                                              6

SEQ ID NO: 220            moltype = AA   length = 5
FEATURE                   Location/Qualifiers
REGION                    1..5
                          note = Synthetic peptide
source                    1..5
                          mol_type = protein
                          organism = synthetic construct
SEQUENCE: 220
PVDLS                                                               5

SEQ ID NO: 221            moltype = AA   length = 4
FEATURE                   Location/Qualifiers
REGION                    1..4
                          note = Synthetic peptide
source                    1..4
                          mol_type = protein
                          organism = synthetic construct
SEQUENCE: 221
VDLS                                                                4

SEQ ID NO: 222            moltype =    length =
SEQUENCE: 222
000

SEQ ID NO: 223            moltype = AA   length = 10
FEATURE                   Location/Qualifiers
REGION                    1..10
```

```
                         note = Synthetic peptide
source                   1..10
                         mol_type = protein
                         organism = synthetic construct
SEQUENCE: 223
IVYKPVDLSK                                                                    10

SEQ ID NO: 224           moltype = AA   length = 9
FEATURE                  Location/Qualifiers
REGION                   1..9
                         note = Synthetic peptide
source                   1..9
                         mol_type = protein
                         organism = synthetic construct
SEQUENCE: 224
VYKPVDLSK                                                                      9

SEQ ID NO: 225           moltype = AA   length = 8
FEATURE                  Location/Qualifiers
REGION                   1..8
                         note = Synthetic peptide
source                   1..8
                         mol_type = protein
                         organism = synthetic construct
SEQUENCE: 225
YKPVDLSK                                                                       8

SEQ ID NO: 226           moltype = AA   length = 7
FEATURE                  Location/Qualifiers
REGION                   1..7
                         note = Synthetic peptide
source                   1..7
                         mol_type = protein
                         organism = synthetic construct
SEQUENCE: 226
KPVDLSK                                                                        7

SEQ ID NO: 227           moltype = AA   length = 6
FEATURE                  Location/Qualifiers
REGION                   1..6
                         note = Synthetic peptide
source                   1..6
                         mol_type = protein
                         organism = synthetic construct
SEQUENCE: 227
PVDLSK                                                                         6

SEQ ID NO: 228           moltype = AA   length = 5
FEATURE                  Location/Qualifiers
REGION                   1..5
                         note = Synthetic peptide
source                   1..5
                         mol_type = protein
                         organism = synthetic construct
SEQUENCE: 228
VDLSK                                                                          5

SEQ ID NO: 229           moltype = AA   length = 4
FEATURE                  Location/Qualifiers
REGION                   1..4
                         note = Synthetic peptide
source                   1..4
                         mol_type = protein
                         organism = synthetic construct
SEQUENCE: 229
DLSK                                                                           4

SEQ ID NO: 230           moltype =    length =
SEQUENCE: 230
000

SEQ ID NO: 231           moltype = AA   length = 10
FEATURE                  Location/Qualifiers
REGION                   1..10
                         note = Synthetic peptide
source                   1..10
                         mol_type = protein
                         organism = synthetic construct
SEQUENCE: 231
```

```
VYKPVDLSKV                                                                      10

SEQ ID NO: 232         moltype = AA  length = 9
FEATURE                Location/Qualifiers
REGION                 1..9
                       note = Synthetic peptide
source                 1..9
                       mol_type = protein
                       organism = synthetic construct
SEQUENCE: 232
YKPVDLSKV                                                                       9

SEQ ID NO: 233         moltype = AA  length = 8
FEATURE                Location/Qualifiers
REGION                 1..8
                       note = Synthetic peptide
source                 1..8
                       mol_type = protein
                       organism = synthetic construct
SEQUENCE: 233
KPVDLSKV                                                                        8

SEQ ID NO: 234         moltype = AA  length = 7
FEATURE                Location/Qualifiers
REGION                 1..7
                       note = Synthetic peptide
source                 1..7
                       mol_type = protein
                       organism = synthetic construct
SEQUENCE: 234
PVDLSKV                                                                         7

SEQ ID NO: 235         moltype = AA  length = 6
FEATURE                Location/Qualifiers
REGION                 1..6
                       note = Synthetic peptide
source                 1..6
                       mol_type = protein
                       organism = synthetic construct
SEQUENCE: 235
VDLSKV                                                                          6

SEQ ID NO: 236         moltype = AA  length = 5
FEATURE                Location/Qualifiers
REGION                 1..5
                       note = Synthetic peptide
source                 1..5
                       mol_type = protein
                       organism = synthetic construct
SEQUENCE: 236
DLSKV                                                                           5

SEQ ID NO: 237         moltype = AA  length = 4
FEATURE                Location/Qualifiers
REGION                 1..4
                       note = Synthetic peptide
source                 1..4
                       mol_type = protein
                       organism = synthetic construct
SEQUENCE: 237
LSKV                                                                            4

SEQ ID NO: 238         moltype =    length =
SEQUENCE: 238
000

SEQ ID NO: 239         moltype = AA  length = 10
FEATURE                Location/Qualifiers
REGION                 1..10
                       note = Synthetic peptide
source                 1..10
                       mol_type = protein
                       organism = synthetic construct
SEQUENCE: 239
YKPVDLSKVT                                                                      10

SEQ ID NO: 240         moltype = AA  length = 9
FEATURE                Location/Qualifiers
REGION                 1..9
```

```
                           note = Synthetic peptide
source                     1..9
                           mol_type = protein
                           organism = synthetic construct
SEQUENCE: 240
KPVDLSKVT                                                                    9

SEQ ID NO: 241             moltype = AA  length = 8
FEATURE                    Location/Qualifiers
REGION                     1..8
                           note = Synthetic peptide
source                     1..8
                           mol_type = protein
                           organism = synthetic construct
SEQUENCE: 241
PVDLSKVT                                                                     8

SEQ ID NO: 242             moltype = AA  length = 7
FEATURE                    Location/Qualifiers
REGION                     1..7
                           note = Synthetic peptide
source                     1..7
                           mol_type = protein
                           organism = synthetic construct
SEQUENCE: 242
VDLSKVT                                                                      7

SEQ ID NO: 243             moltype = AA  length = 10
FEATURE                    Location/Qualifiers
REGION                     1..10
                           note = Synthetic peptide
source                     1..10
                           mol_type = protein
                           organism = synthetic construct
SEQUENCE: 243
AKTDHGAEIV                                                                  10

SEQ ID NO: 244             moltype = AA  length = 9
FEATURE                    Location/Qualifiers
REGION                     1..9
                           note = Synthetic peptide
source                     1..9
                           mol_type = protein
                           organism = synthetic construct
SEQUENCE: 244
KTDHGAEIV                                                                    9

SEQ ID NO: 245             moltype = AA  length = 8
FEATURE                    Location/Qualifiers
REGION                     1..8
                           note = Synthetic peptide
source                     1..8
                           mol_type = protein
                           organism = synthetic construct
SEQUENCE: 245
TDHGAEIV                                                                     8

SEQ ID NO: 246             moltype = AA  length = 7
FEATURE                    Location/Qualifiers
REGION                     1..7
                           note = Synthetic peptide
source                     1..7
                           mol_type = protein
                           organism = synthetic construct
SEQUENCE: 246
DHGAEIV                                                                      7

SEQ ID NO: 247             moltype = AA  length = 6
FEATURE                    Location/Qualifiers
REGION                     1..6
                           note = Synthetic peptide
source                     1..6
                           mol_type = protein
                           organism = synthetic construct
SEQUENCE: 247
HGAEIV                                                                       6

SEQ ID NO: 248             moltype = AA  length = 5
FEATURE                    Location/Qualifiers
```

```
REGION                  1..5
                        note = Synthetic peptide
source                  1..5
                        mol_type = protein
                        organism = synthetic construct
SEQUENCE: 248
GAEIV                                                                         5

SEQ ID NO: 249          moltype = AA  length = 4
FEATURE                 Location/Qualifiers
REGION                  1..4
                        note = Synthetic peptide
source                  1..4
                        mol_type = protein
                        organism = synthetic construct
SEQUENCE: 249
AEIV                                                                          4

SEQ ID NO: 250          moltype =     length =
SEQUENCE: 250
000

SEQ ID NO: 251          moltype = AA  length = 10
FEATURE                 Location/Qualifiers
REGION                  1..10
                        note = Synthetic peptide
source                  1..10
                        mol_type = protein
                        organism = synthetic construct
SEQUENCE: 251
KTDHGAEIVY                                                                   10

SEQ ID NO: 252          moltype = AA  length = 9
FEATURE                 Location/Qualifiers
REGION                  1..9
                        note = Synthetic peptide
source                  1..9
                        mol_type = protein
                        organism = synthetic construct
SEQUENCE: 252
TDHGAEIVY                                                                     9

SEQ ID NO: 253          moltype = AA  length = 8
FEATURE                 Location/Qualifiers
REGION                  1..8
                        note = Synthetic peptide
source                  1..8
                        mol_type = protein
                        organism = synthetic construct
SEQUENCE: 253
DHGAEIVY                                                                      8

SEQ ID NO: 254          moltype = AA  length = 7
FEATURE                 Location/Qualifiers
REGION                  1..7
                        note = Synthetic peptide
source                  1..7
                        mol_type = protein
                        organism = synthetic construct
SEQUENCE: 254
HGAEIVY                                                                       7

SEQ ID NO: 255          moltype = AA  length = 6
FEATURE                 Location/Qualifiers
REGION                  1..6
                        note = Synthetic peptide
source                  1..6
                        mol_type = protein
                        organism = synthetic construct
SEQUENCE: 255
GAEIVY                                                                        6

SEQ ID NO: 256          moltype = AA  length = 5
FEATURE                 Location/Qualifiers
REGION                  1..5
                        note = Synthetic peptide
source                  1..5
                        mol_type = protein
                        organism = synthetic construct
```

| | | |
|---|---|---|
| SEQUENCE: 256 | | |
| AEIVY | | 5 |
| | | |
| SEQ ID NO: 257 | moltype = AA  length = 4 | |
| FEATURE | Location/Qualifiers | |
| REGION | 1..4 | |
| | note = Synthetic peptide | |
| source | 1..4 | |
| | mol_type = protein | |
| | organism = synthetic construct | |
| SEQUENCE: 257 | | |
| EIVY | | 4 |
| | | |
| SEQ ID NO: 258 | moltype =   length = | |
| SEQUENCE: 258 | | |
| 000 | | |
| | | |
| SEQ ID NO: 259 | moltype = AA  length = 10 | |
| FEATURE | Location/Qualifiers | |
| REGION | 1..10 | |
| | note = Synthetic peptide | |
| source | 1..10 | |
| | mol_type = protein | |
| | organism = synthetic construct | |
| SEQUENCE: 259 | | |
| TDHGAEIVYK | | 10 |
| | | |
| SEQ ID NO: 260 | moltype = AA  length = 9 | |
| FEATURE | Location/Qualifiers | |
| REGION | 1..9 | |
| | note = Synthetic peptide | |
| source | 1..9 | |
| | mol_type = protein | |
| | organism = synthetic construct | |
| SEQUENCE: 260 | | |
| DHGAEIVYK | | 9 |
| | | |
| SEQ ID NO: 261 | moltype = AA  length = 8 | |
| FEATURE | Location/Qualifiers | |
| REGION | 1..8 | |
| | note = Synthetic peptide | |
| source | 1..8 | |
| | mol_type = protein | |
| | organism = synthetic construct | |
| SEQUENCE: 261 | | |
| HGAEIVYK | | 8 |
| | | |
| SEQ ID NO: 262 | moltype = AA  length = 7 | |
| FEATURE | Location/Qualifiers | |
| REGION | 1..7 | |
| | note = Synthetic peptide | |
| source | 1..7 | |
| | mol_type = protein | |
| | organism = synthetic construct | |
| SEQUENCE: 262 | | |
| GAEIVYK | | 7 |
| | | |
| SEQ ID NO: 263 | moltype = AA  length = 6 | |
| FEATURE | Location/Qualifiers | |
| REGION | 1..6 | |
| | note = Synthetic peptide | |
| source | 1..6 | |
| | mol_type = protein | |
| | organism = synthetic construct | |
| SEQUENCE: 263 | | |
| AEIVYK | | 6 |
| | | |
| SEQ ID NO: 264 | moltype = AA  length = 5 | |
| FEATURE | Location/Qualifiers | |
| REGION | 1..5 | |
| | note = Synthetic peptide | |
| source | 1..5 | |
| | mol_type = protein | |
| | organism = synthetic construct | |
| SEQUENCE: 264 | | |
| EIVYK | | 5 |
| | | |
| SEQ ID NO: 265 | moltype = AA  length = 4 | |
| FEATURE | Location/Qualifiers | |

```
REGION                  1..4
                        note = Synthetic peptide
source                  1..4
                        mol_type = protein
                        organism = synthetic construct
SEQUENCE: 265
IVYK                                                                    4

SEQ ID NO: 266          moltype = AA   length = 10
FEATURE                 Location/Qualifiers
REGION                  1..10
                        note = Synthetic peptide
source                  1..10
                        mol_type = protein
                        organism = synthetic construct
SEQUENCE: 266
DHGAEIVYKS                                                             10

SEQ ID NO: 267          moltype = AA   length = 9
FEATURE                 Location/Qualifiers
REGION                  1..9
                        note = Synthetic peptide
source                  1..9
                        mol_type = protein
                        organism = synthetic construct
SEQUENCE: 267
HGAEIVYKS                                                               9

SEQ ID NO: 268          moltype = AA   length = 8
FEATURE                 Location/Qualifiers
REGION                  1..8
                        note = Synthetic peptide
source                  1..8
                        mol_type = protein
                        organism = synthetic construct
SEQUENCE: 268
GAEIVYKS                                                                8

SEQ ID NO: 269          moltype = AA   length = 7
FEATURE                 Location/Qualifiers
REGION                  1..7
                        note = Synthetic peptide
source                  1..7
                        mol_type = protein
                        organism = synthetic construct
SEQUENCE: 269
AEIVYKS                                                                 7

SEQ ID NO: 270          moltype = AA   length = 6
FEATURE                 Location/Qualifiers
REGION                  1..6
                        note = Synthetic peptide
source                  1..6
                        mol_type = protein
                        organism = synthetic construct
SEQUENCE: 270
EIVYKS                                                                  6

SEQ ID NO: 271          moltype = AA   length = 5
FEATURE                 Location/Qualifiers
REGION                  1..5
                        note = Synthetic peptide
source                  1..5
                        mol_type = protein
                        organism = synthetic construct
SEQUENCE: 271
IVYKS                                                                   5

SEQ ID NO: 272          moltype = AA   length = 4
FEATURE                 Location/Qualifiers
REGION                  1..4
                        note = Synthetic peptide
source                  1..4
                        mol_type = protein
                        organism = synthetic construct
SEQUENCE: 272
VYKS                                                                    4

SEQ ID NO: 273          moltype =    length =
```

```
SEQUENCE: 273
000

SEQ ID NO: 274           moltype = AA  length = 10
FEATURE                  Location/Qualifiers
REGION                   1..10
                         note = Synthetic peptide
source                   1..10
                         mol_type = protein
                         organism = synthetic construct
SEQUENCE: 274
HGAEIVYKSP                                                                  10

SEQ ID NO: 275           moltype = AA  length = 9
FEATURE                  Location/Qualifiers
REGION                   1..9
                         note = Synthetic peptide
source                   1..9
                         mol_type = protein
                         organism = synthetic construct
SEQUENCE: 275
GAEIVYKSP                                                                    9

SEQ ID NO: 276           moltype = AA  length = 8
FEATURE                  Location/Qualifiers
REGION                   1..8
                         note = Synthetic peptide
source                   1..8
                         mol_type = protein
                         organism = synthetic construct
SEQUENCE: 276
AEIVYKSP                                                                     8

SEQ ID NO: 277           moltype = AA  length = 7
FEATURE                  Location/Qualifiers
REGION                   1..7
                         note = Synthetic peptide
source                   1..7
                         mol_type = protein
                         organism = synthetic construct
SEQUENCE: 277
EIVYKSP                                                                      7

SEQ ID NO: 278           moltype = AA  length = 6
FEATURE                  Location/Qualifiers
REGION                   1..6
                         note = Synthetic peptide
source                   1..6
                         mol_type = protein
                         organism = synthetic construct
SEQUENCE: 278
IVYKSP                                                                       6

SEQ ID NO: 279           moltype = AA  length = 5
FEATURE                  Location/Qualifiers
REGION                   1..5
                         note = Synthetic peptide
source                   1..5
                         mol_type = protein
                         organism = synthetic construct
SEQUENCE: 279
VYKSP                                                                        5

SEQ ID NO: 280           moltype = AA  length = 4
FEATURE                  Location/Qualifiers
REGION                   1..4
                         note = Synthetic peptide
source                   1..4
                         mol_type = protein
                         organism = synthetic construct
SEQUENCE: 280
YKSP                                                                         4

SEQ ID NO: 281           moltype =     length =
SEQUENCE: 281
000

SEQ ID NO: 282           moltype = AA  length = 10
FEATURE                  Location/Qualifiers
```

```
REGION                  1..10
                        note = Synthetic peptide
source                  1..10
                        mol_type = protein
                        organism = synthetic construct
SEQUENCE: 282
GAEIVYKSPV                                                                   10

SEQ ID NO: 283          moltype = AA  length = 9
FEATURE                 Location/Qualifiers
REGION                  1..9
                        note = Synthetic peptide
source                  1..9
                        mol_type = protein
                        organism = synthetic construct
SEQUENCE: 283
AEIVYKSPV                                                                    9

SEQ ID NO: 284          moltype = AA  length = 8
FEATURE                 Location/Qualifiers
REGION                  1..8
                        note = Synthetic peptide
source                  1..8
                        mol_type = protein
                        organism = synthetic construct
SEQUENCE: 284
EIVYKSPV                                                                     8

SEQ ID NO: 285          moltype = AA  length = 7
FEATURE                 Location/Qualifiers
REGION                  1..7
                        note = Synthetic peptide
source                  1..7
                        mol_type = protein
                        organism = synthetic construct
SEQUENCE: 285
IVYKSPV                                                                      7

SEQ ID NO: 286          moltype = AA  length = 6
FEATURE                 Location/Qualifiers
REGION                  1..6
                        note = Synthetic peptide
source                  1..6
                        mol_type = protein
                        organism = synthetic construct
SEQUENCE: 286
VYKSPV                                                                       6

SEQ ID NO: 287          moltype = AA  length = 5
FEATURE                 Location/Qualifiers
REGION                  1..5
                        note = Synthetic peptide
source                  1..5
                        mol_type = protein
                        organism = synthetic construct
SEQUENCE: 287
YKSPV                                                                        5

SEQ ID NO: 288          moltype = AA  length = 4
FEATURE                 Location/Qualifiers
REGION                  1..4
                        note = Synthetic peptide
source                  1..4
                        mol_type = protein
                        organism = synthetic construct
SEQUENCE: 288
KSPV                                                                         4

SEQ ID NO: 289          moltype =    length =
SEQUENCE: 289
000

SEQ ID NO: 290          moltype = AA  length = 10
FEATURE                 Location/Qualifiers
REGION                  1..10
                        note = Synthetic peptide
source                  1..10
                        mol_type = protein
                        organism = synthetic construct
```

```
SEQUENCE: 290
AEIVYKSPVV                                                                10

SEQ ID NO: 291         moltype = AA  length = 9
FEATURE                Location/Qualifiers
REGION                 1..9
                       note = Synthetic peptide
source                 1..9
                       mol_type = protein
                       organism = synthetic construct
SEQUENCE: 291
EIVYKSPVV                                                                  9

SEQ ID NO: 292         moltype = AA  length = 8
FEATURE                Location/Qualifiers
REGION                 1..8
                       note = Synthetic peptide
source                 1..8
                       mol_type = protein
                       organism = synthetic construct
SEQUENCE: 292
IVYKSPVV                                                                   8

SEQ ID NO: 293         moltype = AA  length = 7
FEATURE                Location/Qualifiers
REGION                 1..7
                       note = Synthetic peptide
source                 1..7
                       mol_type = protein
                       organism = synthetic construct
SEQUENCE: 293
VYKSPVV                                                                    7

SEQ ID NO: 294         moltype = AA  length = 6
FEATURE                Location/Qualifiers
REGION                 1..6
                       note = Synthetic peptide
source                 1..6
                       mol_type = protein
                       organism = synthetic construct
SEQUENCE: 294
YKSPVV                                                                     6

SEQ ID NO: 295         moltype = AA  length = 5
FEATURE                Location/Qualifiers
REGION                 1..5
                       note = Synthetic peptide
source                 1..5
                       mol_type = protein
                       organism = synthetic construct
SEQUENCE: 295
KSPVV                                                                      5

SEQ ID NO: 296         moltype = AA  length = 4
FEATURE                Location/Qualifiers
REGION                 1..4
                       note = Synthetic peptide
source                 1..4
                       mol_type = protein
                       organism = synthetic construct
SEQUENCE: 296
SPVV                                                                       4

SEQ ID NO: 297         moltype =     length =
SEQUENCE: 297
000

SEQ ID NO: 298         moltype = AA  length = 10
FEATURE                Location/Qualifiers
REGION                 1..10
                       note = Synthetic peptide
source                 1..10
                       mol_type = protein
                       organism = synthetic construct
SEQUENCE: 298
EIVYKSPVVS                                                                10

SEQ ID NO: 299         moltype = AA  length = 9
FEATURE                Location/Qualifiers
```

```
REGION                  1..9
                        note = Synthetic peptide
source                  1..9
                        mol_type = protein
                        organism = synthetic construct
SEQUENCE: 299
IVYKSPVVS                                                                        9

SEQ ID NO: 300          moltype = AA  length = 8
FEATURE                 Location/Qualifiers
REGION                  1..8
                        note = Synthetic peptide
source                  1..8
                        mol_type = protein
                        organism = synthetic construct
SEQUENCE: 300
VYKSPVVS                                                                         8

SEQ ID NO: 301          moltype = AA  length = 7
FEATURE                 Location/Qualifiers
REGION                  1..7
                        note = Synthetic peptide
source                  1..7
                        mol_type = protein
                        organism = synthetic construct
SEQUENCE: 301
YKSPVVS                                                                          7

SEQ ID NO: 302          moltype = AA  length = 6
FEATURE                 Location/Qualifiers
REGION                  1..6
                        note = Synthetic peptide
source                  1..6
                        mol_type = protein
                        organism = synthetic construct
SEQUENCE: 302
KSPVVS                                                                           6

SEQ ID NO: 303          moltype = AA  length = 5
FEATURE                 Location/Qualifiers
REGION                  1..5
                        note = Synthetic peptide
source                  1..5
                        mol_type = protein
                        organism = synthetic construct
SEQUENCE: 303
SPVVS                                                                            5

SEQ ID NO: 304          moltype = AA  length = 4
FEATURE                 Location/Qualifiers
REGION                  1..4
                        note = Synthetic peptide
source                  1..4
                        mol_type = protein
                        organism = synthetic construct
SEQUENCE: 304
PVVS                                                                             4

SEQ ID NO: 305          moltype =     length =
SEQUENCE: 305
000

SEQ ID NO: 306          moltype = AA  length = 10
FEATURE                 Location/Qualifiers
REGION                  1..10
                        note = Synthetic peptide
source                  1..10
                        mol_type = protein
                        organism = synthetic construct
SEQUENCE: 306
IVYKSPVVSG                                                                      10

SEQ ID NO: 307          moltype = AA  length = 9
FEATURE                 Location/Qualifiers
REGION                  1..9
                        note = Synthetic peptide
source                  1..9
                        mol_type = protein
                        organism = synthetic construct
```

```
SEQUENCE: 307
VYKSPVVSG                                                                        9

SEQ ID NO: 308           moltype = AA  length = 8
FEATURE                  Location/Qualifiers
REGION                   1..8
                         note = Synthetic peptide
source                   1..8
                         mol_type = protein
                         organism = synthetic construct
SEQUENCE: 308
YKSPVVSG                                                                         8

SEQ ID NO: 309           moltype = AA  length = 7
FEATURE                  Location/Qualifiers
REGION                   1..7
                         note = Synthetic peptide
source                   1..7
                         mol_type = protein
                         organism = synthetic construct
SEQUENCE: 309
KSPVVSG                                                                          7

SEQ ID NO: 310           moltype = AA  length = 6
FEATURE                  Location/Qualifiers
REGION                   1..6
                         note = Synthetic peptide
source                   1..6
                         mol_type = protein
                         organism = synthetic construct
SEQUENCE: 310
SPVVSG                                                                           6

SEQ ID NO: 311           moltype = AA  length = 5
FEATURE                  Location/Qualifiers
REGION                   1..5
                         note = Synthetic peptide
source                   1..5
                         mol_type = protein
                         organism = synthetic construct
SEQUENCE: 311
PVVSG                                                                            5

SEQ ID NO: 312           moltype = AA  length = 4
FEATURE                  Location/Qualifiers
REGION                   1..4
                         note = Synthetic peptide
source                   1..4
                         mol_type = protein
                         organism = synthetic construct
SEQUENCE: 312
VVSG                                                                             4

SEQ ID NO: 313           moltype =    length =
SEQUENCE: 313
000

SEQ ID NO: 314           moltype = AA  length = 10
FEATURE                  Location/Qualifiers
REGION                   1..10
                         note = Synthetic peptide
source                   1..10
                         mol_type = protein
                         organism = synthetic construct
SEQUENCE: 314
VYKSPVVSGD                                                                      10

SEQ ID NO: 315           moltype = AA  length = 9
FEATURE                  Location/Qualifiers
REGION                   1..9
                         note = Synthetic peptide
source                   1..9
                         mol_type = protein
                         organism = synthetic construct
SEQUENCE: 315
YKSPVVSGD                                                                        9

SEQ ID NO: 316           moltype = AA  length = 8
FEATURE                  Location/Qualifiers
```

```
REGION                  1..8
                        note = Synthetic peptide
source                  1..8
                        mol_type = protein
                        organism = synthetic construct
SEQUENCE: 316
KSPVVSGD                                                                        8

SEQ ID NO: 317          moltype = AA  length = 7
FEATURE                 Location/Qualifiers
REGION                  1..7
                        note = Synthetic peptide
source                  1..7
                        mol_type = protein
                        organism = synthetic construct
SEQUENCE: 317
SPVVSGD                                                                         7

SEQ ID NO: 318          moltype = AA  length = 6
FEATURE                 Location/Qualifiers
REGION                  1..6
                        note = Synthetic peptide
source                  1..6
                        mol_type = protein
                        organism = synthetic construct
SEQUENCE: 318
PVVSGD                                                                          6

SEQ ID NO: 319          moltype = AA  length = 5
FEATURE                 Location/Qualifiers
REGION                  1..5
                        note = Synthetic peptide
source                  1..5
                        mol_type = protein
                        organism = synthetic construct
SEQUENCE: 319
VVSGD                                                                           5

SEQ ID NO: 320          moltype = AA  length = 4
FEATURE                 Location/Qualifiers
REGION                  1..4
                        note = Synthetic peptide
source                  1..4
                        mol_type = protein
                        organism = synthetic construct
SEQUENCE: 320
VSGD                                                                            4

SEQ ID NO: 321          moltype =     length =
SEQUENCE: 321
000

SEQ ID NO: 322          moltype = AA  length = 10
FEATURE                 Location/Qualifiers
REGION                  1..10
                        note = Synthetic peptide
source                  1..10
                        mol_type = protein
                        organism = synthetic construct
SEQUENCE: 322
YKSPVVSGDT                                                                      10

SEQ ID NO: 323          moltype = AA  length = 9
FEATURE                 Location/Qualifiers
REGION                  1..9
                        note = Synthetic peptide
source                  1..9
                        mol_type = protein
                        organism = synthetic construct
SEQUENCE: 323
KSPVVSGDT                                                                       9

SEQ ID NO: 324          moltype = AA  length = 8
FEATURE                 Location/Qualifiers
REGION                  1..8
                        note = Synthetic peptide
source                  1..8
                        mol_type = protein
                        organism = synthetic construct
```

```
SEQUENCE: 324
SPVVSGDT                                                                        8

SEQ ID NO: 325          moltype = AA  length = 7
FEATURE                 Location/Qualifiers
REGION                  1..7
                        note = Synthetic peptide
source                  1..7
                        mol_type = protein
                        organism = synthetic construct
SEQUENCE: 325
PVVSGDT                                                                         7

SEQ ID NO: 326          moltype = AA  length = 6
FEATURE                 Location/Qualifiers
REGION                  1..6
                        note = Synthetic peptide
source                  1..6
                        mol_type = protein
                        organism = synthetic construct
SEQUENCE: 326
VVSGDT                                                                          6

SEQ ID NO: 327          moltype = AA  length = 5
FEATURE                 Location/Qualifiers
REGION                  1..5
                        note = Synthetic peptide
source                  1..5
                        mol_type = protein
                        organism = synthetic construct
SEQUENCE: 327
VSGDT                                                                           5

SEQ ID NO: 328          moltype = AA  length = 4
FEATURE                 Location/Qualifiers
REGION                  1..4
                        note = Synthetic peptide
source                  1..4
                        mol_type = protein
                        organism = synthetic construct
SEQUENCE: 328
SGDT                                                                            4

SEQ ID NO: 329          moltype =    length =
SEQUENCE: 329
000

SEQ ID NO: 330          moltype = AA  length = 10
FEATURE                 Location/Qualifiers
REGION                  1..10
                        note = Synthetic peptide
source                  1..10
                        mol_type = protein
                        organism = synthetic construct
SEQUENCE: 330
KSPVVSGDTS                                                                     10

SEQ ID NO: 331          moltype = AA  length = 9
FEATURE                 Location/Qualifiers
REGION                  1..9
                        note = Synthetic peptide
source                  1..9
                        mol_type = protein
                        organism = synthetic construct
SEQUENCE: 331
SPVVSGDTS                                                                       9

SEQ ID NO: 332          moltype = AA  length = 8
FEATURE                 Location/Qualifiers
REGION                  1..8
                        note = Synthetic peptide
source                  1..8
                        mol_type = protein
                        organism = synthetic construct
SEQUENCE: 332
PVVSGDTS                                                                        8

SEQ ID NO: 333          moltype = AA  length = 7
FEATURE                 Location/Qualifiers
```

```
REGION                   1..7
                         note = Synthetic peptide
source                   1..7
                         mol_type = protein
                         organism = synthetic construct
SEQUENCE: 333
VVSGDTS                                                                    7

SEQ ID NO: 334           moltype = AA  length = 6
FEATURE                  Location/Qualifiers
REGION                   1..6
                         note = Synthetic peptide
source                   1..6
                         mol_type = protein
                         organism = synthetic construct
SEQUENCE: 334
VSGDTS                                                                     6

SEQ ID NO: 335           moltype = AA  length = 5
FEATURE                  Location/Qualifiers
REGION                   1..5
                         note = Synthetic peptide
source                   1..5
                         mol_type = protein
                         organism = synthetic construct
SEQUENCE: 335
SGDTS                                                                      5

SEQ ID NO: 336           moltype = AA  length = 4
FEATURE                  Location/Qualifiers
REGION                   1..4
                         note = Synthetic peptide
source                   1..4
                         mol_type = protein
                         organism = synthetic construct
SEQUENCE: 336
GDTS                                                                       4

SEQ ID NO: 337           moltype =     length =
SEQUENCE: 337
000

SEQ ID NO: 338           moltype = AA  length = 10
FEATURE                  Location/Qualifiers
REGION                   1..10
                         note = Synthetic peptide
source                   1..10
                         mol_type = protein
                         organism = synthetic construct
SEQUENCE: 338
SPVVSGDTSP                                                                10

SEQ ID NO: 339           moltype = AA  length = 9
FEATURE                  Location/Qualifiers
REGION                   1..9
                         note = Synthetic peptide
source                   1..9
                         mol_type = protein
                         organism = synthetic construct
SEQUENCE: 339
PVVSGDTSP                                                                  9

SEQ ID NO: 340           moltype = AA  length = 8
FEATURE                  Location/Qualifiers
REGION                   1..8
                         note = Synthetic peptide
source                   1..8
                         mol_type = protein
                         organism = synthetic construct
SEQUENCE: 340
VVSGDTSP                                                                   8

SEQ ID NO: 341           moltype = AA  length = 7
FEATURE                  Location/Qualifiers
REGION                   1..7
                         note = Synthetic peptide
source                   1..7
                         mol_type = protein
                         organism = synthetic construct
```

```
SEQUENCE: 341
VSGDTSP                                                                 7

SEQ ID NO: 342          moltype = AA  length = 6
FEATURE                 Location/Qualifiers
REGION                  1..6
                        note = Synthetic peptide
source                  1..6
                        mol_type = protein
                        organism = synthetic construct
SEQUENCE: 342
SGDTSP                                                                  6

SEQ ID NO: 343          moltype = AA  length = 5
FEATURE                 Location/Qualifiers
REGION                  1..5
                        note = Synthetic peptide
source                  1..5
                        mol_type = protein
                        organism = synthetic construct
SEQUENCE: 343
GDTSP                                                                   5

SEQ ID NO: 344          moltype = AA  length = 4
FEATURE                 Location/Qualifiers
REGION                  1..4
                        note = Synthetic peptide
source                  1..4
                        mol_type = protein
                        organism = synthetic construct
SEQUENCE: 344
DTSP                                                                    4

SEQ ID NO: 345          moltype =    length =
SEQUENCE: 345
000

SEQ ID NO: 346          moltype = AA  length = 10
FEATURE                 Location/Qualifiers
REGION                  1..10
                        note = Synthetic peptide
source                  1..10
                        mol_type = protein
                        organism = synthetic construct
SEQUENCE: 346
PVVSGDTSPR                                                             10

SEQ ID NO: 347          moltype = AA  length = 9
FEATURE                 Location/Qualifiers
REGION                  1..9
                        note = Synthetic peptide
source                  1..9
                        mol_type = protein
                        organism = synthetic construct
SEQUENCE: 347
VVSGDTSPR                                                               9

SEQ ID NO: 348          moltype = AA  length = 8
FEATURE                 Location/Qualifiers
REGION                  1..8
                        note = Synthetic peptide
source                  1..8
                        mol_type = protein
                        organism = synthetic construct
SEQUENCE: 348
VSGDTSPR                                                                8

SEQ ID NO: 349          moltype = AA  length = 7
FEATURE                 Location/Qualifiers
REGION                  1..7
                        note = Synthetic peptide
source                  1..7
                        mol_type = protein
                        organism = synthetic construct
SEQUENCE: 349
SGDTSPR                                                                 7

SEQ ID NO: 350          moltype = AA  length = 6
FEATURE                 Location/Qualifiers
```

```
REGION                  1..6
                        note = Synthetic peptide
source                  1..6
                        mol_type = protein
                        organism = synthetic construct
SEQUENCE: 350
GDTSPR                                                                   6

SEQ ID NO: 351          moltype = AA  length = 5
FEATURE                 Location/Qualifiers
REGION                  1..5
                        note = Synthetic peptide
source                  1..5
                        mol_type = protein
                        organism = synthetic construct
SEQUENCE: 351
DTSPR                                                                    5

SEQ ID NO: 352          moltype = AA  length = 4
FEATURE                 Location/Qualifiers
REGION                  1..4
                        note = Synthetic peptide
source                  1..4
                        mol_type = protein
                        organism = synthetic construct
SEQUENCE: 352
TSPR                                                                     4

SEQ ID NO: 353          moltype =    length =
SEQUENCE: 353
000

SEQ ID NO: 354          moltype = AA  length = 10
FEATURE                 Location/Qualifiers
REGION                  1..10
                        note = Synthetic peptide
source                  1..10
                        mol_type = protein
                        organism = synthetic construct
SEQUENCE: 354
HQPGGGKVQI                                                              10

SEQ ID NO: 355          moltype = AA  length = 9
FEATURE                 Location/Qualifiers
REGION                  1..9
                        note = Synthetic peptide
source                  1..9
                        mol_type = protein
                        organism = synthetic construct
SEQUENCE: 355
QPGGGKVQI                                                                9

SEQ ID NO: 356          moltype = AA  length = 8
FEATURE                 Location/Qualifiers
REGION                  1..8
                        note = Synthetic peptide
source                  1..8
                        mol_type = protein
                        organism = synthetic construct
SEQUENCE: 356
PGGGKVQI                                                                 8

SEQ ID NO: 357          moltype = AA  length = 7
FEATURE                 Location/Qualifiers
REGION                  1..7
                        note = Synthetic peptide
source                  1..7
                        mol_type = protein
                        organism = synthetic construct
SEQUENCE: 357
GGGKVQI                                                                  7

SEQ ID NO: 358          moltype = AA  length = 6
FEATURE                 Location/Qualifiers
REGION                  1..6
                        note = Synthetic peptide
source                  1..6
                        mol_type = protein
                        organism = synthetic construct
```

```
SEQUENCE: 358
GGKVQI                                                                           6

SEQ ID NO: 359         moltype = AA  length = 5
FEATURE                Location/Qualifiers
REGION                 1..5
                       note = Synthetic peptide
source                 1..5
                       mol_type = protein
                       organism = synthetic construct
SEQUENCE: 359
GKVQI                                                                            5

SEQ ID NO: 360         moltype = AA  length = 4
FEATURE                Location/Qualifiers
REGION                 1..4
                       note = Synthetic peptide
source                 1..4
                       mol_type = protein
                       organism = synthetic construct
SEQUENCE: 360
KVQI                                                                             4

SEQ ID NO: 361         moltype =   length =
SEQUENCE: 361
000

SEQ ID NO: 362         moltype = AA  length = 10
FEATURE                Location/Qualifiers
REGION                 1..10
                       note = Synthetic peptide
source                 1..10
                       mol_type = protein
                       organism = synthetic construct
SEQUENCE: 362
QPGGGKVQII                                                                      10

SEQ ID NO: 363         moltype = AA  length = 9
FEATURE                Location/Qualifiers
REGION                 1..9
                       note = Synthetic peptide
source                 1..9
                       mol_type = protein
                       organism = synthetic construct
SEQUENCE: 363
PGGGKVQII                                                                        9

SEQ ID NO: 364         moltype = AA  length = 6
FEATURE                Location/Qualifiers
REGION                 1..6
                       note = Synthetic peptide
source                 1..6
                       mol_type = protein
                       organism = synthetic construct
SEQUENCE: 364
SVDLSK                                                                           6

SEQ ID NO: 365         moltype = AA  length = 8
FEATURE                Location/Qualifiers
REGION                 1..8
                       note = Synthetic peptide
source                 1..8
                       mol_type = protein
                       organism = synthetic construct
SEQUENCE: 365
GGGKVQII                                                                         8

SEQ ID NO: 366         moltype = AA  length = 7
FEATURE                Location/Qualifiers
REGION                 1..7
                       note = Synthetic peptide
source                 1..7
                       mol_type = protein
                       organism = synthetic construct
SEQUENCE: 366
GGKVQII                                                                          7

SEQ ID NO: 367         moltype = AA  length = 6
FEATURE                Location/Qualifiers
```

```
REGION                  1..6
                        note = Synthetic peptide
source                  1..6
                        mol_type = protein
                        organism = synthetic construct
SEQUENCE: 367
GKVQII                                                                    6

SEQ ID NO: 368          moltype = AA  length = 5
FEATURE                 Location/Qualifiers
REGION                  1..5
                        note = Synthetic peptide
source                  1..5
                        mol_type = protein
                        organism = synthetic construct
SEQUENCE: 368
KVQII                                                                     5

SEQ ID NO: 369          moltype = AA  length = 4
FEATURE                 Location/Qualifiers
REGION                  1..4
                        note = Synthetic peptide
source                  1..4
                        mol_type = protein
                        organism = synthetic construct
SEQUENCE: 369
VQII                                                                      4

SEQ ID NO: 370          moltype =     length =
SEQUENCE: 370
000

SEQ ID NO: 371          moltype = AA  length = 10
FEATURE                 Location/Qualifiers
REGION                  1..10
                        note = Synthetic peptide
source                  1..10
                        mol_type = protein
                        organism = synthetic construct
SEQUENCE: 371
PGGGKVQIIN                                                               10

SEQ ID NO: 372          moltype = AA  length = 9
FEATURE                 Location/Qualifiers
REGION                  1..9
                        note = Synthetic peptide
source                  1..9
                        mol_type = protein
                        organism = synthetic construct
SEQUENCE: 372
GGGKVQIIN                                                                 9

SEQ ID NO: 373          moltype = AA  length = 8
FEATURE                 Location/Qualifiers
REGION                  1..8
                        note = Synthetic peptide
source                  1..8
                        mol_type = protein
                        organism = synthetic construct
SEQUENCE: 373
GGKVQIIN                                                                  8

SEQ ID NO: 374          moltype = AA  length = 7
FEATURE                 Location/Qualifiers
REGION                  1..7
                        note = Synthetic peptide
source                  1..7
                        mol_type = protein
                        organism = synthetic construct
SEQUENCE: 374
GKVQIIN                                                                   7

SEQ ID NO: 375          moltype = AA  length = 6
FEATURE                 Location/Qualifiers
REGION                  1..6
                        note = Synthetic peptide
source                  1..6
                        mol_type = protein
                        organism = synthetic construct
```

```
SEQUENCE: 375
KVQIIN                                                                6

SEQ ID NO: 376          moltype = AA  length = 5
FEATURE                 Location/Qualifiers
REGION                  1..5
                        note = Synthetic peptide
source                  1..5
                        mol_type = protein
                        organism = synthetic construct
SEQUENCE: 376
VQIIN                                                                 5

SEQ ID NO: 377          moltype = AA  length = 4
FEATURE                 Location/Qualifiers
REGION                  1..4
                        note = Synthetic peptide
source                  1..4
                        mol_type = protein
                        organism = synthetic construct
SEQUENCE: 377
QIIN                                                                  4

SEQ ID NO: 378          moltype =   length =
SEQUENCE: 378
000

SEQ ID NO: 379          moltype = AA  length = 10
FEATURE                 Location/Qualifiers
REGION                  1..10
                        note = Synthetic peptide
source                  1..10
                        mol_type = protein
                        organism = synthetic construct
SEQUENCE: 379
GGGKVQIINK                                                           10

SEQ ID NO: 380          moltype = AA  length = 9
FEATURE                 Location/Qualifiers
REGION                  1..9
                        note = Synthetic peptide
source                  1..9
                        mol_type = protein
                        organism = synthetic construct
SEQUENCE: 380
GGKVQIINK                                                             9

SEQ ID NO: 381          moltype = AA  length = 8
FEATURE                 Location/Qualifiers
REGION                  1..8
                        note = Synthetic peptide
source                  1..8
                        mol_type = protein
                        organism = synthetic construct
SEQUENCE: 381
GKVQIINK                                                              8

SEQ ID NO: 382          moltype = AA  length = 7
FEATURE                 Location/Qualifiers
REGION                  1..7
                        note = Synthetic peptide
source                  1..7
                        mol_type = protein
                        organism = synthetic construct
SEQUENCE: 382
KVQIINK                                                               7

SEQ ID NO: 383          moltype = AA  length = 4
FEATURE                 Location/Qualifiers
REGION                  1..4
                        note = Synthetic peptide
source                  1..4
                        mol_type = protein
                        organism = synthetic construct
SEQUENCE: 383
IINK                                                                  4

SEQ ID NO: 384          moltype =   length =
SEQUENCE: 384
```

```
000

SEQ ID NO: 385          moltype = AA  length = 10
FEATURE                 Location/Qualifiers
REGION                  1..10
                        note = Synthetic peptide
source                  1..10
                        mol_type = protein
                        organism = synthetic construct
SEQUENCE: 385
GGKVQIINKK                                                              10

SEQ ID NO: 386          moltype = AA  length = 9
FEATURE                 Location/Qualifiers
REGION                  1..9
                        note = Synthetic peptide
source                  1..9
                        mol_type = protein
                        organism = synthetic construct
SEQUENCE: 386
GKVQIINKK                                                                9

SEQ ID NO: 387          moltype = AA  length = 8
FEATURE                 Location/Qualifiers
REGION                  1..8
                        note = Synthetic peptide
source                  1..8
                        mol_type = protein
                        organism = synthetic construct
SEQUENCE: 387
KVQIINKK                                                                 8

SEQ ID NO: 388          moltype = AA  length = 5
FEATURE                 Location/Qualifiers
REGION                  1..5
                        note = Synthetic peptide
source                  1..5
                        mol_type = protein
                        organism = synthetic construct
SEQUENCE: 388
IINKK                                                                    5

SEQ ID NO: 389          moltype = AA  length = 4
FEATURE                 Location/Qualifiers
REGION                  1..4
                        note = Synthetic peptide
source                  1..4
                        mol_type = protein
                        organism = synthetic construct
SEQUENCE: 389
INKK                                                                     4

SEQ ID NO: 390          moltype =     length =
SEQUENCE: 390
000

SEQ ID NO: 391          moltype = AA  length = 10
FEATURE                 Location/Qualifiers
REGION                  1..10
                        note = Synthetic peptide
source                  1..10
                        mol_type = protein
                        organism = synthetic construct
SEQUENCE: 391
GKVQIINKKL                                                              10

SEQ ID NO: 392          moltype = AA  length = 9
FEATURE                 Location/Qualifiers
REGION                  1..9
                        note = Synthetic peptide
source                  1..9
                        mol_type = protein
                        organism = synthetic construct
SEQUENCE: 392
KVQIINKKL                                                                9

SEQ ID NO: 393          moltype = AA  length = 6
FEATURE                 Location/Qualifiers
REGION                  1..6
```

```
                        note = Synthetic peptide
source                  1..6
                        mol_type = protein
                        organism = synthetic construct
SEQUENCE: 393
IINKKL                                                                        6

SEQ ID NO: 394          moltype = AA  length = 5
FEATURE                 Location/Qualifiers
REGION                  1..5
                        note = Synthetic peptide
source                  1..5
                        mol_type = protein
                        organism = synthetic construct
SEQUENCE: 394
INKKL                                                                         5

SEQ ID NO: 395          moltype = AA  length = 4
FEATURE                 Location/Qualifiers
REGION                  1..4
                        note = Synthetic peptide
source                  1..4
                        mol_type = protein
                        organism = synthetic construct
SEQUENCE: 395
NKKL                                                                          4

SEQ ID NO: 396          moltype =    length =
SEQUENCE: 396
000

SEQ ID NO: 397          moltype = AA  length = 10
FEATURE                 Location/Qualifiers
REGION                  1..10
                        note = Synthetic peptide
source                  1..10
                        mol_type = protein
                        organism = synthetic construct
SEQUENCE: 397
KVQIINKKLD                                                                   10

SEQ ID NO: 398          moltype = AA  length = 9
FEATURE                 Location/Qualifiers
REGION                  1..9
                        note = Synthetic peptide
source                  1..9
                        mol_type = protein
                        organism = synthetic construct
SEQUENCE: 398
VQIINKKLD                                                                     9

SEQ ID NO: 399          moltype = AA  length = 8
FEATURE                 Location/Qualifiers
REGION                  1..8
                        note = Synthetic peptide
source                  1..8
                        mol_type = protein
                        organism = synthetic construct
SEQUENCE: 399
QIINKKLD                                                                      8

SEQ ID NO: 400          moltype = AA  length = 7
FEATURE                 Location/Qualifiers
REGION                  1..7
                        note = Synthetic peptide
source                  1..7
                        mol_type = protein
                        organism = synthetic construct
SEQUENCE: 400
IINKKLD                                                                       7

SEQ ID NO: 401          moltype = AA  length = 6
FEATURE                 Location/Qualifiers
REGION                  1..6
                        note = Synthetic peptide
source                  1..6
                        mol_type = protein
                        organism = synthetic construct
SEQUENCE: 401
```

```
INKKLD                                                                          6

SEQ ID NO: 402         moltype = AA  length = 5
FEATURE                Location/Qualifiers
REGION                 1..5
                       note = Synthetic peptide
source                 1..5
                       mol_type = protein
                       organism = synthetic construct
SEQUENCE: 402
NKKLD                                                                           5

SEQ ID NO: 403         moltype = AA  length = 4
FEATURE                Location/Qualifiers
REGION                 1..4
                       note = Synthetic peptide
source                 1..4
                       mol_type = protein
                       organism = synthetic construct
SEQUENCE: 403
KKLD                                                                            4

SEQ ID NO: 404         moltype =     length =
SEQUENCE: 404
000

SEQ ID NO: 405         moltype = AA  length = 10
FEATURE                Location/Qualifiers
REGION                 1..10
                       note = Synthetic peptide
source                 1..10
                       mol_type = protein
                       organism = synthetic construct
SEQUENCE: 405
VQIINKKLDL                                                                     10

SEQ ID NO: 406         moltype = AA  length = 9
FEATURE                Location/Qualifiers
REGION                 1..9
                       note = Synthetic peptide
source                 1..9
                       mol_type = protein
                       organism = synthetic construct
SEQUENCE: 406
QIINKKLDL                                                                       9

SEQ ID NO: 407         moltype = AA  length = 8
FEATURE                Location/Qualifiers
REGION                 1..8
                       note = Synthetic peptide
source                 1..8
                       mol_type = protein
                       organism = synthetic construct
SEQUENCE: 407
IINKKLDL                                                                        8

SEQ ID NO: 408         moltype = AA  length = 7
FEATURE                Location/Qualifiers
REGION                 1..7
                       note = Synthetic peptide
source                 1..7
                       mol_type = protein
                       organism = synthetic construct
SEQUENCE: 408
INKKLDL                                                                         7

SEQ ID NO: 409         moltype = AA  length = 6
FEATURE                Location/Qualifiers
REGION                 1..6
                       note = Synthetic peptide
source                 1..6
                       mol_type = protein
                       organism = synthetic construct
SEQUENCE: 409
NKKLDL                                                                          6

SEQ ID NO: 410         moltype = AA  length = 5
FEATURE                Location/Qualifiers
REGION                 1..5
```

```
                            note = Synthetic peptide
source                      1..5
                            mol_type = protein
                            organism = synthetic construct
SEQUENCE: 410
KKLDL                                                                    5

SEQ ID NO: 411              moltype = AA  length = 4
FEATURE                     Location/Qualifiers
REGION                      1..4
                            note = Synthetic peptide
source                      1..4
                            mol_type = protein
                            organism = synthetic construct
SEQUENCE: 411
KLDL                                                                     4

SEQ ID NO: 412              moltype =   length =
SEQUENCE: 412
000

SEQ ID NO: 413              moltype = AA  length = 10
FEATURE                     Location/Qualifiers
REGION                      1..10
                            note = Synthetic peptide
source                      1..10
                            mol_type = protein
                            organism = synthetic construct
SEQUENCE: 413
QIINKKLDLS                                                              10

SEQ ID NO: 414              moltype = AA  length = 9
FEATURE                     Location/Qualifiers
REGION                      1..9
                            note = Synthetic peptide
source                      1..9
                            mol_type = protein
                            organism = synthetic construct
SEQUENCE: 414
IINKKLDLS                                                                9

SEQ ID NO: 415              moltype = AA  length = 8
FEATURE                     Location/Qualifiers
REGION                      1..8
                            note = Synthetic peptide
source                      1..8
                            mol_type = protein
                            organism = synthetic construct
SEQUENCE: 415
INKKLDLS                                                                 8

SEQ ID NO: 416              moltype = AA  length = 7
FEATURE                     Location/Qualifiers
REGION                      1..7
                            note = Synthetic peptide
source                      1..7
                            mol_type = protein
                            organism = synthetic construct
SEQUENCE: 416
NKKLDLS                                                                  7

SEQ ID NO: 417              moltype = AA  length = 6
FEATURE                     Location/Qualifiers
REGION                      1..6
                            note = Synthetic peptide
source                      1..6
                            mol_type = protein
                            organism = synthetic construct
SEQUENCE: 417
KKLDLS                                                                   6

SEQ ID NO: 418              moltype = AA  length = 5
FEATURE                     Location/Qualifiers
REGION                      1..5
                            note = Synthetic peptide
source                      1..5
                            mol_type = protein
                            organism = synthetic construct
SEQUENCE: 418
```

```
KLDLS                                                                          5

SEQ ID NO: 419         moltype = AA  length = 4
FEATURE                Location/Qualifiers
REGION                 1..4
                       note = Synthetic peptide
source                 1..4
                       mol_type = protein
                       organism = synthetic construct
SEQUENCE: 419
LDLS                                                                           4

SEQ ID NO: 420         moltype = AA  length = 10
FEATURE                Location/Qualifiers
REGION                 1..10
                       note = Synthetic peptide
source                 1..10
                       mol_type = protein
                       organism = synthetic construct
SEQUENCE: 420
IINKKLDLSN                                                                    10

SEQ ID NO: 421         moltype = AA  length = 9
FEATURE                Location/Qualifiers
REGION                 1..9
                       note = Synthetic peptide
source                 1..9
                       mol_type = protein
                       organism = synthetic construct
SEQUENCE: 421
INKKLDLSN                                                                      9

SEQ ID NO: 422         moltype = AA  length = 8
FEATURE                Location/Qualifiers
REGION                 1..8
                       note = Synthetic peptide
source                 1..8
                       mol_type = protein
                       organism = synthetic construct
SEQUENCE: 422
NKKLDLSN                                                                       8

SEQ ID NO: 423         moltype = AA  length = 7
FEATURE                Location/Qualifiers
REGION                 1..7
                       note = Synthetic peptide
source                 1..7
                       mol_type = protein
                       organism = synthetic construct
SEQUENCE: 423
KKLDLSN                                                                        7

SEQ ID NO: 424         moltype = AA  length = 6
FEATURE                Location/Qualifiers
REGION                 1..6
                       note = Synthetic peptide
source                 1..6
                       mol_type = protein
                       organism = synthetic construct
SEQUENCE: 424
KLDLSN                                                                         6

SEQ ID NO: 425         moltype = AA  length = 5
FEATURE                Location/Qualifiers
REGION                 1..5
                       note = Synthetic peptide
source                 1..5
                       mol_type = protein
                       organism = synthetic construct
SEQUENCE: 425
LDLSN                                                                          5

SEQ ID NO: 426         moltype = AA  length = 4
FEATURE                Location/Qualifiers
REGION                 1..4
                       note = Synthetic peptide
source                 1..4
                       mol_type = protein
                       organism = synthetic construct
```

```
SEQUENCE: 426
DLSN                                                                      4

SEQ ID NO: 427          moltype =    length =
SEQUENCE: 427
000

SEQ ID NO: 428          moltype = AA   length = 10
FEATURE                 Location/Qualifiers
REGION                  1..10
                        note = Synthetic peptide
source                  1..10
                        mol_type = protein
                        organism = synthetic construct
SEQUENCE: 428
INKKLDLSNV                                                               10

SEQ ID NO: 429          moltype = AA   length = 9
FEATURE                 Location/Qualifiers
REGION                  1..9
                        note = Synthetic peptide
source                  1..9
                        mol_type = protein
                        organism = synthetic construct
SEQUENCE: 429
NKKLDLSNV                                                                 9

SEQ ID NO: 430          moltype = AA   length = 8
FEATURE                 Location/Qualifiers
REGION                  1..8
                        note = Synthetic peptide
source                  1..8
                        mol_type = protein
                        organism = synthetic construct
SEQUENCE: 430
KKLDLSNV                                                                  8

SEQ ID NO: 431          moltype = AA   length = 7
FEATURE                 Location/Qualifiers
REGION                  1..7
                        note = Synthetic peptide
source                  1..7
                        mol_type = protein
                        organism = synthetic construct
SEQUENCE: 431
KLDLSNV                                                                   7

SEQ ID NO: 432          moltype = AA   length = 6
FEATURE                 Location/Qualifiers
REGION                  1..6
                        note = Synthetic peptide
source                  1..6
                        mol_type = protein
                        organism = synthetic construct
SEQUENCE: 432
LDLSNV                                                                    6

SEQ ID NO: 433          moltype = AA   length = 5
FEATURE                 Location/Qualifiers
REGION                  1..5
                        note = Synthetic peptide
source                  1..5
                        mol_type = protein
                        organism = synthetic construct
SEQUENCE: 433
DLSNV                                                                     5

SEQ ID NO: 434          moltype = AA   length = 4
FEATURE                 Location/Qualifiers
REGION                  1..4
                        note = Synthetic peptide
source                  1..4
                        mol_type = protein
                        organism = synthetic construct
SEQUENCE: 434
LSNV                                                                      4

SEQ ID NO: 435          moltype =    length =
SEQUENCE: 435
```

```
000

SEQ ID NO: 436            moltype = AA   length = 10
FEATURE                   Location/Qualifiers
REGION                    1..10
                          note = Synthetic peptide
source                    1..10
                          mol_type = protein
                          organism = synthetic construct
SEQUENCE: 436
NKKLDLSNVQ                                                              10

SEQ ID NO: 437            moltype = AA   length = 9
FEATURE                   Location/Qualifiers
REGION                    1..9
                          note = Synthetic peptide
source                    1..9
                          mol_type = protein
                          organism = synthetic construct
SEQUENCE: 437
KKLDLSNVQ                                                                9

SEQ ID NO: 438            moltype = AA   length = 8
FEATURE                   Location/Qualifiers
REGION                    1..8
                          note = Synthetic peptide
source                    1..8
                          mol_type = protein
                          organism = synthetic construct
SEQUENCE: 438
KLDLSNVQ                                                                 8

SEQ ID NO: 439            moltype = AA   length = 7
FEATURE                   Location/Qualifiers
REGION                    1..7
                          note = Synthetic peptide
source                    1..7
                          mol_type = protein
                          organism = synthetic construct
SEQUENCE: 439
LDLSNVQ                                                                  7

SEQ ID NO: 440            moltype = AA   length = 6
FEATURE                   Location/Qualifiers
REGION                    1..6
                          note = Synthetic peptide
source                    1..6
                          mol_type = protein
                          organism = synthetic construct
SEQUENCE: 440
DLSNVQ                                                                   6

SEQ ID NO: 441            moltype = AA   length = 5
FEATURE                   Location/Qualifiers
REGION                    1..5
                          note = Synthetic peptide
source                    1..5
                          mol_type = protein
                          organism = synthetic construct
SEQUENCE: 441
LSNVQ                                                                    5

SEQ ID NO: 442            moltype = AA   length = 4
FEATURE                   Location/Qualifiers
REGION                    1..4
                          note = Synthetic peptide
source                    1..4
                          mol_type = protein
                          organism = synthetic construct
SEQUENCE: 442
SNVQ                                                                     4

SEQ ID NO: 443            moltype =     length =
SEQUENCE: 443
000

SEQ ID NO: 444            moltype = AA   length = 10
FEATURE                   Location/Qualifiers
REGION                    1..10
```

```
                        note = Synthetic peptide
source                  1..10
                        mol_type = protein
                        organism = synthetic construct
SEQUENCE: 444
KKLDLSNVQS                                                                  10

SEQ ID NO: 445          moltype = AA  length = 9
FEATURE                 Location/Qualifiers
REGION                  1..9
                        note = Synthetic peptide
source                  1..9
                        mol_type = protein
                        organism = synthetic construct
SEQUENCE: 445
KLDLSNVQS                                                                    9

SEQ ID NO: 446          moltype = AA  length = 8
FEATURE                 Location/Qualifiers
REGION                  1..8
                        note = Synthetic peptide
source                  1..8
                        mol_type = protein
                        organism = synthetic construct
SEQUENCE: 446
LDLSNVQS                                                                     8

SEQ ID NO: 447          moltype = AA  length = 7
FEATURE                 Location/Qualifiers
REGION                  1..7
                        note = Synthetic peptide
source                  1..7
                        mol_type = protein
                        organism = synthetic construct
SEQUENCE: 447
DLSNVQS                                                                      7

SEQ ID NO: 448          moltype = AA  length = 6
FEATURE                 Location/Qualifiers
REGION                  1..6
                        note = Synthetic peptide
source                  1..6
                        mol_type = protein
                        organism = synthetic construct
SEQUENCE: 448
LSNVQS                                                                       6

SEQ ID NO: 449          moltype = AA  length = 5
FEATURE                 Location/Qualifiers
REGION                  1..5
                        note = Synthetic peptide
source                  1..5
                        mol_type = protein
                        organism = synthetic construct
SEQUENCE: 449
SNVQS                                                                        5

SEQ ID NO: 450          moltype = AA  length = 4
FEATURE                 Location/Qualifiers
REGION                  1..4
                        note = Synthetic peptide
source                  1..4
                        mol_type = protein
                        organism = synthetic construct
SEQUENCE: 450
NVQS                                                                         4

SEQ ID NO: 451          moltype =     length =
SEQUENCE: 451
000

SEQ ID NO: 452          moltype = AA  length = 10
FEATURE                 Location/Qualifiers
REGION                  1..10
                        note = Synthetic peptide
source                  1..10
                        mol_type = protein
                        organism = synthetic construct
SEQUENCE: 452
```

```
SKCGSKDNIK                                                                 10

SEQ ID NO: 453          moltype = AA  length = 9
FEATURE                 Location/Qualifiers
REGION                  1..9
                        note = Synthetic peptide
source                  1..9
                        mol_type = protein
                        organism = synthetic construct
SEQUENCE: 453
KCGSKDNIK                                                                   9

SEQ ID NO: 454          moltype = AA  length = 8
FEATURE                 Location/Qualifiers
REGION                  1..8
                        note = Synthetic peptide
source                  1..8
                        mol_type = protein
                        organism = synthetic construct
SEQUENCE: 454
CGSKDNIK                                                                    8

SEQ ID NO: 455          moltype = AA  length = 7
FEATURE                 Location/Qualifiers
REGION                  1..7
                        note = Synthetic peptide
source                  1..7
                        mol_type = protein
                        organism = synthetic construct
SEQUENCE: 455
GSKDNIK                                                                     7

SEQ ID NO: 456          moltype = AA  length = 6
FEATURE                 Location/Qualifiers
REGION                  1..6
                        note = Synthetic peptide
source                  1..6
                        mol_type = protein
                        organism = synthetic construct
SEQUENCE: 456
SKDNIK                                                                      6

SEQ ID NO: 457          moltype = AA  length = 5
FEATURE                 Location/Qualifiers
REGION                  1..5
                        note = Synthetic peptide
source                  1..5
                        mol_type = protein
                        organism = synthetic construct
SEQUENCE: 457
KDNIK                                                                       5

SEQ ID NO: 458          moltype = AA  length = 4
FEATURE                 Location/Qualifiers
REGION                  1..4
                        note = Synthetic peptide
source                  1..4
                        mol_type = protein
                        organism = synthetic construct
SEQUENCE: 458
DNIK                                                                        4

SEQ ID NO: 459          moltype =    length =
SEQUENCE: 459
000

SEQ ID NO: 460          moltype = AA  length = 10
FEATURE                 Location/Qualifiers
REGION                  1..10
                        note = Synthetic peptide
source                  1..10
                        mol_type = protein
                        organism = synthetic construct
SEQUENCE: 460
KCGSKDNIKH                                                                 10

SEQ ID NO: 461          moltype = AA  length = 9
FEATURE                 Location/Qualifiers
REGION                  1..9
```

```
                        note = Synthetic peptide
source                  1..9
                        mol_type = protein
                        organism = synthetic construct
SEQUENCE: 461
CGSKDNIKH                                                                       9

SEQ ID NO: 462          moltype = AA  length = 8
FEATURE                 Location/Qualifiers
REGION                  1..8
                        note = Synthetic peptide
source                  1..8
                        mol_type = protein
                        organism = synthetic construct
SEQUENCE: 462
GSKDNIKH                                                                        8

SEQ ID NO: 463          moltype = AA  length = 7
FEATURE                 Location/Qualifiers
REGION                  1..7
                        note = Synthetic peptide
source                  1..7
                        mol_type = protein
                        organism = synthetic construct
SEQUENCE: 463
SKDNIKH                                                                         7

SEQ ID NO: 464          moltype = AA  length = 6
FEATURE                 Location/Qualifiers
REGION                  1..6
                        note = Synthetic peptide
source                  1..6
                        mol_type = protein
                        organism = synthetic construct
SEQUENCE: 464
KDNIKH                                                                          6

SEQ ID NO: 465          moltype = AA  length = 5
FEATURE                 Location/Qualifiers
REGION                  1..5
                        note = Synthetic peptide
source                  1..5
                        mol_type = protein
                        organism = synthetic construct
SEQUENCE: 465
DNIKH                                                                           5

SEQ ID NO: 466          moltype = AA  length = 4
FEATURE                 Location/Qualifiers
REGION                  1..4
                        note = Synthetic peptide
source                  1..4
                        mol_type = protein
                        organism = synthetic construct
SEQUENCE: 466
NIKH                                                                            4

SEQ ID NO: 467          moltype =     length =
SEQUENCE: 467
000

SEQ ID NO: 468          moltype = AA  length = 10
FEATURE                 Location/Qualifiers
REGION                  1..10
                        note = Synthetic peptide
source                  1..10
                        mol_type = protein
                        organism = synthetic construct
SEQUENCE: 468
CGSKDNIKHV                                                                     10

SEQ ID NO: 469          moltype = AA  length = 9
FEATURE                 Location/Qualifiers
REGION                  1..9
                        note = Synthetic peptide
source                  1..9
                        mol_type = protein
                        organism = synthetic construct
SEQUENCE: 469
```

```
GSKDNIKHV                                                                  9

SEQ ID NO: 470          moltype = AA   length = 8
FEATURE                 Location/Qualifiers
REGION                  1..8
                        note = Synthetic peptide
source                  1..8
                        mol_type = protein
                        organism = synthetic construct
SEQUENCE: 470
SKDNIKHV                                                                   8

SEQ ID NO: 471          moltype = AA   length = 7
FEATURE                 Location/Qualifiers
REGION                  1..7
                        note = Synthetic peptide
source                  1..7
                        mol_type = protein
                        organism = synthetic construct
SEQUENCE: 471
KDNIKHV                                                                    7

SEQ ID NO: 472          moltype = AA   length = 6
FEATURE                 Location/Qualifiers
REGION                  1..6
                        note = Synthetic peptide
source                  1..6
                        mol_type = protein
                        organism = synthetic construct
SEQUENCE: 472
DNIKHV                                                                     6

SEQ ID NO: 473          moltype = AA   length = 5
FEATURE                 Location/Qualifiers
REGION                  1..5
                        note = Synthetic peptide
source                  1..5
                        mol_type = protein
                        organism = synthetic construct
SEQUENCE: 473
NIKHV                                                                      5

SEQ ID NO: 474          moltype = AA   length = 4
FEATURE                 Location/Qualifiers
REGION                  1..4
                        note = Synthetic peptide
source                  1..4
                        mol_type = protein
                        organism = synthetic construct
SEQUENCE: 474
IKHV                                                                       4

SEQ ID NO: 475          moltype =      length =
SEQUENCE: 475
000

SEQ ID NO: 476          moltype = AA   length = 10
FEATURE                 Location/Qualifiers
REGION                  1..10
                        note = Synthetic peptide
source                  1..10
                        mol_type = protein
                        organism = synthetic construct
SEQUENCE: 476
GSKDNIKHVP                                                                10

SEQ ID NO: 477          moltype = AA   length = 9
FEATURE                 Location/Qualifiers
REGION                  1..9
                        note = Synthetic peptide
source                  1..9
                        mol_type = protein
                        organism = synthetic construct
SEQUENCE: 477
SKDNIKHVP                                                                  9

SEQ ID NO: 478          moltype = AA   length = 8
FEATURE                 Location/Qualifiers
REGION                  1..8
```

```
                        note = Synthetic peptide
source                  1..8
                        mol_type = protein
                        organism = synthetic construct
SEQUENCE: 478
KDNIKHVP                                                                     8

SEQ ID NO: 479          moltype = AA   length = 7
FEATURE                 Location/Qualifiers
REGION                  1..7
                        note = Synthetic peptide
source                  1..7
                        mol_type = protein
                        organism = synthetic construct
SEQUENCE: 479
DNIKHVP                                                                      7

SEQ ID NO: 480          moltype = AA   length = 5
FEATURE                 Location/Qualifiers
REGION                  1..5
                        note = Synthetic peptide
source                  1..5
                        mol_type = protein
                        organism = synthetic construct
SEQUENCE: 480
IKHVP                                                                        5

SEQ ID NO: 481          moltype = AA   length = 4
FEATURE                 Location/Qualifiers
REGION                  1..4
                        note = Synthetic peptide
source                  1..4
                        mol_type = protein
                        organism = synthetic construct
SEQUENCE: 481
KHVP                                                                         4

SEQ ID NO: 482          moltype =     length =
SEQUENCE: 482
000

SEQ ID NO: 483          moltype = AA   length = 10
FEATURE                 Location/Qualifiers
REGION                  1..10
                        note = Synthetic peptide
source                  1..10
                        mol_type = protein
                        organism = synthetic construct
SEQUENCE: 483
SKDNIKHVPG                                                                  10

SEQ ID NO: 484          moltype = AA   length = 9
FEATURE                 Location/Qualifiers
REGION                  1..9
                        note = Synthetic peptide
source                  1..9
                        mol_type = protein
                        organism = synthetic construct
SEQUENCE: 484
KDNIKHVPG                                                                    9

SEQ ID NO: 485          moltype = AA   length = 8
FEATURE                 Location/Qualifiers
REGION                  1..8
                        note = Synthetic peptide
source                  1..8
                        mol_type = protein
                        organism = synthetic construct
SEQUENCE: 485
DNIKHVPG                                                                     8

SEQ ID NO: 486          moltype = AA   length = 7
FEATURE                 Location/Qualifiers
REGION                  1..7
                        note = Synthetic peptide
source                  1..7
                        mol_type = protein
                        organism = synthetic construct
SEQUENCE: 486
```

```
NIKHVPG                                                                    7

SEQ ID NO: 487        moltype = AA  length = 6
FEATURE               Location/Qualifiers
REGION                1..6
                      note = Synthetic peptide
source                1..6
                      mol_type = protein
                      organism = synthetic construct
SEQUENCE: 487
IKHVPG                                                                     6

SEQ ID NO: 488        moltype = AA  length = 5
FEATURE               Location/Qualifiers
REGION                1..5
                      note = Synthetic peptide
source                1..5
                      mol_type = protein
                      organism = synthetic construct
SEQUENCE: 488
KHVPG                                                                      5

SEQ ID NO: 489        moltype = AA  length = 4
FEATURE               Location/Qualifiers
REGION                1..4
                      note = Synthetic peptide
source                1..4
                      mol_type = protein
                      organism = synthetic construct
SEQUENCE: 489
HVPG                                                                       4

SEQ ID NO: 490        moltype =     length =
SEQUENCE: 490
000

SEQ ID NO: 491        moltype = AA  length = 10
FEATURE               Location/Qualifiers
REGION                1..10
                      note = Synthetic peptide
source                1..10
                      mol_type = protein
                      organism = synthetic construct
SEQUENCE: 491
KDNIKHVPGG                                                                 10

SEQ ID NO: 492        moltype = AA  length = 9
FEATURE               Location/Qualifiers
REGION                1..9
                      note = Synthetic peptide
source                1..9
                      mol_type = protein
                      organism = synthetic construct
SEQUENCE: 492
DNIKHVPGG                                                                  9

SEQ ID NO: 493        moltype = AA  length = 8
FEATURE               Location/Qualifiers
REGION                1..8
                      note = Synthetic peptide
source                1..8
                      mol_type = protein
                      organism = synthetic construct
SEQUENCE: 493
NIKHVPGG                                                                   8

SEQ ID NO: 494        moltype = AA  length = 7
FEATURE               Location/Qualifiers
REGION                1..7
                      note = Synthetic peptide
source                1..7
                      mol_type = protein
                      organism = synthetic construct
SEQUENCE: 494
IKHVPGG                                                                    7

SEQ ID NO: 495        moltype = AA  length = 6
FEATURE               Location/Qualifiers
REGION                1..6
```

```
                        note = Synthetic peptide
source                  1..6
                        mol_type = protein
                        organism = synthetic construct
SEQUENCE: 495
KHVPGG                                                                   6

SEQ ID NO: 496          moltype = AA  length = 4
FEATURE                 Location/Qualifiers
REGION                  1..4
                        note = Synthetic peptide
source                  1..4
                        mol_type = protein
                        organism = synthetic construct
SEQUENCE: 496
VPGG                                                                     4

SEQ ID NO: 497          moltype =     length =
SEQUENCE: 497
000

SEQ ID NO: 498          moltype = AA  length = 10
FEATURE                 Location/Qualifiers
REGION                  1..10
                        note = Synthetic peptide
source                  1..10
                        mol_type = protein
                        organism = synthetic construct
SEQUENCE: 498
DNIKHVPGGG                                                              10

SEQ ID NO: 499          moltype = AA  length = 9
FEATURE                 Location/Qualifiers
REGION                  1..9
                        note = Synthetic peptide
source                  1..9
                        mol_type = protein
                        organism = synthetic construct
SEQUENCE: 499
NIKHVPGGG                                                                9

SEQ ID NO: 500          moltype = AA  length = 8
FEATURE                 Location/Qualifiers
REGION                  1..8
                        note = Synthetic peptide
source                  1..8
                        mol_type = protein
                        organism = synthetic construct
SEQUENCE: 500
IKHVPGGG                                                                 8

SEQ ID NO: 501          moltype = AA  length = 5
FEATURE                 Location/Qualifiers
REGION                  1..5
                        note = Synthetic peptide
source                  1..5
                        mol_type = protein
                        organism = synthetic construct
SEQUENCE: 501
VPGGG                                                                    5

SEQ ID NO: 502          moltype = AA  length = 4
FEATURE                 Location/Qualifiers
REGION                  1..4
                        note = Synthetic peptide
source                  1..4
                        mol_type = protein
                        organism = synthetic construct
SEQUENCE: 502
PGGG                                                                     4

SEQ ID NO: 503          moltype =     length =
SEQUENCE: 503
000

SEQ ID NO: 504          moltype = AA  length = 10
FEATURE                 Location/Qualifiers
REGION                  1..10
                        note = Synthetic peptide
```

```
source                  1..10
                        mol_type = protein
                        organism = synthetic construct
SEQUENCE: 504
NIKHVPGGGS                                                                  10

SEQ ID NO: 505          moltype = AA   length = 9
FEATURE                 Location/Qualifiers
REGION                  1..9
                        note = Synthetic peptide
source                  1..9
                        mol_type = protein
                        organism = synthetic construct
SEQUENCE: 505
IKHVPGGGS                                                                   9

SEQ ID NO: 506          moltype = AA   length = 8
FEATURE                 Location/Qualifiers
REGION                  1..8
                        note = Synthetic peptide
source                  1..8
                        mol_type = protein
                        organism = synthetic construct
SEQUENCE: 506
KHVPGGGS                                                                    8

SEQ ID NO: 507          moltype = AA   length = 7
FEATURE                 Location/Qualifiers
REGION                  1..7
                        note = Synthetic peptide
source                  1..7
                        mol_type = protein
                        organism = synthetic construct
SEQUENCE: 507
HVPGGGS                                                                     7

SEQ ID NO: 508          moltype = AA   length = 6
FEATURE                 Location/Qualifiers
REGION                  1..6
                        note = Synthetic peptide
source                  1..6
                        mol_type = protein
                        organism = synthetic construct
SEQUENCE: 508
VPGGGS                                                                      6

SEQ ID NO: 509          moltype = AA   length = 5
FEATURE                 Location/Qualifiers
REGION                  1..5
                        note = Synthetic peptide
source                  1..5
                        mol_type = protein
                        organism = synthetic construct
SEQUENCE: 509
PGGGS                                                                       5

SEQ ID NO: 510          moltype = AA   length = 4
FEATURE                 Location/Qualifiers
REGION                  1..4
                        note = Synthetic peptide
source                  1..4
                        mol_type = protein
                        organism = synthetic construct
SEQUENCE: 510
GGGS                                                                        4

SEQ ID NO: 511          moltype =    length =
SEQUENCE: 511
000

SEQ ID NO: 512          moltype = AA   length = 10
FEATURE                 Location/Qualifiers
REGION                  1..10
                        note = Synthetic peptide
source                  1..10
                        mol_type = protein
                        organism = synthetic construct
SEQUENCE: 512
IKHVPGGGSV                                                                  10
```

```
SEQ ID NO: 513          moltype = AA   length = 9
FEATURE                 Location/Qualifiers
REGION                  1..9
                        note = Synthetic peptide
source                  1..9
                        mol_type = protein
                        organism = synthetic construct
SEQUENCE: 513
KHVPGGGSV                                                                 9

SEQ ID NO: 514          moltype = AA   length = 8
FEATURE                 Location/Qualifiers
REGION                  1..8
                        note = Synthetic peptide
source                  1..8
                        mol_type = protein
                        organism = synthetic construct
SEQUENCE: 514
HVPGGGSV                                                                  8

SEQ ID NO: 515          moltype = AA   length = 7
FEATURE                 Location/Qualifiers
REGION                  1..7
                        note = Synthetic peptide
source                  1..7
                        mol_type = protein
                        organism = synthetic construct
SEQUENCE: 515
VPGGGSV                                                                   7

SEQ ID NO: 516          moltype = AA   length = 6
FEATURE                 Location/Qualifiers
REGION                  1..6
                        note = Synthetic peptide
source                  1..6
                        mol_type = protein
                        organism = synthetic construct
SEQUENCE: 516
PGGGSV                                                                    6

SEQ ID NO: 517          moltype = AA   length = 5
FEATURE                 Location/Qualifiers
REGION                  1..5
                        note = Synthetic peptide
source                  1..5
                        mol_type = protein
                        organism = synthetic construct
SEQUENCE: 517
GGGSV                                                                     5

SEQ ID NO: 518          moltype = AA   length = 4
FEATURE                 Location/Qualifiers
REGION                  1..4
                        note = Synthetic peptide
source                  1..4
                        mol_type = protein
                        organism = synthetic construct
SEQUENCE: 518
GGSV                                                                      4

SEQ ID NO: 519          moltype =    length =
SEQUENCE: 519
000

SEQ ID NO: 520          moltype = AA   length = 10
FEATURE                 Location/Qualifiers
REGION                  1..10
                        note = Synthetic peptide
source                  1..10
                        mol_type = protein
                        organism = synthetic construct
SEQUENCE: 520
KHVPGGGSVQ                                                               10

SEQ ID NO: 521          moltype = AA   length = 9
FEATURE                 Location/Qualifiers
REGION                  1..9
                        note = Synthetic peptide
```

-continued

| | | |
|---|---|---|
| source | 1..9<br>mol_type = protein<br>organism = synthetic construct | |
| SEQUENCE: 521<br>HVPGGGSVQ | | 9 |
| SEQ ID NO: 522<br>FEATURE<br>REGION | moltype = AA   length = 8<br>Location/Qualifiers<br>1..8<br>note = Synthetic peptide | |
| source | 1..8<br>mol_type = protein<br>organism = synthetic construct | |
| SEQUENCE: 522<br>VPGGGSVQ | | 8 |
| SEQ ID NO: 523<br>FEATURE<br>REGION | moltype = AA   length = 7<br>Location/Qualifiers<br>1..7<br>note = Synthetic peptide | |
| source | 1..7<br>mol_type = protein<br>organism = synthetic construct | |
| SEQUENCE: 523<br>PGGGSVQ | | 7 |
| SEQ ID NO: 524<br>FEATURE<br>REGION | moltype = AA   length = 6<br>Location/Qualifiers<br>1..6<br>note = Synthetic peptide | |
| source | 1..6<br>mol_type = protein<br>organism = synthetic construct | |
| SEQUENCE: 524<br>GGGSVQ | | 6 |
| SEQ ID NO: 525<br>FEATURE<br>REGION | moltype = AA   length = 5<br>Location/Qualifiers<br>1..5<br>note = Synthetic peptide | |
| source | 1..5<br>mol_type = protein<br>organism = synthetic construct | |
| SEQUENCE: 525<br>GGSVQ | | 5 |
| SEQ ID NO: 526<br>FEATURE<br>REGION | moltype = AA   length = 4<br>Location/Qualifiers<br>1..4<br>note = Synthetic peptide | |
| source | 1..4<br>mol_type = protein<br>organism = synthetic construct | |
| SEQUENCE: 526<br>GSVQ | | 4 |
| SEQ ID NO: 527<br>SEQUENCE: 527<br>000 | moltype =    length = | |
| SEQ ID NO: 528<br>FEATURE<br>REGION | moltype = AA   length = 10<br>Location/Qualifiers<br>1..10<br>note = Synthetic peptide | |
| source | 1..10<br>mol_type = protein<br>organism = synthetic construct | |
| SEQUENCE: 528<br>HVPGGGSVQI | | 10 |
| SEQ ID NO: 529<br>FEATURE<br>REGION | moltype = AA   length = 9<br>Location/Qualifiers<br>1..9<br>note = Synthetic peptide | |
| source | 1..9<br>mol_type = protein<br>organism = synthetic construct | |
| SEQUENCE: 529<br>VPGGGSVQI | | 9 |

```
SEQ ID NO: 530          moltype = AA   length = 8
FEATURE                 Location/Qualifiers
REGION                  1..8
                        note = Synthetic peptide
source                  1..8
                        mol_type = protein
                        organism = synthetic construct
SEQUENCE: 530
PGGGSVQI                                                                  8

SEQ ID NO: 531          moltype = AA   length = 7
FEATURE                 Location/Qualifiers
REGION                  1..7
                        note = Synthetic peptide
source                  1..7
                        mol_type = protein
                        organism = synthetic construct
SEQUENCE: 531
GGGSVQI                                                                   7

SEQ ID NO: 532          moltype = AA   length = 6
FEATURE                 Location/Qualifiers
REGION                  1..6
                        note = Synthetic peptide
source                  1..6
                        mol_type = protein
                        organism = synthetic construct
SEQUENCE: 532
GGSVQI                                                                    6

SEQ ID NO: 533          moltype = AA   length = 5
FEATURE                 Location/Qualifiers
REGION                  1..5
                        note = Synthetic peptide
source                  1..5
                        mol_type = protein
                        organism = synthetic construct
SEQUENCE: 533
GSVQI                                                                     5

SEQ ID NO: 534          moltype = AA   length = 4
FEATURE                 Location/Qualifiers
REGION                  1..4
                        note = Synthetic peptide
source                  1..4
                        mol_type = protein
                        organism = synthetic construct
SEQUENCE: 534
SVQI                                                                      4

SEQ ID NO: 535          moltype = AA   length = 10
FEATURE                 Location/Qualifiers
REGION                  1..10
                        note = Synthetic peptide
source                  1..10
                        mol_type = protein
                        organism = synthetic construct
SEQUENCE: 535
GGSVQIVYKS                                                               10

SEQ ID NO: 536          moltype = AA   length = 9
FEATURE                 Location/Qualifiers
REGION                  1..9
                        note = Synthetic peptide
source                  1..9
                        mol_type = protein
                        organism = synthetic construct
SEQUENCE: 536
GSVQIVYKS                                                                 9

SEQ ID NO: 537          moltype = AA   length = 8
FEATURE                 Location/Qualifiers
REGION                  1..8
                        note = Synthetic peptide
source                  1..8
                        mol_type = protein
                        organism = synthetic construct
SEQUENCE: 537
```

SVQIVYKS                                                                          8

SEQ ID NO: 538          moltype = AA   length = 7
FEATURE                 Location/Qualifiers
REGION                  1..7
                        note = Synthetic peptide
source                  1..7
                        mol_type = protein
                        organism = synthetic construct
SEQUENCE: 538
VQIVYKS                                                                           7

SEQ ID NO: 539          moltype = AA   length = 6
FEATURE                 Location/Qualifiers
REGION                  1..6
                        note = Synthetic peptide
source                  1..6
                        mol_type = protein
                        organism = synthetic construct
SEQUENCE: 539
QIVYKS                                                                            6

SEQ ID NO: 540          moltype = AA   length = 5
FEATURE                 Location/Qualifiers
REGION                  1..5
                        note = Synthetic peptide
source                  1..5
                        mol_type = protein
                        organism = synthetic construct
SEQUENCE: 540
IVYKS                                                                             5

SEQ ID NO: 541          moltype = AA   length = 4
FEATURE                 Location/Qualifiers
REGION                  1..4
                        note = Synthetic peptide
source                  1..4
                        mol_type = protein
                        organism = synthetic construct
SEQUENCE: 541
VYKS                                                                              4

SEQ ID NO: 542          moltype =      length =
SEQUENCE: 542
000

SEQ ID NO: 543          moltype = AA   length = 10
FEATURE                 Location/Qualifiers
REGION                  1..10
                        note = Synthetic peptide
source                  1..10
                        mol_type = protein
                        organism = synthetic construct
SEQUENCE: 543
GSVQIVYKSV                                                                        10

SEQ ID NO: 544          moltype = AA   length = 9
FEATURE                 Location/Qualifiers
REGION                  1..9
                        note = Synthetic peptide
source                  1..9
                        mol_type = protein
                        organism = synthetic construct
SEQUENCE: 544
SVQIVYKSV                                                                         9

SEQ ID NO: 545          moltype = AA   length = 8
FEATURE                 Location/Qualifiers
REGION                  1..8
                        note = Synthetic peptide
source                  1..8
                        mol_type = protein
                        organism = synthetic construct
SEQUENCE: 545
VQIVYKSV                                                                          8

SEQ ID NO: 546          moltype = AA   length = 7
FEATURE                 Location/Qualifiers
REGION                  1..7

```
                        note = Synthetic peptide
source                  1..7
                        mol_type = protein
                        organism = synthetic construct
SEQUENCE: 546
QIVYKSV                                                                 7

SEQ ID NO: 547          moltype = AA   length = 6
FEATURE                 Location/Qualifiers
REGION                  1..6
                        note = Synthetic peptide
source                  1..6
                        mol_type = protein
                        organism = synthetic construct
SEQUENCE: 547
IVYKSV                                                                  6

SEQ ID NO: 548          moltype = AA   length = 5
FEATURE                 Location/Qualifiers
REGION                  1..5
                        note = Synthetic peptide
source                  1..5
                        mol_type = protein
                        organism = synthetic construct
SEQUENCE: 548
VYKSV                                                                   5

SEQ ID NO: 549          moltype = AA   length = 4
FEATURE                 Location/Qualifiers
REGION                  1..4
                        note = Synthetic peptide
source                  1..4
                        mol_type = protein
                        organism = synthetic construct
SEQUENCE: 549
YKSV                                                                    4

SEQ ID NO: 550          moltype = AA   length = 10
FEATURE                 Location/Qualifiers
REGION                  1..10
                        note = Synthetic peptide
source                  1..10
                        mol_type = protein
                        organism = synthetic construct
SEQUENCE: 550
SVQIVYKSVD                                                             10

SEQ ID NO: 551          moltype = AA   length = 9
FEATURE                 Location/Qualifiers
REGION                  1..9
                        note = Synthetic peptide
source                  1..9
                        mol_type = protein
                        organism = synthetic construct
SEQUENCE: 551
VQIVYKSVD                                                               9

SEQ ID NO: 552          moltype = AA   length = 8
FEATURE                 Location/Qualifiers
REGION                  1..8
                        note = Synthetic peptide
source                  1..8
                        mol_type = protein
                        organism = synthetic construct
SEQUENCE: 552
QIVYKSVD                                                                8

SEQ ID NO: 553          moltype = AA   length = 7
FEATURE                 Location/Qualifiers
REGION                  1..7
                        note = Synthetic peptide
source                  1..7
                        mol_type = protein
                        organism = synthetic construct
SEQUENCE: 553
IVYKSVD                                                                 7

SEQ ID NO: 554          moltype = AA   length = 6
FEATURE                 Location/Qualifiers
```

```
REGION                  1..6
                        note = Synthetic peptide
source                  1..6
                        mol_type = protein
                        organism = synthetic construct
SEQUENCE: 554
VYKSVD                                                                      6

SEQ ID NO: 555          moltype = AA  length = 5
FEATURE                 Location/Qualifiers
REGION                  1..5
                        note = Synthetic peptide
source                  1..5
                        mol_type = protein
                        organism = synthetic construct
SEQUENCE: 555
YKSVD                                                                       5

SEQ ID NO: 556          moltype = AA  length = 4
FEATURE                 Location/Qualifiers
REGION                  1..4
                        note = Synthetic peptide
source                  1..4
                        mol_type = protein
                        organism = synthetic construct
SEQUENCE: 556
KSVD                                                                        4

SEQ ID NO: 557          moltype =   length =
SEQUENCE: 557
000

SEQ ID NO: 558          moltype = AA  length = 10
FEATURE                 Location/Qualifiers
REGION                  1..10
                        note = Synthetic peptide
source                  1..10
                        mol_type = protein
                        organism = synthetic construct
SEQUENCE: 558
VQIVYKSVDL                                                                 10

SEQ ID NO: 559          moltype = AA  length = 9
FEATURE                 Location/Qualifiers
REGION                  1..9
                        note = Synthetic peptide
source                  1..9
                        mol_type = protein
                        organism = synthetic construct
SEQUENCE: 559
QIVYKSVDL                                                                   9

SEQ ID NO: 560          moltype = AA  length = 8
FEATURE                 Location/Qualifiers
REGION                  1..8
                        note = Synthetic peptide
source                  1..8
                        mol_type = protein
                        organism = synthetic construct
SEQUENCE: 560
IVYKSVDL                                                                    8

SEQ ID NO: 561          moltype = AA  length = 7
FEATURE                 Location/Qualifiers
REGION                  1..7
                        note = Synthetic peptide
source                  1..7
                        mol_type = protein
                        organism = synthetic construct
SEQUENCE: 561
VYKSVDL                                                                     7

SEQ ID NO: 562          moltype = AA  length = 6
FEATURE                 Location/Qualifiers
REGION                  1..6
                        note = Synthetic peptide
source                  1..6
                        mol_type = protein
                        organism = synthetic construct
```

```
SEQUENCE: 562
YKSVDL                                                                          6

SEQ ID NO: 563          moltype = AA  length = 5
FEATURE                 Location/Qualifiers
REGION                  1..5
                        note = Synthetic peptide
source                  1..5
                        mol_type = protein
                        organism = synthetic construct
SEQUENCE: 563
KSVDL                                                                           5

SEQ ID NO: 564          moltype = AA  length = 4
FEATURE                 Location/Qualifiers
REGION                  1..4
                        note = Synthetic peptide
source                  1..4
                        mol_type = protein
                        organism = synthetic construct
SEQUENCE: 564
SVDL                                                                            4

SEQ ID NO: 565          moltype = AA  length = 10
FEATURE                 Location/Qualifiers
REGION                  1..10
                        note = Synthetic peptide
source                  1..10
                        mol_type = protein
                        organism = synthetic construct
SEQUENCE: 565
QIVYKSVDLS                                                                     10

SEQ ID NO: 566          moltype = AA  length = 9
FEATURE                 Location/Qualifiers
REGION                  1..9
                        note = Synthetic peptide
source                  1..9
                        mol_type = protein
                        organism = synthetic construct
SEQUENCE: 566
IVYKSVDLS                                                                       9

SEQ ID NO: 567          moltype = AA  length = 8
FEATURE                 Location/Qualifiers
REGION                  1..8
                        note = Synthetic peptide
source                  1..8
                        mol_type = protein
                        organism = synthetic construct
SEQUENCE: 567
VYKSVDLS                                                                        8

SEQ ID NO: 568          moltype = AA  length = 7
FEATURE                 Location/Qualifiers
REGION                  1..7
                        note = Synthetic peptide
source                  1..7
                        mol_type = protein
                        organism = synthetic construct
SEQUENCE: 568
YKSVDLS                                                                         7

SEQ ID NO: 569          moltype = AA  length = 6
FEATURE                 Location/Qualifiers
REGION                  1..6
                        note = Synthetic peptide
source                  1..6
                        mol_type = protein
                        organism = synthetic construct
SEQUENCE: 569
KSVDLS                                                                          6

SEQ ID NO: 570          moltype = AA  length = 5
FEATURE                 Location/Qualifiers
REGION                  1..5
                        note = Synthetic peptide
source                  1..5
                        mol_type = protein
```

```
                        organism = synthetic construct
SEQUENCE: 570
SVDLS                                                                   5

SEQ ID NO: 571          moltype = AA   length = 10
FEATURE                 Location/Qualifiers
REGION                  1..10
                        note = Synthetic peptide
source                  1..10
                        mol_type = protein
                        organism = synthetic construct
SEQUENCE: 571
IVYKSVDLSK                                                             10

SEQ ID NO: 572          moltype = AA   length = 9
FEATURE                 Location/Qualifiers
REGION                  1..9
                        note = Synthetic peptide
source                  1..9
                        mol_type = protein
                        organism = synthetic construct
SEQUENCE: 572
VYKSVDLSK                                                               9

SEQ ID NO: 573          moltype = AA   length = 8
FEATURE                 Location/Qualifiers
REGION                  1..8
                        note = Synthetic peptide
source                  1..8
                        mol_type = protein
                        organism = synthetic construct
SEQUENCE: 573
YKSVDLSK                                                                8

SEQ ID NO: 574          moltype = AA   length = 7
FEATURE                 Location/Qualifiers
REGION                  1..7
                        note = Synthetic peptide
source                  1..7
                        mol_type = protein
                        organism = synthetic construct
SEQUENCE: 574
KSVDLSK                                                                 7

SEQ ID NO: 575          moltype = AA   length = 10
FEATURE                 Location/Qualifiers
REGION                  1..10
                        note = Synthetic peptide
source                  1..10
                        mol_type = protein
                        organism = synthetic construct
SEQUENCE: 575
VYKSVDLSKV                                                             10

SEQ ID NO: 576          moltype = AA   length = 9
FEATURE                 Location/Qualifiers
REGION                  1..9
                        note = Synthetic peptide
source                  1..9
                        mol_type = protein
                        organism = synthetic construct
SEQUENCE: 576
YKSVDLSKV                                                               9

SEQ ID NO: 577          moltype = AA   length = 8
FEATURE                 Location/Qualifiers
REGION                  1..8
                        note = Synthetic peptide
source                  1..8
                        mol_type = protein
                        organism = synthetic construct
SEQUENCE: 577
KSVDLSKV                                                                8

SEQ ID NO: 578          moltype = AA   length = 7
FEATURE                 Location/Qualifiers
REGION                  1..7
                        note = Synthetic peptide
source                  1..7
```

```
SEQUENCE: 578
SVDLSKV                                                              7

SEQ ID NO: 579        moltype = AA  length = 10
FEATURE               Location/Qualifiers
REGION                1..10
                      note = Synthetic peptide
source                1..10
                      mol_type = protein
                      organism = synthetic construct
SEQUENCE: 579
YKSVDLSKVT                                                          10

SEQ ID NO: 580        moltype = AA  length = 9
FEATURE               Location/Qualifiers
REGION                1..9
                      note = Synthetic peptide
source                1..9
                      mol_type = protein
                      organism = synthetic construct
SEQUENCE: 580
KSVDLSKVT                                                            9

SEQ ID NO: 581        moltype = AA  length = 8
FEATURE               Location/Qualifiers
REGION                1..8
                      note = Synthetic peptide
source                1..8
                      mol_type = protein
                      organism = synthetic construct
SEQUENCE: 581
SVDLSKVT                                                             8

SEQ ID NO: 582        moltype = AA  length = 6
FEATURE               Location/Qualifiers
REGION                1..6
                      note = Synthetic peptide
source                1..6
                      mol_type = protein
                      organism = synthetic construct
SEQUENCE: 582
DLSKVT                                                               6

SEQ ID NO: 583        moltype = AA  length = 5
FEATURE               Location/Qualifiers
REGION                1..5
                      note = Synthetic peptide
source                1..5
                      mol_type = protein
                      organism = synthetic construct
SEQUENCE: 583
LSKVT                                                                5

SEQ ID NO: 584        moltype = AA  length = 4
FEATURE               Location/Qualifiers
REGION                1..4
                      note = Synthetic peptide
source                1..4
                      mol_type = protein
                      organism = synthetic construct
SEQUENCE: 584
SKVT                                                                 4

SEQ ID NO: 585        moltype =    length =
SEQUENCE: 585
000

SEQ ID NO: 586        moltype = AA  length = 10
FEATURE               Location/Qualifiers
REGION                1..10
                      note = Synthetic peptide
source                1..10
                      mol_type = protein
                      organism = synthetic construct
SEQUENCE: 586
HGAEIVYKSV                                                          10
```

```
SEQ ID NO: 587            moltype = AA   length = 9
FEATURE                   Location/Qualifiers
REGION                    1..9
                          note = Synthetic peptide
source                    1..9
                          mol_type = protein
                          organism = synthetic construct
SEQUENCE: 587
GAEIVYKSV                                                                 9

SEQ ID NO: 588            moltype = AA   length = 8
FEATURE                   Location/Qualifiers
REGION                    1..8
                          note = Synthetic peptide
source                    1..8
                          mol_type = protein
                          organism = synthetic construct
SEQUENCE: 588
AEIVYKSV                                                                  8

SEQ ID NO: 589            moltype = AA   length = 10
FEATURE                   Location/Qualifiers
REGION                    1..10
                          note = Synthetic peptide
source                    1..10
                          mol_type = protein
                          organism = synthetic construct
SEQUENCE: 589
GAEIVYKSVV                                                                10

SEQ ID NO: 590            moltype = AA   length = 9
FEATURE                   Location/Qualifiers
REGION                    1..9
                          note = Synthetic peptide
source                    1..9
                          mol_type = protein
                          organism = synthetic construct
SEQUENCE: 590
AEIVYKSVV                                                                 9

SEQ ID NO: 591            moltype = AA   length = 8
FEATURE                   Location/Qualifiers
REGION                    1..8
                          note = Synthetic peptide
source                    1..8
                          mol_type = protein
                          organism = synthetic construct
SEQUENCE: 591
EIVYKSVV                                                                  8

SEQ ID NO: 592            moltype = AA   length = 7
FEATURE                   Location/Qualifiers
REGION                    1..7
                          note = Synthetic peptide
source                    1..7
                          mol_type = protein
                          organism = synthetic construct
SEQUENCE: 592
IVYKSVV                                                                   7

SEQ ID NO: 593            moltype = AA   length = 6
FEATURE                   Location/Qualifiers
REGION                    1..6
                          note = Synthetic peptide
source                    1..6
                          mol_type = protein
                          organism = synthetic construct
SEQUENCE: 593
VYKSVV                                                                    6

SEQ ID NO: 594            moltype = AA   length = 5
FEATURE                   Location/Qualifiers
REGION                    1..5
                          note = Synthetic peptide
source                    1..5
                          mol_type = protein
                          organism = synthetic construct
SEQUENCE: 594
YKSVV                                                                     5
```

```
SEQ ID NO: 595          moltype = AA   length = 4
FEATURE                 Location/Qualifiers
REGION                  1..4
                        note = Synthetic peptide
source                  1..4
                        mol_type = protein
                        organism = synthetic construct
SEQUENCE: 595
KSVV                                                                    4

SEQ ID NO: 596          moltype =    length =
SEQUENCE: 596
000

SEQ ID NO: 597          moltype = AA   length = 10
FEATURE                 Location/Qualifiers
REGION                  1..10
                        note = Synthetic peptide
source                  1..10
                        mol_type = protein
                        organism = synthetic construct
SEQUENCE: 597
AEIVYKSVVS                                                             10

SEQ ID NO: 598          moltype = AA   length = 9
FEATURE                 Location/Qualifiers
REGION                  1..9
                        note = Synthetic peptide
source                  1..9
                        mol_type = protein
                        organism = synthetic construct
SEQUENCE: 598
EIVYKSVVS                                                               9

SEQ ID NO: 599          moltype = AA   length = 8
FEATURE                 Location/Qualifiers
REGION                  1..8
                        note = Synthetic peptide
source                  1..8
                        mol_type = protein
                        organism = synthetic construct
SEQUENCE: 599
IVYKSVVS                                                                8

SEQ ID NO: 600          moltype = AA   length = 7
FEATURE                 Location/Qualifiers
REGION                  1..7
                        note = Synthetic peptide
source                  1..7
                        mol_type = protein
                        organism = synthetic construct
SEQUENCE: 600
VYKSVVS                                                                 7

SEQ ID NO: 601          moltype = AA   length = 6
FEATURE                 Location/Qualifiers
REGION                  1..6
                        note = Synthetic peptide
source                  1..6
                        mol_type = protein
                        organism = synthetic construct
SEQUENCE: 601
YKSVVS                                                                  6

SEQ ID NO: 602          moltype = AA   length = 5
FEATURE                 Location/Qualifiers
REGION                  1..5
                        note = Synthetic peptide
source                  1..5
                        mol_type = protein
                        organism = synthetic construct
SEQUENCE: 602
KSVVS                                                                   5

SEQ ID NO: 603          moltype = AA   length = 4
FEATURE                 Location/Qualifiers
REGION                  1..4
                        note = Synthetic peptide
```

```
                        -continued source                  1..4
                        mol_type = protein
                        organism = synthetic construct
SEQUENCE: 603
SVVS                                                                    4

SEQ ID NO: 604          moltype = AA  length = 10
FEATURE                 Location/Qualifiers
REGION                  1..10
                        note = Synthetic peptide
source                  1..10
                        mol_type = protein
                        organism = synthetic construct
SEQUENCE: 604
EIVYKSVVSG                                                             10

SEQ ID NO: 605          moltype = AA  length = 9
FEATURE                 Location/Qualifiers
REGION                  1..9
                        note = Synthetic peptide
source                  1..9
                        mol_type = protein
                        organism = synthetic construct
SEQUENCE: 605
IVYKSVVSG                                                               9

SEQ ID NO: 606          moltype = AA  length = 8
FEATURE                 Location/Qualifiers
REGION                  1..8
                        note = Synthetic peptide
source                  1..8
                        mol_type = protein
                        organism = synthetic construct
SEQUENCE: 606
VYKSVVSG                                                                8

SEQ ID NO: 607          moltype = AA  length = 7
FEATURE                 Location/Qualifiers
REGION                  1..7
                        note = Synthetic peptide
source                  1..7
                        mol_type = protein
                        organism = synthetic construct
SEQUENCE: 607
YKSVVSG                                                                 7

SEQ ID NO: 608          moltype = AA  length = 6
FEATURE                 Location/Qualifiers
REGION                  1..6
                        note = Synthetic peptide
source                  1..6
                        mol_type = protein
                        organism = synthetic construct
SEQUENCE: 608
KSVVSG                                                                  6

SEQ ID NO: 609          moltype = AA  length = 5
FEATURE                 Location/Qualifiers
REGION                  1..5
                        note = Synthetic peptide
source                  1..5
                        mol_type = protein
                        organism = synthetic construct
SEQUENCE: 609
SVVSG                                                                   5

SEQ ID NO: 610          moltype = AA  length = 4
FEATURE                 Location/Qualifiers
REGION                  1..4
                        note = Synthetic peptide
source                  1..4
                        mol_type = protein
                        organism = synthetic construct
SEQUENCE: 610
VVSG                                                                    4

SEQ ID NO: 611          moltype =     length =
SEQUENCE: 611
000
```

| | | |
|---|---|---|
| SEQ ID NO: 612<br>FEATURE<br>REGION<br><br>source<br><br>SEQUENCE: 612<br>IVYKSVVSGD | moltype = AA   length = 10<br>Location/Qualifiers<br>1..10<br>note = Synthetic peptide<br>1..10<br>mol_type = protein<br>organism = synthetic construct | <br><br><br><br><br><br><br>10 |
| SEQ ID NO: 613<br>FEATURE<br>REGION<br><br>source<br><br>SEQUENCE: 613<br>VYKSVVSGD | moltype = AA   length = 9<br>Location/Qualifiers<br>1..9<br>note = Synthetic peptide<br>1..9<br>mol_type = protein<br>organism = synthetic construct | <br><br><br><br><br><br><br>9 |
| SEQ ID NO: 614<br>FEATURE<br>REGION<br><br>source<br><br>SEQUENCE: 614<br>YKSVVSGD | moltype = AA   length = 8<br>Location/Qualifiers<br>1..8<br>note = Synthetic peptide<br>1..8<br>mol_type = protein<br>organism = synthetic construct | <br><br><br><br><br><br><br>8 |
| SEQ ID NO: 615<br>FEATURE<br>REGION<br><br>source<br><br>SEQUENCE: 615<br>KSVVSGD | moltype = AA   length = 7<br>Location/Qualifiers<br>1..7<br>note = Synthetic peptide<br>1..7<br>mol_type = protein<br>organism = synthetic construct | <br><br><br><br><br><br><br>7 |
| SEQ ID NO: 616<br>FEATURE<br>REGION<br><br>source<br><br>SEQUENCE: 616<br>SVVSGD | moltype = AA   length = 6<br>Location/Qualifiers<br>1..6<br>note = Synthetic peptide<br>1..6<br>mol_type = protein<br>organism = synthetic construct | <br><br><br><br><br><br><br>6 |
| SEQ ID NO: 617<br>FEATURE<br>REGION<br><br>source<br><br>SEQUENCE: 617<br>VVSGD | moltype = AA   length = 5<br>Location/Qualifiers<br>1..5<br>note = Synthetic peptide<br>1..5<br>mol_type = protein<br>organism = synthetic construct | <br><br><br><br><br><br><br>5 |
| SEQ ID NO: 618<br>FEATURE<br>REGION<br><br>source<br><br>SEQUENCE: 618<br>VYKSVVSGDT | moltype = AA   length = 10<br>Location/Qualifiers<br>1..10<br>note = Synthetic peptide<br>1..10<br>mol_type = protein<br>organism = synthetic construct | <br><br><br><br><br><br><br>10 |
| SEQ ID NO: 619<br>FEATURE<br>REGION<br><br>source<br><br>SEQUENCE: 619 | moltype = AA   length = 9<br>Location/Qualifiers<br>1..9<br>note = Synthetic peptide<br>1..9<br>mol_type = protein<br>organism = synthetic construct | |

```
YKSVVSGDT                                                                      9

SEQ ID NO: 620      moltype = AA  length = 8
FEATURE             Location/Qualifiers
REGION              1..8
                    note = Synthetic peptide
source              1..8
                    mol_type = protein
                    organism = synthetic construct
SEQUENCE: 620
KSVVSGDT                                                                       8

SEQ ID NO: 621      moltype = AA  length = 7
FEATURE             Location/Qualifiers
REGION              1..7
                    note = Synthetic peptide
source              1..7
                    mol_type = protein
                    organism = synthetic construct
SEQUENCE: 621
SVVSGDT                                                                        7

SEQ ID NO: 622      moltype = AA  length = 10
FEATURE             Location/Qualifiers
REGION              1..10
                    note = Synthetic peptide
source              1..10
                    mol_type = protein
                    organism = synthetic construct
SEQUENCE: 622
YKSVVSGDTS                                                                    10

SEQ ID NO: 623      moltype = AA  length = 9
FEATURE             Location/Qualifiers
REGION              1..9
                    note = Synthetic peptide
source              1..9
                    mol_type = protein
                    organism = synthetic construct
SEQUENCE: 623
KSVVSGDTS                                                                      9

SEQ ID NO: 624      moltype = AA  length = 8
FEATURE             Location/Qualifiers
REGION              1..8
                    note = Synthetic peptide
source              1..8
                    mol_type = protein
                    organism = synthetic construct
SEQUENCE: 624
SVVSGDTS                                                                       8

SEQ ID NO: 625      moltype = AA  length = 10
FEATURE             Location/Qualifiers
REGION              1..10
                    note = Synthetic peptide
source              1..10
                    mol_type = protein
                    organism = synthetic construct
SEQUENCE: 625
YKSVVSGDTS                                                                    10

SEQ ID NO: 626      moltype = AA  length = 9
FEATURE             Location/Qualifiers
REGION              1..9
                    note = Synthetic peptide
source              1..9
                    mol_type = protein
                    organism = synthetic construct
SEQUENCE: 626
KSVVSGDTS                                                                      9

SEQ ID NO: 627      moltype = AA  length = 8
FEATURE             Location/Qualifiers
REGION              1..8
                    note = Synthetic peptide
source              1..8
                    mol_type = protein
                    organism = synthetic construct
```

-continued

```
SEQUENCE: 627
SVVSGDTS                                                               8

SEQ ID NO: 628          moltype = AA  length = 7
FEATURE                 Location/Qualifiers
REGION                  1..7
                        note = Synthetic peptide
source                  1..7
                        mol_type = protein
                        organism = synthetic construct
SEQUENCE: 628
VVSGDTS                                                                7

SEQ ID NO: 629          moltype = AA  length = 10
FEATURE                 Location/Qualifiers
REGION                  1..10
                        note = Synthetic peptide
source                  1..10
                        mol_type = protein
                        organism = synthetic construct
SEQUENCE: 629
KSVVSGDTSP                                                            10

SEQ ID NO: 630          moltype = AA  length = 9
FEATURE                 Location/Qualifiers
REGION                  1..9
                        note = Synthetic peptide
source                  1..9
                        mol_type = protein
                        organism = synthetic construct
SEQUENCE: 630
SVVSGDTSP                                                              9

SEQ ID NO: 631          moltype = AA  length = 10
FEATURE                 Location/Qualifiers
REGION                  1..10
                        note = Synthetic peptide
source                  1..10
                        mol_type = protein
                        organism = synthetic construct
SEQUENCE: 631
SVVSGDTSPR                                                            10

SEQ ID NO: 632          moltype = AA  length = 10
FEATURE                 Location/Qualifiers
REGION                  1..10
                        note = Synthetic peptide
source                  1..10
                        mol_type = protein
                        organism = synthetic construct
SEQUENCE: 632
DHGAEIVYKP                                                            10

SEQ ID NO: 633          moltype = AA  length = 9
FEATURE                 Location/Qualifiers
REGION                  1..9
                        note = Synthetic peptide
source                  1..9
                        mol_type = protein
                        organism = synthetic construct
SEQUENCE: 633
HGAEIVYKP                                                              9

SEQ ID NO: 634          moltype = AA  length = 8
FEATURE                 Location/Qualifiers
REGION                  1..8
                        note = Synthetic peptide
source                  1..8
                        mol_type = protein
                        organism = synthetic construct
SEQUENCE: 634
GAEIVYKP                                                               8

SEQ ID NO: 635          moltype = AA  length = 7
FEATURE                 Location/Qualifiers
REGION                  1..7
                        note = Synthetic peptide
source                  1..7
                        mol_type = protein
```

```
                       -continued
                       organism = synthetic construct
SEQUENCE: 635
AEIVYKP                                                                 7

SEQ ID NO: 636         moltype = AA   length = 10
FEATURE                Location/Qualifiers
REGION                 1..10
                       note = Synthetic peptide
source                 1..10
                       mol_type = protein
                       organism = synthetic construct
SEQUENCE: 636
HGAEIVYKPV                                                             10

SEQ ID NO: 637         moltype = AA   length = 9
FEATURE                Location/Qualifiers
REGION                 1..9
                       note = Synthetic peptide
source                 1..9
                       mol_type = protein
                       organism = synthetic construct
SEQUENCE: 637
GAEIVYKPV                                                               9

SEQ ID NO: 638         moltype = AA   length = 8
FEATURE                Location/Qualifiers
REGION                 1..8
                       note = Synthetic peptide
source                 1..8
                       mol_type = protein
                       organism = synthetic construct
SEQUENCE: 638
AEIVYKPV                                                                8

SEQ ID NO: 639         moltype = AA   length = 10
FEATURE                Location/Qualifiers
REGION                 1..10
                       note = Synthetic peptide
source                 1..10
                       mol_type = protein
                       organism = synthetic construct
SEQUENCE: 639
GAEIVYKPVV                                                             10

SEQ ID NO: 640         moltype = AA   length = 9
FEATURE                Location/Qualifiers
REGION                 1..9
                       note = Synthetic peptide
source                 1..9
                       mol_type = protein
                       organism = synthetic construct
SEQUENCE: 640
AEIVYKPVV                                                               9

SEQ ID NO: 641         moltype = AA   length = 8
FEATURE                Location/Qualifiers
REGION                 1..8
                       note = Synthetic peptide
source                 1..8
                       mol_type = protein
                       organism = synthetic construct
SEQUENCE: 641
EIVYKPVV                                                                8

SEQ ID NO: 642         moltype = AA   length = 7
FEATURE                Location/Qualifiers
REGION                 1..7
                       note = Synthetic peptide
source                 1..7
                       mol_type = protein
                       organism = synthetic construct
SEQUENCE: 642
IVYKPVV                                                                 7

SEQ ID NO: 643         moltype = AA   length = 6
FEATURE                Location/Qualifiers
REGION                 1..6
                       note = Synthetic peptide
source                 1..6
```

```
                                          mol_type = protein
                                          organism = synthetic construct
SEQUENCE: 643
VYKPVV                                                                        6

SEQ ID NO: 644          moltype = AA  length = 5
FEATURE                 Location/Qualifiers
REGION                  1..5
                        note = Synthetic peptide
source                  1..5
                        mol_type = protein
                        organism = synthetic construct
SEQUENCE: 644
YKPVV                                                                         5

SEQ ID NO: 645          moltype = AA  length = 4
FEATURE                 Location/Qualifiers
REGION                  1..4
                        note = Synthetic peptide
source                  1..4
                        mol_type = protein
                        organism = synthetic construct
SEQUENCE: 645
KPVV                                                                          4

SEQ ID NO: 646          moltype = AA  length = 10
FEATURE                 Location/Qualifiers
REGION                  1..10
                        note = Synthetic peptide
source                  1..10
                        mol_type = protein
                        organism = synthetic construct
SEQUENCE: 646
AEIVYKPVVS                                                                   10

SEQ ID NO: 647          moltype = AA  length = 9
FEATURE                 Location/Qualifiers
REGION                  1..9
                        note = Synthetic peptide
source                  1..9
                        mol_type = protein
                        organism = synthetic construct
SEQUENCE: 647
EIVYKPVVS                                                                     9

SEQ ID NO: 648          moltype = AA  length = 8
FEATURE                 Location/Qualifiers
REGION                  1..8
                        note = Synthetic peptide
source                  1..8
                        mol_type = protein
                        organism = synthetic construct
SEQUENCE: 648
IVYKPVVS                                                                      8

SEQ ID NO: 649          moltype = AA  length = 7
FEATURE                 Location/Qualifiers
REGION                  1..7
                        note = Synthetic peptide
source                  1..7
                        mol_type = protein
                        organism = synthetic construct
SEQUENCE: 649
VYKPVVS                                                                       7

SEQ ID NO: 650          moltype = AA  length = 6
FEATURE                 Location/Qualifiers
REGION                  1..6
                        note = Synthetic peptide
source                  1..6
                        mol_type = protein
                        organism = synthetic construct
SEQUENCE: 650
YKPVVS                                                                        6

SEQ ID NO: 651          moltype = AA  length = 5
FEATURE                 Location/Qualifiers
REGION                  1..5
                        note = Synthetic peptide
```

```
                         -continued source                  1..5
                        mol_type = protein
                        organism = synthetic construct
SEQUENCE: 651
KPVVS                                                                    5

SEQ ID NO: 652          moltype = AA  length = 10
FEATURE                 Location/Qualifiers
REGION                  1..10
                        note = Synthetic peptide
source                  1..10
                        mol_type = protein
                        organism = synthetic construct
SEQUENCE: 652
EIVYKPVVSG                                                              10

SEQ ID NO: 653          moltype = AA  length = 9
FEATURE                 Location/Qualifiers
REGION                  1..9
                        note = Synthetic peptide
source                  1..9
                        mol_type = protein
                        organism = synthetic construct
SEQUENCE: 653
IVYKPVVSG                                                                9

SEQ ID NO: 654          moltype = AA  length = 8
FEATURE                 Location/Qualifiers
REGION                  1..8
                        note = Synthetic peptide
source                  1..8
                        mol_type = protein
                        organism = synthetic construct
SEQUENCE: 654
VYKPVVSG                                                                 8

SEQ ID NO: 655          moltype = AA  length = 7
FEATURE                 Location/Qualifiers
REGION                  1..7
                        note = Synthetic peptide
source                  1..7
                        mol_type = protein
                        organism = synthetic construct
SEQUENCE: 655
YKPVVSG                                                                  7

SEQ ID NO: 656          moltype = AA  length = 6
FEATURE                 Location/Qualifiers
REGION                  1..6
                        note = Synthetic peptide
source                  1..6
                        mol_type = protein
                        organism = synthetic construct
SEQUENCE: 656
KPVVSG                                                                   6

SEQ ID NO: 657          moltype = AA  length = 10
FEATURE                 Location/Qualifiers
REGION                  1..10
                        note = Synthetic peptide
source                  1..10
                        mol_type = protein
                        organism = synthetic construct
SEQUENCE: 657
IVYKPVVSGD                                                              10

SEQ ID NO: 658          moltype = AA  length = 9
FEATURE                 Location/Qualifiers
REGION                  1..9
                        note = Synthetic peptide
source                  1..9
                        mol_type = protein
                        organism = synthetic construct
SEQUENCE: 658
VYKPVVSGD                                                                9

SEQ ID NO: 659          moltype = AA  length = 8
FEATURE                 Location/Qualifiers
REGION                  1..8
```

```
                        note         = Synthetic peptide
source                  1..8
                        mol_type     = protein
                        organism     = synthetic construct
SEQUENCE: 659
YKPVVSGD                                                                    8

SEQ ID NO: 660          moltype = AA   length = 7
FEATURE                 Location/Qualifiers
REGION                  1..7
                        note         = Synthetic peptide
source                  1..7
                        mol_type     = protein
                        organism     = synthetic construct
SEQUENCE: 660
KPVVSGD                                                                     7

SEQ ID NO: 661          moltype = AA   length = 10
FEATURE                 Location/Qualifiers
REGION                  1..10
                        note         = Synthetic peptide
source                  1..10
                        mol_type     = protein
                        organism     = synthetic construct
SEQUENCE: 661
VYKPVVSGDT                                                                 10

SEQ ID NO: 662          moltype = AA   length = 9
FEATURE                 Location/Qualifiers
REGION                  1..9
                        note         = Synthetic peptide
source                  1..9
                        mol_type     = protein
                        organism     = synthetic construct
SEQUENCE: 662
YKPVVSGDT                                                                   9

SEQ ID NO: 663          moltype = AA   length = 8
FEATURE                 Location/Qualifiers
REGION                  1..8
                        note         = Synthetic peptide
source                  1..8
                        mol_type     = protein
                        organism     = synthetic construct
SEQUENCE: 663
KPVVSGDT                                                                    8

SEQ ID NO: 664          moltype = AA   length = 10
FEATURE                 Location/Qualifiers
REGION                  1..10
                        note         = Synthetic peptide
source                  1..10
                        mol_type     = protein
                        organism     = synthetic construct
SEQUENCE: 664
YKPVVSGDTS                                                                 10

SEQ ID NO: 665          moltype = AA   length = 9
FEATURE                 Location/Qualifiers
REGION                  1..9
                        note         = Synthetic peptide
source                  1..9
                        mol_type     = protein
                        organism     = synthetic construct
SEQUENCE: 665
KPVVSGDTS                                                                   9

SEQ ID NO: 666          moltype = AA   length = 8
FEATURE                 Location/Qualifiers
REGION                  1..8
                        note         = Synthetic peptide
source                  1..8
                        mol_type     = protein
                        organism     = synthetic construct
SEQUENCE: 666
PVVSGDTS                                                                    8

SEQ ID NO: 667          moltype = AA   length = 7
FEATURE                 Location/Qualifiers
```

```
REGION                    1..7
                          note = Synthetic peptide
source                    1..7
                          mol_type = protein
                          organism = synthetic construct
SEQUENCE: 667
VVSGDTS                                                              7

SEQ ID NO: 668            moltype = AA  length = 10
FEATURE                   Location/Qualifiers
REGION                    1..10
                          note = Synthetic peptide
source                    1..10
                          mol_type = protein
                          organism = synthetic construct
SEQUENCE: 668
KPVVSGDTSP                                                          10

SEQ ID NO: 669            moltype = AA  length = 4
FEATURE                   Location/Qualifiers
REGION                    1..4
                          note = Synthetic peptide
source                    1..4
                          mol_type = protein
                          organism = synthetic construct
SEQUENCE: 669
CNIK                                                                 4

SEQ ID NO: 670            moltype = AA  length = 5
FEATURE                   Location/Qualifiers
REGION                    1..5
                          note = Synthetic peptide
source                    1..5
                          mol_type = protein
                          organism = synthetic construct
SEQUENCE: 670
CNIKH                                                                5

SEQ ID NO: 671            moltype = AA  length = 6
FEATURE                   Location/Qualifiers
REGION                    1..6
                          note = Synthetic peptide
source                    1..6
                          mol_type = protein
                          organism = synthetic construct
SEQUENCE: 671
CNIKHV                                                               6

SEQ ID NO: 672            moltype = AA  length = 9
FEATURE                   Location/Qualifiers
REGION                    1..9
                          note = Synthetic peptide
source                    1..9
                          mol_type = protein
                          organism = synthetic construct
SEQUENCE: 672
CNIKHVPGG                                                            9

SEQ ID NO: 673            moltype = AA  length = 10
FEATURE                   Location/Qualifiers
REGION                    1..10
                          note = Synthetic peptide
source                    1..10
                          mol_type = protein
                          organism = synthetic construct
SEQUENCE: 673
CNIKHVPGGG                                                          10

SEQ ID NO: 674            moltype = AA  length = 11
FEATURE                   Location/Qualifiers
REGION                    1..11
                          note = Synthetic peptide
source                    1..11
                          mol_type = protein
                          organism = synthetic construct
SEQUENCE: 674
CNIKHVPGGG S                                                        11

SEQ ID NO: 675            moltype = AA  length = 10
```

```
FEATURE                Location/Qualifiers
REGION                 1..10
                       note = Synthetic peptide
source                 1..10
                       mol_type = protein
                       organism = synthetic construct
SEQUENCE: 675
ENLKHQPGGG                                                                    10

SEQ ID NO: 676         moltype = AA  length = 9
FEATURE                Location/Qualifiers
REGION                 1..9
                       note = Synthetic peptide
source                 1..9
                       mol_type = protein
                       organism = synthetic construct
SEQUENCE: 676
NLKHQPGGG                                                                     9

SEQ ID NO: 677         moltype = AA  length = 8
FEATURE                Location/Qualifiers
REGION                 1..8
                       note = Synthetic peptide
source                 1..8
                       mol_type = protein
                       organism = synthetic construct
SEQUENCE: 677
LKHQPGGG                                                                      8

SEQ ID NO: 678         moltype = AA  length = 7
FEATURE                Location/Qualifiers
REGION                 1..7
                       note = Synthetic peptide
source                 1..7
                       mol_type = protein
                       organism = synthetic construct
SEQUENCE: 678
KHQPGGG                                                                       7

SEQ ID NO: 679         moltype = AA  length = 6
FEATURE                Location/Qualifiers
REGION                 1..6
                       note = Synthetic peptide
source                 1..6
                       mol_type = protein
                       organism = synthetic construct
SEQUENCE: 679
HQPGGG                                                                        6

SEQ ID NO: 680         moltype = AA  length = 5
FEATURE                Location/Qualifiers
REGION                 1..5
                       note = Synthetic peptide
source                 1..5
                       mol_type = protein
                       organism = synthetic construct
SEQUENCE: 680
QPGGG                                                                         5

SEQ ID NO: 681         moltype = AA  length = 10
FEATURE                Location/Qualifiers
REGION                 1..10
                       note = Synthetic peptide
source                 1..10
                       mol_type = protein
                       organism = synthetic construct
SEQUENCE: 681
TENLKHQPGG                                                                    10

SEQ ID NO: 682         moltype = AA  length = 9
FEATURE                Location/Qualifiers
REGION                 1..9
                       note = Synthetic peptide
source                 1..9
                       mol_type = protein
                       organism = synthetic construct
SEQUENCE: 682
ENLKHQPGG                                                                     9
```

```
SEQ ID NO: 683            moltype = AA  length = 8
FEATURE                   Location/Qualifiers
REGION                    1..8
                          note = Synthetic peptide
source                    1..8
                          mol_type = protein
                          organism = synthetic construct
SEQUENCE: 683
NLKHQPGG                                                                   8

SEQ ID NO: 684            moltype = AA  length = 7
FEATURE                   Location/Qualifiers
REGION                    1..7
                          note = Synthetic peptide
source                    1..7
                          mol_type = protein
                          organism = synthetic construct
SEQUENCE: 684
LKHQPGG                                                                    7

SEQ ID NO: 685            moltype = AA  length = 6
FEATURE                   Location/Qualifiers
REGION                    1..6
                          note = Synthetic peptide
source                    1..6
                          mol_type = protein
                          organism = synthetic construct
SEQUENCE: 685
KHQPGG                                                                     6

SEQ ID NO: 686            moltype = AA  length = 5
FEATURE                   Location/Qualifiers
REGION                    1..5
                          note = Synthetic peptide
source                    1..5
                          mol_type = protein
                          organism = synthetic construct
SEQUENCE: 686
HQPGG                                                                      5

SEQ ID NO: 687            moltype = AA  length = 4
FEATURE                   Location/Qualifiers
REGION                    1..4
                          note = Synthetic peptide
source                    1..4
                          mol_type = protein
                          organism = synthetic construct
SEQUENCE: 687
QPGG                                                                       4

SEQ ID NO: 688            moltype = AA  length = 9
FEATURE                   Location/Qualifiers
REGION                    1..9
                          note = Synthetic peptide
source                    1..9
                          mol_type = protein
                          organism = synthetic construct
SEQUENCE: 688
TENLKHQPG                                                                  9

SEQ ID NO: 689            moltype = AA  length = 8
FEATURE                   Location/Qualifiers
REGION                    1..8
                          note = Synthetic peptide
source                    1..8
                          mol_type = protein
                          organism = synthetic construct
SEQUENCE: 689
ENLKHQPG                                                                   8

SEQ ID NO: 690            moltype = AA  length = 7
FEATURE                   Location/Qualifiers
REGION                    1..7
                          note = Synthetic peptide
source                    1..7
                          mol_type = protein
                          organism = synthetic construct
SEQUENCE: 690
NLKHQPG                                                                    7
```

```
SEQ ID NO: 691          moltype = AA   length = 6
FEATURE                 Location/Qualifiers
REGION                  1..6
                        note = Synthetic peptide
source                  1..6
                        mol_type = protein
                        organism = synthetic construct
SEQUENCE: 691
LKHQPG                                                                      6

SEQ ID NO: 692          moltype = AA   length = 5
FEATURE                 Location/Qualifiers
REGION                  1..5
                        note = Synthetic peptide
source                  1..5
                        mol_type = protein
                        organism = synthetic construct
SEQUENCE: 692
KHQPG                                                                       5

SEQ ID NO: 693          moltype = AA   length = 4
FEATURE                 Location/Qualifiers
REGION                  1..4
                        note = Synthetic peptide
source                  1..4
                        mol_type = protein
                        organism = synthetic construct
SEQUENCE: 693
HQPG                                                                        4

SEQ ID NO: 694          moltype =     length =
SEQUENCE: 694
000

SEQ ID NO: 695          moltype = AA   length = 8
FEATURE                 Location/Qualifiers
REGION                  1..8
                        note = Synthetic peptide
source                  1..8
                        mol_type = protein
                        organism = synthetic construct
SEQUENCE: 695
TENLKHQP                                                                    8

SEQ ID NO: 696          moltype = AA   length = 7
FEATURE                 Location/Qualifiers
REGION                  1..7
                        note = Synthetic peptide
source                  1..7
                        mol_type = protein
                        organism = synthetic construct
SEQUENCE: 696
ENLKHQP                                                                     7

SEQ ID NO: 697          moltype = AA   length = 6
FEATURE                 Location/Qualifiers
REGION                  1..6
                        note = Synthetic peptide
source                  1..6
                        mol_type = protein
                        organism = synthetic construct
SEQUENCE: 697
NLKHQP                                                                      6

SEQ ID NO: 698          moltype = AA   length = 5
FEATURE                 Location/Qualifiers
REGION                  1..5
                        note = Synthetic peptide
source                  1..5
                        mol_type = protein
                        organism = synthetic construct
SEQUENCE: 698
LKHQP                                                                       5

SEQ ID NO: 699          moltype = AA   length = 4
FEATURE                 Location/Qualifiers
REGION                  1..4
                        note = Synthetic peptide
```

```
source                 1..4
                       mol_type = protein
                       organism = synthetic construct
SEQUENCE: 699
KHQP                                                                    4

SEQ ID NO: 700         moltype =    length =
SEQUENCE: 700
000

SEQ ID NO: 701         moltype = AA   length = 7
FEATURE                Location/Qualifiers
REGION                 1..7
                       note = Synthetic peptide
source                 1..7
                       mol_type = protein
                       organism = synthetic construct
SEQUENCE: 701
TENLKHQ                                                                 7

SEQ ID NO: 702         moltype = AA   length = 6
FEATURE                Location/Qualifiers
REGION                 1..6
                       note = Synthetic peptide
source                 1..6
                       mol_type = protein
                       organism = synthetic construct
SEQUENCE: 702
ENLKHQ                                                                  6

SEQ ID NO: 703         moltype = AA   length = 5
FEATURE                Location/Qualifiers
REGION                 1..5
                       note = Synthetic peptide
source                 1..5
                       mol_type = protein
                       organism = synthetic construct
SEQUENCE: 703
NLKHQ                                                                   5

SEQ ID NO: 704         moltype = AA   length = 4
FEATURE                Location/Qualifiers
REGION                 1..4
                       note = Synthetic peptide
source                 1..4
                       mol_type = protein
                       organism = synthetic construct
SEQUENCE: 704
LKHQ                                                                    4

SEQ ID NO: 705         moltype =    length =
SEQUENCE: 705
000

SEQ ID NO: 706         moltype = AA   length = 6
FEATURE                Location/Qualifiers
REGION                 1..6
                       note = Synthetic peptide
source                 1..6
                       mol_type = protein
                       organism = synthetic construct
SEQUENCE: 706
TENLKH                                                                  6

SEQ ID NO: 707         moltype = AA   length = 5
FEATURE                Location/Qualifiers
REGION                 1..5
                       note = Synthetic peptide
source                 1..5
                       mol_type = protein
                       organism = synthetic construct
SEQUENCE: 707
ENLKH                                                                   5

SEQ ID NO: 708         moltype = AA   length = 4
FEATURE                Location/Qualifiers
REGION                 1..4
                       note = Synthetic peptide
source                 1..4
```

|                              |                                                                                                |    |
|------------------------------|------------------------------------------------------------------------------------------------|----|
|                              | mol_type = protein<br>organism = synthetic construct                                           |    |
| SEQUENCE: 708<br>NLKH        |                                                                                                | 4  |
| SEQ ID NO: 709<br>SEQUENCE: 709<br>000 | moltype =   length =                                                                  |    |
| SEQ ID NO: 710<br>FEATURE<br>REGION<br>source | moltype = AA  length = 5<br>Location/Qualifiers<br>1..5<br>note = Synthetic peptide<br>1..5<br>mol_type = protein<br>organism = synthetic construct |    |
| SEQUENCE: 710<br>TENLK       |                                                                                                | 5  |
| SEQ ID NO: 711<br>FEATURE<br>REGION<br>source | moltype = AA  length = 4<br>Location/Qualifiers<br>1..4<br>note = Synthetic peptide<br>1..4<br>mol_type = protein<br>organism = synthetic construct |    |
| SEQUENCE: 711<br>ENLK        |                                                                                                | 4  |
| SEQ ID NO: 712<br>SEQUENCE: 712<br>000 | moltype =   length =                                                                  |    |
| SEQ ID NO: 713<br>FEATURE<br>REGION<br>source | moltype = AA  length = 4<br>Location/Qualifiers<br>1..4<br>note = Synthetic peptide<br>1..4<br>mol_type = protein<br>organism = synthetic construct |    |
| SEQUENCE: 713<br>TENL        |                                                                                                | 4  |
| SEQ ID NO: 714<br>SEQUENCE: 714<br>000 | moltype =   length =                                                                  |    |
| SEQ ID NO: 715<br>SEQUENCE: 715<br>000 | moltype =   length =                                                                  |    |
| SEQ ID NO: 716<br>FEATURE<br>REGION<br>source | moltype = AA  length = 11<br>Location/Qualifiers<br>1..11<br>note = Synthetic peptide<br>1..11<br>mol_type = protein<br>organism = synthetic construct |    |
| SEQUENCE: 716<br>KDNIKHVPGG G |                                                                                                | 11 |
| SEQ ID NO: 717<br>FEATURE<br>REGION<br>source | moltype = AA  length = 4<br>Location/Qualifiers<br>1..4<br>note = Synthetic peptide<br>1..4<br>mol_type = protein<br>organism = synthetic construct |    |
| SEQUENCE: 717<br>KDNI        |                                                                                                | 4  |
| SEQ ID NO: 718<br>SEQUENCE: 718<br>000 | moltype =   length =                                                                  |    |
| SEQ ID NO: 719<br>FEATURE<br>REGION | moltype = AA  length = 7<br>Location/Qualifiers<br>1..7<br>note = Synthetic peptide          |    |

```
                        -continued source                  1..7
                        mol_type = protein
                        organism = synthetic construct
SEQUENCE: 719
IKHVGGG                                                                 7

SEQ ID NO: 720          moltype = AA  length = 6
FEATURE                 Location/Qualifiers
REGION                  1..6
                        note = Synthetic peptide
source                  1..6
                        mol_type = protein
                        organism = synthetic construct
SEQUENCE: 720
IKHVGG                                                                  6

SEQ ID NO: 721          moltype = AA  length = 5
FEATURE                 Location/Qualifiers
REGION                  1..5
                        note = Synthetic peptide
source                  1..5
                        mol_type = protein
                        organism = synthetic construct
SEQUENCE: 721
IKHVG                                                                   5

SEQ ID NO: 722          moltype = AA  length = 6
FEATURE                 Location/Qualifiers
REGION                  1..6
                        note = Synthetic peptide
source                  1..6
                        mol_type = protein
                        organism = synthetic construct
SEQUENCE: 722
KHVGGG                                                                  6

SEQ ID NO: 723          moltype = AA  length = 5
FEATURE                 Location/Qualifiers
REGION                  1..5
                        note = Synthetic peptide
source                  1..5
                        mol_type = protein
                        organism = synthetic construct
SEQUENCE: 723
KHVGG                                                                   5

SEQ ID NO: 724          moltype = AA  length = 4
FEATURE                 Location/Qualifiers
REGION                  1..4
                        note = Synthetic peptide
source                  1..4
                        mol_type = protein
                        organism = synthetic construct
SEQUENCE: 724
KHVG                                                                    4

SEQ ID NO: 725          moltype = AA  length = 11
FEATURE                 Location/Qualifiers
REGION                  1..11
                        note = Synthetic peptide
source                  1..11
                        mol_type = protein
                        organism = synthetic construct
SEQUENCE: 725
LGNIHHKPGG G                                                           11

SEQ ID NO: 726          moltype = AA  length = 10
FEATURE                 Location/Qualifiers
REGION                  1..10
                        note = Synthetic peptide
source                  1..10
                        mol_type = protein
                        organism = synthetic construct
SEQUENCE: 726
GNIHHKPGGG                                                             10

SEQ ID NO: 727          moltype = AA  length = 9
FEATURE                 Location/Qualifiers
REGION                  1..9
```

```
                        note = Synthetic peptide
source                  1..9
                        mol_type = protein
                        organism = synthetic construct
SEQUENCE: 727
NIHHKPGGG                                                                       9

SEQ ID NO: 728          moltype = AA  length = 8
FEATURE                 Location/Qualifiers
REGION                  1..8
                        note = Synthetic peptide
source                  1..8
                        mol_type = protein
                        organism = synthetic construct
SEQUENCE: 728
IHHKPGGG                                                                        8

SEQ ID NO: 729          moltype = AA  length = 7
FEATURE                 Location/Qualifiers
REGION                  1..7
                        note = Synthetic peptide
source                  1..7
                        mol_type = protein
                        organism = synthetic construct
SEQUENCE: 729
HHKPGGG                                                                         7

SEQ ID NO: 730          moltype = AA  length = 5
FEATURE                 Location/Qualifiers
REGION                  1..5
                        note = Synthetic peptide
source                  1..5
                        mol_type = protein
                        organism = synthetic construct
SEQUENCE: 730
KPGGG                                                                           5

SEQ ID NO: 731          moltype = AA  length = 10
FEATURE                 Location/Qualifiers
REGION                  1..10
                        note = Synthetic peptide
source                  1..10
                        mol_type = protein
                        organism = synthetic construct
SEQUENCE: 731
LGNIHHKPGG                                                                     10

SEQ ID NO: 732          moltype = AA  length = 9
FEATURE                 Location/Qualifiers
REGION                  1..9
                        note = Synthetic peptide
source                  1..9
                        mol_type = protein
                        organism = synthetic construct
SEQUENCE: 732
GNIHHKPGG                                                                       9

SEQ ID NO: 733          moltype = AA  length = 8
FEATURE                 Location/Qualifiers
REGION                  1..8
                        note = Synthetic peptide
source                  1..8
                        mol_type = protein
                        organism = synthetic construct
SEQUENCE: 733
NIHHKPGG                                                                        8

SEQ ID NO: 734          moltype = AA  length = 7
FEATURE                 Location/Qualifiers
REGION                  1..7
                        note = Synthetic peptide
source                  1..7
                        mol_type = protein
                        organism = synthetic construct
SEQUENCE: 734
IHHKPGG                                                                         7

SEQ ID NO: 735          moltype = AA  length = 6
FEATURE                 Location/Qualifiers
```

```
REGION                  1..6
                        note = Synthetic peptide
source                  1..6
                        mol_type = protein
                        organism = synthetic construct
SEQUENCE: 735
HHKPGG                                                                   6

SEQ ID NO: 736          moltype = AA  length = 4
FEATURE                 Location/Qualifiers
REGION                  1..4
                        note = Synthetic peptide
source                  1..4
                        mol_type = protein
                        organism = synthetic construct
SEQUENCE: 736
KPGG                                                                     4

SEQ ID NO: 737          moltype = AA  length = 9
FEATURE                 Location/Qualifiers
REGION                  1..9
                        note = Synthetic peptide
source                  1..9
                        mol_type = protein
                        organism = synthetic construct
SEQUENCE: 737
LGNIHHKPG                                                                9

SEQ ID NO: 738          moltype = AA  length = 8
FEATURE                 Location/Qualifiers
REGION                  1..8
                        note = Synthetic peptide
source                  1..8
                        mol_type = protein
                        organism = synthetic construct
SEQUENCE: 738
GNIHHKPG                                                                 8

SEQ ID NO: 739          moltype = AA  length = 7
FEATURE                 Location/Qualifiers
REGION                  1..7
                        note = Synthetic peptide
source                  1..7
                        mol_type = protein
                        organism = synthetic construct
SEQUENCE: 739
NIHHKPG                                                                  7

SEQ ID NO: 740          moltype = AA  length = 6
FEATURE                 Location/Qualifiers
REGION                  1..6
                        note = Synthetic peptide
source                  1..6
                        mol_type = protein
                        organism = synthetic construct
SEQUENCE: 740
IHHKPG                                                                   6

SEQ ID NO: 741          moltype = AA  length = 5
FEATURE                 Location/Qualifiers
REGION                  1..5
                        note = Synthetic peptide
source                  1..5
                        mol_type = protein
                        organism = synthetic construct
SEQUENCE: 741
HHKPG                                                                    5

SEQ ID NO: 742          moltype = AA  length = 4
FEATURE                 Location/Qualifiers
REGION                  1..4
                        note = Synthetic peptide
source                  1..4
                        mol_type = protein
                        organism = synthetic construct
SEQUENCE: 742
HKPG                                                                     4

SEQ ID NO: 743          moltype =     length =
```

```
SEQUENCE: 743
000

SEQ ID NO: 744          moltype = AA  length = 8
FEATURE                 Location/Qualifiers
REGION                  1..8
                        note = Synthetic peptide
source                  1..8
                        mol_type = protein
                        organism = synthetic construct
SEQUENCE: 744
LGNIHHKP                                                                 8

SEQ ID NO: 745          moltype = AA  length = 7
FEATURE                 Location/Qualifiers
REGION                  1..7
                        note = Synthetic peptide
source                  1..7
                        mol_type = protein
                        organism = synthetic construct
SEQUENCE: 745
GNIHHKP                                                                  7

SEQ ID NO: 746          moltype = AA  length = 6
FEATURE                 Location/Qualifiers
REGION                  1..6
                        note = Synthetic peptide
source                  1..6
                        mol_type = protein
                        organism = synthetic construct
SEQUENCE: 746
NIHHKP                                                                   6

SEQ ID NO: 747          moltype = AA  length = 5
FEATURE                 Location/Qualifiers
REGION                  1..5
                        note = Synthetic peptide
source                  1..5
                        mol_type = protein
                        organism = synthetic construct
SEQUENCE: 747
IHHKP                                                                    5

SEQ ID NO: 748          moltype = AA  length = 4
FEATURE                 Location/Qualifiers
REGION                  1..4
                        note = Synthetic peptide
source                  1..4
                        mol_type = protein
                        organism = synthetic construct
SEQUENCE: 748
HHKP                                                                     4

SEQ ID NO: 749          moltype =     length =
SEQUENCE: 749
000

SEQ ID NO: 750          moltype = AA  length = 7
FEATURE                 Location/Qualifiers
REGION                  1..7
                        note = Synthetic peptide
source                  1..7
                        mol_type = protein
                        organism = synthetic construct
SEQUENCE: 750
LGNIHHK                                                                  7

SEQ ID NO: 751          moltype = AA  length = 6
FEATURE                 Location/Qualifiers
REGION                  1..6
                        note = Synthetic peptide
source                  1..6
                        mol_type = protein
                        organism = synthetic construct
SEQUENCE: 751
GNIHHK                                                                   6

SEQ ID NO: 752          moltype = AA  length = 5
FEATURE                 Location/Qualifiers
```

```
REGION                  1..5
                        note = Synthetic peptide
source                  1..5
                        mol_type = protein
                        organism = synthetic construct
SEQUENCE: 752
NIHHK                                                                    5

SEQ ID NO: 753          moltype = AA   length = 4
FEATURE                 Location/Qualifiers
REGION                  1..4
                        note = Synthetic peptide
source                  1..4
                        mol_type = protein
                        organism = synthetic construct
SEQUENCE: 753
IHHK                                                                     4

SEQ ID NO: 754          moltype =   length =
SEQUENCE: 754
000

SEQ ID NO: 755          moltype = AA   length = 6
FEATURE                 Location/Qualifiers
REGION                  1..6
                        note = Synthetic peptide
source                  1..6
                        mol_type = protein
                        organism = synthetic construct
SEQUENCE: 755
LGNIHH                                                                   6

SEQ ID NO: 756          moltype = AA   length = 5
FEATURE                 Location/Qualifiers
REGION                  1..5
                        note = Synthetic peptide
source                  1..5
                        mol_type = protein
                        organism = synthetic construct
SEQUENCE: 756
GNIHH                                                                    5

SEQ ID NO: 757          moltype = AA   length = 4
FEATURE                 Location/Qualifiers
REGION                  1..4
                        note = Synthetic peptide
source                  1..4
                        mol_type = protein
                        organism = synthetic construct
SEQUENCE: 757
NIHH                                                                     4

SEQ ID NO: 758          moltype =   length =
SEQUENCE: 758
000

SEQ ID NO: 759          moltype = AA   length = 5
FEATURE                 Location/Qualifiers
REGION                  1..5
                        note = Synthetic peptide
source                  1..5
                        mol_type = protein
                        organism = synthetic construct
SEQUENCE: 759
LGNIH                                                                    5

SEQ ID NO: 760          moltype = AA   length = 4
FEATURE                 Location/Qualifiers
REGION                  1..4
                        note = Synthetic peptide
source                  1..4
                        mol_type = protein
                        organism = synthetic construct
SEQUENCE: 760
GNIH                                                                     4

SEQ ID NO: 761          moltype =   length =
SEQUENCE: 761
000
```

```
SEQ ID NO: 762          moltype = AA  length = 4
FEATURE                 Location/Qualifiers
REGION                  1..4
                        note = Synthetic peptide
source                  1..4
                        mol_type = protein
                        organism = synthetic construct
SEQUENCE: 762
LGNI                                                                    4

SEQ ID NO: 763          moltype =   length =
SEQUENCE: 763
000

SEQ ID NO: 764          moltype =   length =
SEQUENCE: 764
000

SEQ ID NO: 765          moltype = AA  length = 11
FEATURE                 Location/Qualifiers
REGION                  1..11
                        note = Synthetic peptide
source                  1..11
                        mol_type = protein
                        organism = synthetic construct
SEQUENCE: 765
LDNITHVPGG G                                                           11

SEQ ID NO: 766          moltype = AA  length = 10
FEATURE                 Location/Qualifiers
REGION                  1..10
                        note = Synthetic peptide
source                  1..10
                        mol_type = protein
                        organism = synthetic construct
SEQUENCE: 766
DNITHVPGGG                                                             10

SEQ ID NO: 767          moltype = AA  length = 9
FEATURE                 Location/Qualifiers
REGION                  1..9
                        note = Synthetic peptide
source                  1..9
                        mol_type = protein
                        organism = synthetic construct
SEQUENCE: 767
NITHVPGGG                                                               9

SEQ ID NO: 768          moltype = AA  length = 8
FEATURE                 Location/Qualifiers
REGION                  1..8
                        note = Synthetic peptide
source                  1..8
                        mol_type = protein
                        organism = synthetic construct
SEQUENCE: 768
ITHVPGGG                                                                8

SEQ ID NO: 769          moltype = AA  length = 7
FEATURE                 Location/Qualifiers
REGION                  1..7
                        note = Synthetic peptide
source                  1..7
                        mol_type = protein
                        organism = synthetic construct
SEQUENCE: 769
THVPGGG                                                                 7

SEQ ID NO: 770          moltype = AA  length = 10
FEATURE                 Location/Qualifiers
REGION                  1..10
                        note = Synthetic peptide
source                  1..10
                        mol_type = protein
                        organism = synthetic construct
SEQUENCE: 770
LDNITHVPGG                                                             10
```

```
SEQ ID NO: 771         moltype = AA   length = 9
FEATURE                Location/Qualifiers
REGION                 1..9
                       note = Synthetic peptide
source                 1..9
                       mol_type = protein
                       organism = synthetic construct
SEQUENCE: 771
DNITHVPGG                                                                9

SEQ ID NO: 772         moltype = AA   length = 8
FEATURE                Location/Qualifiers
REGION                 1..8
                       note = Synthetic peptide
source                 1..8
                       mol_type = protein
                       organism = synthetic construct
SEQUENCE: 772
NITHVPGG                                                                 8

SEQ ID NO: 773         moltype = AA   length = 7
FEATURE                Location/Qualifiers
REGION                 1..7
                       note = Synthetic peptide
source                 1..7
                       mol_type = protein
                       organism = synthetic construct
SEQUENCE: 773
ITHVPGG                                                                  7

SEQ ID NO: 774         moltype = AA   length = 6
FEATURE                Location/Qualifiers
REGION                 1..6
                       note = Synthetic peptide
source                 1..6
                       mol_type = protein
                       organism = synthetic construct
SEQUENCE: 774
THVPGG                                                                   6

SEQ ID NO: 775         moltype = AA   length = 9
FEATURE                Location/Qualifiers
REGION                 1..9
                       note = Synthetic peptide
source                 1..9
                       mol_type = protein
                       organism = synthetic construct
SEQUENCE: 775
LDNITHVPG                                                                9

SEQ ID NO: 776         moltype = AA   length = 8
FEATURE                Location/Qualifiers
REGION                 1..8
                       note = Synthetic peptide
source                 1..8
                       mol_type = protein
                       organism = synthetic construct
SEQUENCE: 776
DNITHVPG                                                                 8

SEQ ID NO: 777         moltype = AA   length = 7
FEATURE                Location/Qualifiers
REGION                 1..7
                       note = Synthetic peptide
source                 1..7
                       mol_type = protein
                       organism = synthetic construct
SEQUENCE: 777
NITHVPG                                                                  7

SEQ ID NO: 778         moltype = AA   length = 6
FEATURE                Location/Qualifiers
REGION                 1..6
                       note = Synthetic peptide
source                 1..6
                       mol_type = protein
                       organism = synthetic construct
SEQUENCE: 778
ITHVPG                                                                   6
```

```
SEQ ID NO: 779         moltype = AA   length = 5
FEATURE                Location/Qualifiers
REGION                 1..5
                       note = Synthetic peptide
source                 1..5
                       mol_type = protein
                       organism = synthetic construct
SEQUENCE: 779
THVPG                                                                   5

SEQ ID NO: 780         moltype = AA   length = 8
FEATURE                Location/Qualifiers
REGION                 1..8
                       note = Synthetic peptide
source                 1..8
                       mol_type = protein
                       organism = synthetic construct
SEQUENCE: 780
LDNITHVP                                                                8

SEQ ID NO: 781         moltype = AA   length = 7
FEATURE                Location/Qualifiers
REGION                 1..7
                       note = Synthetic peptide
source                 1..7
                       mol_type = protein
                       organism = synthetic construct
SEQUENCE: 781
DNITHVP                                                                 7

SEQ ID NO: 782         moltype = AA   length = 6
FEATURE                Location/Qualifiers
REGION                 1..6
                       note = Synthetic peptide
source                 1..6
                       mol_type = protein
                       organism = synthetic construct
SEQUENCE: 782
NITHVP                                                                  6

SEQ ID NO: 783         moltype = AA   length = 5
FEATURE                Location/Qualifiers
REGION                 1..5
                       note = Synthetic peptide
source                 1..5
                       mol_type = protein
                       organism = synthetic construct
SEQUENCE: 783
ITHVP                                                                   5

SEQ ID NO: 784         moltype = AA   length = 4
FEATURE                Location/Qualifiers
REGION                 1..4
                       note = Synthetic peptide
source                 1..4
                       mol_type = protein
                       organism = synthetic construct
SEQUENCE: 784
THVP                                                                    4

SEQ ID NO: 785         moltype = AA   length = 7
FEATURE                Location/Qualifiers
REGION                 1..7
                       note = Synthetic peptide
source                 1..7
                       mol_type = protein
                       organism = synthetic construct
SEQUENCE: 785
LDNITHV                                                                 7

SEQ ID NO: 786         moltype = AA   length = 6
FEATURE                Location/Qualifiers
REGION                 1..6
                       note = Synthetic peptide
source                 1..6
                       mol_type = protein
                       organism = synthetic construct
SEQUENCE: 786
```

```
DNITHV                                                                       6

SEQ ID NO: 787          moltype = AA  length = 5
FEATURE                 Location/Qualifiers
REGION                  1..5
                        note = Synthetic peptide
source                  1..5
                        mol_type = protein
                        organism = synthetic construct
SEQUENCE: 787
NITHV                                                                        5

SEQ ID NO: 788          moltype = AA  length = 4
FEATURE                 Location/Qualifiers
REGION                  1..4
                        note = Synthetic peptide
source                  1..4
                        mol_type = protein
                        organism = synthetic construct
SEQUENCE: 788
ITHV                                                                         4

SEQ ID NO: 789          moltype =     length =
SEQUENCE: 789
000

SEQ ID NO: 790          moltype = AA  length = 6
FEATURE                 Location/Qualifiers
REGION                  1..6
                        note = Synthetic peptide
source                  1..6
                        mol_type = protein
                        organism = synthetic construct
SEQUENCE: 790
LDNITH                                                                       6

SEQ ID NO: 791          moltype = AA  length = 5
FEATURE                 Location/Qualifiers
REGION                  1..5
                        note = Synthetic peptide
source                  1..5
                        mol_type = protein
                        organism = synthetic construct
SEQUENCE: 791
DNITH                                                                        5

SEQ ID NO: 792          moltype = AA  length = 4
FEATURE                 Location/Qualifiers
REGION                  1..4
                        note = Synthetic peptide
source                  1..4
                        mol_type = protein
                        organism = synthetic construct
SEQUENCE: 792
NITH                                                                         4

SEQ ID NO: 793          moltype =     length =
SEQUENCE: 793
000

SEQ ID NO: 794          moltype = AA  length = 5
FEATURE                 Location/Qualifiers
REGION                  1..5
                        note = Synthetic peptide
source                  1..5
                        mol_type = protein
                        organism = synthetic construct
SEQUENCE: 794
LDNIT                                                                        5

SEQ ID NO: 795          moltype = AA  length = 4
FEATURE                 Location/Qualifiers
REGION                  1..4
                        note = Synthetic peptide
source                  1..4
                        mol_type = protein
                        organism = synthetic construct
SEQUENCE: 795
DNIT                                                                         4
```

```
SEQ ID NO: 796           moltype =    length =
SEQUENCE: 796
000

SEQ ID NO: 797           moltype = AA   length = 4
FEATURE                  Location/Qualifiers
REGION                   1..4
                         note = Synthetic peptide
source                   1..4
                         mol_type = protein
                         organism = synthetic construct
SEQUENCE: 797
LDNI                                                                      4

SEQ ID NO: 798           moltype =    length =
SEQUENCE: 798
000

SEQ ID NO: 799           moltype = AA   length = 10
FEATURE                  Location/Qualifiers
REGION                   1..10
                         note = Synthetic peptide
source                   1..10
                         mol_type = protein
                         organism = synthetic construct
SEQUENCE: 799
KNVKSKIGST                                                               10

SEQ ID NO: 800           moltype = AA   length = 9
FEATURE                  Location/Qualifiers
REGION                   1..9
                         note = Synthetic peptide
source                   1..9
                         mol_type = protein
                         organism = synthetic construct
SEQUENCE: 800
NVKSKIGST                                                                 9

SEQ ID NO: 801           moltype = AA   length = 8
FEATURE                  Location/Qualifiers
REGION                   1..8
                         note = Synthetic peptide
source                   1..8
                         mol_type = protein
                         organism = synthetic construct
SEQUENCE: 801
VKSKIGST                                                                  8

SEQ ID NO: 802           moltype = AA   length = 7
FEATURE                  Location/Qualifiers
REGION                   1..7
                         note = Synthetic peptide
source                   1..7
                         mol_type = protein
                         organism = synthetic construct
SEQUENCE: 802
KSKIGST                                                                   7

SEQ ID NO: 803           moltype = AA   length = 6
FEATURE                  Location/Qualifiers
REGION                   1..6
                         note = Synthetic peptide
source                   1..6
                         mol_type = protein
                         organism = synthetic construct
SEQUENCE: 803
SKIGST                                                                    6

SEQ ID NO: 804           moltype = AA   length = 5
FEATURE                  Location/Qualifiers
REGION                   1..5
                         note = Synthetic peptide
source                   1..5
                         mol_type = protein
                         organism = synthetic construct
SEQUENCE: 804
KIGST                                                                     5
```

| | | |
|---|---|---|
| SEQ ID NO: 805 | moltype = AA length = 4 | |
| FEATURE | Location/Qualifiers | |
| REGION | 1..4 | |
| | note = Synthetic peptide | |
| source | 1..4 | |
| | mol_type = protein | |
| | organism = synthetic construct | |
| SEQUENCE: 805 | | |
| IGST | | 4 |
| | | |
| SEQ ID NO: 806 | moltype = length = | |
| SEQUENCE: 806 | | |
| 000 | | |
| | | |
| SEQ ID NO: 807 | moltype = AA length = 10 | |
| FEATURE | Location/Qualifiers | |
| REGION | 1..10 | |
| | note = Synthetic peptide | |
| source | 1..10 | |
| | mol_type = protein | |
| | organism = synthetic construct | |
| SEQUENCE: 807 | | |
| NVKSKIGSTE | | 10 |
| | | |
| SEQ ID NO: 808 | moltype = AA length = 9 | |
| FEATURE | Location/Qualifiers | |
| REGION | 1..9 | |
| | note = Synthetic peptide | |
| source | 1..9 | |
| | mol_type = protein | |
| | organism = synthetic construct | |
| SEQUENCE: 808 | | |
| VKSKIGSTE | | 9 |
| | | |
| SEQ ID NO: 809 | moltype = AA length = 8 | |
| FEATURE | Location/Qualifiers | |
| REGION | 1..8 | |
| | note = Synthetic peptide | |
| source | 1..8 | |
| | mol_type = protein | |
| | organism = synthetic construct | |
| SEQUENCE: 809 | | |
| KSKIGSTE | | 8 |
| | | |
| SEQ ID NO: 810 | moltype = AA length = 7 | |
| FEATURE | Location/Qualifiers | |
| REGION | 1..7 | |
| | note = Synthetic peptide | |
| source | 1..7 | |
| | mol_type = protein | |
| | organism = synthetic construct | |
| SEQUENCE: 810 | | |
| SKIGSTE | | 7 |
| | | |
| SEQ ID NO: 811 | moltype = AA length = 6 | |
| FEATURE | Location/Qualifiers | |
| REGION | 1..6 | |
| | note = Synthetic peptide | |
| source | 1..6 | |
| | mol_type = protein | |
| | organism = synthetic construct | |
| SEQUENCE: 811 | | |
| KIGSTE | | 6 |
| | | |
| SEQ ID NO: 812 | moltype = AA length = 5 | |
| FEATURE | Location/Qualifiers | |
| REGION | 1..5 | |
| | note = Synthetic peptide | |
| source | 1..5 | |
| | mol_type = protein | |
| | organism = synthetic construct | |
| SEQUENCE: 812 | | |
| IGSTE | | 5 |
| | | |
| SEQ ID NO: 813 | moltype = AA length = 4 | |
| FEATURE | Location/Qualifiers | |
| REGION | 1..4 | |
| | note = Synthetic peptide | |
| source | 1..4 | |

```
                            mol_type = protein
                            organism = synthetic construct
SEQUENCE: 813
GSTE                                                                    4

SEQ ID NO: 814              moltype =    length =
SEQUENCE: 814
000

SEQ ID NO: 815              moltype = AA   length = 10
FEATURE                     Location/Qualifiers
REGION                      1..10
                            note = Synthetic peptide
source                      1..10
                            mol_type = protein
                            organism = synthetic construct
SEQUENCE: 815
VKSKIGSTEN                                                             10

SEQ ID NO: 816              moltype = AA   length = 9
FEATURE                     Location/Qualifiers
REGION                      1..9
                            note = Synthetic peptide
source                      1..9
                            mol_type = protein
                            organism = synthetic construct
SEQUENCE: 816
KSKIGSTEN                                                               9

SEQ ID NO: 817              moltype = AA   length = 8
FEATURE                     Location/Qualifiers
REGION                      1..8
                            note = Synthetic peptide
source                      1..8
                            mol_type = protein
                            organism = synthetic construct
SEQUENCE: 817
SKIGSTEN                                                                8

SEQ ID NO: 818              moltype = AA   length = 7
FEATURE                     Location/Qualifiers
REGION                      1..7
                            note = Synthetic peptide
source                      1..7
                            mol_type = protein
                            organism = synthetic construct
SEQUENCE: 818
KIGSTEN                                                                 7

SEQ ID NO: 819              moltype = AA   length = 6
FEATURE                     Location/Qualifiers
REGION                      1..6
                            note = Synthetic peptide
source                      1..6
                            mol_type = protein
                            organism = synthetic construct
SEQUENCE: 819
IGSTEN                                                                  6

SEQ ID NO: 820              moltype = AA   length = 5
FEATURE                     Location/Qualifiers
REGION                      1..5
                            note = Synthetic peptide
source                      1..5
                            mol_type = protein
                            organism = synthetic construct
SEQUENCE: 820
GSTEN                                                                   5

SEQ ID NO: 821              moltype = AA   length = 4
FEATURE                     Location/Qualifiers
REGION                      1..4
                            note = Synthetic peptide
source                      1..4
                            mol_type = protein
                            organism = synthetic construct
SEQUENCE: 821
STEN                                                                    4
```

-continued

| | | |
|---|---|---|
| SEQ ID NO: 822<br>FEATURE<br>REGION<br><br>source | moltype = AA  length = 10<br>Location/Qualifiers<br>1..10<br>note = Synthetic peptide<br>1..10<br>mol_type = protein<br>organism = synthetic construct | |
| SEQUENCE: 822<br>KSKIGSTENL | | 10 |
| SEQ ID NO: 823<br>FEATURE<br>REGION<br><br>source | moltype = AA  length = 9<br>Location/Qualifiers<br>1..9<br>note = Synthetic peptide<br>1..9<br>mol_type = protein<br>organism = synthetic construct | |
| SEQUENCE: 823<br>SKIGSTENL | | 9 |
| SEQ ID NO: 824<br>FEATURE<br>REGION<br><br>source | moltype = AA  length = 8<br>Location/Qualifiers<br>1..8<br>note = Synthetic peptide<br>1..8<br>mol_type = protein<br>organism = synthetic construct | |
| SEQUENCE: 824<br>KIGSTENL | | 8 |
| SEQ ID NO: 825<br>FEATURE<br>REGION<br><br>source | moltype = AA  length = 7<br>Location/Qualifiers<br>1..7<br>note = Synthetic peptide<br>1..7<br>mol_type = protein<br>organism = synthetic construct | |
| SEQUENCE: 825<br>IGSTENL | | 7 |
| SEQ ID NO: 826<br>FEATURE<br>REGION<br><br>source | moltype = AA  length = 6<br>Location/Qualifiers<br>1..6<br>note = Synthetic peptide<br>1..6<br>mol_type = protein<br>organism = synthetic construct | |
| SEQUENCE: 826<br>GSTENL | | 6 |
| SEQ ID NO: 827<br>FEATURE<br>REGION<br><br>source | moltype = AA  length = 5<br>Location/Qualifiers<br>1..5<br>note = Synthetic peptide<br>1..5<br>mol_type = protein<br>organism = synthetic construct | |
| SEQUENCE: 827<br>STENL | | 5 |
| SEQ ID NO: 828<br>FEATURE<br>REGION<br><br>source | moltype = AA  length = 10<br>Location/Qualifiers<br>1..10<br>note = Synthetic peptide<br>1..10<br>mol_type = protein<br>organism = synthetic construct | |
| SEQUENCE: 828<br>SKIGSTENLK | | 10 |
| SEQ ID NO: 829<br>FEATURE<br>REGION<br><br>source | moltype = AA  length = 9<br>Location/Qualifiers<br>1..9<br>note = Synthetic peptide<br>1..9<br>mol_type = protein<br>organism = synthetic construct | |
| SEQUENCE: 829<br>KIGSTENLK | | 9 |

| | |
|---|---|
| SEQ ID NO: 830<br>FEATURE<br>REGION<br><br>source | moltype = AA  length = 8<br>Location/Qualifiers<br>1..8<br>note = Synthetic peptide<br>1..8<br>mol_type = protein<br>organism = synthetic construct |
| SEQUENCE: 830<br>IGSTENLK | 8 |
| SEQ ID NO: 831<br>FEATURE<br>REGION<br><br>source | moltype = AA  length = 7<br>Location/Qualifiers<br>1..7<br>note = Synthetic peptide<br>1..7<br>mol_type = protein<br>organism = synthetic construct |
| SEQUENCE: 831<br>GSTENLK | 7 |
| SEQ ID NO: 832<br>FEATURE<br>REGION<br><br>source | moltype = AA  length = 6<br>Location/Qualifiers<br>1..6<br>note = Synthetic peptide<br>1..6<br>mol_type = protein<br>organism = synthetic construct |
| SEQUENCE: 832<br>STENLK | 6 |
| SEQ ID NO: 833<br>FEATURE<br>REGION<br><br>source | moltype = AA  length = 10<br>Location/Qualifiers<br>1..10<br>note = Synthetic peptide<br>1..10<br>mol_type = protein<br>organism = synthetic construct |
| SEQUENCE: 833<br>KIGSTENLKH | 10 |
| SEQ ID NO: 834<br>FEATURE<br>REGION<br><br>source | moltype = AA  length = 9<br>Location/Qualifiers<br>1..9<br>note = Synthetic peptide<br>1..9<br>mol_type = protein<br>organism = synthetic construct |
| SEQUENCE: 834<br>IGSTENLKH | 9 |
| SEQ ID NO: 835<br>FEATURE<br>REGION<br><br>source | moltype = AA  length = 8<br>Location/Qualifiers<br>1..8<br>note = Synthetic peptide<br>1..8<br>mol_type = protein<br>organism = synthetic construct |
| SEQUENCE: 835<br>GSTENLKH | 8 |
| SEQ ID NO: 836<br>FEATURE<br>REGION<br><br>source | moltype = AA  length = 7<br>Location/Qualifiers<br>1..7<br>note = Synthetic peptide<br>1..7<br>mol_type = protein<br>organism = synthetic construct |
| SEQUENCE: 836<br>STENLKH | 7 |
| SEQ ID NO: 837<br>FEATURE<br>REGION<br><br>source | moltype = AA  length = 10<br>Location/Qualifiers<br>1..10<br>note = Synthetic peptide<br>1..10<br>mol_type = protein<br>organism = synthetic construct |
| SEQUENCE: 837 | |

```
IGSTENLKHQ                                                                    10

SEQ ID NO: 838          moltype = AA   length = 9
FEATURE                 Location/Qualifiers
REGION                  1..9
                        note = Synthetic peptide
source                  1..9
                        mol_type = protein
                        organism = synthetic construct
SEQUENCE: 838
GSTENLKHQ                                                                      9

SEQ ID NO: 839          moltype = AA   length = 8
FEATURE                 Location/Qualifiers
REGION                  1..8
                        note = Synthetic peptide
source                  1..8
                        mol_type = protein
                        organism = synthetic construct
SEQUENCE: 839
STENLKHQ                                                                       8

SEQ ID NO: 840          moltype = AA   length = 10
FEATURE                 Location/Qualifiers
REGION                  1..10
                        note = Synthetic peptide
source                  1..10
                        mol_type = protein
                        organism = synthetic construct
SEQUENCE: 840
GSTENLKHQP                                                                    10

SEQ ID NO: 841          moltype = AA   length = 9
FEATURE                 Location/Qualifiers
REGION                  1..9
                        note = Synthetic peptide
source                  1..9
                        mol_type = protein
                        organism = synthetic construct
SEQUENCE: 841
STENLKHQP                                                                      9

SEQ ID NO: 842          moltype = AA   length = 10
FEATURE                 Location/Qualifiers
REGION                  1..10
                        note = Synthetic peptide
source                  1..10
                        mol_type = protein
                        organism = synthetic construct
SEQUENCE: 842
STENLKHQPG                                                                    10

SEQ ID NO: 843          moltype = AA   length = 10
FEATURE                 Location/Qualifiers
REGION                  1..10
                        note = Synthetic peptide
source                  1..10
                        mol_type = protein
                        organism = synthetic construct
SEQUENCE: 843
SNVQSKCGSK                                                                    10

SEQ ID NO: 844          moltype = AA   length = 9
FEATURE                 Location/Qualifiers
REGION                  1..9
                        note = Synthetic peptide
source                  1..9
                        mol_type = protein
                        organism = synthetic construct
SEQUENCE: 844
NVQSKCGSK                                                                      9

SEQ ID NO: 845          moltype = AA   length = 8
FEATURE                 Location/Qualifiers
REGION                  1..8
                        note = Synthetic peptide
source                  1..8
                        mol_type = protein
                        organism = synthetic construct
```

```
SEQUENCE: 845
VQSKCGSK                                                                    8

SEQ ID NO: 846          moltype = AA  length = 7
FEATURE                 Location/Qualifiers
REGION                  1..7
                        note = Synthetic peptide
source                  1..7
                        mol_type = protein
                        organism = synthetic construct
SEQUENCE: 846
QSKCGSK                                                                     7

SEQ ID NO: 847          moltype = AA  length = 6
FEATURE                 Location/Qualifiers
REGION                  1..6
                        note = Synthetic peptide
source                  1..6
                        mol_type = protein
                        organism = synthetic construct
SEQUENCE: 847
SKCGSK                                                                      6

SEQ ID NO: 848          moltype = AA  length = 5
FEATURE                 Location/Qualifiers
REGION                  1..5
                        note = Synthetic peptide
source                  1..5
                        mol_type = protein
                        organism = synthetic construct
SEQUENCE: 848
KCGSK                                                                       5

SEQ ID NO: 849          moltype = AA  length = 4
FEATURE                 Location/Qualifiers
REGION                  1..4
                        note = Synthetic peptide
source                  1..4
                        mol_type = protein
                        organism = synthetic construct
SEQUENCE: 849
CGSK                                                                        4

SEQ ID NO: 850          moltype =     length =
SEQUENCE: 850
000

SEQ ID NO: 851          moltype = AA  length = 10
FEATURE                 Location/Qualifiers
REGION                  1..10
                        note = Synthetic peptide
source                  1..10
                        mol_type = protein
                        organism = synthetic construct
SEQUENCE: 851
NVQSKCGSKD                                                                 10

SEQ ID NO: 852          moltype = AA  length = 9
FEATURE                 Location/Qualifiers
REGION                  1..9
                        note = Synthetic peptide
source                  1..9
                        mol_type = protein
                        organism = synthetic construct
SEQUENCE: 852
VQSKCGSKD                                                                   9

SEQ ID NO: 853          moltype = AA  length = 8
FEATURE                 Location/Qualifiers
REGION                  1..8
                        note = Synthetic peptide
source                  1..8
                        mol_type = protein
                        organism = synthetic construct
SEQUENCE: 853
QSKCGSKD                                                                    8

SEQ ID NO: 854          moltype = AA  length = 7
FEATURE                 Location/Qualifiers
```

```
REGION                      1..7
                            note = Synthetic peptide
source                      1..7
                            mol_type = protein
                            organism = synthetic construct
SEQUENCE: 854
SKCGSKD                                                                     7

SEQ ID NO: 855              moltype = AA  length = 6
FEATURE                     Location/Qualifiers
REGION                      1..6
                            note = Synthetic peptide
source                      1..6
                            mol_type = protein
                            organism = synthetic construct
SEQUENCE: 855
KCGSKD                                                                      6

SEQ ID NO: 856              moltype = AA  length = 5
FEATURE                     Location/Qualifiers
REGION                      1..5
                            note = Synthetic peptide
source                      1..5
                            mol_type = protein
                            organism = synthetic construct
SEQUENCE: 856
CGSKD                                                                       5

SEQ ID NO: 857              moltype = AA  length = 4
FEATURE                     Location/Qualifiers
REGION                      1..4
                            note = Synthetic peptide
source                      1..4
                            mol_type = protein
                            organism = synthetic construct
SEQUENCE: 857
GSKD                                                                        4

SEQ ID NO: 858              moltype =     length =
SEQUENCE: 858
000

SEQ ID NO: 859              moltype = AA  length = 10
FEATURE                     Location/Qualifiers
REGION                      1..10
                            note = Synthetic peptide
source                      1..10
                            mol_type = protein
                            organism = synthetic construct
SEQUENCE: 859
VQSKCGSKDN                                                                 10

SEQ ID NO: 860              moltype = AA  length = 9
FEATURE                     Location/Qualifiers
REGION                      1..9
                            note = Synthetic peptide
source                      1..9
                            mol_type = protein
                            organism = synthetic construct
SEQUENCE: 860
QSKCGSKDN                                                                   9

SEQ ID NO: 861              moltype = AA  length = 8
FEATURE                     Location/Qualifiers
REGION                      1..8
                            note = Synthetic peptide
source                      1..8
                            mol_type = protein
                            organism = synthetic construct
SEQUENCE: 861
SKCGSKDN                                                                    8

SEQ ID NO: 862              moltype = AA  length = 7
FEATURE                     Location/Qualifiers
REGION                      1..7
                            note = Synthetic peptide
source                      1..7
                            mol_type = protein
                            organism = synthetic construct
```

```
SEQUENCE: 862
KCGSKDN                                                              7

SEQ ID NO: 863         moltype = AA  length = 6
FEATURE                Location/Qualifiers
REGION                 1..6
                       note = Synthetic peptide
source                 1..6
                       mol_type = protein
                       organism = synthetic construct
SEQUENCE: 863
CGSKDN                                                               6

SEQ ID NO: 864         moltype = AA  length = 5
FEATURE                Location/Qualifiers
REGION                 1..5
                       note = Synthetic peptide
source                 1..5
                       mol_type = protein
                       organism = synthetic construct
SEQUENCE: 864
GSKDN                                                                5

SEQ ID NO: 865         moltype = AA  length = 4
FEATURE                Location/Qualifiers
REGION                 1..4
                       note = Synthetic peptide
source                 1..4
                       mol_type = protein
                       organism = synthetic construct
SEQUENCE: 865
SKDN                                                                 4

SEQ ID NO: 866         moltype = AA  length = 10
FEATURE                Location/Qualifiers
REGION                 1..10
                       note = Synthetic peptide
source                 1..10
                       mol_type = protein
                       organism = synthetic construct
SEQUENCE: 866
QSKCGSKDNI                                                          10

SEQ ID NO: 867         moltype = AA  length = 9
FEATURE                Location/Qualifiers
REGION                 1..9
                       note = Synthetic peptide
source                 1..9
                       mol_type = protein
                       organism = synthetic construct
SEQUENCE: 867
SKCGSKDNI                                                            9

SEQ ID NO: 868         moltype = AA  length = 8
FEATURE                Location/Qualifiers
REGION                 1..8
                       note = Synthetic peptide
source                 1..8
                       mol_type = protein
                       organism = synthetic construct
SEQUENCE: 868
KCGSKDNI                                                             8

SEQ ID NO: 869         moltype = AA  length = 7
FEATURE                Location/Qualifiers
REGION                 1..7
                       note = Synthetic peptide
source                 1..7
                       mol_type = protein
                       organism = synthetic construct
SEQUENCE: 869
CGSKDNI                                                              7

SEQ ID NO: 870         moltype = AA  length = 6
FEATURE                Location/Qualifiers
REGION                 1..6
                       note = Synthetic peptide
source                 1..6
                       mol_type = protein
```

```
                           organism = synthetic construct
SEQUENCE: 870
GSKDNI                                                                          6

SEQ ID NO: 871             moltype = AA   length = 5
FEATURE                    Location/Qualifiers
REGION                     1..5
                           note = Synthetic peptide
source                     1..5
                           mol_type = protein
                           organism = synthetic construct
SEQUENCE: 871
SKDNI                                                                           5

SEQ ID NO: 872             moltype = AA   length = 10
FEATURE                    Location/Qualifiers
REGION                     1..10
                           note = Synthetic peptide
source                     1..10
                           mol_type = protein
                           organism = synthetic construct
SEQUENCE: 872
SKVTSKCGSL                                                                     10

SEQ ID NO: 873             moltype = AA   length = 9
FEATURE                    Location/Qualifiers
REGION                     1..9
                           note = Synthetic peptide
source                     1..9
                           mol_type = protein
                           organism = synthetic construct
SEQUENCE: 873
KVTSKCGSL                                                                       9

SEQ ID NO: 874             moltype = AA   length = 8
FEATURE                    Location/Qualifiers
REGION                     1..8
                           note = Synthetic peptide
source                     1..8
                           mol_type = protein
                           organism = synthetic construct
SEQUENCE: 874
VTSKCGSL                                                                        8

SEQ ID NO: 875             moltype = AA   length = 7
FEATURE                    Location/Qualifiers
REGION                     1..7
                           note = Synthetic peptide
source                     1..7
                           mol_type = protein
                           organism = synthetic construct
SEQUENCE: 875
TSKCGSL                                                                         7

SEQ ID NO: 876             moltype = AA   length = 6
FEATURE                    Location/Qualifiers
REGION                     1..6
                           note = Synthetic peptide
source                     1..6
                           mol_type = protein
                           organism = synthetic construct
SEQUENCE: 876
SKCGSL                                                                          6

SEQ ID NO: 877             moltype = AA   length = 5
FEATURE                    Location/Qualifiers
REGION                     1..5
                           note = Synthetic peptide
source                     1..5
                           mol_type = protein
                           organism = synthetic construct
SEQUENCE: 877
KCGSL                                                                           5

SEQ ID NO: 878             moltype = AA   length = 4
FEATURE                    Location/Qualifiers
REGION                     1..4
                           note = Synthetic peptide
source                     1..4
```

```
                        mol_type = protein
                        organism = synthetic construct
SEQUENCE: 878
CGSL                                                                    4

SEQ ID NO: 879          moltype =   length =
SEQUENCE: 879
000

SEQ ID NO: 880          moltype = AA   length = 10
FEATURE                 Location/Qualifiers
REGION                  1..10
                        note = Synthetic peptide
source                  1..10
                        mol_type = protein
                        organism = synthetic construct
SEQUENCE: 880
KVTSKCGSLG                                                             10

SEQ ID NO: 881          moltype = AA   length = 9
FEATURE                 Location/Qualifiers
REGION                  1..9
                        note = Synthetic peptide
source                  1..9
                        mol_type = protein
                        organism = synthetic construct
SEQUENCE: 881
VTSKCGSLG                                                               9

SEQ ID NO: 882          moltype = AA   length = 8
FEATURE                 Location/Qualifiers
REGION                  1..8
                        note = Synthetic peptide
source                  1..8
                        mol_type = protein
                        organism = synthetic construct
SEQUENCE: 882
TSKCGSLG                                                                8

SEQ ID NO: 883          moltype = AA   length = 7
FEATURE                 Location/Qualifiers
REGION                  1..7
                        note = Synthetic peptide
source                  1..7
                        mol_type = protein
                        organism = synthetic construct
SEQUENCE: 883
SKCGSLG                                                                 7

SEQ ID NO: 884          moltype = AA   length = 6
FEATURE                 Location/Qualifiers
REGION                  1..6
                        note = Synthetic peptide
source                  1..6
                        mol_type = protein
                        organism = synthetic construct
SEQUENCE: 884
KCGSLG                                                                  6

SEQ ID NO: 885          moltype = AA   length = 5
FEATURE                 Location/Qualifiers
REGION                  1..5
                        note = Synthetic peptide
source                  1..5
                        mol_type = protein
                        organism = synthetic construct
SEQUENCE: 885
CGSLG                                                                   5

SEQ ID NO: 886          moltype = AA   length = 4
FEATURE                 Location/Qualifiers
REGION                  1..4
                        note = Synthetic peptide
source                  1..4
                        mol_type = protein
                        organism = synthetic construct
SEQUENCE: 886
GSLG                                                                    4
```

| | | |
|---|---|---|
| SEQ ID NO: 887<br>SEQUENCE: 887<br>000 | moltype =   length = | |
| SEQ ID NO: 888<br>FEATURE<br>REGION<br><br>source | moltype = AA   length = 10<br>Location/Qualifiers<br>1..10<br>note = Synthetic peptide<br>1..10<br>mol_type = protein<br>organism = synthetic construct | |
| SEQUENCE: 888<br>VTSKCGSLGN | | 10 |
| SEQ ID NO: 889<br>FEATURE<br>REGION<br><br>source | moltype = AA   length = 9<br>Location/Qualifiers<br>1..9<br>note = Synthetic peptide<br>1..9<br>mol_type = protein<br>organism = synthetic construct | |
| SEQUENCE: 889<br>TSKCGSLGN | | 9 |
| SEQ ID NO: 890<br>FEATURE<br>REGION<br><br>source | moltype = AA   length = 8<br>Location/Qualifiers<br>1..8<br>note = Synthetic peptide<br>1..8<br>mol_type = protein<br>organism = synthetic construct | |
| SEQUENCE: 890<br>SKCGSLGN | | 8 |
| SEQ ID NO: 891<br>FEATURE<br>REGION<br><br>source | moltype = AA   length = 7<br>Location/Qualifiers<br>1..7<br>note = Synthetic peptide<br>1..7<br>mol_type = protein<br>organism = synthetic construct | |
| SEQUENCE: 891<br>KCGSLGN | | 7 |
| SEQ ID NO: 892<br>FEATURE<br>REGION<br><br>source | moltype = AA   length = 6<br>Location/Qualifiers<br>1..6<br>note = Synthetic peptide<br>1..6<br>mol_type = protein<br>organism = synthetic construct | |
| SEQUENCE: 892<br>CGSLGN | | 6 |
| SEQ ID NO: 893<br>FEATURE<br>REGION<br><br>source | moltype = AA   length = 5<br>Location/Qualifiers<br>1..5<br>note = Synthetic peptide<br>1..5<br>mol_type = protein<br>organism = synthetic construct | |
| SEQUENCE: 893<br>GSLGN | | 5 |
| SEQ ID NO: 894<br>FEATURE<br>REGION<br><br>source | moltype = AA   length = 4<br>Location/Qualifiers<br>1..4<br>note = Synthetic peptide<br>1..4<br>mol_type = protein<br>organism = synthetic construct | |
| SEQUENCE: 894<br>SLGN | | 4 |
| SEQ ID NO: 895<br>FEATURE<br>REGION<br><br>source | moltype = AA   length = 10<br>Location/Qualifiers<br>1..10<br>note = Synthetic peptide<br>1..10 | |

```
                              mol_type = protein
                              organism = synthetic construct
SEQUENCE: 895
TSKCGSLGNI                                                                  10

SEQ ID NO: 896            moltype = AA   length = 9
FEATURE                   Location/Qualifiers
REGION                    1..9
                          note = Synthetic peptide
source                    1..9
                          mol_type = protein
                          organism = synthetic construct
SEQUENCE: 896
SKCGSLGNI                                                                   9

SEQ ID NO: 897            moltype = AA   length = 8
FEATURE                   Location/Qualifiers
REGION                    1..8
                          note = Synthetic peptide
source                    1..8
                          mol_type = protein
                          organism = synthetic construct
SEQUENCE: 897
KCGSLGNI                                                                    8

SEQ ID NO: 898            moltype = AA   length = 7
FEATURE                   Location/Qualifiers
REGION                    1..7
                          note = Synthetic peptide
source                    1..7
                          mol_type = protein
                          organism = synthetic construct
SEQUENCE: 898
CGSLGNI                                                                     7

SEQ ID NO: 899            moltype = AA   length = 6
FEATURE                   Location/Qualifiers
REGION                    1..6
                          note = Synthetic peptide
source                    1..6
                          mol_type = protein
                          organism = synthetic construct
SEQUENCE: 899
GSLGNI                                                                      6

SEQ ID NO: 900            moltype = AA   length = 5
FEATURE                   Location/Qualifiers
REGION                    1..5
                          note = Synthetic peptide
source                    1..5
                          mol_type = protein
                          organism = synthetic construct
SEQUENCE: 900
SLGNI                                                                       5

SEQ ID NO: 901            moltype = AA   length = 10
FEATURE                   Location/Qualifiers
REGION                    1..10
                          note = Synthetic peptide
source                    1..10
                          mol_type = protein
                          organism = synthetic construct
SEQUENCE: 901
SKCGSLGNIH                                                                  10

SEQ ID NO: 902            moltype = AA   length = 9
FEATURE                   Location/Qualifiers
REGION                    1..9
                          note = Synthetic peptide
source                    1..9
                          mol_type = protein
                          organism = synthetic construct
SEQUENCE: 902
KCGSLGNIH                                                                   9

SEQ ID NO: 903            moltype = AA   length = 8
FEATURE                   Location/Qualifiers
REGION                    1..8
                          note = Synthetic peptide
```

```
                         -continued source                   1..8
                         mol_type = protein
                         organism = synthetic construct
SEQUENCE: 903
CGSLGNIH                                                            8

SEQ ID NO: 904           moltype = AA   length = 7
FEATURE                  Location/Qualifiers
REGION                   1..7
                         note = Synthetic peptide
source                   1..7
                         mol_type = protein
                         organism = synthetic construct
SEQUENCE: 904
GSLGNIH                                                             7

SEQ ID NO: 905           moltype = AA   length = 6
FEATURE                  Location/Qualifiers
REGION                   1..6
                         note = Synthetic peptide
source                   1..6
                         mol_type = protein
                         organism = synthetic construct
SEQUENCE: 905
SLGNIH                                                              6

SEQ ID NO: 906           moltype = AA   length = 10
FEATURE                  Location/Qualifiers
REGION                   1..10
                         note = Synthetic peptide
source                   1..10
                         mol_type = protein
                         organism = synthetic construct
SEQUENCE: 906
KCGSLGNIHH                                                         10

SEQ ID NO: 907           moltype = AA   length = 9
FEATURE                  Location/Qualifiers
REGION                   1..9
                         note = Synthetic peptide
source                   1..9
                         mol_type = protein
                         organism = synthetic construct
SEQUENCE: 907
CGSLGNIHH                                                           9

SEQ ID NO: 908           moltype = AA   length = 8
FEATURE                  Location/Qualifiers
REGION                   1..8
                         note = Synthetic peptide
source                   1..8
                         mol_type = protein
                         organism = synthetic construct
SEQUENCE: 908
GSLGNIHH                                                            8

SEQ ID NO: 909           moltype = AA   length = 7
FEATURE                  Location/Qualifiers
REGION                   1..7
                         note = Synthetic peptide
source                   1..7
                         mol_type = protein
                         organism = synthetic construct
SEQUENCE: 909
SLGNIHH                                                             7

SEQ ID NO: 910           moltype = AA   length = 10
FEATURE                  Location/Qualifiers
REGION                   1..10
                         note = Synthetic peptide
source                   1..10
                         mol_type = protein
                         organism = synthetic construct
SEQUENCE: 910
CGSLGNIHHK                                                         10

SEQ ID NO: 911           moltype = AA   length = 9
FEATURE                  Location/Qualifiers
REGION                   1..9
```

```
                        note = Synthetic peptide
source                  1..9
                        mol_type = protein
                        organism = synthetic construct
SEQUENCE: 911
GSLGNIHHK                                                                    9

SEQ ID NO: 912          moltype = AA  length = 8
FEATURE                 Location/Qualifiers
REGION                  1..8
                        note = Synthetic peptide
source                  1..8
                        mol_type = protein
                        organism = synthetic construct
SEQUENCE: 912
SLGNIHHK                                                                     8

SEQ ID NO: 913          moltype = AA  length = 10
FEATURE                 Location/Qualifiers
REGION                  1..10
                        note = Synthetic peptide
source                  1..10
                        mol_type = protein
                        organism = synthetic construct
SEQUENCE: 913
GSLGNIHHKP                                                                  10

SEQ ID NO: 914          moltype = AA  length = 9
FEATURE                 Location/Qualifiers
REGION                  1..9
                        note = Synthetic peptide
source                  1..9
                        mol_type = protein
                        organism = synthetic construct
SEQUENCE: 914
SLGNIHHKP                                                                    9

SEQ ID NO: 915          moltype = AA  length = 10
FEATURE                 Location/Qualifiers
REGION                  1..10
                        note = Synthetic peptide
source                  1..10
                        mol_type = protein
                        organism = synthetic construct
SEQUENCE: 915
SLGNIHHKPG                                                                  10

SEQ ID NO: 916          moltype = AA  length = 10
FEATURE                 Location/Qualifiers
REGION                  1..10
                        note = Synthetic peptide
source                  1..10
                        mol_type = protein
                        organism = synthetic construct
SEQUENCE: 916
DRVQSKIGSL                                                                  10

SEQ ID NO: 917          moltype = AA  length = 9
FEATURE                 Location/Qualifiers
REGION                  1..9
                        note = Synthetic peptide
source                  1..9
                        mol_type = protein
                        organism = synthetic construct
SEQUENCE: 917
RVQSKIGSL                                                                    9

SEQ ID NO: 918          moltype = AA  length = 8
FEATURE                 Location/Qualifiers
REGION                  1..8
                        note = Synthetic peptide
source                  1..8
                        mol_type = protein
                        organism = synthetic construct
SEQUENCE: 918
VQSKIGSL                                                                     8

SEQ ID NO: 919          moltype = AA  length = 7
FEATURE                 Location/Qualifiers
```

```
REGION                  1..7
                        note = Synthetic peptide
source                  1..7
                        mol_type = protein
                        organism = synthetic construct
SEQUENCE: 919
QSKIGSL                                                                     7

SEQ ID NO: 920          moltype = AA  length = 6
FEATURE                 Location/Qualifiers
REGION                  1..6
                        note = Synthetic peptide
source                  1..6
                        mol_type = protein
                        organism = synthetic construct
SEQUENCE: 920
SKIGSL                                                                      6

SEQ ID NO: 921          moltype = AA  length = 5
FEATURE                 Location/Qualifiers
REGION                  1..5
                        note = Synthetic peptide
source                  1..5
                        mol_type = protein
                        organism = synthetic construct
SEQUENCE: 921
KIGSL                                                                       5

SEQ ID NO: 922          moltype = AA  length = 4
FEATURE                 Location/Qualifiers
REGION                  1..4
                        note = Synthetic peptide
source                  1..4
                        mol_type = protein
                        organism = synthetic construct
SEQUENCE: 922
IGSL                                                                        4

SEQ ID NO: 923          moltype = AA  length = 10
FEATURE                 Location/Qualifiers
REGION                  1..10
                        note = Synthetic peptide
source                  1..10
                        mol_type = protein
                        organism = synthetic construct
SEQUENCE: 923
RVQSKIGSLD                                                                 10

SEQ ID NO: 924          moltype = AA  length = 9
FEATURE                 Location/Qualifiers
REGION                  1..9
                        note = Synthetic peptide
source                  1..9
                        mol_type = protein
                        organism = synthetic construct
SEQUENCE: 924
VQSKIGSLD                                                                   9

SEQ ID NO: 925          moltype = AA  length = 8
FEATURE                 Location/Qualifiers
REGION                  1..8
                        note = Synthetic peptide
source                  1..8
                        mol_type = protein
                        organism = synthetic construct
SEQUENCE: 925
QSKIGSLD                                                                    8

SEQ ID NO: 926          moltype = AA  length = 7
FEATURE                 Location/Qualifiers
REGION                  1..7
                        note = Synthetic peptide
source                  1..7
                        mol_type = protein
                        organism = synthetic construct
SEQUENCE: 926
SKIGSLD                                                                     7

SEQ ID NO: 927          moltype = AA  length = 6
```

```
FEATURE             Location/Qualifiers
REGION              1..6
                    note = Synthetic peptide
source              1..6
                    mol_type = protein
                    organism = synthetic construct
SEQUENCE: 927
KIGSLD                                                                  6

SEQ ID NO: 928      moltype = AA  length = 5
FEATURE             Location/Qualifiers
REGION              1..5
                    note = Synthetic peptide
source              1..5
                    mol_type = protein
                    organism = synthetic construct
SEQUENCE: 928
IGSLD                                                                   5

SEQ ID NO: 929      moltype = AA  length = 4
FEATURE             Location/Qualifiers
REGION              1..4
                    note = Synthetic peptide
source              1..4
                    mol_type = protein
                    organism = synthetic construct
SEQUENCE: 929
GSLD                                                                    4

SEQ ID NO: 930      moltype =   length =
SEQUENCE: 930
000

SEQ ID NO: 931      moltype = AA  length = 10
FEATURE             Location/Qualifiers
REGION              1..10
                    note = Synthetic peptide
source              1..10
                    mol_type = protein
                    organism = synthetic construct
SEQUENCE: 931
VQSKIGSLDN                                                             10

SEQ ID NO: 932      moltype = AA  length = 9
FEATURE             Location/Qualifiers
REGION              1..9
                    note = Synthetic peptide
source              1..9
                    mol_type = protein
                    organism = synthetic construct
SEQUENCE: 932
QSKIGSLDN                                                               9

SEQ ID NO: 933      moltype = AA  length = 8
FEATURE             Location/Qualifiers
REGION              1..8
                    note = Synthetic peptide
source              1..8
                    mol_type = protein
                    organism = synthetic construct
SEQUENCE: 933
SKIGSLDN                                                                8

SEQ ID NO: 934      moltype = AA  length = 7
FEATURE             Location/Qualifiers
REGION              1..7
                    note = Synthetic peptide
source              1..7
                    mol_type = protein
                    organism = synthetic construct
SEQUENCE: 934
KIGSLDN                                                                 7

SEQ ID NO: 935      moltype = AA  length = 6
FEATURE             Location/Qualifiers
REGION              1..6
                    note = Synthetic peptide
source              1..6
                    mol_type = protein
```

```
                         -continued organism = synthetic construct
SEQUENCE: 935
IGSLDN                                                                    6

SEQ ID NO: 936           moltype = AA  length = 5
FEATURE                  Location/Qualifiers
REGION                   1..5
                         note = Synthetic peptide
source                   1..5
                         mol_type = protein
                         organism = synthetic construct
SEQUENCE: 936
GSLDN                                                                     5

SEQ ID NO: 937           moltype = AA  length = 4
FEATURE                  Location/Qualifiers
REGION                   1..4
                         note = Synthetic peptide
source                   1..4
                         mol_type = protein
                         organism = synthetic construct
SEQUENCE: 937
SLDN                                                                      4

SEQ ID NO: 938           moltype = AA  length = 10
FEATURE                  Location/Qualifiers
REGION                   1..10
                         note = Synthetic peptide
source                   1..10
                         mol_type = protein
                         organism = synthetic construct
SEQUENCE: 938
QSKIGSLDNI                                                               10

SEQ ID NO: 939           moltype = AA  length = 9
FEATURE                  Location/Qualifiers
REGION                   1..9
                         note = Synthetic peptide
source                   1..9
                         mol_type = protein
                         organism = synthetic construct
SEQUENCE: 939
SKIGSLDNI                                                                 9

SEQ ID NO: 940           moltype = AA  length = 8
FEATURE                  Location/Qualifiers
REGION                   1..8
                         note = Synthetic peptide
source                   1..8
                         mol_type = protein
                         organism = synthetic construct
SEQUENCE: 940
KIGSLDNI                                                                  8

SEQ ID NO: 941           moltype = AA  length = 7
FEATURE                  Location/Qualifiers
REGION                   1..7
                         note = Synthetic peptide
source                   1..7
                         mol_type = protein
                         organism = synthetic construct
SEQUENCE: 941
IGSLDNI                                                                   7

SEQ ID NO: 942           moltype = AA  length = 6
FEATURE                  Location/Qualifiers
REGION                   1..6
                         note = Synthetic peptide
source                   1..6
                         mol_type = protein
                         organism = synthetic construct
SEQUENCE: 942
GSLDNI                                                                    6

SEQ ID NO: 943           moltype = AA  length = 10
FEATURE                  Location/Qualifiers
REGION                   1..10
                         note = Synthetic peptide
source                   1..10
```

```
                        mol_type = protein
                        organism = synthetic construct
SEQUENCE: 943
SKIGSLDNIT                                                                    10

SEQ ID NO: 944          moltype = AA   length = 9
FEATURE                 Location/Qualifiers
REGION                  1..9
                        note = Synthetic peptide
source                  1..9
                        mol_type = protein
                        organism = synthetic construct
SEQUENCE: 944
KIGSLDNIT                                                                      9

SEQ ID NO: 945          moltype = AA   length = 8
FEATURE                 Location/Qualifiers
REGION                  1..8
                        note = Synthetic peptide
source                  1..8
                        mol_type = protein
                        organism = synthetic construct
SEQUENCE: 945
IGSLDNIT                                                                       8

SEQ ID NO: 946          moltype = AA   length = 7
FEATURE                 Location/Qualifiers
REGION                  1..7
                        note = Synthetic peptide
source                  1..7
                        mol_type = protein
                        organism = synthetic construct
SEQUENCE: 946
GSLDNIT                                                                        7

SEQ ID NO: 947          moltype = AA   length = 6
FEATURE                 Location/Qualifiers
REGION                  1..6
                        note = Synthetic peptide
source                  1..6
                        mol_type = protein
                        organism = synthetic construct
SEQUENCE: 947
SLDNIT                                                                         6

SEQ ID NO: 948          moltype = AA   length = 10
FEATURE                 Location/Qualifiers
REGION                  1..10
                        note = Synthetic peptide
source                  1..10
                        mol_type = protein
                        organism = synthetic construct
SEQUENCE: 948
KIGSLDNITH                                                                    10

SEQ ID NO: 949          moltype = AA   length = 9
FEATURE                 Location/Qualifiers
REGION                  1..9
                        note = Synthetic peptide
source                  1..9
                        mol_type = protein
                        organism = synthetic construct
SEQUENCE: 949
IGSLDNITH                                                                      9

SEQ ID NO: 950          moltype = AA   length = 8
FEATURE                 Location/Qualifiers
REGION                  1..8
                        note = Synthetic peptide
source                  1..8
                        mol_type = protein
                        organism = synthetic construct
SEQUENCE: 950
GSLDNITH                                                                       8

SEQ ID NO: 951          moltype = AA   length = 7
FEATURE                 Location/Qualifiers
REGION                  1..7
                        note = Synthetic peptide
```

```
source                      1..7
                            mol_type = protein
                            organism = synthetic construct
SEQUENCE: 951
SLDNITH                                                                          7

SEQ ID NO: 952              moltype = AA  length = 10
FEATURE                     Location/Qualifiers
REGION                      1..10
                            note = Synthetic peptide
source                      1..10
                            mol_type = protein
                            organism = synthetic construct
SEQUENCE: 952
IGSLDNITHV                                                                      10

SEQ ID NO: 953              moltype = AA  length = 9
FEATURE                     Location/Qualifiers
REGION                      1..9
                            note = Synthetic peptide
source                      1..9
                            mol_type = protein
                            organism = synthetic construct
SEQUENCE: 953
GSLDNITHV                                                                        9

SEQ ID NO: 954              moltype = AA  length = 8
FEATURE                     Location/Qualifiers
REGION                      1..8
                            note = Synthetic peptide
source                      1..8
                            mol_type = protein
                            organism = synthetic construct
SEQUENCE: 954
SLDNITHV                                                                         8

SEQ ID NO: 955              moltype = AA  length = 10
FEATURE                     Location/Qualifiers
REGION                      1..10
                            note = Synthetic peptide
source                      1..10
                            mol_type = protein
                            organism = synthetic construct
SEQUENCE: 955
GSLDNITHVP                                                                      10

SEQ ID NO: 956              moltype = AA  length = 9
FEATURE                     Location/Qualifiers
REGION                      1..9
                            note = Synthetic peptide
source                      1..9
                            mol_type = protein
                            organism = synthetic construct
SEQUENCE: 956
SLDNITHVP                                                                        9

SEQ ID NO: 957              moltype = AA  length = 10
FEATURE                     Location/Qualifiers
REGION                      1..10
                            note = Synthetic peptide
source                      1..10
                            mol_type = protein
                            organism = synthetic construct
SEQUENCE: 957
SLDNITHVPG                                                                      10

SEQ ID NO: 958              moltype = AA  length = 8
FEATURE                     Location/Qualifiers
REGION                      1..8
                            note = Synthetic peptide
source                      1..8
                            mol_type = protein
                            organism = synthetic construct
SEQUENCE: 958
PDLKNVKS                                                                         8

SEQ ID NO: 959              moltype = AA  length = 8
FEATURE                     Location/Qualifiers
REGION                      1..8
```

|  |  |  |
|---|---|---|
|  | note = Synthetic peptide | |
| source | 1..8 | |
|  | mol_type = protein | |
|  | organism = synthetic construct | |
| SEQUENCE: 959 | | |
| DLKNVKSK | | 8 |
| SEQ ID NO: 960 | moltype = AA  length = 8 | |
| FEATURE | Location/Qualifiers | |
| REGION | 1..8 | |
|  | note = Synthetic peptide | |
| source | 1..8 | |
|  | mol_type = protein | |
|  | organism = synthetic construct | |
| SEQUENCE: 960 | | |
| LKNVKSKI | | 8 |
| SEQ ID NO: 961 | moltype = AA  length = 8 | |
| FEATURE | Location/Qualifiers | |
| REGION | 1..8 | |
|  | note = Synthetic peptide | |
| source | 1..8 | |
|  | mol_type = protein | |
|  | organism = synthetic construct | |
| SEQUENCE: 961 | | |
| KNVKSKIG | | 8 |
| SEQ ID NO: 962 | moltype = AA  length = 8 | |
| FEATURE | Location/Qualifiers | |
| REGION | 1..8 | |
|  | note = Synthetic peptide | |
| source | 1..8 | |
|  | mol_type = protein | |
|  | organism = synthetic construct | |
| SEQUENCE: 962 | | |
| NVKSKIGS | | 8 |
| SEQ ID NO: 963 | moltype = AA  length = 8 | |
| FEATURE | Location/Qualifiers | |
| REGION | 1..8 | |
|  | note = Synthetic peptide | |
| source | 1..8 | |
|  | mol_type = protein | |
|  | organism = synthetic construct | |
| SEQUENCE: 963 | | |
| DLSNVQSK | | 8 |
| SEQ ID NO: 964 | moltype = AA  length = 8 | |
| FEATURE | Location/Qualifiers | |
| REGION | 1..8 | |
|  | note = Synthetic peptide | |
| source | 1..8 | |
|  | mol_type = protein | |
|  | organism = synthetic construct | |
| SEQUENCE: 964 | | |
| LSNVQSKC | | 8 |
| SEQ ID NO: 965 | moltype = AA  length = 8 | |
| FEATURE | Location/Qualifiers | |
| REGION | 1..8 | |
|  | note = Synthetic peptide | |
| source | 1..8 | |
|  | mol_type = protein | |
|  | organism = synthetic construct | |
| SEQUENCE: 965 | | |
| SNVQSKCG | | 8 |
| SEQ ID NO: 966 | moltype = AA  length = 8 | |
| FEATURE | Location/Qualifiers | |
| REGION | 1..8 | |
|  | note = Synthetic peptide | |
| source | 1..8 | |
|  | mol_type = protein | |
|  | organism = synthetic construct | |
| SEQUENCE: 966 | | |
| NVQSKCGS | | 8 |
| SEQ ID NO: 967 | moltype = AA  length = 8 | |
| FEATURE | Location/Qualifiers | |

```
                       -continued

REGION                 1..8
                       note = Synthetic peptide
source                 1..8
                       mol_type = protein
                       organism = synthetic construct
SEQUENCE: 967
VDLSKVTS                                                             8

SEQ ID NO: 968         moltype = AA  length = 8
FEATURE                Location/Qualifiers
REGION                 1..8
                       note = Synthetic peptide
source                 1..8
                       mol_type = protein
                       organism = synthetic construct
SEQUENCE: 968
DLSKVTSK                                                             8

SEQ ID NO: 969         moltype = AA  length = 8
FEATURE                Location/Qualifiers
REGION                 1..8
                       note = Synthetic peptide
source                 1..8
                       mol_type = protein
                       organism = synthetic construct
SEQUENCE: 969
LSKVTSKC                                                             8

SEQ ID NO: 970         moltype = AA  length = 8
FEATURE                Location/Qualifiers
REGION                 1..8
                       note = Synthetic peptide
source                 1..8
                       mol_type = protein
                       organism = synthetic construct
SEQUENCE: 970
SKVTSKCG                                                             8

SEQ ID NO: 971         moltype = AA  length = 8
FEATURE                Location/Qualifiers
REGION                 1..8
                       note = Synthetic peptide
source                 1..8
                       mol_type = protein
                       organism = synthetic construct
SEQUENCE: 971
KVTSKCGS                                                             8

SEQ ID NO: 972         moltype = AA  length = 8
FEATURE                Location/Qualifiers
REGION                 1..8
                       note = Synthetic peptide
source                 1..8
                       mol_type = protein
                       organism = synthetic construct
SEQUENCE: 972
LDFKDRVQ                                                             8

SEQ ID NO: 973         moltype = AA  length = 8
FEATURE                Location/Qualifiers
REGION                 1..8
                       note = Synthetic peptide
source                 1..8
                       mol_type = protein
                       organism = synthetic construct
SEQUENCE: 973
DFKDRVQS                                                             8

SEQ ID NO: 974         moltype = AA  length = 8
FEATURE                Location/Qualifiers
REGION                 1..8
                       note = Synthetic peptide
source                 1..8
                       mol_type = protein
                       organism = synthetic construct
SEQUENCE: 974
FKDRVQSK                                                             8

SEQ ID NO: 975         moltype = AA  length = 8
```

```
FEATURE                 Location/Qualifiers
REGION                  1..8
                        note = Synthetic peptide
source                  1..8
                        mol_type = protein
                        organism = synthetic construct
SEQUENCE: 975
KDRVQSKI                                                                    8

SEQ ID NO: 976          moltype = AA  length = 8
FEATURE                 Location/Qualifiers
REGION                  1..8
                        note = Synthetic peptide
source                  1..8
                        mol_type = protein
                        organism = synthetic construct
SEQUENCE: 976
DRVQSKIG                                                                    8

SEQ ID NO: 977          moltype = AA  length = 8
FEATURE                 Location/Qualifiers
REGION                  1..8
                        note = Synthetic peptide
source                  1..8
                        mol_type = protein
                        organism = synthetic construct
SEQUENCE: 977
RVQSKIGS                                                                    8

SEQ ID NO: 978          moltype = AA  length = 11
FEATURE                 Location/Qualifiers
REGION                  1..11
                        note = Synthetic peptide
source                  1..11
                        mol_type = protein
                        organism = synthetic construct
SEQUENCE: 978
SKIGSTENLK H                                                               11

SEQ ID NO: 979          moltype = AA  length = 11
FEATURE                 Location/Qualifiers
REGION                  1..11
                        note = Synthetic peptide
source                  1..11
                        mol_type = protein
                        organism = synthetic construct
SEQUENCE: 979
SKIGSTENIK H                                                               11

SEQ ID NO: 980          moltype = AA  length = 11
FEATURE                 Location/Qualifiers
REGION                  1..11
                        note = Synthetic peptide
source                  1..11
                        mol_type = protein
                        organism = synthetic construct
SEQUENCE: 980
SKIGSKDNLK H                                                               11

SEQ ID NO: 981          moltype = AA  length = 11
FEATURE                 Location/Qualifiers
REGION                  1..11
                        note = Synthetic peptide
source                  1..11
                        mol_type = protein
                        organism = synthetic construct
SEQUENCE: 981
SKIGSKENIK H                                                               11

SEQ ID NO: 982          moltype = AA  length = 11
FEATURE                 Location/Qualifiers
REGION                  1..11
                        note = Synthetic peptide
source                  1..11
                        mol_type = protein
                        organism = synthetic construct
SEQUENCE: 982
SKIGSLENLK H                                                               11
```

```
SEQ ID NO: 983         moltype = AA   length = 11
FEATURE                Location/Qualifiers
REGION                 1..11
                       note = Synthetic peptide
source                 1..11
                       mol_type = protein
                       organism = synthetic construct
SEQUENCE: 983
SKIGSLENIK H                                                              11

SEQ ID NO: 984         moltype = AA   length = 11
FEATURE                Location/Qualifiers
REGION                 1..11
                       note = Synthetic peptide
source                 1..11
                       mol_type = protein
                       organism = synthetic construct
SEQUENCE: 984
SKIGSTDNLK H                                                              11

SEQ ID NO: 985         moltype = AA   length = 11
FEATURE                Location/Qualifiers
REGION                 1..11
                       note = Synthetic peptide
source                 1..11
                       mol_type = protein
                       organism = synthetic construct
SEQUENCE: 985
SKIGSTDNIK H                                                              11

SEQ ID NO: 986         moltype = AA   length = 11
FEATURE                Location/Qualifiers
REGION                 1..11
                       note = Synthetic peptide
source                 1..11
                       mol_type = protein
                       organism = synthetic construct
SEQUENCE: 986
SKIGSKDNIK H                                                              11

SEQ ID NO: 987         moltype = AA   length = 11
FEATURE                Location/Qualifiers
REGION                 1..11
                       note = Synthetic peptide
source                 1..11
                       mol_type = protein
                       organism = synthetic construct
SEQUENCE: 987
SKIGSLDNLK H                                                              11

SEQ ID NO: 988         moltype = AA   length = 11
FEATURE                Location/Qualifiers
REGION                 1..11
                       note = Synthetic peptide
source                 1..11
                       mol_type = protein
                       organism = synthetic construct
SEQUENCE: 988
SKIGSLDNIK H                                                              11

SEQ ID NO: 989         moltype = AA   length = 11
FEATURE                Location/Qualifiers
REGION                 1..11
                       note = Synthetic peptide
source                 1..11
                       mol_type = protein
                       organism = synthetic construct
SEQUENCE: 989
SKIGSTGNLK H                                                              11

SEQ ID NO: 990         moltype = AA   length = 11
FEATURE                Location/Qualifiers
REGION                 1..11
                       note = Synthetic peptide
source                 1..11
                       mol_type = protein
                       organism = synthetic construct
SEQUENCE: 990
SKIGSTGNIK H                                                              11
```

```
SEQ ID NO: 991           moltype = AA   length = 11
FEATURE                  Location/Qualifiers
REGION                   1..11
                         note = Synthetic peptide
source                   1..11
                         mol_type = protein
                         organism = synthetic construct
SEQUENCE: 991
SKIGSKGNLK H                                                              11

SEQ ID NO: 992           moltype = AA   length = 11
FEATURE                  Location/Qualifiers
REGION                   1..11
                         note = Synthetic peptide
source                   1..11
                         mol_type = protein
                         organism = synthetic construct
SEQUENCE: 992
SKIGSKGNIK H                                                              11

SEQ ID NO: 993           moltype = AA   length = 11
FEATURE                  Location/Qualifiers
REGION                   1..11
                         note = Synthetic peptide
source                   1..11
                         mol_type = protein
                         organism = synthetic construct
SEQUENCE: 993
SKIGSLGNLK H                                                              11

SEQ ID NO: 994           moltype = AA   length = 11
FEATURE                  Location/Qualifiers
REGION                   1..11
                         note = Synthetic peptide
source                   1..11
                         mol_type = protein
                         organism = synthetic construct
SEQUENCE: 994
SKIGSLGNIK H                                                              11

SEQ ID NO: 995           moltype = AA   length = 10
FEATURE                  Location/Qualifiers
REGION                   1..10
                         note = Synthetic peptide
VAR_SEQ                  2
                         note = MISC_FEATURE - Xaa is I or C
VAR_SEQ                  3
                         note = MISC_FEATURE - Xaa is G
VAR_SEQ                  5
                         note = MISC_FEATURE - Xaa is T or K or L
VAR_SEQ                  6
                         note = MISC_FEATURE - Xaa is E or D or G
VAR_SEQ                  8
                         note = MISC_FEATURE - Xaa is L or I
VAR_SEQ                  9
                         note = MISC_FEATURE - Xaa is K or H or T
source                   1..10
                         mol_type = protein
                         organism = synthetic construct
SEQUENCE: 995
KXXSXXNXXH                                                                10

SEQ ID NO: 996           moltype = AA   length = 6
FEATURE                  Location/Qualifiers
REGION                   1..6
                         note = Synthetic peptide
VAR_SEQ                  1
                         note = MISC_FEATURE - Xaa can be Q or E
VAR_SEQ                  6
                         note = MISC_FEATURE - Xaa can be S or P
source                   1..6
                         mol_type = protein
                         organism = synthetic construct
SEQUENCE: 996
XIVYKX                                                                    6

SEQ ID NO: 997           moltype = AA   length = 20
FEATURE                  Location/Qualifiers
```

```
REGION                   1..20
                         note = Synthetic peptide
source                   1..20
                         mol_type = protein
                         organism = synthetic construct
SEQUENCE: 997
DAEFRHDRRV KSKIGSTGGC                                              20

SEQ ID NO: 998           moltype = AA  length = 20
FEATURE                  Location/Qualifiers
REGION                   1..20
                         note = Synthetic peptide
source                   1..20
                         mol_type = protein
                         organism = synthetic construct
SEQUENCE: 998
DAEFRHDRRS KIGSTENGGC                                              20

SEQ ID NO: 999           moltype = AA  length = 20
FEATURE                  Location/Qualifiers
REGION                   1..20
                         note = Synthetic peptide
source                   1..20
                         mol_type = protein
                         organism = synthetic construct
SEQUENCE: 999
DAEFRHDRRT ENLKHQPGGC                                              20

SEQ ID NO: 1000          moltype = AA  length = 20
FEATURE                  Location/Qualifiers
REGION                   1..20
                         note = Synthetic peptide
source                   1..20
                         mol_type = protein
                         organism = synthetic construct
SEQUENCE: 1000
DAEFRHDRRE NLKHQPGGGC                                              20

SEQ ID NO: 1001          moltype = AA  length = 23
FEATURE                  Location/Qualifiers
REGION                   1..23
                         note = Synthetic peptide
source                   1..23
                         mol_type = protein
                         organism = synthetic construct
SEQUENCE: 1001
DAEFRHDRRS KIGSKDNIKH GGC                                          23

SEQ ID NO: 1002          moltype = AA  length = 10
FEATURE                  Location/Qualifiers
REGION                   1..10
                         note = Synthetic peptide
source                   1..10
                         mol_type = protein
                         organism = synthetic construct
SEQUENCE: 1002
VHHQKLVFFA                                                         10

SEQ ID NO: 1003          moltype = AA  length = 9
FEATURE                  Location/Qualifiers
REGION                   1..9
                         note = Synthetic peptide
source                   1..9
                         mol_type = protein
                         organism = synthetic construct
SEQUENCE: 1003
VHHQKLVFF                                                          9

SEQ ID NO: 1004          moltype = AA  length = 8
FEATURE                  Location/Qualifiers
REGION                   1..8
                         note = Synthetic peptide
source                   1..8
                         mol_type = protein
                         organism = synthetic construct
SEQUENCE: 1004
VHHQKLVF                                                           8

SEQ ID NO: 1005          moltype = AA  length = 7
```

```
FEATURE              Location/Qualifiers
REGION               1..7
                     note = Synthetic peptide
source               1..7
                     mol_type = protein
                     organism = synthetic construct
SEQUENCE: 1005
VHHQKLV                                                                         7

SEQ ID NO: 1006      moltype = AA  length = 6
FEATURE              Location/Qualifiers
REGION               1..6
                     note = Synthetic peptide
source               1..6
                     mol_type = protein
                     organism = synthetic construct
SEQUENCE: 1006
VHHQKL                                                                          6

SEQ ID NO: 1007      moltype = AA  length = 10
FEATURE              Location/Qualifiers
REGION               1..10
                     note = Synthetic peptide
source               1..10
                     mol_type = protein
                     organism = synthetic construct
SEQUENCE: 1007
HHQKLVFFAE                                                                     10

SEQ ID NO: 1008      moltype = AA  length = 9
FEATURE              Location/Qualifiers
REGION               1..9
                     note = Synthetic peptide
source               1..9
                     mol_type = protein
                     organism = synthetic construct
SEQUENCE: 1008
HHQKLVFFA                                                                       9

SEQ ID NO: 1009      moltype = AA  length = 8
FEATURE              Location/Qualifiers
REGION               1..8
                     note = Synthetic peptide
source               1..8
                     mol_type = protein
                     organism = synthetic construct
SEQUENCE: 1009
HHQKLVFF                                                                        8

SEQ ID NO: 1010      moltype = AA  length = 7
FEATURE              Location/Qualifiers
REGION               1..7
                     note = Synthetic peptide
source               1..7
                     mol_type = protein
                     organism = synthetic construct
SEQUENCE: 1010
HHQKLVF                                                                         7

SEQ ID NO: 1011      moltype = AA  length = 6
FEATURE              Location/Qualifiers
REGION               1..6
                     note = Synthetic peptide
source               1..6
                     mol_type = protein
                     organism = synthetic construct
SEQUENCE: 1011
HHQKLV                                                                          6

SEQ ID NO: 1012      moltype = AA  length = 5
FEATURE              Location/Qualifiers
REGION               1..5
                     note = Synthetic peptide
source               1..5
                     mol_type = protein
                     organism = synthetic construct
SEQUENCE: 1012
HHQKL                                                                           5
```

-continued

```
SEQ ID NO: 1013         moltype = AA   length = 10
FEATURE                 Location/Qualifiers
REGION                  1..10
                        note = Synthetic peptide
source                  1..10
                        mol_type = protein
                        organism = synthetic construct
SEQUENCE: 1013
HQKLVFFAED                                                                  10

SEQ ID NO: 1014         moltype = AA   length = 9
FEATURE                 Location/Qualifiers
REGION                  1..9
                        note = Synthetic peptide
source                  1..9
                        mol_type = protein
                        organism = synthetic construct
SEQUENCE: 1014
HQKLVFFAE                                                                    9

SEQ ID NO: 1015         moltype = AA   length = 8
FEATURE                 Location/Qualifiers
REGION                  1..8
                        note = Synthetic peptide
source                  1..8
                        mol_type = protein
                        organism = synthetic construct
SEQUENCE: 1015
HQKLVFFA                                                                     8

SEQ ID NO: 1016         moltype = AA   length = 7
FEATURE                 Location/Qualifiers
REGION                  1..7
                        note = Synthetic peptide
source                  1..7
                        mol_type = protein
                        organism = synthetic construct
SEQUENCE: 1016
HQKLVFF                                                                      7

SEQ ID NO: 1017         moltype = AA   length = 6
FEATURE                 Location/Qualifiers
REGION                  1..6
                        note = Synthetic peptide
source                  1..6
                        mol_type = protein
                        organism = synthetic construct
SEQUENCE: 1017
HQKLVF                                                                       6

SEQ ID NO: 1018         moltype = AA   length = 5
FEATURE                 Location/Qualifiers
REGION                  1..5
                        note = Synthetic peptide
source                  1..5
                        mol_type = protein
                        organism = synthetic construct
SEQUENCE: 1018
HQKLV                                                                        5

SEQ ID NO: 1019         moltype = AA   length = 4
FEATURE                 Location/Qualifiers
REGION                  1..4
                        note = Synthetic peptide
source                  1..4
                        mol_type = protein
                        organism = synthetic construct
SEQUENCE: 1019
HQKL                                                                         4

SEQ ID NO: 1020         moltype = AA   length = 10
FEATURE                 Location/Qualifiers
REGION                  1..10
                        note = Synthetic peptide
source                  1..10
                        mol_type = protein
                        organism = synthetic construct
SEQUENCE: 1020
QKLVFFAEDV                                                                  10
```

```
SEQ ID NO: 1021        moltype = AA   length = 9
FEATURE                Location/Qualifiers
REGION                 1..9
                       note = Synthetic peptide
source                 1..9
                       mol_type = protein
                       organism = synthetic construct
SEQUENCE: 1021
QKLVFFAED                                                                  9

SEQ ID NO: 1022        moltype = AA   length = 8
FEATURE                Location/Qualifiers
REGION                 1..8
                       note = Synthetic peptide
source                 1..8
                       mol_type = protein
                       organism = synthetic construct
SEQUENCE: 1022
QKLVFFAE                                                                   8

SEQ ID NO: 1023        moltype = AA   length = 7
FEATURE                Location/Qualifiers
REGION                 1..7
                       note = Synthetic peptide
source                 1..7
                       mol_type = protein
                       organism = synthetic construct
SEQUENCE: 1023
QKLVFFA                                                                    7

SEQ ID NO: 1024        moltype = AA   length = 6
FEATURE                Location/Qualifiers
REGION                 1..6
                       note = Synthetic peptide
source                 1..6
                       mol_type = protein
                       organism = synthetic construct
SEQUENCE: 1024
QKLVFF                                                                     6

SEQ ID NO: 1025        moltype = AA   length = 5
FEATURE                Location/Qualifiers
REGION                 1..5
                       note = Synthetic peptide
source                 1..5
                       mol_type = protein
                       organism = synthetic construct
SEQUENCE: 1025
QKLVF                                                                      5

SEQ ID NO: 1026        moltype = AA   length = 4
FEATURE                Location/Qualifiers
REGION                 1..4
                       note = Synthetic peptide
source                 1..4
                       mol_type = protein
                       organism = synthetic construct
SEQUENCE: 1026
QKLV                                                                       4

SEQ ID NO: 1027        moltype =    length =
SEQUENCE: 1027
000

SEQ ID NO: 1028        moltype = AA   length = 10
FEATURE                Location/Qualifiers
REGION                 1..10
                       note = Synthetic peptide
source                 1..10
                       mol_type = protein
                       organism = synthetic construct
SEQUENCE: 1028
KLVFFAEDVG                                                                10

SEQ ID NO: 1029        moltype = AA   length = 9
FEATURE                Location/Qualifiers
REGION                 1..9
                       note = Synthetic peptide
```

-continued

```
source                   1..9
                         mol_type = protein
                         organism = synthetic construct
SEQUENCE: 1029
KLVFFAEDV                                                                        9

SEQ ID NO: 1030          moltype = AA   length = 8
FEATURE                  Location/Qualifiers
REGION                   1..8
                         note = Synthetic peptide
source                   1..8
                         mol_type = protein
                         organism = synthetic construct
SEQUENCE: 1030
KLVFFAED                                                                         8

SEQ ID NO: 1031          moltype = AA   length = 7
FEATURE                  Location/Qualifiers
REGION                   1..7
                         note = Synthetic peptide
source                   1..7
                         mol_type = protein
                         organism = synthetic construct
SEQUENCE: 1031
KLVFFAE                                                                          7

SEQ ID NO: 1032          moltype = AA   length = 6
FEATURE                  Location/Qualifiers
REGION                   1..6
                         note = Synthetic peptide
source                   1..6
                         mol_type = protein
                         organism = synthetic construct
SEQUENCE: 1032
KLVFFA                                                                           6

SEQ ID NO: 1033          moltype = AA   length = 5
FEATURE                  Location/Qualifiers
REGION                   1..5
                         note = Synthetic peptide
source                   1..5
                         mol_type = protein
                         organism = synthetic construct
SEQUENCE: 1033
KLVFF                                                                            5

SEQ ID NO: 1034          moltype = AA   length = 4
FEATURE                  Location/Qualifiers
REGION                   1..4
                         note = Synthetic peptide
source                   1..4
                         mol_type = protein
                         organism = synthetic construct
SEQUENCE: 1034
KLVF                                                                             4

SEQ ID NO: 1035          moltype = AA   length = 4
FEATURE                  Location/Qualifiers
REGION                   1..4
                         note = Synthetic peptide
source                   1..4
                         mol_type = protein
                         organism = synthetic construct
SEQUENCE: 1035
KLVF                                                                             4

SEQ ID NO: 1036          moltype = AA   length = 9
FEATURE                  Location/Qualifiers
REGION                   1..9
                         note = Synthetic peptide
source                   1..9
                         mol_type = protein
                         organism = synthetic construct
SEQUENCE: 1036
LVFFAEDVG                                                                        9

SEQ ID NO: 1037          moltype = AA   length = 8
FEATURE                  Location/Qualifiers
REGION                   1..8
```

```
                            note = Synthetic peptide
source                      1..8
                            mol_type = protein
                            organism = synthetic construct
SEQUENCE: 1037
LVFFAEDV                                                            8

SEQ ID NO: 1038             moltype = AA  length = 7
FEATURE                     Location/Qualifiers
REGION                      1..7
                            note = Synthetic peptide
source                      1..7
                            mol_type = protein
                            organism = synthetic construct
SEQUENCE: 1038
LVFFAED                                                             7

SEQ ID NO: 1039             moltype = AA  length = 6
FEATURE                     Location/Qualifiers
REGION                      1..6
                            note = Synthetic peptide
source                      1..6
                            mol_type = protein
                            organism = synthetic construct
SEQUENCE: 1039
LVFFAE                                                              6

SEQ ID NO: 1040             moltype = AA  length = 5
FEATURE                     Location/Qualifiers
REGION                      1..5
                            note = Synthetic peptide
source                      1..5
                            mol_type = protein
                            organism = synthetic construct
SEQUENCE: 1040
LVFFA                                                               5

SEQ ID NO: 1041             moltype = AA  length = 4
FEATURE                     Location/Qualifiers
REGION                      1..4
                            note = Synthetic peptide
source                      1..4
                            mol_type = protein
                            organism = synthetic construct
SEQUENCE: 1041
LVFF                                                                4

SEQ ID NO: 1042             moltype =   length =
SEQUENCE: 1042
000

SEQ ID NO: 1043             moltype = AA  length = 8
FEATURE                     Location/Qualifiers
REGION                      1..8
                            note = Synthetic peptide
source                      1..8
                            mol_type = protein
                            organism = synthetic construct
SEQUENCE: 1043
VFFAEDVG                                                            8

SEQ ID NO: 1044             moltype = AA  length = 7
FEATURE                     Location/Qualifiers
REGION                      1..7
                            note = Synthetic peptide
source                      1..7
                            mol_type = protein
                            organism = synthetic construct
SEQUENCE: 1044
VFFAEDV                                                             7

SEQ ID NO: 1045             moltype = AA  length = 6
FEATURE                     Location/Qualifiers
REGION                      1..6
                            note = Synthetic peptide
source                      1..6
                            mol_type = protein
                            organism = synthetic construct
SEQUENCE: 1045
```

-continued

```
VFFAED                                                                6

SEQ ID NO: 1046         moltype = AA  length = 5
FEATURE                 Location/Qualifiers
REGION                  1..5
                        note = Synthetic peptide
source                  1..5
                        mol_type = protein
                        organism = synthetic construct
SEQUENCE: 1046
VFFAE                                                                 5

SEQ ID NO: 1047         moltype = AA  length = 4
FEATURE                 Location/Qualifiers
REGION                  1..4
                        note = Synthetic peptide
source                  1..4
                        mol_type = protein
                        organism = synthetic construct
SEQUENCE: 1047
VFFA                                                                  4

SEQ ID NO: 1048         moltype =     length =
SEQUENCE: 1048
000

SEQ ID NO: 1049         moltype = AA  length = 7
FEATURE                 Location/Qualifiers
REGION                  1..7
                        note = Synthetic peptide
source                  1..7
                        mol_type = protein
                        organism = synthetic construct
SEQUENCE: 1049
FFAEDVG                                                               7

SEQ ID NO: 1050         moltype = AA  length = 6
FEATURE                 Location/Qualifiers
REGION                  1..6
                        note = Synthetic peptide
source                  1..6
                        mol_type = protein
                        organism = synthetic construct
SEQUENCE: 1050
FFAEDV                                                                6

SEQ ID NO: 1051         moltype = AA  length = 5
FEATURE                 Location/Qualifiers
REGION                  1..5
                        note = Synthetic peptide
source                  1..5
                        mol_type = protein
                        organism = synthetic construct
SEQUENCE: 1051
FFAED                                                                 5

SEQ ID NO: 1052         moltype = AA  length = 4
FEATURE                 Location/Qualifiers
REGION                  1..4
                        note = Synthetic peptide
source                  1..4
                        mol_type = protein
                        organism = synthetic construct
SEQUENCE: 1052
FFAE                                                                  4

SEQ ID NO: 1053         moltype =     length =
SEQUENCE: 1053
000

SEQ ID NO: 1054         moltype = AA  length = 6
FEATURE                 Location/Qualifiers
REGION                  1..6
                        note = Synthetic peptide
source                  1..6
                        mol_type = protein
                        organism = synthetic construct
SEQUENCE: 1054
FAEDVG                                                                6
```

```
SEQ ID NO: 1055        moltype = AA  length = 5
FEATURE                Location/Qualifiers
REGION                 1..5
                       note = Synthetic peptide
source                 1..5
                       mol_type = protein
                       organism = synthetic construct
SEQUENCE: 1055
FAEDV                                                                          5

SEQ ID NO: 1056        moltype = AA  length = 4
FEATURE                Location/Qualifiers
REGION                 1..4
                       note = Synthetic peptide
source                 1..4
                       mol_type = protein
                       organism = synthetic construct
SEQUENCE: 1056
FAED                                                                           4

SEQ ID NO: 1057        moltype =   length =
SEQUENCE: 1057
000

SEQ ID NO: 1058        moltype = AA  length = 31
FEATURE                Location/Qualifiers
REGION                 1..31
                       note = Synthetic peptide
source                 1..31
                       mol_type = protein
                       organism = synthetic construct
SEQUENCE: 1058
QTAPVPMPDL KNVKSKIGST ENLKHQPGGG K                                            31

SEQ ID NO: 1059        moltype = AA  length = 31
FEATURE                Location/Qualifiers
REGION                 1..31
                       note = Synthetic peptide
source                 1..31
                       mol_type = protein
                       organism = synthetic construct
SEQUENCE: 1059
VQIINKKLDL SNVQSKCGSK DNIKHVPGGG S                                            31

SEQ ID NO: 1060        moltype = AA  length = 31
FEATURE                Location/Qualifiers
REGION                 1..31
                       note = Synthetic peptide
source                 1..31
                       mol_type = protein
                       organism = synthetic construct
SEQUENCE: 1060
VQIVYKPVDL SKVTSKCGSL GNIHHKPGGG Q                                            31

SEQ ID NO: 1061        moltype = AA  length = 32
FEATURE                Location/Qualifiers
REGION                 1..32
                       note = Synthetic peptide
source                 1..32
                       mol_type = protein
                       organism = synthetic construct
SEQUENCE: 1061
VEVKSEKLDF KDRVQSKIGS LDNITHVPGG GN                                           32

SEQ ID NO: 1062        moltype = AA  length = 4
FEATURE                Location/Qualifiers
REGION                 1..4
                       note = linker
source                 1..4
                       mol_type = protein
                       organism = synthetic construct
SEQUENCE: 1062
GGGS                                                                           4

SEQ ID NO: 1063        moltype = AA  length = 5
FEATURE                Location/Qualifiers
REGION                 1..5
                       note = linker
```

```
source          1..5
                mol_type = protein
                organism = synthetic construct
SEQUENCE: 1063
GGGGS                                          5
```

What is claimed is:

1. A polypeptide comprising a first peptide comprising amino acid sequence EFR and comprising sequence 3-10 amino acids from residues 1-10 of SEQ ID NO:01 linked to a second peptide comprising amino acid sequence NLK and comprising 3-13 amino acids from residues 244-372 of SEQ ID NO:02.

2. The polypeptide of claim 1, wherein the first peptide is N-terminal to the second peptide.

3. The polypeptide of claim 1, wherein the first peptide is C-terminal to the second peptide.

4. The polypeptide of claim 1, wherein:

(a) the first peptide comprises an amino acid sequence selected from the group consisting of DAEFRHDSGY,   (SEQ ID NO: 03)
DAEFRHDSG,    (SEQ ID NO: 04)
DAEFRHDS,     (SEQ ID NO: 05)
DAEFRHD,      (SEQ ID NO: 06)
DAEFRH,       (SEQ ID NO: 07)
DAEFR,        (SEQ ID NO: 08)
DAEF,         (SEQ ID NO: 09)
DAE,          (SEQ ID NO: 10)
AEFRHDSGY,    (SEQ ID NO: 11)
AEFRHDSG,     (SEQ ID NO: 12)
AEFRHDS,      (SEQ ID NO: 13)
AEFRHD,       (SEQ ID NO: 14)
AEFRH,        (SEQ ID NO: 15)
AEFR,         (SEQ ID NO: 16)
AEF,          (SEQ ID NO: 17)
EFRHDSGY,     (SEQ ID NO: 18)
EFRHDSG,      (SEQ ID NO: 19)
EFRHDS,       (SEQ ID NO: 20)
EFRHD,        (SEQ ID NO: 21)
EFRH,         (SEQ ID NO: 22)
EFR,          (SEQ ID NO: 23)
FRHDSGY,      (SEQ ID NO: 24)
FRHDSG,       (SEQ ID NO: 25)
FRHDS,        (SEQ ID NO: 26)
FRHD,         (SEQ ID NO: 27)
FRH,          (SEQ ID NO: 28)
RHDSGY,       (SEQ ID NO: 29)
RHDSG,        (SEQ ID NO: 30)
RHDS,         (SEQ ID NO: 31)
RHD,          (SEQ ID NO: 32)
HDSGY,        (SEQ ID NO: 33)
HDSG,         (SEQ ID NO: 34)
HDS,          (SEQ ID NO: 35)
DSGY,         (SEQ ID NO: 36)
DSG,          (SEQ ID NO: 37)
and
SGY;          (SEQ ID NO: 38)

and (b) the second peptide comprises an amino acid sequence selected from the group consisting of

HQPGGG,       (SEQ ID NO: 55)
HQPGG,        (SEQ ID NO: 56)

-continued

VKSKIGST, (SEQ ID NO: 801)

SKIGSTEN, (SEQ ID NO: 817)

TENLKHQP, (SEQ ID NO: 695)

ENLKHQPG. (SEQ ID NO: 689)

5. The polypeptide of claim 1, wherein the first peptide and second peptide are linked by a cleavable linker.

6. The polypeptide of claim 5, wherein the cleavable linker comprises an amino acid sequence and the amino acid sequence comprises arginine-arginine (Arg-Arg), arginine-valine-arginine-arginine (Arg-Val-Arg-Arg (SEQ ID NO:69)), valine-citrulline (Val-Cit), valine-arginine (Val-Arg), valine-lysine (Val-Lys), valine-alanine (Val-Ala), phenylalanine-lysine (Phe-Lys), glycine-alanine-glycine-alanine (Gly-Ala-Gly-Ala; SEQ ID NO:80), alanine-glycine-alanine-glycine (Ala-Gly-Ala-Gly; SEQ ID NO:81), or lysine-glycine-lysine-glycine (Lys-Gly-Lys-Gly; SEQ ID NO:82).

7. The polypeptide of claim 1, further comprising a linker to a carrier at either a C-terminal portion of the polypeptide, or a N-terminal portion of the polypeptide.

8. The polypeptide of claim 7, wherein the linker comprises an amino acid sequence selected from the group consisting of GG, GGG, AA, AAA, KK, KKK, SS, SSS, GAGA (SEQ ID NO:80), AGAG (SEQ ID NO:81), and KGKG (SEQ ID NO:82).

9. The polypeptide of claim 7, wherein the linker to the carrier, if present, further comprises a C-terminal cysteine (C).

10. The polypeptide of claim 1, comprising an amino acid sequence selected from the group consisting of DAE-FRHDRRTENLKHQPGGC (SEQ ID NO:999), DAE-FRHDRRENLKHQPGGGC (SEQ ID NO:1000).

11. An immunotherapy composition, comprising the polypeptide of claim 1, wherein the polypeptide is linked to a carrier.

12. The immunotherapy composition of claim 11, wherein the carrier comprises serum albumins, immunoglobulin molecules, thyroglobulin, ovalbumin, tetanus toxoid (TT), diphtheria toxoid (DT), a genetically modified cross-reacting material (CRM) of diphtheria toxin, CRM197, meningococcal outer membrane protein complex (OMPC) and *H. influenzae* protein D (HiD), rEPA (*Pseudomonas aeruginosa* exotoxin A), KLH (keyhole limpet hemocyanin), and flagellin.

13. A pharmaceutical formulation comprising (a) the immunotherapy composition of claim 11 and (b) at least one adjuvant.

14. The pharmaceutical formulation of claim 13, wherein the adjuvant is selected from the group consisting of aluminum hydroxide, aluminum phosphate, aluminum sulfate, 3 De-O-acylated monophosphoryl lipid A (MPL), QS-21, TQL1055, QS-18, QS-17, QS-7, Complete Freund's Adjuvant (CFA), Incomplete Freund's Adjuvant (IFA), oil in water emulsions (such as squalene or peanut oil), CpG, polyglutamic acid, polylysine, AddaVax™, MF59®, and combinations thereof.

15. The pharmaceutical formulation of claim 13, wherein the adjuvant comprises a liposomal formulation.

16. The pharmaceutical formulation of claim 13, wherein the composition comprises at least one pharmaceutically acceptable diluent.

17. The pharmaceutical formulation of claim 13, comprising a multiple antigen presenting system (MAP).

18. The pharmaceutical formulation of claim 17, wherein the MAP comprises one or more of a Lys-based dendritic scaffold, helper T-cell epitopes, immune stimulating lipophilic moieties, cell penetrating peptides, radical induced polymerization, self-assembling nanoparticles as antigen-presenting platforms and gold nanoparticles.

19. A nucleic acid comprising a nucleic acid sequence encoding a polypeptide of claim 1.

20. A nucleic acid immunotherapy composition comprising the nucleic acid of claim 19 and at least one adjuvant.

21. An immunization kit comprising the immunotherapy composition of claim 11.

22. The kit of claim 21, further comprising an adjuvant.

23. The kit of claim 22, wherein the immunotherapy composition is in a first container and the adjuvant is in a second container.

24. A kit comprising the nucleic acid immunotherapy composition of claim 20.

25. The kit of claim 24, further comprising an adjuvant.

26. The kit of claim 25, wherein the nucleic acid is in a first container and the adjuvant is in a second container.

* * * * *